US 9,512,090 B2

(12) United States Patent
Shioda et al.

(10) Patent No.: US 9,512,090 B2
(45) Date of Patent: *Dec. 6, 2016

(54) TETRAZOLINONE COMPOUND AND USE THEREOF

(71) Applicant: Sumitomo Chemical Company, Limited, Tokyo (JP)

(72) Inventors: Takayuki Shioda, Takarazuka (JP); Sadayuki Arimori, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/907,699

(22) PCT Filed: Jul. 29, 2014

(86) PCT No.: PCT/JP2014/070414
§ 371 (c)(1),
(2) Date: Jan. 26, 2016

(87) PCT Pub. No.: WO2015/016373
PCT Pub. Date: Feb. 5, 2015

(65) Prior Publication Data
US 2016/0159755 A1    Jun. 9, 2016

(30) Foreign Application Priority Data

Jul. 31, 2013 (JP) .................. 2013-158726
Oct. 30, 2013 (JP) .................. 2013-225026

(51) Int. Cl.
C07D 257/04    (2006.01)
C07D 401/12    (2006.01)
C07D 403/12    (2006.01)
A01N 43/713    (2006.01)

(52) U.S. Cl.
CPC ........... *C07D 257/04* (2013.01); *A01N 43/713* (2013.01); *C07D 401/12* (2013.01); *C07D 403/12* (2013.01)

(58) Field of Classification Search
CPC    C07D 257/04; C07D 403/12; C07D 401/12; A01N 43/713
USPC ....................................................... 514/274
See application file for complete search history.

(56) References Cited

U.S. PATENT DOCUMENTS 6,583,090 B1 * 6/2003 Gewehr ............... C07D 231/12
504/280
2015/0031733 A1    1/2015 Yoshimoto et al.
2015/0051171 A1    2/2015 Yoshimoto et al.
2015/0203511 A1    7/2015 Arimori et al.
2015/0336908 A1   11/2015 Shioda et al.
2016/0081339 A1 *  3/2016 Yoshimoto ........... C07D 403/12
514/236.2

FOREIGN PATENT DOCUMENTS

| JP | H109208565 A | 8/1997 |
|---|---|---|
| WO | 9626191 A1 | 8/1996 |
| WO | 9636229 A1 | 11/1996 |
| WO | 9823156 A1 | 6/1998 |
| WO | 2013162072 A1 | 10/2013 |
| WO | 2013162077 A1 | 10/2013 |
| WO | 2014051165 A1 | 4/2014 |
| WO | 2014104384 A1 | 7/2014 |
| WO | 2015016372 A1 | 2/2015 |

OTHER PUBLICATIONS

International Search Report and Written Opinion (English language) issued Oct. 28, 2014 in International Application No. PCT/JP2014/070414.

* cited by examiner

*Primary Examiner* — Yong Chu
(74) *Attorney, Agent, or Firm* — Panitch Schwarze Belisario & Nadel LLP

(57) ABSTRACT

A tetrazolinone compound represented by formula (1):

(1)

Wherein $R^1$, $R^2$, $R^3$, and $R^{11}$ each represents a halogen atom, a C1-C6 alkyl group, etc.; $R^4$ and $R^5$ each represents a hydrogen atom, a halogen atom, a C1-C3 alkyl group, etc.; $R^6$ represents a C1-C3 alkyl group optionally having one or more halogen atoms, etc.; $R^7$, $R^8$, and $R^9$ each represents a hydrogen atom, a halogen atom, etc.; $R^{10}$ represents a C1-C3 alkyl group, etc.; and $R^{12}$ represents a phenyl group optionally having one or more atoms or groups selected from Group $P^3$, a phenoxy group optionally having one or more atoms or groups Group $P^3$, etc., has excellent control activity against pests.

7 Claims, No Drawings

TETRAZOLINONE COMPOUND AND USE THEREOF

CROSS-REFERENCE TO RELATED APPLICATION

This application is a Section 371 of International Application No. PCT/JP2014/070414, filed Jul. 29, 2014, which was published in the Japanese language on Feb. 5, 2015, under International Publication No. WO 2015/016373 A1, and the disclosure of which is incorporated herein by reference.

TECHNICAL FIELD

The present invention relates to a tetrazolinone compound and use thereof.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by formula (A):

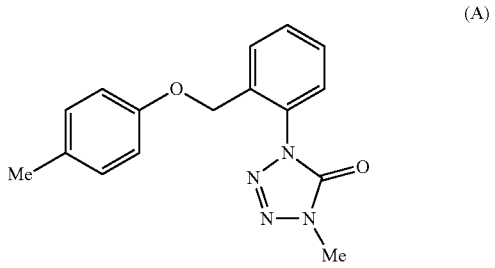

(A)

(see WO 96/036229 A).

DISCLOSURE OF THE INVENTION

The present invention provides compounds having excellent control activity against pests.

The present inventors have intensively studied so as to find compounds having excellent control activity against pests, and found that a tetrazolinone compound represented by the following formula (1) has excellent control activity against pests, thus completing the present invention.

The present invention includes the followings [1] to [8].

[1] A tetrazolinone compound represented by formula (1):

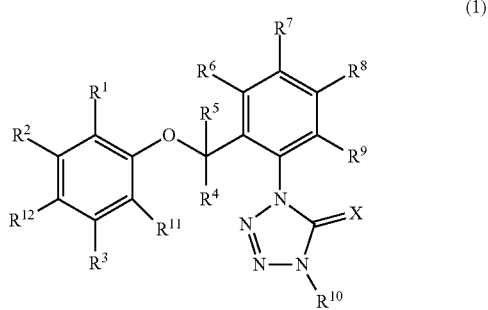

(1)

wherein $R^1$, $R^2$, $R^3$, and $R^{11}$ each independently represents a C1-C6 alkyl group optionally having one or more atoms or groups selected from Group $P^1$, a halogen atom, a hydrogen atom, a C1-C6 alkoxy group optionally having one or more halogen atoms, a cyano group, a nitro group, a C2-C6 alkenyl group optionally having one or more halogen atoms, a C2-C6 alkynyl group optionally having one or more halogen atoms, a C1-C8 alkylamino group optionally having one or more halogen atoms, a C1-C6 alkylthio group optionally having one or more halogen atoms, a C1-C6 alkylsulfinyl group optionally having one or more halogen atoms, a C1-C6 alkylsulfonyl group optionally having one or more halogen atoms, a pentafluorosulfanyl group, a C3-C9 trialkylsilyl group, a C2-C6 alkylcarbonyl group, a C2-C6 alkoxycarbonyl group, or an aminocarbonyl group optionally having a C1-C6 alkyl group;

$R^4$ and $R^5$ each independently represents a hydrogen atom, a halogen atom, or a C1-C3 alkyl group;

$R^6$ represents a C1-C6 alkyl group optionally having one or more halogen atoms, a C1-C6 alkoxy group optionally having one or more halogen atoms, a C3-C6 cycloalkyl group optionally having one or more halogen atoms, a halogen atom, a C2-C6 alkenyl group optionally having one or more halogen atoms, a cyano group, a C1-C6 alkylthio group optionally having one or more halogen atoms, a C2-C6 alkynyl group optionally having one or more halogen atoms, a nitro group, an aminocarbonyl group optionally having one or more C1-C6 alkyl groups, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkoxycarbonyl group, a hydroxy group, a sulfanyl group, a C1-C8 alkylamino group optionally having one or more halogen atoms, a pentafluorosulfanyl group, a C3-C9 trialkylsilyl group, a C1-C6 alkylsulfonyl group optionally having one or more halogen atoms, a C1-C6 alkylsulfinyl group optionally having one or more halogen atoms, a C2-C6 alkylcarbonyl group, a C2-C5 alkoxyalkyl group, or a C2-C5 alkylthioalkyl group;

$R^7$, $R^8$, and $R^9$ each independently represents a hydrogen atom, a halogen atom, a C1-C3 alkyl group optionally having one or more halogen atoms, a C2-C3 alkenyl group optionally having one or more halogen atoms, or a C1-C3 alkoxy group optionally having one or more halogen atoms;

$R^{10}$ represents a C1-C3 alkyl group optionally having one or more halogen atoms, a C2-C3 alkenyl group optionally having one or more halogen atoms, a C2-C3 alkynyl group optionally having one or more halogen atoms, or a C3-C5 cycloalkyl group optionally having one or more halogen atoms;

$R^{12}$ represents a C6-C16 aryl group optionally having one or more atoms or groups selected from Group $P^2$, a C6-C16 aryloxy group optionally having one or more atoms or groups selected from Group $P^2$, a C6-C16 arylthio group optionally having one or more atoms or groups selected from Group $P^2$, a C7-C18 aralkyl group optionally having one or more atoms or groups selected from Group $P^2$, a C7-C18 aralkyloxy group optionally having one or more atoms or groups selected from Group $P^2$, a C7-C16 aryloxyalkyl group optionally having one or more atoms or groups selected from Group $P^2$, an anilino group optionally having one or more atoms or groups selected from Group $P^2$, a C2-C5 alkylthioalkyl group, a C1-C6 alkyl group optionally having one or more C1-C3 alkoxy groups and/or halogen atoms, a C1-C6 alkoxy group optionally having one or more halogen atoms, a C2-C6 alkenyl group optionally having one or more halogen atoms, a C3-C6 cycloalkyl group optionally having one or more halogen atoms, a C3-C6 cycloalkenyl group optionally having one or more halogen atoms, a C1-C8 alkylamino group optionally having one or more halogen atoms, a C2-C9 heteroaryloxy group optionally having one or more atoms or groups selected from Group $P^2$ (provided that the heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring), $R^{13}R^{14}N-N=CH-$, $R^{13}R^{14}N-CH=N-$, a C1-C6 alkylsulfinyl group optionally having one or more halogen atoms, a C1-C6 alkylsulfonyl group optionally having one or more halogen atoms, a pentafluorosulfanyl group, a C2-C6 alkoxycarbonyl group, a C2-C6 alkylcarbonyloxy group, an aminocarbonyl group optionally having a C1-C6 alkyl group, or a C3-C9 trialkylsilyl group;

$R^{43}$ and $R^{14}$ each independently represents a hydrogen atom or a C1-C3 alkyl group; and X represents an oxygen atom or a sulfur atom:

Group $P^1$: Group consisting of a halogen atom, a cyano group, a C3-C6 cycloalkyl group optionally having one or more halogen atoms, a C1-C4 alkoxy group optionally having one or more halogen atoms, and a C1-C4 alkylthio group optionally having one or more halogen atoms; and Group $P^2$: Group consisting of a C1-C6 alkyl group optionally having one or more halogen atoms, a halogen atom, a cyano group, a hydroxy group, a C3-C6 cycloalkyl group optionally having one or more halogen atoms, a C1-C6 alkoxy group optionally having one or more halogen atoms, a C1-C6 alkylthio group optionally having one or more halogen atoms, a C2-C6 alkenyl group optionally having one or more halogen atoms, a C2-C6 alkynyl group optionally having one or more halogen atoms, a C1-C8 alkylamino group optionally having one or more halogen atoms, a C1-C6 alkylsulfinyl group optionally having one or more halogen atoms, a C1-C6 alkylsulfonyl group optionally having one or more halogen atoms, a pentafluorosulfanyl group, a C2-C6 alkoxycarbonyl group, a C2-C6 alkylcarbonyl group, a C2-C6 alkylcarbonyloxy group, a C2-C6 alkylcarbonylamino group, an aminocarbonyl group optionally having a C1-C6 alkyl group, and a C3-C9 trialkylsilyl group.

[2] The tetrazolinone compound according to [1], wherein $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms;

$R^2$ and $R^3$ represent a hydrogen atom, a halogen atom, a C1-C4 alkyl group optionally having one or more halogen atoms, a C1-C4 alkoxy group optionally having one or more halogen atoms, or a cyano group;

$R^4$, $R^5$, $R^7$, $R^8$, $R^9$, and $R^{11}$ are hydrogen atoms;

$R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group;

$R^{10}$ is a methyl group; or

X is an oxygen atom.

[3] The tetrazolinone compound according to [1] or [2], wherein $R^{12}$ is a phenyl group optionally having one or more atoms or groups selected from the following Group $P^3$:

Group $P^3$: Group consisting of a C1-C3 alkyl group optionally having one or more halogen atoms, a halogen atom, a cyano group, a C1-C3 alkoxy group optionally having one or more halogen atoms, a C3-C4 cycloalkyl group optionally having one or more halogen atoms, and a C1-C3 alkylthio group optionally having one or more halogen atoms.

[4] The tetrazolinone compound according to [1] or [2], wherein $R^{12}$ is a phenoxy group optionally having one or more atoms or groups selected from the following Group $P^3$:

Group $P^3$: Group consisting of a C1-C3 alkyl group optionally having one or more halogen atoms, a halogen atom, a cyano group, a C1-C3 alkoxy group optionally having one or more halogen atoms, a C3-C4 cycloalkyl group optionally having one or more halogen atoms, and a C1-C3 alkylthio group optionally having one or more halogen atoms.

[5] The tetrazolinone compound according to [1] or [2], wherein $R^1$ is a C1-C3 alkyl group optionally having one or more halogen atoms, a hydrogen atom, or a C1-C3 alkoxy group optionally having one or more halogen atoms;

$R^2$ is a hydrogen atom, a halogen atom, a C1-C4 alkyl group optionally having one or more halogen atoms, a C1-C4 alkoxy group optionally having one or more halogen atoms, or a cyano group;

$R^3$ is a hydrogen atom, a halogen atom, or a C1-C4 alkyl group optionally having one or more halogen atoms;

$R^4$, $R^5$, $R^6$, $R^7$, $R^8$, $R^9$, and $R^{11}$ are hydrogen atoms;

$R^6$ is a C1-C4 alkyl group optionally having one or more halogen atoms, a halogen atom, a C1-C4 alkoxy group optionally having one or more halogen atoms, or a C3-C5 cycloalkyl group optionally having one or more halogen atoms;

$R^{10}$ is a methyl group;

X is an oxygen atom;

$R^{12}$ is a phenyl group optionally having one or more atoms or groups selected from the following Group $P^3$, or a phenoxy group optionally having one or more atoms or groups selected from the following Group $P^3$:

Group $P^3$: Group consisting of a C1-C3 alkyl group optionally having one or more halogen atoms, a halogen atom, a cyano group, and a C1-C3 alkoxy group optionally having one or more halogen atoms.

[6] A pest control agent comprising the tetrazolinone compound according to any one of [1] to [5].

[7] A method for controlling pests, which comprises treating plants or soil with an effective amount of the tetrazolinone compound according to any one of [1] to [5].

[8] Use of the tetrazolinone compound according to any one of [1] to [5] for controlling pests.

According to the present invention, pests can be controlled.

MODE FOR CARRYING OUT THE INVENTION

A compound of the present invention (hereinafter referred to as the present compound) is a tetrazolinone compound represented by formula (1):

Formula (1)

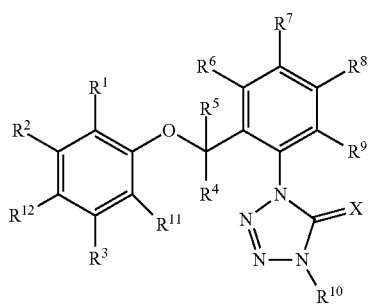

wherein symbols are the same as defined above.

Substituents as used herein will be mentioned in detail below.

Examples of the halogen atom include a fluorine atom, a chlorine atom, a bromine atom, and an iodine atom.

The C1-C6 alkyl group optionally having one or more halogen atoms represents a group in which one or more hydrogen atoms of a straight or branched alkyl group having 1-6 carbon atoms are optionally substituted with a halogen atom, and examples thereof include a methyl group, an ethyl group, a propyl group, an isopropyl group, a butyl group, an isobutyl group, a sec-butyl group, a tert-butyl group, a pentyl group, a hexyl group, a fluoromethyl group, a chloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, and a 2,2-difluoroethyl group.

The C1-C4 alkyl group optionally having one or more halogen atoms represents a group in which one or more hydrogen atoms of a straight or branched alkyl group having 1-4 carbon atoms are optionally substituted with a halogen atom, and examples thereof include a methyl group, an ethyl group, a propyl group, an isopropyl group, a butyl group, an isobutyl group, a sec-butyl group, a tert-butyl group, a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, and a 2,2-difluoroethyl group.

The C1-C6 alkyl group optionally having one or more atoms or groups selected from Group $P^1$ represents a C1-C6 alkyl in which a hydrogen atom is optionally substituted with one or more atoms or groups selected from Group $P^1$ and, when the C1-C6 alkyl group has two or more atoms or groups selected from Group $P^1$, those atoms and groups selected from Group $P^1$ may be the same or different to each other.

Examples of the C1-C6 alkyl group optionally having one or more atoms or groups selected from Group $P^1$ include a methyl group, an ethyl group, a propyl group, an isopropyl group, a butyl group, an isobutyl group, a sec-butyl group, a tert-butyl group, a pentyl group, a hexyl group, a 2,2,2-trifluoroethyl group, a 2,2,2-trichloroethyl group, a 3,3,3-trifluoropropyl group, a 2,2-difluoroethyl group, a 1,1-difluoroethyl group, a pentafluoroethyl group, a heptafluoroisopropyl group, a 1,1,2,2-tetrafluoroethyl group, a 2,2,3,3,3-pentafluoropropyl group, a 2,2,3,3,3-pentafluorobutyl group, a 2-(cyclopropyl)ethyl group, a 3-(cyclopropyl)propyl group, a 4-(cyclopropyl)butyl group, a 2-(cyclobutyl)ethyl group, a 3-cyclopropyl-2,2-difluoropropyl group, 2-methoxyethyl group, a 2-ethoxyethyl group, a 2-tert-butoxyethyl group, a 3-methoxypropyl group, a 3-ethoxypropyl group, a 2-(trifluoromethoxy)ethyl group, a 2-methylthioethyl group, a 3-methylthiopropyl group, a 2-ethylthioethyl group, a 3-ethylthiopropyl group, a 2-(tert-butylthio)-ethyl group, a 3-(tert-butylthio)-propyl group, a 2-(trifluoromethylthio)ethyl group, a 2-cyanoethyl group, a 3-cyanopropyl group, a 1-cyanoethyl group, a 2-cyano-2-methylethyl group, and a 2-cyano-2-methylpropyl group.

The C3-C6 cycloalkyl group optionally having one or more atoms or groups selected from Group $P^1$ represents a C3-C6 cycloalkyl in which a hydrogen atom is optionally substituted with one or more atoms or groups selected from Group $P^1$ and, when the C3-C6 cycloalkyl group has two or more atoms or groups selected from Group $P^1$, those atoms and groups selected from Group $P^1$ may be the same or different to each other.

Examples of the C3-C6 cycloalkyl group optionally having one or more atoms or groups selected from Group $P^1$ include a cyclopropyl group, a 1-fluorocyclopropyl group, a 2,2-difluorocyclopropyl group, a 1-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group, a 4,4-difluorocyclohexyl group, a 1-cyclopropylcyclopropyl group, a 2-cyclopropylcyclopropyl group, a 1-methoxycyclopropyl group, a 1-isopropoxycyclohexyl group, a 1-(trifluoromethoxy)cyclopropyl group, a 1-ethylthiocyclopropyl group, a 2-methylthiocyclopropyl group, a 1-(trifluoromethylthio)cyclopropyl group, a 2-(trifluoromethylthio)cyclopropyl group, a 1-cyanocyclopropyl group, a 2-cyanocyclopropyl group, and a 2,2-dicyanocyclopropyl group.

The C2-C6 alkenyl group optionally having one or more halogen atoms represents a group in which one or more hydrogen atoms of a straight or branched alkenyl group having 1-6 carbon atoms are optionally substituted with a halogen atom, and examples thereof include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 2-chlorovinyl group, a 2-bromovinyl group, a 2-iodovinyl group, a 3-chloro-2-propenyl group, a 1-trifluoromethylvinyl group, and a 4,4-difluoro-3-methyl-3-butenyl group.

The C2-C3 alkenyl group optionally having one or more halogen atoms represents a group in which one or more hydrogen atoms of a straight or branched alkenyl group having 1-3 carbon atoms are optionally substituted with a halogen atom, and examples thereof include a vinyl group, a 1-propenyl group, an isopropenyl group, a 2-propenyl group, a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, and a 2,3,3-trichloro-2-propenyl group.

The C2-C6 alkynyl group optionally having one or more halogen atoms represents a group in which one or more hydrogen atoms of a straight or branched alkynyl group having 1-6 carbon atoms are optionally substituted with a halogen atom, and examples thereof include an ethynyl group, a propargyl group, a 1-butyn-3-yl group, a 3-methyl-1-butyn-3-yl group, a 2-butynyl group, a 3-butynyl group, a 2-pentynyl group, a 3-pentynyl group, a 4-pentynyl group, a 1-hexynyl group, a 5-hexynyl group, a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3-fluoro-2-propynyl group, a perfluoro-2-butynyl group, a perfluoro-2-pentynyl group, a perfluoro-3-pentynyl group, and a perfluoro-1-hexynyl group.

The C2-C3 alkynyl group optionally having one or more halogen atoms represents a group in which one or more hydrogen atoms of a straight or branched alkynyl group having 1-3 carbon atoms are optionally substituted with a halogen atom, and examples thereof include an ethynyl group, a propargyl group, a fluoroethynyl group, a 3-chloro-2-propynyl group, a 3-bromo-2-propynyl group, a 3-iodo-2-propynyl group, and a 3-chloro-1-propynyl group.

The C3-C6 cycloalkyl group optionally having one or more halogen atoms represents a group in which one or more hydrogen atoms of a cycloalkyl group having 3-6 carbon atoms are optionally substituted with a halogen atom, and examples thereof include a cyclopropyl group, a cyclobutyl group, a cyclopentyl group, a cyclohexyl group, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2,2,3,3-tetrafluorocyclobutyl group, a 2-chlorocyclohexyl group, a 4,4-difluorocyclohexyl group, and a 4-chlorocyclohexyl group.

The C1-C6 alkoxy group optionally having one or more halogen atoms represents a group in which one or more hydrogen atoms of a straight or branched alkoxy group having 1-6 carbon atoms are optionally substituted with a halogen atom, and examples thereof include a methoxy group, an ethoxy group, a propoxy group, an isopropoxy group, a butoxy group, an isobutoxy group, a sec-butoxy group, a tert-butoxy group, a pentoxy group, an isoamyloxy group, a neopentoxy group, a 2-pentoxy group, a 3-pentoxy group, a 2-methylbutoxy group, a hexyloxy group, a trifluoromethoxy group, a trichloromethoxy group, a chloromethoxy group, a dichloromethoxy group, a fluoromethoxy group, a difluoromethoxy group, a pentafluoroethoxy group, a 2,2,2-trifluoroethoxy group, a 2-chloroethoxy group, a 2,2-difluoroethoxy group, a heptafluoropropoxy group, a 3,3,3-trifluoropropoxy group, a perfluoropentoxy group, a perchloropentoxy group, a perbromopentoxy group, a perfluorohexyloxy group, a perchlorohexyloxy group, a perbromohexyloxy group, and a periodohexyloxy group.

The C1-C3 alkoxy group optionally having one or more halogen atoms represents a group in which one or more hydrogen atoms of a straight or branched alkoxy group having 1-3 carbon atoms may be substituted with a halogen atom, and examples thereof include a methoxy group, an ethoxy group, a propoxy group, an isopropoxy group, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trifluoroethoxy group, a heptafluoropropoxy group, and a 3,3,3-trifluoropropoxy group.

The C1-C6 alkylthio group optionally having one or more halogen atoms represents a group in which at least one hydrogen atom of a straight or branched alkylthio group having 1-6 carbon atoms is optionally substituted with a halogen atom, and examples thereof include a methylthio group, an ethylthio group, a propylthio group, an isopropylthio group, a butylthio group, a sec-butylthio group, a tert-butylthio group, a pentylthio group, an isopentylthio group, a neopentylthio group, a hexylthio group, a monofluoromethylthio group, a difluoromethylthio group, a trifluoromethylthio group, a pentafluoroethylthio group, a 2,2,2-trifluoroethylthio group, a heptafluoropropylthio group, a 3,3,3-trifluoropropylthio group, a 3,3,3-trichloropropylthio group, a 3,3,3-tribromopropylthio group, a 3,3,3-triiodopropylthio group, and a periodohexylthio group.

The C3-C6 cycloalkyloxy group optionally having one or more halogen atoms represents a group in which one or more hydrogen atoms of a cycloalkyloxy group having 3-6 carbon atoms are optionally substituted with a halogen atom, and examples thereof include a cyclopropyloxy group, a cyclobutyloxy group, a cyclopentyloxy group, a cyclohexyloxy group, a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2,3,3-tetrafluorocyclobutyloxy group, a 2-chlorocyclohexyloxy group, a 4,4-difluorocyclohexyloxy group, and a 4-chlorocyclohexyloxy group.

The C3-C6 cycloalkylthio group optionally having one or more halogen atoms represents a group in which one or more hydrogen atoms of a cycloalkylthio group having 3-6 carbon atoms are optionally substituted with a halogen atom, and examples thereof include a cyclopropylthio group, a 2,2-difluorocyclopropylthio group, a cyclobutylthio group, a cyclopentylthio group, and a cyclohexylthio group.

The C3-C6 alkenyloxy group optionally having one or more halogen atoms represents a group in which one or more hydrogen atoms of a straight or branched alkenyloxy group having 3-6 carbon atoms are optionally substituted with a halogen atom, and examples thereof include a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 5-hexenyloxy group, a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 4,4,4-trifluoro-2-butenyloxy group, and a 5-bromo-4,5,5-trifluoro-4-trifluoromethyl-2-pentenyloxy group.

The C3-C6 alkynyloxy group optionally having one or more halogen atoms represents a group in which one or more hydrogen atoms of a straight or branched alkynyloxy group having 3-6 carbon atoms are optionally substituted with a halogen atom, and examples thereof include a propargyloxy group, a 1-butyn-3-yloxy group, a 3-methyl-1-butyn-3-yloxy group, a 2-butynyloxy group, a 3-butynyloxy group, a 2-pentynyloxy group, a 3-pentynyloxy group, a 4-pentynyloxy group, a 5-hexynyloxy group, a 3-chloro-2-propynyloxy group, a 3-bromo-2-propynyloxy group, a 3-iodo-2-propynyloxy group, a 5-chloro-4-pentynyloxy group, a 3-fluoro-2-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group.

The C3-C6 alkenylthio group optionally having one or more halogen atoms represents a group in which one or more hydrogen atoms of a straight or branched alkenylthio group having 3-6 carbon atoms are optionally substituted with a halogen atom, and examples thereof include a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 5-hexenylthio group, a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, and a 5-bromo-4,5,5-trifluoro-4-trifluoromethyl-2-pentenylthio group.

The C3-C6 alkynylthio group optionally having one or more halogen atoms represents a group in which one or more hydrogen atoms of a straight or branched alkynylthio group having 3-6 carbon atoms are optionally substituted with a halogen atom, and examples thereof include a propargylthio group, a 1-butyn-3-ylthio group, a 3-methyl-1-butyn-3-ylthio group, a 2-butynylthio group, a 3-butynylthio group, a 2-pentynylthio group, a 3-pentynylthio group, a 4-pentynylthio group, a 5-hexynylthio group, a 3-chloro-2-propynylthio group, a 3-bromo-2-propynylthio group, a 3-iodo-2-propynylthio group, a 5-chloro-4-pentynylthio group, a 3-fluoro-2-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group.

The C2-C6 alkoxycarbonyl group represents a group in which a C1-C5 alkoxy group and a carbonyl group are bound to each other, and may be either straight or branched, and examples thereof include a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutyloxycarbonyl group.

The aminocarbonyl group optionally having one or more C1-C6 alkyl groups represents an aminocarbonyl group in which one and/or two hydrogen atoms on nitrogen are optionally substituted with the same or different C1-C6 alkyl groups, and examples thereof include an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, a dipropylaminocarbonyl group, a diisopropylaminocarbonyl group, a pentylaminocarbonyl group, and a hexylaminocarbonyl group.

The C6-C16 aryl group optionally having one or more atoms or groups selected from Group $P^1$ represents a C6-C16 aryl group in which hydrogen atoms of an aryl group are optionally substituted with one or more atoms or groups selected from Group $P^2$ and, when the number of atoms or groups selected from Group $P^1$ is 2 or more, those atoms and groups may be the same or different to each other. Examples of the C6-C16 aryl group optionally having one or more atoms or groups selected from Group $P^2$ include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 4-methylphenyl group, a 4-trifluoromethylphenyl group, a 4-methoxyphenyl group, a 4-nitrophenyl group, a 4-dimethylaminophenyl group, a 4-methylthiophenyl group, a 2-cyanophenyl group, a 3-cyanophenyl group, a 4-cyanophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, a 2-bromo-3-fluorophenyl group, a 2-chloro-4-fluorophenyl group, a naphthyl group, a 2-fluoro-1-naphthyl group, a 4-chloro-2-naphthyl group, a 3-fluoro-1-acenaphthyl group, a 9-fluoro-1-phenanthryl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, and a 2-fluoro-4-methylphenyl group.

The phenyl group optionally having one or more atoms or groups selected from Group $P^3$ represents a phenyl group in which hydrogen atoms of a phenyl group are optionally substituted with one or more atoms or groups selected from Group $P^3$ and, when the number of atoms or groups selected from Group $P^3$ is 2 or more, those atoms and groups may be the same or different to each other. Examples of the phenyl group optionally having one or more atoms or groups selected from Group $P^3$ include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 4-methylphenyl group, a 4-trifluoromethylphenyl group, a 4-methoxyphenyl group, a 4-methylthiophenyl group, a 2-cyanophenyl group, a 3-cyanophenyl group, a 4-cyanophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, a 2-bromo-3-fluorophenyl group, a 2-chloro-4-fluorophenyl group, a 3,4,5-trifluorophenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, and a 2-fluoro-4-methylphenyl group:

Group $P^3$: Group consisting of a C1-C3 alkyl group optionally having one or more halogen atoms, a halogen atom, a cyano group, a C1-C3 alkoxy group optionally having one or more halogen atoms, a C3-C4 cycloalkyl group optionally having one or more halogen atoms, and a C1-C3 alkylthio group optionally having one or more halogen atoms.

The phenyl group optionally having one or more atoms or groups selected from Group $P^1$ represents a phenyl group in which hydrogen atoms of a phenyl group are optionally substituted with one or more atoms or groups selected from Group $P^4$ and, when the number of atoms or groups selected from Group $P^4$ is 2 or more, those atoms and groups may be the same or different to each other:

Group $P^4$: Group consisting of a methyl group, an ethyl group, a fluorine atom, a chlorine atom, a cyano group, a methoxy group, an ethoxy group, a trifluoromethyl group, a cyclopropyl group, and a methylthio group.

Examples of the phenyl group optionally having one or more atoms or groups selected from Group $P^1$ include a phenyl group, a 2-fluorophenyl group, a 3-fluorophenyl group, a 4-fluorophenyl group, a 2-chlorophenyl group, a 3-chlorophenyl group, a 4-chlorophenyl group, a 4-methylphenyl group, a 4-trifluoromethylphenyl group, a 4-methoxyphenyl group, a 4-methylthiophenyl group, a 2-cyanophenyl group, a 3-cyanophenyl group, a 4-cyanophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, a 2-chloro-4-fluorophenyl group, a 3,4,5-trifluorophenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, and a 2-fluoro-4-methylphenyl group.

The C6-C16 aryloxy group optionally having one or more atoms or groups selected from Group $P^2$ represents a C6-C16 aryloxy group in which hydrogen atoms of an aryloxy group are optionally substituted with or more atoms or groups selected from Group $P^2$ and, when the number of atoms or groups selected from Group $P^2$ is 2 or more, those atoms and groups may be the same or different to each other. Examples of the C6-C16 aryloxy group optionally having one or more atoms or groups selected from Group $P^2$ include a phenoxy group, a 1-naphthyloxy group, a 2-naphthyloxy group, a 9-anthryloxy group, a 2-fluorophenoxy group, a 3-fluorophenoxy group, a 4-fluorophenoxy group, a 2-chlorophenoxy group, a 3-chlorophenoxy group, a 4-chlorophenoxy group, a 2-bromophenoxy group, a 3-bromophenoxy group, a 4-bromophenoxy group, a 2-iodophenoxy group, a 3-iodophenoxy group, a 4-iodophenoxy group, a 2,4-difluorophenoxy group, a 2,5-dichlorophenoxy group, a 2,4,6-trifluorophenoxy group, a 2,3,4-trichlorophenoxy group, a pentafluorophenoxy group, a 2-bromo-4-fluorophenoxy group, a 2-chloro-3-fluorophenoxy group, a 2-fluoro-1-naphthyloxy group, a 3-chloro-1-naphthyloxy group, a 2-methylphenoxy group, a 3-methylphenoxy group, a 4-methylphenoxy group, a 2-cyanophenoxy group, a 3-cyanophenoxy group, and a 4-cyanophenoxy group.

The phenoxy group optionally having one or more atoms or groups selected from Group $P^3$ represents a phenoxy group in which hydrogen atoms of a phenoxy group are optionally substituted with one or more atoms or groups selected from Group $P^3$ and, when the number of atoms or groups selected from Group $P^3$ is 2 or more, those atoms and groups may be the same or different to each other. Examples of the phenoxy group optionally having one or more atoms or groups selected from Group $P^3$ include a phenoxy group, a 2-fluorophenoxy group, a 3-fluorophenoxy group, a 4-fluorophenoxy group, a 2-chlorophenoxy group, a 3-chlorophenoxy group, a 4-chlorophenoxy group, a 2-bromophenoxy group, a 3-bromophenoxy group, a 4-bromophenoxy group, a 2-iodophenoxy group, a 3-iodophenoxy group, a 4-iodophenoxy group, a 2,4-difluorophenoxy group, a 2,5-dichlorophenoxy group, a 2,4,6-trifluorophenoxy group, a 2,3,4-trichlorophenoxy group, a pentafluorophenoxy group, a pentachlorophenoxy group, a 2-bromo-4-fluorophenoxy group, a 2-chloro-3-fluorophenoxy group, a 2-methylphenoxy group, a 3-methylphenoxy group, a 4-methylphenoxy group, a 2-cyanophenoxy group, a 3-cyanophenoxy group, and a 4-cyanophenoxy group.

The phenoxy group optionally having one or more atoms or groups selected from Group $P^4$ represents a phenoxy group in which hydrogen atoms of a phenoxy group are optionally substituted with one or more atoms or groups selected from Group $P^4$ and, when the number of atoms or groups selected from Group $P^4$ is 2 or more, those atoms and groups may be the same or different to each other. Examples of the phenoxy group optionally having one or more atoms or groups selected from Group $P^4$ include a phenoxy group, a 2-fluorophenoxy group, a 3-fluorophenoxy group, a 4-fluorophenoxy group, a 2-chlorophenoxy group, a 3-chlorophenoxy group, a 4-chlorophenoxy group, a 2,4-difluorophenoxy group, a 2,5-dichlorophenoxy group, a 2,4,6-trifluorophenoxy group, a 2,3,4-trichlorophenoxy group, a pentafluorophenoxy group, a pentachlorophenoxy group, a 2-chloro-3-fluorophenoxy group, a 2-methylphenoxy group, a 3-methylphenoxy group, a 4-methylphenoxy group, a 2-cyanophenoxy group, a 3-cyanophenoxy group, and a 4-cyanophenoxy group.

The C6-C16 arylthio group optionally having one or more atoms or groups selected from Group $P^2$ represents a C6-C16 arylthio group in which hydrogen atoms of an arylthio group are optionally substituted with one or more atoms or groups selected from Group $P^2$ and, when the number of atoms or groups selected from Group $P^2$ is 2 or more, those atoms and groups may be the same or different to each other. Examples of the C6-C16 arylthio group optionally having one or more atoms or groups selected from Group $P^2$ include a phenylthio group, a 1-naphthylthio group, a 2-naphthylthio group, a 1-acenaphthylthio group, a 1-phenanthrylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, a 2-iodophenylthio group, a 3-iodophenylthio group, a 4-iodophenylthio group, a 2,4-difluorophenylthio group, and a 1-fluoro-2-naphthylthio group.

The C7-C18 aralkyl group optionally having one or more atoms or groups selected from Group $P^2$ represents a C7-C18 aralkyl group in which the total number of carbon atoms of the alkyl moiety and the aryl moiety is within a range of 7 to 18, and hydrogen atoms of the alkyl moiety and the aryl moiety are optionally substituted with one or more atoms or groups selected from Group $P^2$ and, when the number of atoms or groups selected from Group $P^2$ is 2 or more, those atoms and groups may be the same or different to each other. Examples of the C7-C18 aralkyl group optionally having one or more atoms or groups selected from Group $P^2$ include a benzyl group, a 2-phenylethyl group, a 3-phenylpropyl group, a 4-phenylbutyl group, a 5-phenylpentyl group, a 6-phenylhexyl group, a 7-phenylheptyl group, a 12-phenyldodecyl group, a 1-methoxy-2-phenylethyl group, a 1-naphthylmethyl group, a 2-(1-naphthyl)ethyl group, a 2-naphthylmethyl group, a 2-(2-naphthyl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2-methylbenzyl group, a 3-methylbenzyl group, a 4-methylbenzyl group, a 2-methoxybenzyl group, a 3-methoxybenzyl group, a 4-methoxybenzyl group, a 2-cyanobenzyl group, a 3-cyanobenzyl group, a 4-cyanobenzyl group, a 2,4-difluorobenzyl group, a 2,5-dichlorobenzyl group, a 2,4,6-trifluorobenzyl group, a 2,3,4-trichlorobenzyl group, a pentafluorobenzyl group, a 2-bromo-3-fluorobenzyl group, a 2-chloro-4-fluorobenzyl group, a 2-(4-bromophenyl)ethyl group, a 6-fluoro-1-naphthylmethyl group, a 4-chloro-2-naphthylmethyl group, a 2-(5-chloro-1-naphthyl)ethyl group, a difluoro(phenyl)methyl group, a hydroxy(phenyl)methyl group, and a methoxy(phenyl)methyl group.

The C7-C10 aralkyl group optionally having one or more C1-C4 alkoxy groups and/or hydroxy groups represents a C7-C18 aralkyl group in which the total number of carbon atoms of the alkyl moiety and the aryl moiety is within a range of 7 to 10, and hydrogen atoms of the alkyl moiety and the aryl moiety are optionally substituted with one or more C1-C4 alkoxy groups and/or hydroxy groups, and examples thereof include a benzyl group, a 2-phenylethyl group, a 3-phenylpropyl group, a 1-hydroxy-1-phenylmethyl group, a 1-methoxy-1-phenylmethyl group, and a 4-phenylbutyl group.

The C7-C18 aralkyloxy group optionally having one or more atoms or groups selected from Group $P^2$ represents an aralkyloxy group in which the total number of carbon atoms of the aryl moiety and the alkoxy moiety of an aralkyl is within a range of 7 to 18, and hydrogen atoms of the alkoxy moiety and the aryl moiety are optionally substituted with one or more atoms or groups selected from Group $P^2$ and, when the number of atoms or groups selected from Group $P^2$ is 2 or more, those atoms or groups may be the same or different to each other.

Examples of the C7-C18 aralkyloxy group optionally having one or more atoms or groups selected from Group $P^2$ include a benzyloxy group, a 2-phenylethyloxy group, a 3-phenylpropyloxy group, a 12-phenyldodecyloxy group, a naphthylmethyloxy group, a naphthylethyloxy group, a 4-fluorobenzyloxy group, a 2-chlorobenzyloxy group, a 3-bromobenzyloxy group, a 4-iodobenzyloxy group, a 2-methylbenzyloxy group, a 3-methylbenzyloxy group, a 4-methylbenzyloxy group, a 2-methoxybenzyloxy group, a 3-methoxybenzyloxy group, a 4-methoxybenzyloxy group, a 2-cyanobenzyloxy group, a 3-cyanobenzyloxy group, a 4-cyanobenzyloxy group, a 2,4-difluorobenzyloxy group, a 2,5-dichlorobenzyloxy group, a 3,4,5-trifluorobenzyloxy group, a 4-bromo-2-fluorobenzyloxy group, a 2-chloro-3-fluorobenzyloxy group, a 2-(3-chlorophenyl)ethyloxy group, a 2-(2-bromophenyl)ethyloxy group, a 3-(4-iodophenyl)propyloxy group, a 12-(4-bromophenyl)dodecyloxy group, a 4-fluoro-1-naphthylmethyloxy group, a 1-chloro-2-naphthylmethyloxy group, and a difluoro(phenyl)methyloxy group.

The C7-C10 aralkyloxy group represents an aralkyloxy group in which the total number of carbon atoms of the aryl moiety and the alkoxy moiety is within a range of 7 to 10, and examples of the C7-C10 aralkyloxy group include a benzyloxy group, a 2-phenylethyloxy group, a 3-phenylpropyloxy group, and a 4-phenylbutyloxy group.

The C7-C10 aryloxyalkyl group represents a group in which an aryloxy group is bound to an alkyl group, and the total number of carbon atoms as the C7-C10 aryloxyalkyl group is within a range of 7 to 10. Examples of the C7-C10 aryloxyalkyl group include a phenoxymethyl group, a phenoxyethyl group, a phenoxypropyl group, and a phenoxybutyl group.

The C7-C16 aryloxyalkyl group optionally having one or more atoms or groups selected from Group $P^2$ represents a C7-C16 aryloxyalkyl group in which the total number of carbon atoms of the aryloxy moiety and the alkyl moiety is within a range of 7 to 16, and hydrogen atoms of an aryloxyalkyl group are optionally substituted with one or more atoms or groups selected from Group $P^2$ and, when the number of atoms or groups selected from Group $P^2$ is 2 or more, those atoms and groups may be the same or different to each other. Examples of the C7-C16 aryloxyalkyl group optionally having one or more atoms or groups selected from Group $P^2$ include a phenoxymethyl group, a 1-naphthyloxymethyl group, a 2-naphthyloxymethyl group, a 3-fluorophenoxymethyl group, a 4-fluorophenoxymethyl group, a 2-chlorophenoxymethyl group, a 3-chlorophenoxymethyl group, a 4-chlorophenoxymethyl group, a phenoxyethyl group, and a naphthyloxyethyl group.

The anilino group optionally having one or more atoms or groups selected from Group $P^2$ represents an anilino group in which hydrogen atoms on phenyl and/or hydrogen atoms on nitrogen are optionally substituted with one or more atoms or groups selected from Group $P^2$ and, when the number of atoms or groups selected from Group $P^2$ is 2 or more, those atoms and groups may be the same or different to each other. Examples of the anilino group optionally having one or more atoms or groups selected from Group $P^2$ include an anilino group, an N-methyl-anilino group, an N-ethyl-anilino group, an N-methyl-2-fluoroanilino group, an N-methyl-3-fluoroanilino group, an N-methyl-4-fluoroanilino group, an N-methyl-4-chloroanilino group, an N-methyl-4-methylanilino group, and an N-methyl-4-cyanoanilino group.

The anilino group optionally having a C1-C4 alkyl group represents an anilino group in which hydrogen atoms on phenyl and/or hydrogen atoms on nitrogen are optionally substituted with an alkyl group.

Examples of the anilino group optionally having a C1-C4 alkyl group include an anilino group, an N-methyl-anilino group, an N-ethyl-anilino group, and an N-methyl-4-methylanilino group.

The C3-C6 cycloalkenyl group optionally having one or more halogen atoms represents a group in which one or more hydrogen atoms of a cycloalkenyl group having 3-6 carbon atoms are optionally substituted with a halogen atom, and examples thereof include a cyclopropenyl group, a cyclobutenyl group, a cyclopentenyl group, a cyclohexenyl group, a 4,4-difluorocyclohexenyl group, and a 4-chlorocyclohexenyl group.

The C2-C9 heteroaryloxy group (provided that the heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring) represents a heteroaryloxy group which has, as a ring-constituent atom, one or more atoms selected from the group consisting of a nitrogen atom, an oxygen atom, and a sulfur atom and, when the C2-C9 heteroaryloxy group has two or more atoms, the atoms may be the same or different to each other, and the heteroaryl moiety is a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring.

Examples of the C2-C9 heteroaryloxy group include a 2-pyridyloxy group, a 3-pyridyloxy group, a 4-pyridyloxy group, a 2-pyrimidyloxy group, a 3-pyridazyloxy group, a 2-pyrazyloxy group, a 2-thiazolyloxy group, a 2-oxazolyloxy group, a 2-benzthiazolyloxy group, a 2-benzoxazolyloxy group, a 2-quinolyloxy group, a 3-pyrazolyloxy group, a 3-furyloxy group, and a 3-thienyloxy group.

The C2-C9 heteroaryloxy group optionally having one or more atoms or groups selected from Group $P^2$ (provided that the heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring) represents a heteroaryloxy group in which hydrogen atoms of a C2-C9 heteroaryloxy group are optionally substituted with one or more atoms or groups selected from Group $P^2$ and, when the number of atoms or groups selected from Group $P^2$ is 2 or more, those atoms and groups may be the same or different to each other. Examples of the C2-C9 heteroaryloxy group optionally having one or more atoms or groups selected from Group $P^2$ include a 2-pyridyloxy group, a 3-pyridyloxy group, a 4-pyridyloxy group, a 2-pyrimidyloxy group, a 3-methyl-2-pyridyloxy group, a 4-methyl-2-pyridyloxy group, a 5-methyl-2-pyridyloxy group, a 6-methyl-2-pyridyloxy group, a 6-cyano-2-pyridyloxy group, a 3-pyridazyloxy group, a 2-pyrazyloxy group, a 2-thiazolyloxy group, a 2-oxazolyloxy group, a 2-benzthiazolyloxy group, a 2-benzoxazolyloxy group, a 2-quinolyloxy group, a 2-pyrazolyloxy group, a 3-furyloxy group, and a 3-thienyloxy group.

The C3-C9 trialkylsilyl group represents an alkylsilyl group in which three hydrogen atoms on a silyl group are substituted with the same or different C1-C4 alkyl groups, and examples thereof include a trimethylsilyl group, a tert-butyldimethylsilyl group, a triethylsilyl group, an isopropyldimethylsilyl group, and a triisopropylsilyl group.

The C1-C6 alkylsulfonyl group optionally having one or more halogen atoms represents a group in which one or more hydrogen atoms of a straight or branched alkylsulfonyl group having 1-6 carbon atoms are optionally substituted with a halogen atom, and examples thereof include a methylsulfonyl group, an ethylsulfonyl group, a propylsulfonyl group, an isopropylsulfonyl group, a butylsulfonyl group, a hexylsulfonyl group, a trifluoromethylsulfonyl group, a pentafluoroethylsulfonyl group, and a periodohexylsulfonyl group.

The C1-C6 alkylsulfinyl group optionally having one or more halogen atoms represents a group in which one or more hydrogen atoms of a straight or branched alkylsulfinyl group having 1-6 carbon atoms are optionally substituted with a halogen atom, and examples thereof include a methylsulfinyl group, an ethylsulfinyl group, a propylsulfinyl group, an isopropylsulfinyl group, a butylsulfinyl group, a hexylsulfinyl group, a trifluoromethylsulfinyl group, a pentafluoroethylsulfinyl group, a 2,2,2-trifluoroethylsulfinyl group, and a periodohexylsulfinyl group.

Examples of the C1-C3 alkyl group include a methyl group, an ethyl group, a propyl group, and an isopropyl group.

The C1-C3 alkyl group optionally having one or more halogen atoms represents a group in which one or more hydrogen atoms of a C1-C3 alkyl group are optionally substituted with a halogen atom, and examples thereof include a methyl group, an ethyl group, a propyl group, an isopropyl group, a chloromethyl group, a dichloromethyl group, a fluoromethyl group, a difluoromethyl group, a chlorofluoromethyl group, a dichlorofluoromethyl group, a chlorodifluoromethyl group, a trifluoromethyl group, a trichloromethyl group, a tribromomethyl group, a 2-fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, a heptafluoropropyl group, and a 1-(fluoromethyl)-2-fluoroethyl group.

The C3-C5 cycloalkyl group optionally having one or more halogen atoms represents a group in which one or more hydrogen atoms of a cycloalkyl group having 3-5 carbon atoms are optionally substituted with a halogen atom, and examples thereof include a cyclopropyl group, a cyclobutyl group, a cyclopentyl group, a 2-methylcyclopropyl group, a 2,2-dimethylcyclopropyl group, a 2,3-dimethylcyclopropyl group, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2-chlorocyclopentyl group, and a 3-chlorocyclopentyl group.

The C1-C4 alkoxy group optionally having one or more halogen atoms represents a group in which one or more hydrogen atoms of a straight or branched alkoxy group having 1-4 carbon atoms are optionally substituted with a halogen atom, and examples thereof include a methoxy group, an ethoxy group, a propyloxy group, an isopropyloxy group, a butyloxy group, an isobutyloxy group, a sec-butyloxy group, a tert-butyloxy group, a trifluoromethoxy group, a trichloromethoxy group, a difluoromethoxy group, a 2,2,2-trifluoroethoxy group, and a nonaiodobutoxy group.

The C1-C8 alkylamino group optionally having one or more halogen atoms represents an amino group in which one and/or two hydrogen atoms on nitrogen are substituted with the same or different C1-C8 alkyl groups, and examples thereof include an N-methylamino group, an N-ethylamino group, an N-propylamino group, an N-isopropylamino group, an N-butylamino group, an N,N-dimethylamino group, an N,N-diethylamino group, an N,N-dipropylamino group, an N,N-dibutylamino group, an N-ethyl-N-methylamino group, and an N-propyl-N-methylamino group.

The aminocarbonyl group optionally having a C1-C6 alkyl group represents an aminocarbonyl group in which one and/or two hydrogen atoms on nitrogen are substituted with the same or different C1-C8 alkyl groups, and examples thereof include an aminocarbonyl group, an N-methylaminocarbonyl group, an N-ethylaminocarbonyl group, an N-propylaminocarbonyl group, an N-isopropylaminocarbonyl group, an N-butylaminocarbonyl group, an N,N-dimethylaminocarbonyl group, an N,N-diethylaminocarbonyl group, an N,N-dipropylaminocarbonyl group, an N-ethyl-N-methylaminocarbonyl group, and an N-propyl-N-methylaminocarbonyl group.

The C2-C5 alkoxyalkyl group represents a group in which the total number of carbon atoms of the alkoxy moiety and the alkyl moiety is within a range of 2 to 5, and may be either straight or branched, and examples thereof include a methoxymethyl group, an ethoxymethyl group, a propyloxymethyl group, an isopropyloxymethyl group, a butyloxymethyl group, an isobutyloxymethyl group, a sec-butyloxymethyl group, a 1-methoxyethyl group, a 2-methoxyethyl group, a 2-propyloxyethyl group, a 2-isopropyloxyethyl group, a 3-methoxypropyl group, a 3-ethoxypropyl group, a 3-methoxybutyl group, and a 4-methoxybutyl group.

The C2-C5 alkylthioalkyl group represents a group in which the total number of carbon atoms of the alkylthio moiety and the alkyl moiety is within a range of 2 to 5, and may be either straight or branched, and examples thereof include a methylthiomethyl group, an ethylthiomethyl group, a propylthiomethyl group, an isopropylthiomethyl group, a butylthiomethyl group, an isobutylthiomethyl group, a sec-butylthiomethyl group, a 1-methylthioethyl group, a 2-methylthioethyl group, a 2-propylthioethyl group, a 2-isopropylthioethyl group, a 3-methylthiopropyl group, a 3-ethylthiopropyl group, a 3-methylthiobutyl group, and a 4-methylthiobutyl group.

The C2-C6 alkylcarbonyl group represents an alkylcarbonyl group having 2-6 carbon atoms, which has a straight or branched alkyl group having 1-5 carbon atoms, and examples thereof include a methylcarbonyl group, an ethylcarbonyl group, a propylcarbonyl group, an isopropylcarbonyl group, a pivaloyl group, a butylcarbonyl group, and a pentylcarbonyl group.

The C2-C6 alkylcarbonyloxy group represents an alkylcarbonyl group having a straight or branched alkyl group having 1-5 carbon atoms, and examples thereof include a methylcarbonyloxy group, an ethylcarbonyloxy group, a propylcarbonyloxy group, an isopropylcarbonyloxy group, a pivaloyloxy group, a butylcarbonyloxy group, and a pentylcarbonyloxy group.

The C1-C4 alkylthio group optionally having one or more halogen atoms represents a group in which one or more hydrogen atoms of a straight or branched alkylthio group having 1-4 carbon atoms are optionally substituted with a halogen atom, and examples thereof include a methylthio group, an ethylthio group, a propylthio group, an isopropylthio group, a butylthio group, an isobutylthio group, a tert-butylthio group, a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-trifluoroethylthio group, a 2,2,2-tribromoethylthio group, a 2,2,2-triiodoethylthio group, and a 2,2-difluoroethylthio group.

The C1-C6 alkyl group optionally having one or more C1-C3 alkoxy groups and/or halogen atoms represents a group in which one or more hydrogen atoms of a straight or branched C1-C6 alkyl group are optionally substituted with one or more C1-C3 alkoxy group and/or halogen atoms, and examples thereof include a methoxymethyl group, an ethoxymethyl group, and a trifluoromethyl group.

The total number of carbon atoms in the alkyl moiety and the carbonyl in the C2-C6 alkylcarbonylamino group is within a range of 2 to 6. Examples of the C2-C6 alkylcarbonylamino group include an acetylamino group, a propionylamino group, a butyrylamino group, an isobutyrylamino group, a pentanoylamino group, a 2-methylbutyrylamino group, and a hexanoylamino group.

The total number of carbon atoms of the alkyl moiety and the carbonyl in the C2-C4 alkylcarbonylamino group is within a range of 2 to 4. Examples of the C2-C4 alkylcarbonylamino group include an acetylamino group, a propionylamino group, a butyrylamino group, and an isobutyrylamino group.

Examples of the aspect of the present compound are compounds in which the substituent in formula (1) is shown below, including:

A compound in which $R^{12}$ is a phenyl group optionally having one or more atoms or groups selected from Group $P^3$;
A compound in which $R^{12}$ is a phenoxy group optionally having one or more atoms or groups selected from Group $P^3$;
A compound in which $R^{12}$ is a C2-C9 heteroaryloxy group optionally having one or more atoms or groups selected from Group $P^1$ (provided that heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring);
A compound in which $R^2$ is a hydrogen atom;
A compound in which $R^3$ is a hydrogen atom;
A compound in which $R^4$ is a hydrogen atom;
A compound in which $R^5$ is a hydrogen atom;
A compound in which $R^7$ is a hydrogen atom;
A compound in which $R^8$ is a hydrogen atom;
A compound in which $R^9$ is a hydrogen atom;
A compound in which $R^{10}$ is a hydrogen atom;
A compound in which $R^{11}$ is a hydrogen atom;
A compound in which $R^1$ is a C1-C3 alkyl group optionally having one or more halogen atoms;
A compound in which $R^1$ is a C3-C4 cycloalkyl group;
A compound in which $R^1$ is a halogen atom;
A compound in which $R^1$ is a methyl group;
A compound in which $R^1$ is an ethyl group;
A compound in which $R^1$ is a cyclopropyl group;
A compound in which $R^1$ is a trifluoromethyl group;
A compound in which $R^1$ is a fluorine atom;
A compound in which $R^1$ is a chlorine atom;
A compound in which $R^1$ is a bromine atom;
A compound in which $R^6$ is a C1-C3 alkyl group optionally having one or more halogen atoms;
A compound in which $R^6$ is a C3-C4 cycloalkyl group; A compound in which $R^6$ is a halogen atom;
A compound in which $R^6$ is a C2-C3 alkenyl group;
A compound in which $R^6$ is a C2-C3 alkynyl group;
A compound in which $R^6$ is a C1-C3 alkoxy group optionally having one or more halogen atoms;
A compound in which $R^6$ is a C1-C3 alkyl group optionally having one or more halogen atoms, a halogen atom, a C3-C4 cycloalkyl group, a C1-C3 alkoxy group optionally having one or more halogen atoms, a C2-C3 alkenyl group, or a C2-C3 alkynyl group;
A compound in which $R^6$ is a methyl group;
A compound in which $R^6$ is an ethyl group;
A compound in which $R^6$ is a propyl group;
A compound in which $R^6$ is a cyclopropyl group;
A compound in which $R^6$ is a trifluoromethyl group;
A compound in which $R^6$ is a difluoromethyl group;
A compound in which $R^6$ is a vinyl group;
A compound in which $R^6$ is a 2-propenyl group;
A compound in which $R^6$ is a chlorine atom;
A compound in which $R^6$ is a bromine atom;
A compound in which $R^6$ is an iodine atom;
A compound in which $R^6$ is a fluorine atom;
A compound in which $R^6$ is a methoxy group;
A compound in which $R^6$ is an ethoxy group;
A compound in which $R^2$ is a hydrogen atom;
A compound in which $R^2$ is a hydrogen atom, a methyl group, a methoxy group, or a cyano group;
A compound in which $R^{10}$ is a methyl group;
A compound in which X is an oxygen atom;
A compound in which X is a sulfur atom;
A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represents a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^4$, $R^4$, $R^3$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^3$, $R^4$, $R^5$, $R^7$, $R^8$, $R^9$, and $R^1$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^1$ is a phenyl group optionally having one or more atoms or groups selected from Group $P^1$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^1$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^E$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^3$, $R^4$, $R^5$, $R^7$, $R^2$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ and $R^1$ represent a hydrogen atom, a halogen atom, a C1-C4 alkyl group optionally having one or more halogen atoms, a C1-C4 alkoxy group optionally having one or more halogen atoms, or a cyano group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^4$, $R^4$, $R^5$, $R^7$, $R^2$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^2$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^4$, $R^4$, $R^4$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, a halogen atom, a C1-C4 alkyl group optionally having one or more halogen atoms, a C1-C4 alkoxy group optionally having one or more halogen atoms, or a cyano group, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a phenoxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenoxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a methyl group, an ethyl group, a fluorine atom, a chlorine atom, a bromine atom, or a trifluoromethyl group, $R^2$ is a hydrogen atom, $R^3$ is a hydrogen atom or a methyl group, $R^6$ is a methyl group, an ethyl group, a cyclopropyl group, a chlorine atom, a bromine atom, a methoxy group, an ethoxy group, or a trifluoromethyl group, $R^{12}$ is a phenyl group optionally having one or more atoms or groups selected from Group $P^4$, or a phenoxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a pyridyloxy group optionally having one or more atoms or groups selected from Group $P^4$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a benzyloxy group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a C2-C5 alkoxyalkyl group, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a C7-C18 aralkyl group optionally having one or more atoms or groups selected from Group $P^2$, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a C7-C18 aralkyloxy group optionally having one or more atoms or groups selected from Group $P^1$, $R^{1'}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a C2-C9 heteroaryloxy group optionally having one or more atoms or groups selected from Group $P^2$ (provided that the heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring), $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a pyrazolyloxy group optionally having one or more atoms or groups selected from Group $P^1$, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is a thiazolyloxy group optionally having one or more atoms or groups selected from Group $P^4$, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, $R^{12}$ is an oxazolyloxy group optionally having one or more atoms or groups selected from Group $P^4$, $R^{10}$ is a methyl group, and X is an oxygen atom;

A tetrazolinone compound in which $R^1$ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R² and R³ represent a hydrogen atom, a halogen atom, a C1-C3 alkyl group optionally having one or more halogen atoms, a C1-C3 alkoxy group optionally having one or more halogen atoms, or a cyano group, R⁶ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, R¹² is a tetrazolyloxy group optionally having one or more atoms or groups selected from Group P⁴, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R² and R³ represent a hydrogen atom, a halogen atom, a C1-C3 alkyl group optionally having one or more halogen atoms, a C1-C3 alkoxy group optionally having one or more halogen atoms, or a cyano group, R⁶ is a C1-C4 alkyl group optionally having one or more halogen atoms, a halogen atom, a C1-C4 alkoxy group optionally having one or more halogen atoms, a C3-C5 cycloalkyl group optionally having one or more halogen atoms, a C2-C4 alkenyl group optionally having one or more halogen atoms, or a C2-C4 alkynyl group, R¹² is a C3-C6 cycloalkyl group optionally having one or more halogen atoms, or a C3-C6 cycloalkenyl group optionally having one or more halogen atoms, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R² and R³ represent a hydrogen atom, a halogen atom, a C1-C4 alkyl group optionally having one or more halogen atoms, a C1-C4 alkoxy group optionally having one or more halogen atoms, or a cyano group, R⁶ is a methyl group, R¹² is a phenyl group optionally having one or more atoms or groups selected from Group P³, R¹, R⁵, R⁷, R⁸, R⁹, and R¹¹ are hydrogen atoms, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R² and R³ represent a hydrogen atom, a halogen atom, a C1-C4 alkyl group optionally having one or more halogen atoms, a C1-C4 alkoxy group optionally having one or more halogen atoms, or a cyano group, R⁶ is an ethyl group, R¹² is a phenyl group optionally having one or more atoms or groups selected from Group P³, R⁴, R⁵, R⁷, R⁸, R⁹, and R¹¹ are hydrogen atoms, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R¹ and R³ represent a hydrogen atom, a halogen atom, a C1-C4 alkyl group optionally having one or more halogen atoms, a C1-C4 alkoxy group optionally having one or more halogen atoms, or a cyano group, R⁶ is a cyclopropyl group, R¹¹ is a phenyl group optionally having one or more atoms or groups selected from Group P³, R⁴, R, R, R, R⁹, and R¹¹ are hydrogen atoms, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R² and R³ represent a hydrogen atom, a halogen atom, a C1-C4 alkyl group optionally having one or more halogen atoms, a C1-C4 alkoxy group optionally having one or more halogen atoms, or a cyano group, R⁶ is a chlorine atom, R¹² is a phenyl group optionally having one or more atoms or groups selected from Group P³, R⁴, R⁵, R⁷, R⁸, R⁹, and R¹¹ are hydrogen atoms, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R² and R³ represent a hydrogen atom, a halogen atom, a C1-C4 alkyl group optionally having one or more halogen atoms, a C1-C4 alkoxy group optionally having one or more halogen atoms, or a cyano group, R⁶ is a bromine atom, R¹² is a phenyl group optionally having one or more atoms or groups selected from Group P³, R⁴, R⁵, R⁷, R⁸, R⁹, and R¹¹ are hydrogen atoms, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R² and R³ represent a hydrogen atom, a halogen atom, a C1-C4 alkyl group optionally having one or more halogen atoms, a C1-C4 alkoxy group optionally having one or more halogen atoms, or a cyano group, R⁶ is a methoxy group, R¹² is a phenyl group optionally having one or more atoms or groups selected from Group P³, R⁴, R⁵, R⁷, R⁸, R⁹, and R¹' are hydrogen atoms, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, R² and R³ represent a hydrogen atom, a halogen atom, a C1-C4 alkyl group optionally having one or more halogen atoms, a C1-C4 alkoxy group optionally having one or more halogen atoms, or a cyano group, R⁶ is an ethoxy group, R¹² is a phenyl group optionally having one or more atoms or groups selected from Group P³, R⁴, R⁵, R⁷, R⁸, R⁹, and R¹¹ are hydrogen atoms, R¹⁰ is a methyl group, and X is an oxygen atom;

A tetrazolinone compound in which R¹ is a C1-C3 alkyl group optionally having one or more halogen atoms, a hydrogen atom, a C2-C3 alkynyl group optionally having one or more halogen atoms, a C3-C5 cycloalkyl group optionally having one or more halogen atoms, or a C1-C3 alkoxy group optionally having one or more halogen atoms, $R^2$ and $R^3$ represent a hydrogen atom, a halogen atom, a C1-C4 alkyl group optionally having one or more halogen atoms, a C1-C4 alkoxy group optionally having one or more halogen atoms, or a cyano group, $R^6$ is a trifluoromethyl group, $R^{12}$ is a phenyl group optionally having one or more atoms or groups selected from Group $P^3$, $R^4$, $R^5$, $R^7$, $R^8$, $R^9$, and $R^{11}$ are hydrogen atoms, $R^{10}$ is a methyl group, and X is an oxygen atom;

A tetrazolinone compound in which $R^1$ is a hydrogen atom, a C1-C6 alkyl group optionally having one or more atoms or groups selected from Group $P^1$, or a halogen atom, $R^2$ is a hydrogen atom, a C1-C6 alkyl group optionally having one or more atoms or groups selected from Group $P^1$, a C1-C6 alkoxy group optionally having one or more halogen atoms, or a cyano group, $R^3$ is a hydrogen atom, or a C1-C6 alkyl group optionally having one or more atoms or groups selected from Group $P^1$, $R^4$, $R^5$, $R^7$, $R^8$, $R^9$, and $R^{11}$ are hydrogen atoms, $R^6$ is a C1-C6 alkyl group optionally having one or more halogen atoms, a C1-C6 alkoxy group optionally having one or more halogen atoms, or a C3-C6 cycloalkyl group optionally having one or more halogen atoms, $R^{10}$ is a C1-C3 alkyl group optionally having one or more halogen atoms, $R^{12}$ is a C6-C16 aryl group optionally having one or more atoms or groups selected from Group $P^2$, a C6-C16 aryloxy group optionally having one or more atoms or groups selected from Group P, a C7-C18 aralkyl group optionally having one or more atoms or groups selected from Group $P^2$, a C7-C18 aralkyloxy group optionally having one or more atoms or groups selected from Group $P^2$, a C7-C16 aryloxyalkyl group optionally having one or more atoms or groups selected from Group $P^2$, an anilino group optionally having one or more atoms or groups selected from Group $P^2$, a C1-C6 alkyl group optionally having a C1-C3 alkoxy group and/or one or more halogen atoms, or a C2-C9 heteroaryloxy group optionally having one or more atoms or groups selected from Group $P^2$ (provided that heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring), and X is an oxygen atom;

A tetrazolinone compound in which $R^1$ is a hydrogen atom, a C1-C6 alkyl group, or a halogen atom, $R^2$ is a hydrogen atom, a C1-C6 alkyl group, a C1-C6 alkoxy group, or a cyano group, $R^3$ is a hydrogen atom or a C1-C6 alkyl group, $R^4$, $R^5$, $R^7$, $R^8$, $R^9$, and $R^{11}$ are hydrogen atoms, $R^6$ is a C1-C6 alkyl group, a C1-C6 alkoxy group, or a C3-C6 cycloalkyl group, $R^{10}$ is a C1-C3 alkyl group, $R^{12}$ is a phenyl group optionally having one or more atoms or groups selected from the group consisting of a C1-C4 alkyl group optionally having one or more halogen atoms, a halogen atom, a C1-C4 alkoxy group, a C1-C4 alkylthio group, a cyano group, a C1-C4 alkylcarbonyl group, a C1-C4 alkylsulfonyl group, and a C2-C4 alkylcarbonylamino group, a phenoxy group optionally having one or more atoms or groups selected from the group consisting of a C1-C4 alkyl group, a C1-C4 alkoxy group, a halogen atom, and a cyano group, a C7-C10 aralkyl group optionally having one or more C1-C4 alkoxy groups and/or hydroxy groups, a C7-C10 aralkyloxy group, a C7-C10 aryloxyalkyl group, an anilino group optionally having a C1-C4 alkyl group, a C1-C6 alkyl group optionally having a C1-C3 alkoxy group and/or one or more halogen atoms, or a C2-C9 heteroaryloxy group (provided that heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring), and X is an oxygen atom:

[Group $P^4$: Group consisting of a methyl group, an ethyl group, a fluorine atom, a chlorine atom, a cyano group, a methoxy group, an ethoxy group, a trifluoromethyl group, a cyclopropyl group, and a methylthio group]; and A tetrazolinone compound in which $R^1$ is a C1-C6 alkyl group optionally having one or more halogen atoms, a halogen atom, or a hydrogen atom, $R^2$ is a C1-C6 alkyl group optionally having one or more halogen atoms, a halogen atom, a hydrogen atom, a cyano group, or a C1-C6 alkoxy group optionally having one or more halogen atoms, $R^3$ is a hydrogen atom, a halogen atom, or a C1-C6 alkyl group, $R^6$ is a C1-C6 alkyl group optionally having one or more halogen atoms, a C1-C6 alkoxy group optionally having one or more halogen atoms, or a C3-C6 cycloalkyl group optionally having one or more halogen atoms, $R^{12}$ is a C6-C16 aryl group optionally having one or more atoms or groups selected from Group $P^2$ (provided that the C6-C16 aryl group optionally has one or more atoms or groups selected from the group consisting of a C1-C6 alkyl group optionally having one or more halogen atoms, a halogen atom, a cyano group, a C1-C6 alkoxy group optionally having one or more halogen atoms, a C1-C6 alkylthio group optionally having one or more halogen atoms, a C1-C6 alkylsulfonyl group optionally having one or more halogen atoms, a C2-C6 alkylcarbonyl group, and a C2-C6 alkylcarbonylamino group), $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom.

[Aspect 1]

A tetrazolinone compound in which $R^1$ is a C1-C6 alkyl group optionally having one or more halogen atoms, a halogen atom, or a hydrogen atom, $R^2$ is a C1-C6 alkyl group optionally having one or more halogen atoms, a halogen atom, a hydrogen atom, a cyano group, or a C1-C6 alkoxy group, $R^3$ is a hydrogen atom, a halogen atom, or a C1-C6 alkyl group, $R^6$ is a C1-C6 alkyl group, a C1-C6 alkoxy group, or a C3-C6 cycloalkyl group, $R^{12}$ is a phenyl group (provided that the phenyl group optionally has one or more atoms or groups selected from the group consisting of a C1-C6 alkyl group optionally having one or more halogen atoms, a halogen atom, a cyano group, a C1-C6 alkoxy group, a C1-C6 alkylthio group, a C1-C6 alkylsulfonyl group, a C2-C6 alkylcarbonyl group, and a C2-C6 alkylcarbonylamino group), $R^4$, $R^5$, $R^7$, $R^8$, $R^9$, and $R^{11}$ are hydrogen atoms, $R^{10}$ is a C1-C3 alkyl group, and X is an oxygen atom;

A tetrazolinone compound in which $R^6$ is a C1-C6 alkyl group in [Aspect 1];

A tetrazolinone compound in which $R^6$ is a C1-C6 alkoxy group in [Aspect 1]; and A tetrazolinone compound in which $R^6$ is a C3-C6 cycloalkyl group in [Aspect 1].

A tetrazolinone compound in which $R^1$ is a C1-C6 alkyl group optionally having one or more halogen atoms, or a hydrogen atom, $R^6$ is a C1-C6 alkyl group optionally having one or more halogen atoms, a C1-C6 alkoxy group optionally having one or more halogen atoms, or a C3-C6 cycloalkyl group optionally having one or more halogen atoms, $R^{12}$ is a phenoxy group (provided that the phenoxy group optionally has one or more atoms or groups selected from the group consisting of a C1-C6 alkyl group optionally having one or more halogen atoms, a halogen atom, a cyano group, and a C1-C6 alkoxy group optionally having one or more halogen atoms), $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom.

[Aspect 2]

A tetrazolinone compound in which $R^1$ is a C1-C6 alkyl group or a hydrogen atom, $R^6$ is a C1-C6 alkyl group, a C1-C6 alkoxy group, or a C3-C6 cycloalkyl group, $R^{12}$ is a phenoxy group (provided that the phenoxy group optionally has one or more atoms or groups selected from the group consisting of a C1-C6 alkyl group, a halogen atom, a cyano group, and a C1-C6 alkoxy group), $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^6$ is a C1-C6 alkyl group in [Aspect 2];

A tetrazolinone compound in which $R^6$ is a C1-C6 alkoxy group in [Aspect 2]; and A tetrazolinone compound in which $R^6$ is a C3-C6 cycloalkyl group in [Aspect 2].

[Aspect 3]

A tetrazolinone compound in which $R^1$ is a C1-C6 alkyl group optionally having one or more halogen atoms, or a hydrogen atom, $R^6$ is a C1-C6 alkyl group optionally having one or more halogen atoms, or a C1-C6 alkoxy group optionally having one or more halogen atoms, $R^{12}$ is a C2-C6 alkoxycarbonyl group, $R^2$, $R^3$, $R^4$, $R^5$, $R^7$, $R^8$, $R^9$, and $R^1$ are hydrogen atoms, $R^{10}$ is a C1-C3 alkyl group optionally having one or more halogen atoms, and X is an oxygen atom;

A tetrazolinone compound in which $R^6$ is a C1-C6 alkyl group in [Aspect 3]; and A tetrazolinone compound in which $R^6$ is a C1-C6 alkoxy group in [Aspect 3].

[Aspect 4]

A tetrazolinone compound in which $R^1$ is a C1-C6 alkyl group optionally having one or more halogen atoms, or a hydrogen atom, $R^6$ is a C1-C6 alkyl group optionally having one or more halogen atoms, or a C1-C6 alkoxy group optionally having one or more halogen atoms, $R^{12}$ is a C7-C18 aralkyl group optionally having one or more atoms or groups selected from a hydroxy group, and a C1-C6 alkoxy group optionally having one or more halogen atoms, $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^6$ is a C1-C6 alkyl group in [Aspect 4]; and A tetrazolinone compound in which $R^6$ is a C1-C6 alkoxy group in [Aspect 4].

[Aspect 5]

A tetrazolinone compound in which $R^1$ is a C1-C6 alkyl group optionally having one or more halogen atoms, or hydrogen atom, $R^6$ is a C1-C6 alkyl group optionally having one or more halogen atoms, or a C1-C6 alkoxy group optionally having one or more halogen atoms, $R^{12}$ is a C2-C6 alkenyl group optionally having one or more halogen atoms, $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^6$ is a C1-C6 alkyl group in [Aspect 5]; and A tetrazolinone compound in which $R^6$ is a C1-C6 alkoxy group in [Aspect 5].

A tetrazolinone compound in which $R^1$ is a C1-C6 alkyl group optionally having one or more halogen atoms, a halogen atom, or a hydrogen atom, $R^6$ is C1-C6 alkyl group optionally having one or more halogen atoms, $R^{12}$ is a C1-C6 alkyl group optionally having one or more C1-C3 alkoxy groups and/or halogen atoms, $R^2$, $R^3$, $R^4$, $R^5$, $R^7$, $R^8$, $R^9$, and $R^1$ are hydrogen atoms, $R^{10}$ is a C1-C3 alkyl group optionally having one or more halogen atoms, and X is an oxygen atom;

A tetrazolinone compound in which $R^6$ is a C1-C6 alkyl group optionally having one or more halogen atoms, $R^{12}$ is a C1-C6 alkylsulfonyl group optionally having one or more halogen atoms, $R^1$, $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^1$ is a C1-C6 alkyl group optionally having one or more halogen atoms, or a hydrogen atom, $R^6$ is a C1-C6 alkyl group optionally having one or more halogen atoms, $R^{12}$ is an anilino group optionally having one or more C1-C6 alkyl groups, $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^1$ is a C1-C6 alkyl group optionally having one or more halogen atoms, or a hydrogen atom, $R^6$ is a C1-C6 alkyl group optionally having one or more halogen atoms, $R^{12}$ is a C7-C18 aralkyloxy group optionally having one or more atoms or groups selected from Group $P^2$, $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^1$ is a C1-C6 alkyl group optionally having one or more halogen atoms, or a hydrogen atom, $R^6$ is a C1-C6 alkyl group optionally having one or more halogen atoms, $R^{12}$ is a C7-C16 aryloxyalkyl group optionally having one or more atoms or groups selected from Group $P^2$, $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^1$ is a C1-C6 alkyl group optionally having one or more halogen atoms, or a hydrogen atom, $R^6$ is a C1-C6 alkyl group optionally having one or more halogen atoms, $R^{12}$ is a C3-C6 cycloalkyl group optionally having one or more halogen atoms, $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^1$ is a C1-C6 alkyl group optionally having one or more halogen atoms, or a hydrogen atom, $R^6$ is a C1-C6 alkyl group optionally having one or more halogen atoms, $R^{12}$ is an aminocarbonyl group optionally having a C1-C6 alkyl group, $R^2$, $R^3$, $R^4$, $R^5$, $R^7$, $R^8$, $R^9$, and $R^{11}$ are hydrogen atoms, $R^{10}$ is a C1-C3 alkyl group optionally having one or more halogen atoms, and X is an oxygen atom;

A tetrazolinone compound in which $R^1$ is a C1-C6 alkyl group optionally having one or more halogen atoms, or a hydrogen atom, R⁶ is a C1-C6 alkyl group optionally having one or more halogen atoms, R¹² is a C3-C6 cycloalkenyl group optionally having one or more halogen atoms, R², R³, R⁴, R⁵, R⁷, R⁸, R⁹, and R¹¹ are hydrogen atoms, R¹⁰ is a C1-C3 alkyl group optionally having one or more halogen atoms, and X is an oxygen atom;

A tetrazolinone compound in which R¹ is a C1-C6 alkyl group optionally having one or more halogen atoms, or a hydrogen atom, R⁶ is a C1-C6 alkyl group optionally having one or more halogen atoms, R¹² is a C2-C6 alkylcarbonyloxy group, R², R³, R⁴, R⁵, R⁷, R⁸, R⁹, and R¹¹ are hydrogen atoms, R¹⁰ is a C1-C3 alkyl group optionally having one or more halogen atoms, and X is an oxygen atom;

A tetrazolinone compound in which R¹ is a C1-C6 alkyl group optionally having one or more halogen atoms, or a hydrogen atom, R⁶ is a C1-C6 alkyl group optionally having one or more halogen atoms, R¹² is R¹³R¹⁴N—CH=N—, R², R³, R⁴, R⁵, R⁷, R⁸, R⁹, and R¹¹ are hydrogen atoms, R¹⁰ is a C1-C3 alkyl group optionally having one or more halogen atoms, and X is an oxygen atom;

A tetrazolinone compound in which R¹ is a C1-C6 alkyl group optionally having one or more halogen atoms, or a hydrogen atom, R⁶ is a C1-C6 alkyl group optionally having one or more halogen atoms, R¹² is R¹³R¹⁴N—N=CH—, R², R³, R⁴, R⁵, R⁷, R⁸, R⁹, and R¹¹ are hydrogen atoms, R¹⁰ is a C1-C3 alkyl group optionally having one or more halogen atoms, and X is an oxygen atom;

A tetrazolinone compound in which R¹ is a C1-C6 alkyl group optionally having one or more halogen atoms, or a hydrogen atom, R⁶ is a C1-C6 alkyl group optionally having one or more halogen atoms, R¹² is a C2-C9 heteroaryloxy group, R², R³, R⁴, R⁵, R⁷, R⁸, R⁹, and R¹¹ are hydrogen atoms, R¹⁰ is a C1-C3 alkyl group optionally having one or more halogen atoms, and X is an oxygen atom;

A tetrazolinone compound in which R¹ is a C1-C6 alkyl group optionally having one or more halogen atoms, R², R⁴, R⁵, R⁷, R⁸, R⁹, and R¹¹ are hydrogen atoms, R³ and R¹⁰ are C1-C3 alkyl groups optionally having one or more halogen atoms, R⁶ is a C1-C4 alkyl group optionally having one or more halogen atoms, a halogen atom, a C1-C4 alkoxy group optionally having one or more halogen atoms, or a C3-C5 cycloalkyl group optionally having one or more halogen atoms, R¹² is a phenyl group (provided that the phenyl group optionally has one or more atoms or groups selected from the group consisting of a C1-C3 alkyl group optionally having one or more halogen atoms, a halogen atom, a cyano group, and a C1-C3 alkoxy group optionally having one or more halogen atoms), a phenoxy group (provided that the phenoxy group optionally has one or more atoms or groups selected from the group consisting of a C1-C3 alkyl group optionally having one or more halogen atoms, a halogen atom, a cyano group, and a C1-C3 alkoxy group optionally having one or more halogen atoms), or a pyridyloxy group, and X is an oxygen atom;

A tetrazolinone compound in which R¹ is a C1-C6 alkyl group optionally having one or more halogen atoms, or a hydrogen atom, R², R⁴, R⁵, R⁷, R⁸, R⁹, and R¹¹ are hydrogen atoms, R³ and R¹⁰ are C1-C3 alkyl groups optionally having one or more halogen atoms, R⁶ is a C1-C6 alkyl group optionally having one or more halogen atoms, a halogen atom, a C1-C4 alkoxy group optionally having one or more halogen atoms, or a C3-C5 cycloalkyl group optionally having one or more halogen atoms, R¹² is a phenyl group (provided that the phenyl group optionally has one or more atoms or groups selected from the group consisting of a C1-C3 alkyl group optionally having one or more halogen atoms, a halogen atom, a cyano group, and a C1-C3 alkoxy group optionally having one or more halogen atoms), and X is an oxygen atom;

A tetrazolinone compound in which R¹ is a C1-C6 alkyl group optionally having one or more halogen atoms, or a hydrogen atom, R², R⁴, R⁵, R⁷, R⁸, R⁹, and R¹¹ are hydrogen atoms, R³ and R¹⁰ are C1-C3 alkyl groups optionally having one or more halogen atoms, R⁶ is a C1-C6 alkyl group optionally having one or more halogen atoms, a halogen atom, a C1-C4 alkoxy group optionally having one or more halogen atoms, or a C3-C5 cycloalkyl group optionally having one or more halogen atoms, R¹² is a phenoxy group (provided that the phenoxy group optionally has one or more atoms or groups selected from the group consisting of a C1-C3 alkyl group optionally having one or more halogen atoms, a halogen atom, a cyano group, and a C1-C3 alkoxy group optionally having one or more halogen atoms), and X is an oxygen atom.

In the present description, the structural formula of the compound may, for the sake of convenience, represent a certain form of an isomer, but the present invention includes all kinds of active isomers arising from the structure of the compound, such as a geometrical isomer, an optical isomer, a stereoisomer, and a tautomeric isomer, and a mixture thereof. Thus, it is not limited to the formula mentioned for the sake of convenience, and can be any single isomer or a mixture thereof. Accordingly, the present compound may have an asymmetric carbon atom in the molecule and may contain an optically active isomer and a racemic isomer, but the present invention is not particularly limited thereto, and includes any cases.

Next, a process for producing the present compound will be described.

The present compound can be produced, for example, by the following Production Processes.

(Production Process A)

A compound represented by formula (1) (hereinafter referred to as the compound (1)) can be produced by reacting a compound represented by formula (A1) (hereinafter referred to as the compound (A1)) with a compound represented by formula (A2) (hereinafter referred to as the compound (A2)) in the presence of a base:

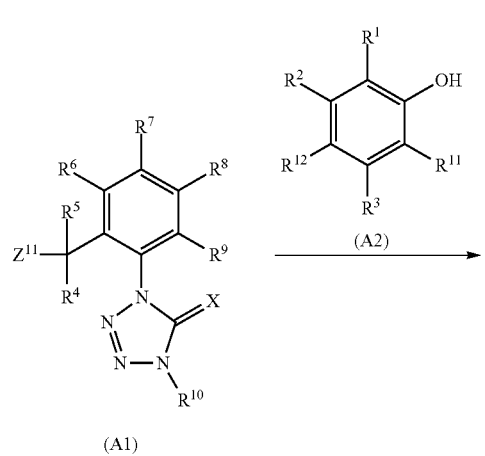

-continued

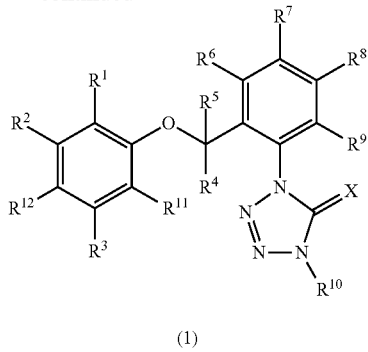

(1)

wherein $R^1$, $R^2$, $R^3$, $R^4$, $R^5$, $R^7$, $R^8$, $R^9$, $R^{10}$, $R^{11}$, $R^{12}$ and X are the same as defined above, and $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used in the proportion of 0.001 to 1.2 mols based on 1 mol of the compound (A1).

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

Among the compounds (1), a compound in which $R^{12}$ is $A^1$ (hereinafter referred to as the compound (1-1)) can be produced by subjecting a compound represented by formula (B1) (hereinafter referred to as the compound (B1)) and a compound represented by formula (B2) (hereinafter referred to as the compound (B2)) to a coupling reaction in the presence of a base and a catalyst:

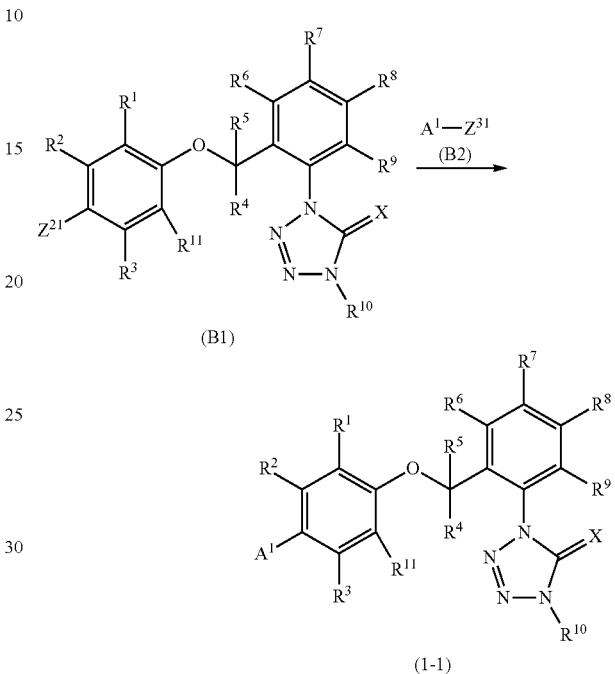

wherein $R^1$, $R^2$, $R^3$, $R^4$, $R^5$, $R^6$, $R^7$, $R^8$, $R^9$, $R^{10}$, $R^{11}$, and X are the same as defined above, $A^1$ represents a C6-C16 aryl group optionally having one or more atoms or groups selected from Group $P^2$, a C3-C6 cycloalkenyl group optionally having one or more halogen atoms, or a C7-C18 aralkyl group optionally having one or more atoms or groups selected from Group $P^2$, $Z^2$ represents a chlorine atom, a bromine atom, or an iodine atom, and $Z^{31}$ represents $B(OH)_2$, an alkoxyboryl group, or a trifluoroborate $BF_3^-K^+$.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. It is possible to produce a boric acid ester derivative by reacting an iodine compound ($A^1$-I) or a bromo compound ($A^1$-Br) with an alkyllithium such as butyllithium, followed by a reaction with a boric acid ester. It is possible to produce a boric acid derivative by optionally hydrolyzing the boric acid ester derivative obtained by the above-mentioned reaction. It is also possible to produce a trifluoroborate $BF_3^-K^+$ by fluorinating the boric acid ester with potassium hydrogen fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphosphaneferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time of the reaction is usually within a range of 0.1 to 24 hours.

After completion of the reaction, the compound (1-1) can be isolated by performing post-treatment operations such as extraction of the reaction mixture with an organic solvent, and drying and concentration of the organic layer. The isolated present compound can be further purified by chromatography, recrystallization, and the like.

(Production Process C)

Among the compounds (1), a compound in which A is $A^1$ (hereinafter referred to as the compound (1-2)) can be produced by subjecting a compound represented by formula (C1) (hereinafter referred to as the compound (C1)) and a compound represented by formula (C2) (hereinafter referred to as the compound (C2)) to a coupling reaction in the presence of a base and a catalyst:

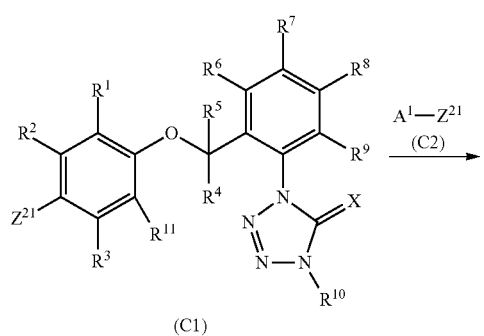

(C1)

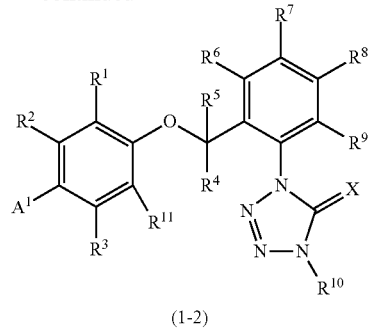

(1-2)

wherein $R^1R^2$, $R^3$, $R^4$, $R^5$, $R^7$, $R^8$, $R^9$, $R^{10}$, $R^{11}$, $A^1$, $Z^{21}$, $Z^{31}$, and X are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is possible to usually use, as the compound (C2) to be used in the reaction, commercially available compounds. Specific examples thereof include bromobenzene, iodobenzene, 1-bromo-2-methylbenzene, and the like.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphosphaneferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time of the reaction is usually within a range of 0.1 to 24 hours.

After completion of the reaction, the compound (1-2) can be isolated by performing post-treatment operations such as extraction of the reaction mixture with an organic solvent, and drying and concentration of the organic layer. The isolated present compound can be further purified by chromatography, recrystallization, and the like.

(Production Process D)

The compound (1) can be produced by reacting a compound represented by formula (1-3) (hereinafter referred to as the compound (1-3)) with a compound represented by formula (E1) (hereinafter referred to as the compound (E1)) in the presence of a base:

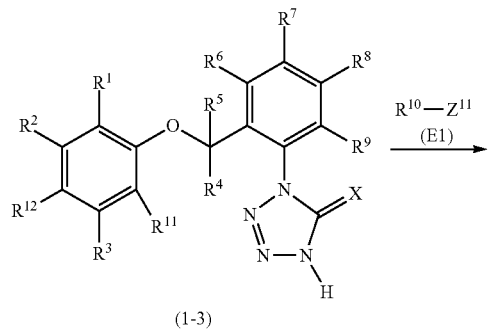

(1-3)

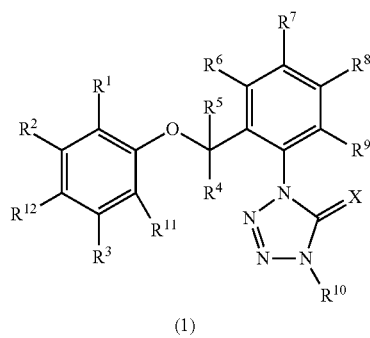

(1)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is possible to usually use, as the compound (E1) to be used in the reaction, commercially available compounds. Specific examples thereof include alkyl halides such as methyl bromide, ethyl bromide, n-propyl bromide, methyl iodide, ethyl iodide, n-propyl bromide, methyl iodide, ethyl iodide, n-propyl iodide, and isopropyl iodide; sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate; and sulfuric acid esters such as dimethyl sulfate, diethyl sulfate, and di-n-propyl sulfate.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide and potassium tert-butoxide.

In the reaction, the compound (E1) is usually used in the proportion within a range of 1 to 10 mols, and the base is usually used in the proportion within a range of 1 to 10 mols, based on 1 mol of the compound (1-3).

The reaction temperature of the reaction is usually within a range of −20 to 150° C. The reaction time is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process E)

Among the compounds (1), a compound in which X is a sulfur atom (hereinafter referred to as the compound (1-S)) can be produced from a compound in which X is an oxygen atom (hereinafter referred to as the compound (1-O)) of the compound (1) by a known sulfidation reaction:

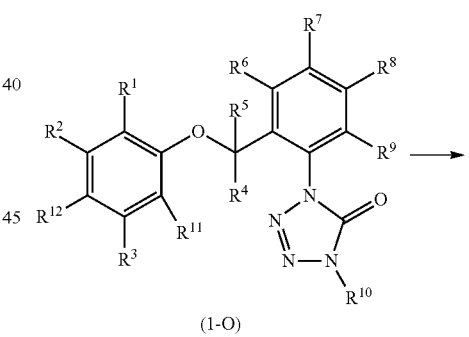

(1-O)

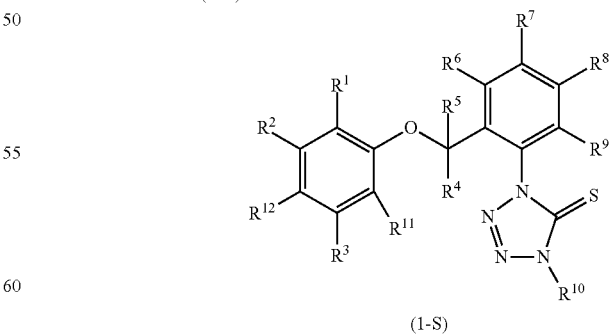

(1-S)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (1-0).

The reaction temperature of the reaction is usually within a range of −20 to 150° C. The reaction time is usually within a range of 0.1 to 24 hours.

In the reaction, if necessary, organic bases such as pyridine and trimethylamine; and inorganic bases such as alkali metal hydroxide and alkali metal carbonate may be added, and the amount of the base to be added is within a range of 0.5 to 1.5 mols based on the compound (1-0).

After completion of the reaction, the compound (1-S) can be isolated by performing post-treatment operations such as extraction of the reaction mixture with an organic solvent, and drying and concentration of the organic layer. The isolated present compound can be further purified by chromatography, recrystallization, and the like.

(Production Process F)

Among the compounds (1), a compound represented by formula (1-4) in which $R^6$ is $R^{71}$ (hereinafter referred to as the compound (1-4)) can be produced by subjecting a compound represented by formula (G1) (hereinafter referred to as the compound (G1)) and a compound represented by formula (G21) (hereinafter referred to as the compound (G21)) to a coupling reaction in the presence of a base and a catalyst:

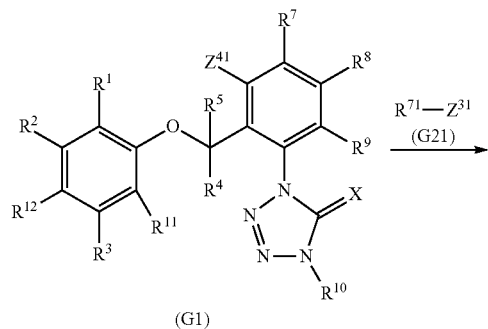

wherein $R^1$, $R^2$, $R^3$, $R^4$, $R^5$, $R^7$, $R^8$, $R^9$, $R^{10}$, $R^{11}$, $R^{12}$, and $Z^{31}$ are the same as defined above, $Z^{41}$ represents a chlorine atom, a bromine atom, an iodine atom, or a trifluoromethanesulfonyloxy group, $R^{71}$ represents a C1-C6 alkyl group optionally having one or more halogen atoms, a C2-C6 alkenyl group optionally having one or more halogen atoms, a C2-C6 alkynyl group optionally having one or more halogen atoms, or a C3-C6 cycloalkyl group optionally having one or more halogen atoms.

The reaction can be carried out in accordance with the reaction mentioned in Production Process B.

Among the compounds (1), a compound represented by formula (1-5) in which $R^7$ is $R^{72}$ (hereinafter referred to as the compound (1-5)) can be produced by subjecting a compound represented by formula (G2) (hereinafter referred to as the compound (G2)) and a compound represented by formula (G22) (hereinafter referred to as the compound (G22)) to a coupling reaction in the presence of a base and a catalyst:

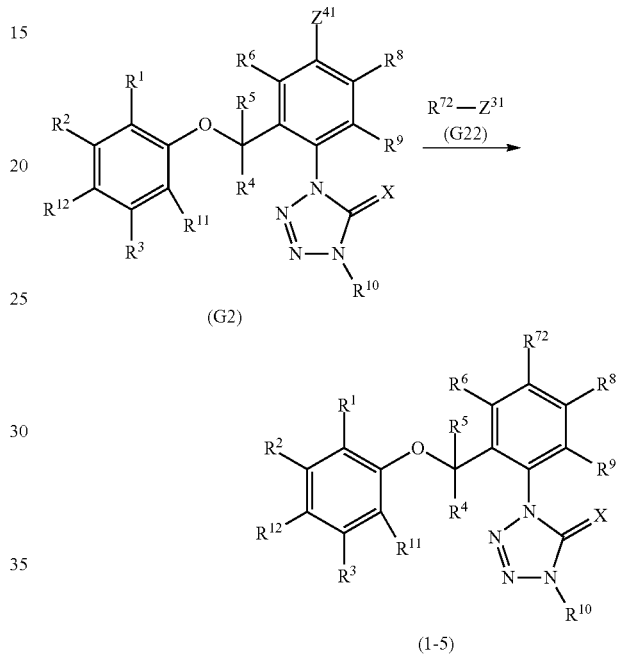

wherein $R^1$, $R^2$, $R^3$, $R^4$, $R^5$, $R^6$, $R^7$, $R^8$, $R^9$, $R^{10}$, $R^{11}$, $R^{12}$, $Z^{31}$, and $Z^{41}$ are the same as defined above, and $R^{72}$ represents a C1-C4 alkyl group optionally having one or more halogen atoms, or a C3-C5 cycloalkyl group optionally having one or more halogen atoms.

The reaction can be carried out in accordance with the reaction mentioned in Production Process B.

Among the compounds (1), a compound represented by formula (1-6) in which $R^8$ is $R^{72}$ (hereinafter referred to as the compound (1-6)) can be produced by subjecting a compound represented by formula (G3) (hereinafter referred to as the compound (G3)) and the compound (G22) to a coupling reaction in the presence of a base and a catalyst:

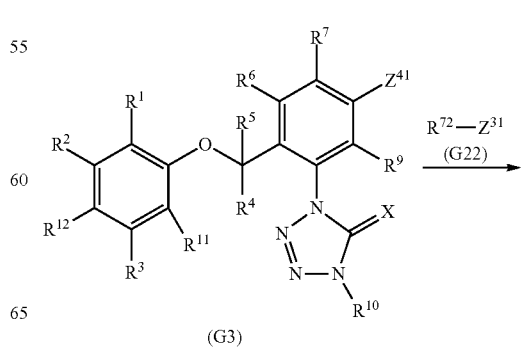

-continued

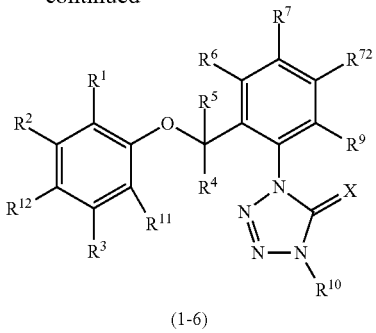

(1-6)

wherein symbols are the same as defined above.

The reaction can be carried out in accordance with the reaction mentioned in Production Process B.

Among the compounds (1), a compound represented by formula (1-7) in which $R^9$ is $R^{72}$ (hereinafter referred to as the compound (1-7)) can be produced by subjecting a compound represented by formula (G4) (hereinafter referred to as the compound (G4)) and the compound (G22) to a coupling reaction in the presence of a base and a catalyst:

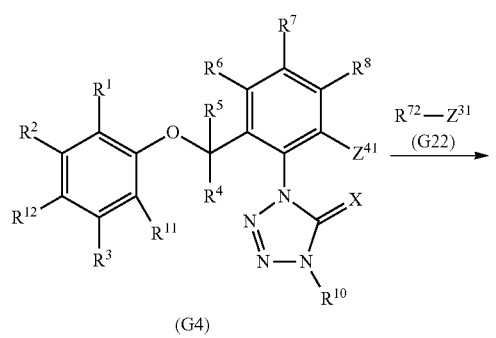

(G4)

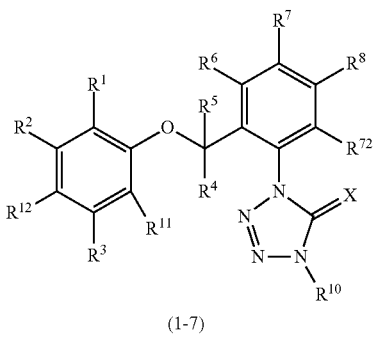

(1-7)

wherein symbols are the same as defined above.

The reaction can be carried out in accordance with the reaction mentioned in Production Process B.

In accordance with Production Process B, it is possible to produce a compound in which two or more substituents selected from $R^6$, $R^7$, $R^8$, and $R^9$ are either $R^{71}$ or $R^{72}$, among the compounds (1).

It is also possible to produce the compound (1) by using the other known coupling reaction in place of the coupling reaction of the Production Process B.

(Production Process G)

Among the compounds (1), a compound represented by formula (1-8) in which $R^1$ is $R^{73}$ (hereinafter referred to as the compound (1-8)) can be produced by subjecting a compound represented by formula (H1) (hereinafter referred to as the compound (H1)) and a compound represented by formula (H21) (hereinafter referred to as the compound (H21)) to a coupling reaction in the presence of a base and a catalyst:

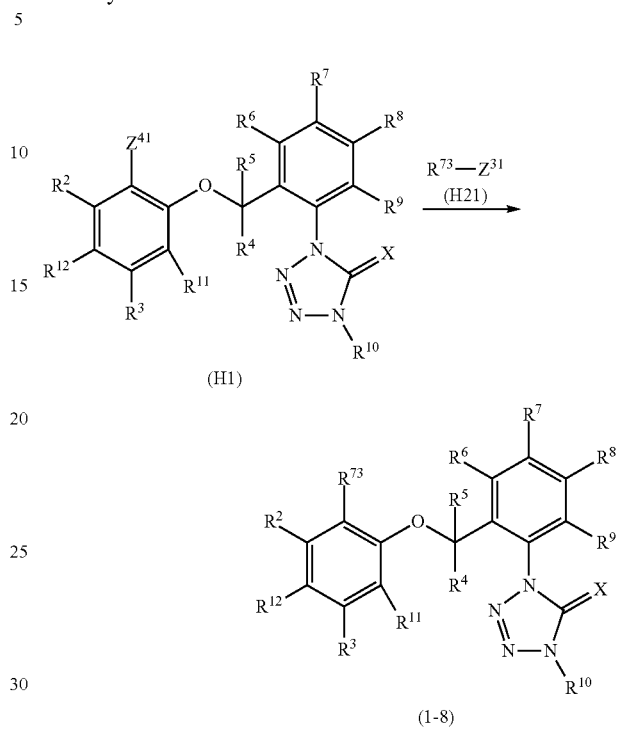

(1-8)

wherein $R^2$, $R^3$, $R^4$, $R^5$, $R^6 R^7$, $R^8$, $R^9$, $R^{10}$, $R^{11}$, $R^{12}$, $Z^{31}$, and $Z^{41}$ are the same as defined above, $R^{73}$ represents a C1-C6 alkyl group optionally having one or more atoms or groups selected from Group $P^1$; a C3-C6 cycloalkyl group optionally having one or more atoms or groups selected from Group $P^1$; a C2-C6 alkenyl group optionally having one or more halogen atoms; or a C2-C6 alkynyl group optionally having one or more halogen atoms.

The reaction can be carried out in accordance with the reaction mentioned in Production Process B.

Among the compounds (1), a compound represented by formula (1-9) in which $R^2$ is $R^{73}$ (hereinafter referred to as the compound (1-9)) can be produced by subjecting a compound represented by formula (H2) (hereinafter referred to as the compound (H2)) and the compound (H21) to a coupling reaction in the presence of a base and a catalyst:

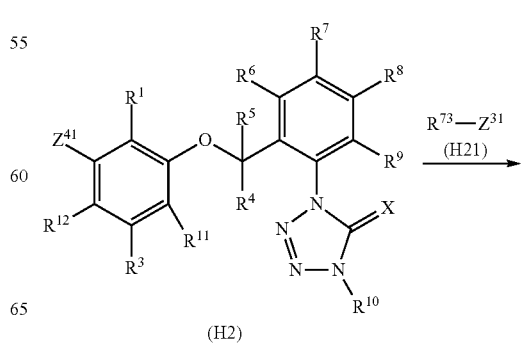

(H2)

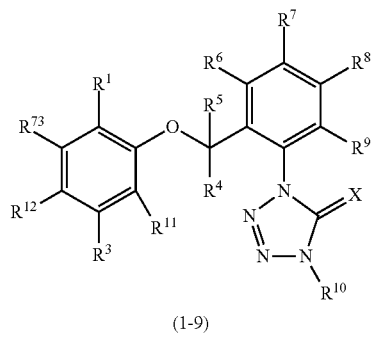

(1-9)

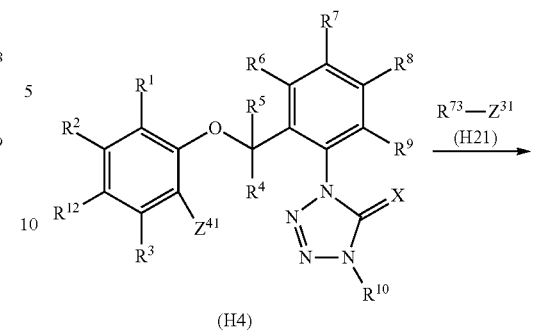

(H4)

wherein symbols are the same as defined above.

The reaction can be carried out in accordance with the reaction mentioned in Production Process B.

Among the compounds (1), a compound represented by formula (1-10) in which $R^3$ is $R^{73}$ (hereinafter referred to as the compound (1-10)) can be produced by subjecting a compound represented by formula (H3) (hereinafter referred to as the compound (H3)) and the compound (H21) to a coupling reaction in the presence of a base and a catalyst:

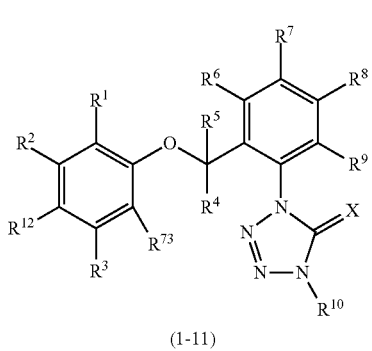

(1-11)

wherein symbols are the same as defined above.

The reaction can be carried out in accordance with the reaction mentioned in Production Process B.

In accordance with Production Process B, it is possible to produce a compound in which two or more substituents selected from $R^1$, $R^2$, $R^3$, and $R^{11}$ are $R^{73}$, among the compounds (1).

It is also possible to produce the compound (1) by using the other known coupling reaction in place of the coupling reaction of the Production Process B.

(Production Process H)

Among the compounds (1), a compound in which $R^{12}$ is $-O-A^2$ (hereinafter referred to as the compound (1-12)) can be produced by reacting a compound represented by formula (I1) (hereinafter referred to as the compound (I1)) and a compound represented by formula (I2) (hereinafter referred to as the compound (I2)) to a coupling reaction in the presence of a base, a catalyst, and a ligand:

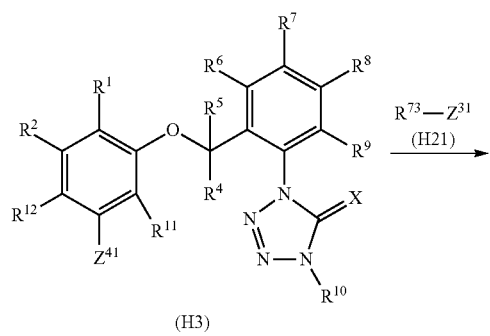

(H3)

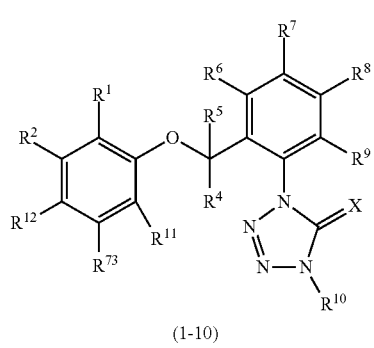

(1-10)

wherein symbols are the same as defined above.

The reaction can be carried out in accordance with the reaction mentioned in Production Process B.

Among the compounds (1), a compound represented by formula (1-11) in which $R^{11}$ is $R^{73}$ (hereinafter referred to as the compound (1-11)) can be produced by subjecting a compound represented by formula (H4) (hereinafter referred to as the compound (H4)) and the compound (H21) to a coupling reaction in the presence of a base and a catalyst:

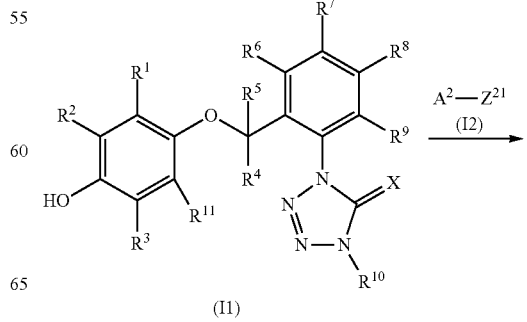

(I1)

-continued

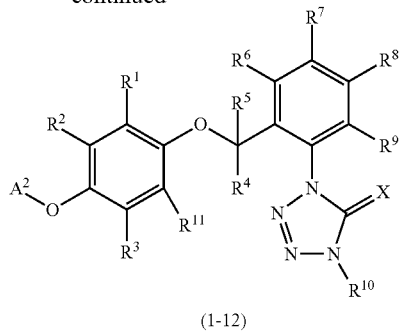

(1-12)

wherein $R^1$, $R^2$, $R^3$, $R^4$, $R^5$, $R^7$, $R^8$, $R^9$, $R^{10}$, $R^1$, $Z^{21}$, and X are the same as defined above, $A^2$ represents a C6-C16 aryl group optionally having one or more atoms or groups selected from Group $P^2$, a C7-C18 aralkyl group optionally having one or more atoms or groups selected from Group $P^2$, or a heteroaryl group optionally having one or more atoms or groups selected from Group $P^2$.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile; and mixtures thereof.

Examples of the catalyst to be used in the reaction include copper(I) iodide, copper(I) bromide, copper(I) chloride, copper(I) oxide, copper(II) acetate, and the like.

Examples of the ligand to be used in the reaction include ethylenediamine, 2-picolinic acid, N-butylimidazole, dipivaloylmethane, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time is usually within a range of 0.1 to 72 hours.

After completion of the reaction, the compound (1-12) can be isolated by performing post-treatment operations such as extraction of the reaction mixture with an organic solvent, and drying and concentration of the organic layer.

The isolated present compound can be further purified by chromatography, recrystallization, and the like.

(Production Process I)

Among the compounds (1), a compound in which $R^{12}$ is $A^4$ (hereinafter referred to as the compound (1-13)) can be produced by subjecting a compound represented by formula (J1) (hereinafter referred to as the compound (J1)) and a compound represented by formula (J2) (hereinafter referred to as the compound (J2)) to a coupling reaction in the presence of a base, a catalyst, and a ligand:

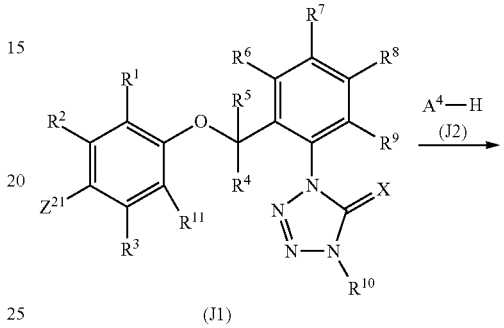

(J1)

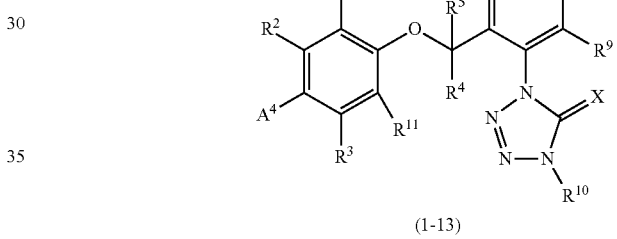

(1-13)

wherein $R^1$, $R^2$, $R^3$, $R^4$, $R^5$, $R^6$, $R^7$, R, $R^9$, $R^{10}$, $R^{11}$, $Z^{21}$, and X are the same as defined above, $A^4$ represents a C6-C16 aryloxy group optionally having one or more atoms or groups selected from Group $P^1$, a C7-C18 aralkyloxy group optionally having one or more atoms or groups selected from Group $P^2$, a C6-C16 arylthio group optionally having one or more atoms or groups selected from Group $P^2$, or a C2-C9 heteroaryloxy group optionally having one or more atoms or groups selected from Group $P^2$ (provided that heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring).

The reaction can be carried out in accordance with the reaction mentioned in Production Process H.

The process for synthesizing an intermediate compound will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)) or a compound represented by formula (XA2) (hereinafter referred to as the compound (XA2)) with an azidation agent:

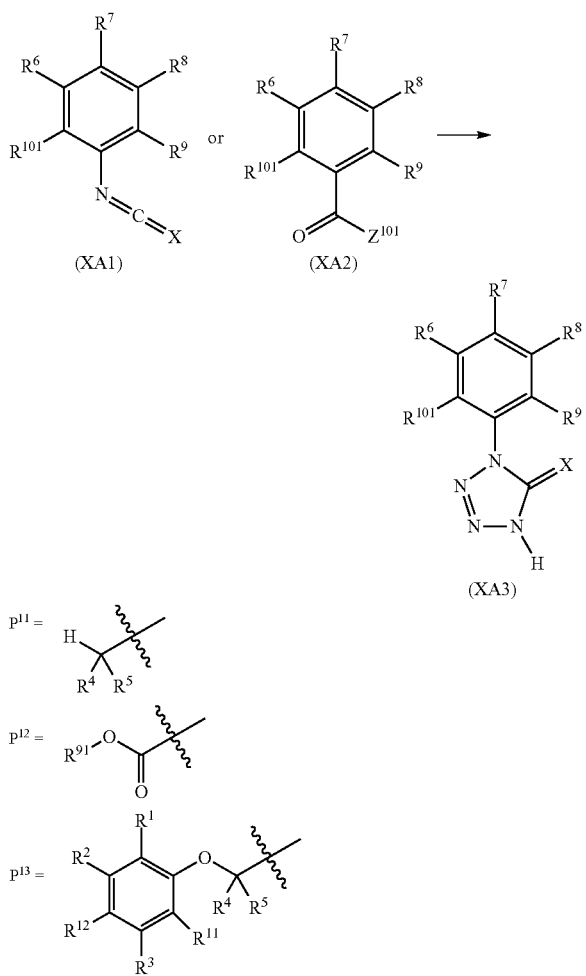

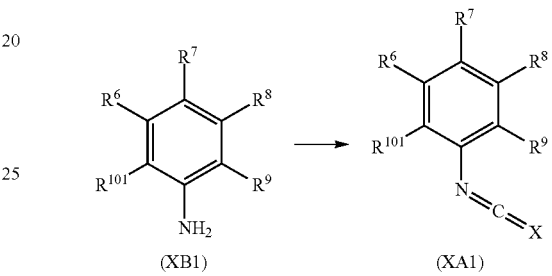

wherein $R^1$, $R^2$, $R^3$, $R^4$, $R^5$, $R^7$, $R^8$, $R^9$, $R^{10}$, $R^{11}$, $R^{12}$, and X are the same as defined above, $R^{101}$ represents $P^{11}$, $P^{12}$, or $P^{13}$, $R^{91}$ represents a C1-C12 alkyl group, $Z^{101}$ represents a chlorine atom or a bromine atom, and the wavy line represents a binding site.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

(Reference Production Process B)

The compound (XA1) can be produced by reacting a compound represented by formula (XB1) (hereinafter referred to as the compound (XB1)) with an isocyanating agent:

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

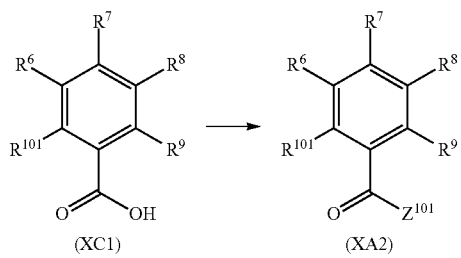

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of −20 to 150° C. The reaction time is usually within a range of 0.1 to 24 hours.

In the reaction, the catalyst may be added and N,N-dimethylformamide, or the like is used. The amount of the catalyst to be used is usually in the proportion within a range of 0.001 to 1 mol based on 1 mol of the compound (XC1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by formula (XD1) (hereinafter referred to as the compound (XD1)), and then reacting the compound (XD1) with an isocyanating agent:

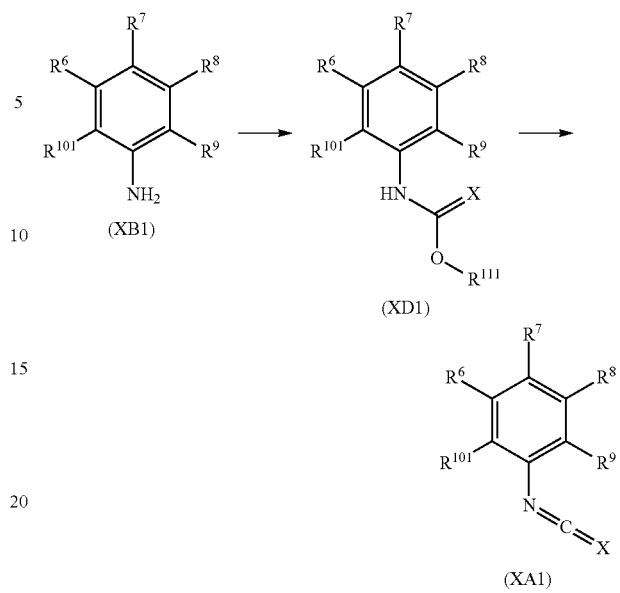

wherein $R^6$, $R^7$, $R^8$, $R^9$, $R^{101}$, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, dioxane, ethylene glycol dimethyl ether, and methyl tert-butyl ether; aromatic hydrocarbons such as toluene and xylene; halogenated hydrocarbons such as carbon tetrachloride, chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the isocyanating agent to be used in the reaction include phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by formula (XE2) (hereinafter referred to as the compound (XE2)) can be produced by reacting a compound represented by formula (XE1) (hereinafter referred to as the compound (XE1)) with hydrogen in the presence of a catalyst:

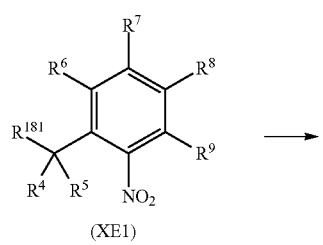

(XE1)

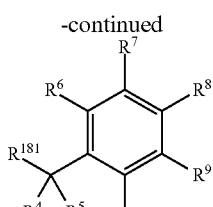

(XE2)

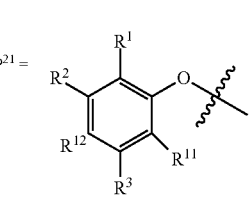

wherein $R^1$, $R^2$, $R^3$, $R^4$, $R^5$, $R^6$, $R^7$, $R^8$, $R^9$, $R^{10}$, $R^{11}$, and $R^{12}$ are the same as defined above, $R^{181}$ represents a hydrogen atom or $P^{21}$, and the wavy line represents a binding site.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as carbon tetrachloride, chloroform, dichloromethane, 1,2-dichloroethane, tetrachloroethane, and chlorobenzene; ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; water; and mixtures thereof.

Examples of the catalyst to be used in the reaction include palladium-carbon (Pd/C), platinum-carbon (Pt/C), osmium-carbon (Os/C), ruthenium-carbon (Ru/C), rhodium-carbon (Rh/C), Raney nickel, and the like.

In the reaction, the catalyst is usually used in the proportion within a range of 0.0001 to 1 mol based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process F)

The compound (XE2) can be produced by reacting the compound (XE1) with a reducing agent in the presence of an acid:

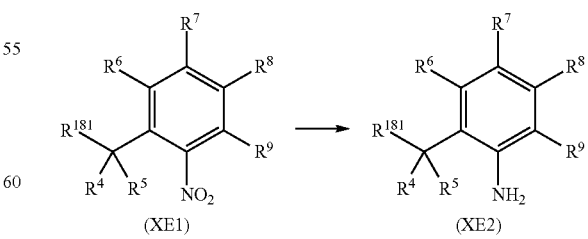

wherein symbols are the same as defined above.

The reaction is usually performed in a solvent.

Examples of the solvent to be used in the reaction include solvent include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, an aqueous ammonium chloride solution, and the like.

In the reaction, the reducing agent is usually used in the proportion within a range of 1 to 30 mols based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XG2) (hereinafter referred to as the compound (XG2)) can be produced by reacting a compound represented by formula (XG1) (hereinafter referred to as the compound (XG1)) with the compound (E1) in the presence of a base:

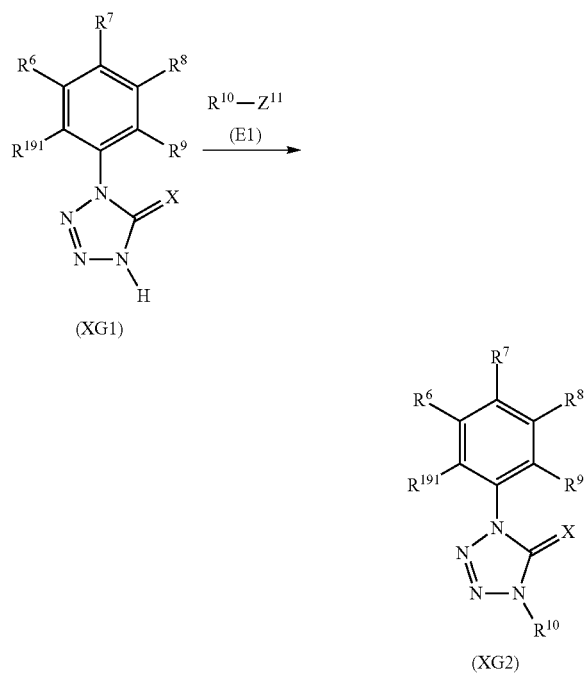

wherein $R^6$, $R^7$, $R^8$, $R^9$, $R^{10}$, and $Z^{11}$ are the same as defined above, and $R^{191}$ represents $P^{11}$ or $P^2$.

The reaction can be carried out in accordance with the reaction mentioned in Production Process D.

(Reference Production Process H)

A compound represented by formula (XH2) (hereinafter referred to as the compound (XH2)) can be produced by reacting a compound represented by formula (XH1) (hereinafter referred to as the compound (XH1)) with a halogenating agent:

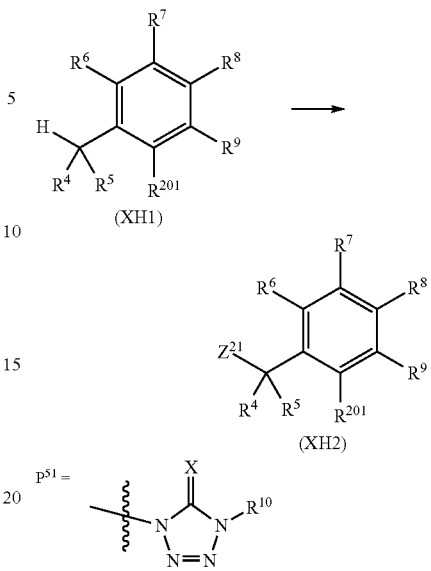

wherein $R^4$, $R^5$, $R^6$, $R^7$, $R^8$, $R^9$, $R^{10}$, $Z^{21}$, and X are the same as defined above, and $R^{201}$ represents $P^{51}$ or a nitro group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, and N-bromophthalimide.

In the reaction, a radical initiator can also be used.

Examples of the radical initiator to be used in the reaction include benzoyl peroxide, azobisisobutyronitrile (AIBN), diacyl peroxide, dialkylperoxydicarbonate, tert-alkylperoxyester, monoperoxycarbonate, di(tert-alkylperoxy)ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XJ2) (hereinafter referred to as the compound (XJ2)) can be produced by reacting the compound (XH2) with a compound represented by formula (XJ1) (hereinafter referred to as the compound (XJ1)):

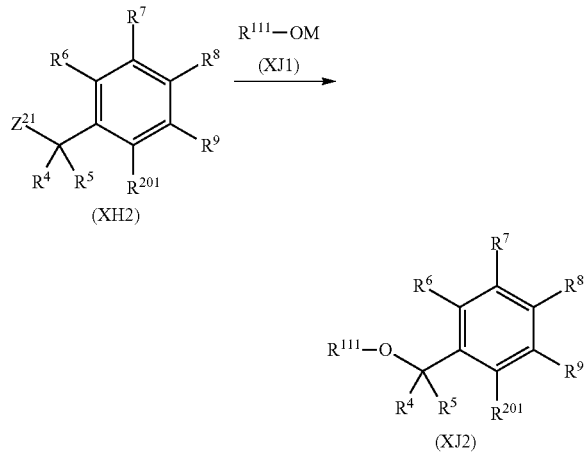

wherein $R^4$, $R^5$, $R^6$, $R^7$, $R^8$, $R^9$, $R^{111}$, and $Z^{21}$ are the same as defined above, and M represents sodium, potassium, or lithium.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-hexane, cyclohexane, toluene, and xylene; halogenated hydrocarbons such as carbon tetrachloride, chloroform, dichloromethane, 1,2-dichloroethane, tetrachloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) usable in the reaction include sodium methoxide, sodium ethoxide, sodium n-propoxide, sodium n-butoxide, sodium isopropoxide, sodium sec-butoxide, sodium tert-butoxide, potassium methoxide, potassium methoxide, potassium n-propoxide, potassium n-butoxide, potassium isopropoxide, potassium sec-butoxide, potassium tert-butoxide, sodium phenoxide, and the like.

In the reaction, the compound (XJ1) is usually used in the proportion within a range of 1 to 10 mols based on 1 mol of the compound (XH2).

The reaction temperature of the reaction is usually within a range of −20 to 150° C. The reaction time is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.
(Reference Production Process J)

A compound represented by formula (XK1) (hereinafter referred to as the compound (XK1)) can be produced by reacting the compound (XH2) with water in the presence of a base:

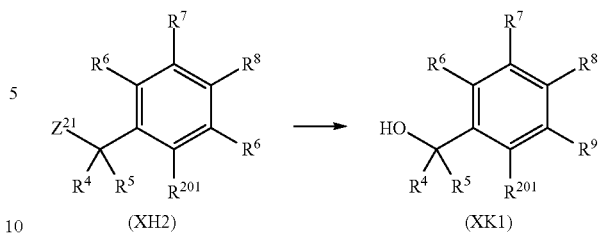

wherein symbols are the same as defined above.

The reaction is usually performed in water, or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-hexane, cyclohexane, toluene, and xylene; halogenated hydrocarbons such as carbon tetrachloride, chloroform, dichloromethane, 1,2-dichloroethane, tetrachloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, 4-dimethylaminopyridine, diisopropylethylamine, and diazabicycloundecene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to large excess based on 1 mol of the compound (XH2).

The reaction temperature of the reaction is usually within a range of −20 to 150° C. The reaction time is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

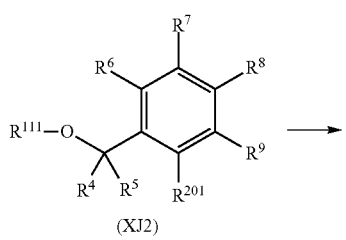

(XJ2)

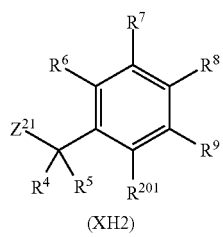

(XH2)

wherein symbols are the same as defined above.

The reaction is usually performed in a solvent.

Examples of the solvent to be used in the reaction include hydrocarbons such as n-hexane, cyclohexane, toluene, and xylene; halogenated hydrocarbons such as carbon tetrachloride, chloroform, dichloromethane, 1,2-dichloroethane, tetrachloroethane, and chlorobenzene; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include hydrochloric acid, hydrobromic acid, and hydroiodic acid.

In the reaction, halogenating agent is usually used in the proportion of 1 mol or more based on 1 mol of the compound (XJ2).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can be produced by reacting the compound (XK1) with a halogenating agent:

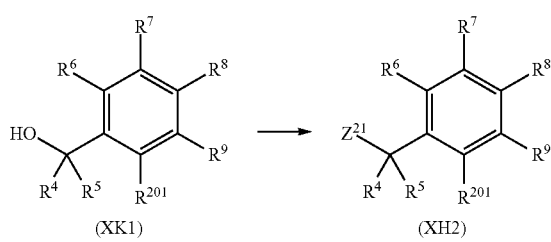

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, acetyl chloride, carbon tetrabromide, N-bromosuccinimide, lithium chloride, sodium iodide, acetyl bromide, and the like.

In the reaction, the halogenating agent is usually used in the proportion within a range of 1 to 10 mols based on 1 mol of the compound (XK1).

In order to accelerate the reaction, additives may be added according to the halogenating agent to be used, and specific examples thereof include zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, trimethylsilyl chloride for sodium iodide, and the like. Any additives are usually used in the proportion within a range of 0.01 to 5 mols based on 1 mol of the compound (XK1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by formula (XM3) (hereinafter referred to as the compound (XM3)) can be produced by reacting the compound (XK1) with a compound represented by formula (XM2) (hereinafter referred to as the compound (XM2)) in the presence of a base:

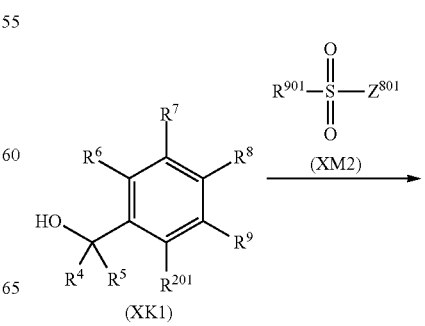

(XK1)

-continued

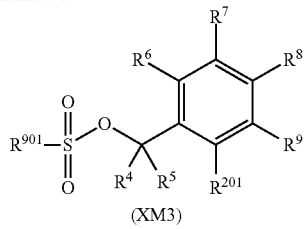

(XM3)

wherein $R^4$, $R^5$, $R^6$, $R^7$, $R^8$, $R^9$, and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

In the reaction, compound (XM2) is usually used in the proportion within a range of 1 to 10 mols, and the base is usually used in the proportion within a range of 1 to 5 mols, based on 1 mol of the compound (XK1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process N)

A compound represented by formula (XN12) (hereinafter referred to as the compound (XN12)) can be produced by subjecting a compound represented by formula (XN11) (hereinafter referred to as the compound (XN11)) and the compound (G21) to a coupling reaction in the presence of a base and a catalyst:

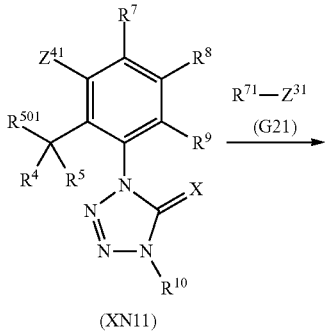

(XN11)

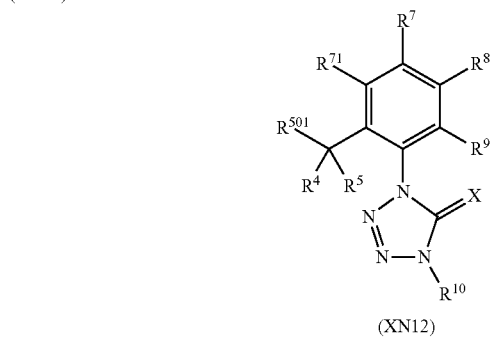

(XN12)

wherein $R^{501}$ represents a hydrogen atom or an $OR^{111}$ group, and $R^{111}$, $R^4$, $R^5$, $R^7$, $R^8 R^9$, $R^{10}$, $R^{71}$, X, $Z^{31}$ and $Z^{41}$ are the same as defined above.

The reaction can be carried out in accordance with the reaction mentioned in Production Process B.

A compound represented by formula (XN22) (hereinafter referred to as the compound (XN22)) can be produced by subjecting a compound represented by formula (XN21) (hereinafter referred to as the compound (XN21)) and the compound (G22) to a coupling reaction in the presence of a base and a catalyst:

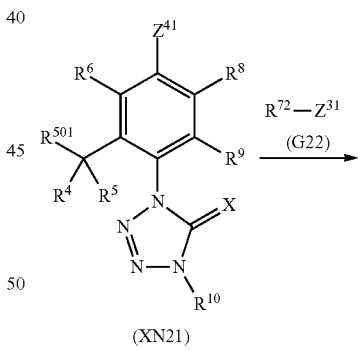

(XN21)

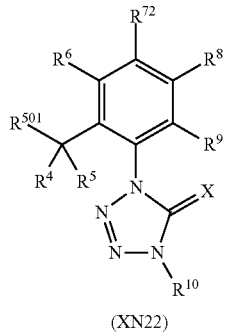

(XN22)

wherein symbols are the same as defined above.

The reaction can be carried out in accordance with the reaction mentioned in Production Process B.

A compound represented by formula (XN32) (hereinafter referred to as the compound (XN32)) can be produced by subjecting a compound represented by formula (XN31) (hereinafter referred to as the compound (XN31)) and the compound (G22) to a coupling reaction in the presence of a base and a catalyst:

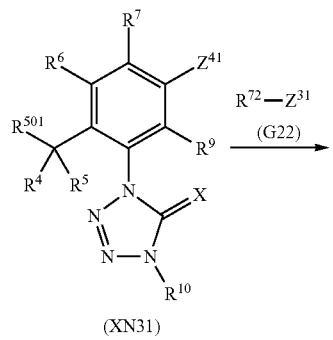

wherein symbols are the same as defined above.

The reaction can be carried out in accordance with the reaction mentioned in Production Process B.

A compound represented by formula (XN42) (hereinafter referred to as the compound (XN42)) can be produced by subjecting a compound represented by formula (XN41) (hereinafter referred to as the compound (XN41)) and the compound (G22) to a coupling reaction in the presence of a base and a catalyst:

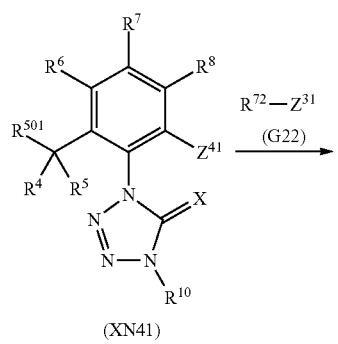

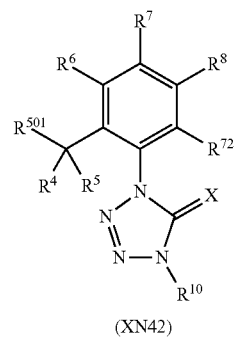

wherein symbols are the same as defined above.

The reaction can be carried out in accordance with the reaction mentioned in Production Process B.

In accordance with Production Process B, it is possible to produce a compound in which two or more substituents selected from $R^6$, $R^7$, $R^8$, and $R^9$ are $R^{71}$ and/or $R^{72}$, among Group of compounds represented by formula (XN50):

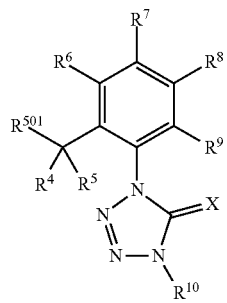

wherein symbols are the same as defined above.

It is also possible to use the other known coupling reaction in place of the coupling reaction mentioned in the Production Process B.

(Reference Production Process O)

A compound represented by formula (XW2) (hereinafter referred to as the compound (XW2)) can be produced by reacting a compound represented by formula (XW1) (hereinafter referred to as the compound (XW1)) with a compound represented by formula (XW3) (hereinafter referred to as the compound (XW3)) in the presence of a reaction accelerator:

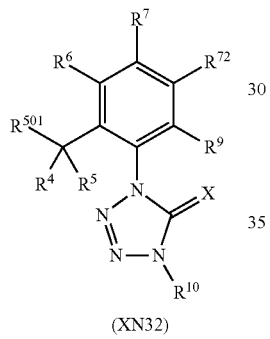

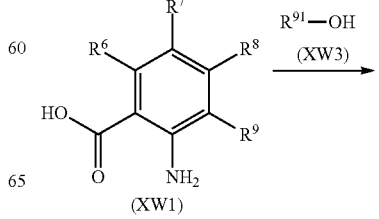

-continued

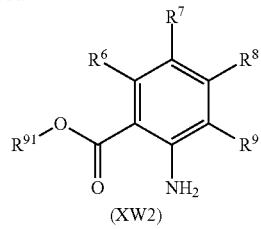

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) usable in the reaction include methyl alcohol, ethyl alcohol, propyl alcohol, isopropyl alcohol, n-butyl alcohol, sec-butyl alcohol, t-butanol, n-pentanol, and the like.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, the reaction accelerator is usually used in the proportion within a range of 0.01 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.001 to 5 mols based on 1 mol of the compound (XW1).

In the reaction, an excess amount of compound (XW3) is used based on the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by formula (XV1) (hereinafter referred to as the compound (XV1)), and then reacting the compound (XV1) with the compound (XW3):

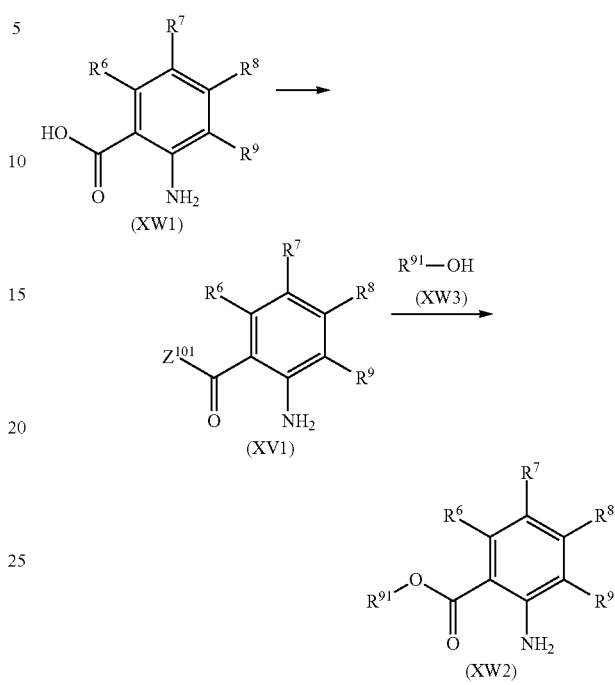

wherein symbols are the same as defined above.

The process in which the compound (XW1) is reacted with a halogenating agent to produce the compound (XV1) can be carried out in accordance with the reaction mentioned in Reference Production Process C.

The process for producing the compound (XW2) from the compound (XV1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

In the reaction, an excess amount of compound (XW3) is used based on the compound (XV1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

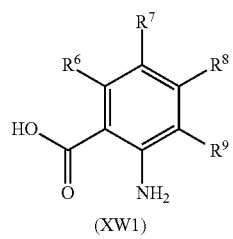

(XW1)

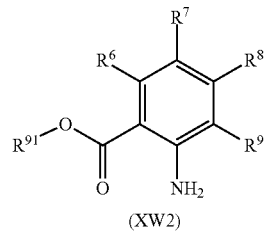

(XW2)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the alkylating agent usable in the reaction include halogenated alkyls such as methyl bromide, ethyl bromide, n-propyl bromide, methyl iodide, ethyl iodide, n-propyl iodide, and isopropyl iodide; sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate; and sulfuric acid esters such as dimethyl sulfate, diethyl sulfate, and di-n-propyl sulfate.

In the reaction, the alkylating agent is usually used in the proportion within a range of 1 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; quaternary ammonium salts such as tetra(n-butyl)ammonium hydroxide may be added, and these compounds are usually used in the proportion within a range of 0.001 to 5 mols based on 1 mol of the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

A compound represented by formula (XS2) (hereinafter referred to as the compound (XS2)) can be produced by reacting a compound represented by formula (XS1) (hereinafter referred to as the compound (XS1)) with the compound (A2) in the presence of a base:

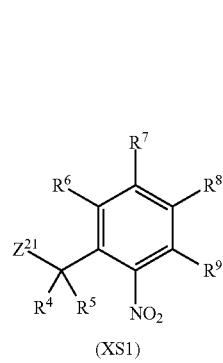

(XS1)

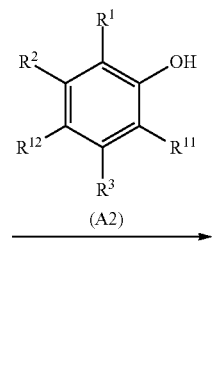

(A2)

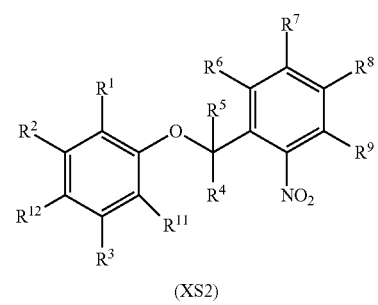

(XS2)

wherein symbols are the same as defined above.

The reaction can be carried out in accordance with the reaction mentioned in Production Process A.

(Reference Production Process U)

A compound represented by formula (XU2) (hereinafter referred to as the compound (XU2)) can be produced by subjecting a compound represented by formula (XU1) (hereinafter referred to as the compound (XU1)) and the compound (B2) to coupling reaction in the presence of a base and a catalyst:

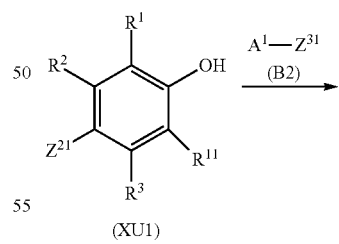

(XU1)

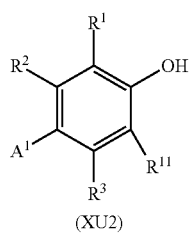

(XU2)

wherein symbols are the same as defined above.

The reaction can be carried out in accordance with the reaction mentioned in Production Process B.

(Reference Production Process V)

The compound (B1) can be produced by reacting a compound represented by formula (XO1) (hereinafter referred to as the compound (XO1)) with the compound (XU1) in the presence of a base:

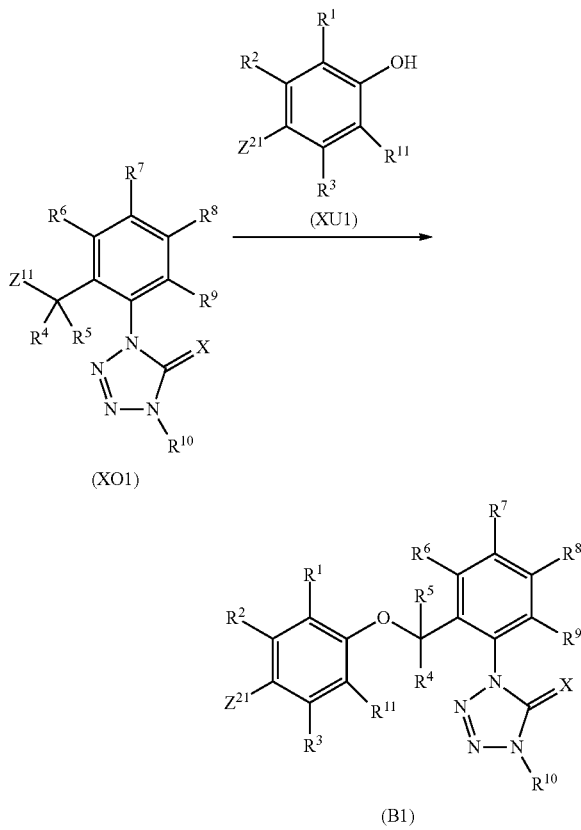

(XO1)

(XU1)

(B1)

wherein symbols are the same as defined above.

The reaction can be carried out in accordance with the reaction mentioned in Production Process A.

(Reference Production Process W)

The compound (C1) can be produced by reacting the compound (B1) with a Borylation reagent in the presence of a base:

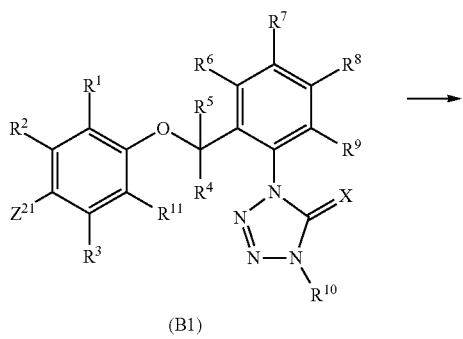

(B1)

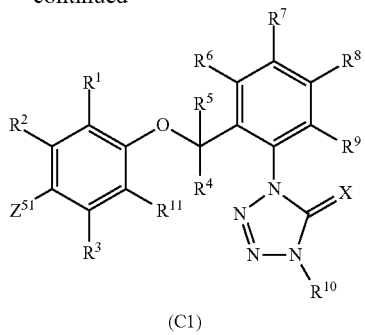

(C1)

wherein $Z^{51}$ represents an alkoxyboranyl group, and $R^1$, $R^2$, $R^3$, $R^4$, $R^5$, $R^6$, $R^7$, $R^8$, $R^9$, $R^{10}$, $R^{11}$, and X are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the Borylation reagent to be used in the reaction include bis(pinacolato)diboron and pinacolborane.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphosphaneferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/ dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the Borylation reagent is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time of the reaction is usually within a range of 0.1 to 24 hours.

After completion of the reaction, the compound (C1) can be isolated by performing post-treatment operations such as extraction of the reaction mixture with an organic solvent, and drying and concentration of the organic layer. The isolated present compound can be further purified by chromatography, recrystallization, and the like.

(Reference Production Process X)

The compound (I1) can be produced by reacting the compound (C1) with a hydrogen peroxide solution in the presence of a base:

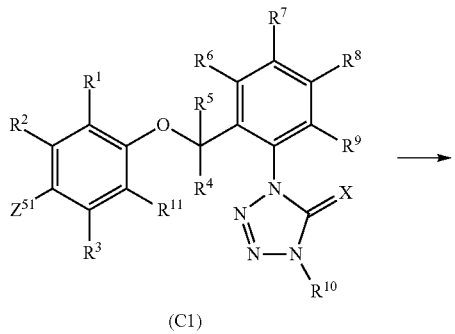

(C1)

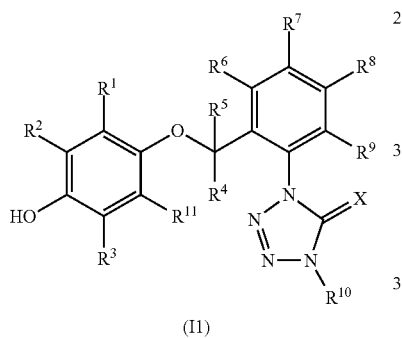

(I1)

wherein symbols are the same as defined above.

The reaction is usually performed in a solvent. Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; nitriles such as acetonitrile; water; and mixtures thereof.

The concentration of the hydrogen peroxide solution to be used in the reaction is usually within a range of 1 to 70%.

Examples of the catalyst to be used in the reaction include palladium(II) acetate, dichlorobis(triphenylphosphine)palladium, tetrakistriphenylphosphinepalladium(0), palladium (II) acetate/tricyclohexylphosphine, bis(diphenylphosphaneferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, a hydrogen peroxide solution is usually used in the proportion within a range of 1 to 10 mols, and the base is usually used in the proportion within a range of 1 to 10 mols, based on 1 mol of the compound (C1).

The reaction temperature of the reaction is usually within a range of −78 to 100° C. The reaction time is usually within a range of 0.1 to 24 hours.

After completion of the reaction, the compound (11) can be isolated by performing post-treatment operations such as extraction of the reaction mixture with an organic solvent, and drying and concentration of the organic layer. The isolated present compound can be further purified by chromatography, recrystallization, and the like.

(Reference Production Process Y)

The compound (1-3) can be produced by reacting a compound represented by formula (Y1) (hereinafter referred to as the compound (Y1)) with an azidation agent:

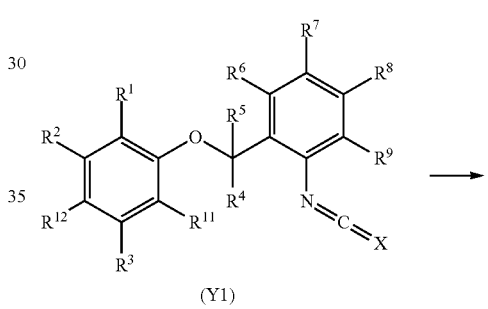

(Y1)

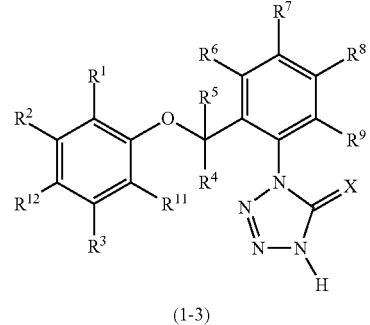

(1-3)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (Y1).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (Y1).

After completion of the reaction, the compound (1-3) can be isolated by performing post-treatment operations such as extraction of the reaction mixture with an organic solvent, and drying and concentration of the organic layer. The isolated present compound can be further purified by chromatography, recrystallization, and the like.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexane, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters, and sugar alcohol derivatives.

Examples of other auxiliary agents for formulation include stickers, dispersers and stabilizers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The method for applying the present compound is not particularly limited, as long as the applying form is a form by which the present compound may be applied substantially, and includes, for example, an application to plants such as a foliage application; an application to area for cultivating plants such as a submerged treatment; and an application to soil such as seed disinfection.

The present control agent may be used as a mixture with various oils or surfactants such as mineral oils or vegetable oils. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the like.

The present compound can also be used as a mixture with or together with other fungicides, insecticides, acaricides, and nematicides.

Examples of these other fungicides include the followings.

(1) Azole Fungicides
such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, and ipconazole;

(2) Amine Fungicides
such as fenpropimorph, tridemorph, fenpropidin, and spiroxamine;

(3) Benzimidazole Fungicides
such as carbendazim, benomyl, thiabendazole, and thiophanate-methyl;

(4) Dicarboxyimide Fungicides
such as procymidone, iprodione, and vinclozolin;

(5) Anilinopyrimidine Fungicides
such as cyprodinil, pyrimethanil, and mepanipyrim;

(6) Phenylpyrrole Fungicides
such as fenpiclonil and fludioxonil;

(7) Strobilurin Fungicides
such as kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin, pyrametostrobin, flufenoxystrobin, fenaminstrobin, enoxastrobin, coumoxystrobin, pyriminostrobin, triclopyricarb, and mandestrobin;

(8) Phenylamide Fungicides
such as metalaxyl, metalaxyl-M or mefenoxam, benalaxyl, and benalaxyl-M or kiralaxyl;

(9) Phenylamide Fungicides
such as dimethomorph, iprovalicarb, benthivalicarb-isopropyl, mandipropamid, and valiphenal;

(10) Carboxamide Fungicides
such as carboxin, mepronil, flutolanil, thifluzamide, furametpyr, boscalid, penthiopyrad, fluopyram, bixafen, penflufen, sedaxane, fluxapyroxad, isopyrazam, benzovindiflupyr, isofetamid, N-[2-(3,4-difluorophenyl)phenyl]-3-trifluoromethylpyrazine-2-carboxylic acid amide, and N-(1,1,3-trimethylindan-4-yl)-1-methyl-3-difluoromethylpyrazole-4-carboxylic acid amide (including a mixture of a racemic body or an enantiomer, an enantiomer of an R-form, and an enantiomer of an S-form at any ratio);

(11) Other Fungicides such as diethofencarb; thiuram; fluazinam; mancozeb; chlorothalonil; captan; dichlofluanid; folpet; quinoxyfen; fenhexanid; fanoxadon; fenamidon; zoxamide; ethaboxam; amisulbrom; cyazofamid; metrafenone; pyriofenone; cyflufenamid; proquinazid; flusulfamide; fluopicolide; fosetyl; cymoxanil; pencycuron; tolclofos-methyl; carpropamid; diclocymet; fenoxanil; tricyclazole; pyroquilon; probenazole; isotianil; tiadinil; tebufloquin; diclomezine; kasugamycin; ferimzone; fthalide; validamycin; hydroxyisoxazole; iminoctadine acetate; isoprothiolane; oxolinic acid; oxytetracycline; streptomycin; copper oxychloride; copper hydroxide; copper hydroxide sulfate; organocopper; sulfur; ametoctradin; fenpyrazamine; oxathiapiprolin; 3-chloro-4-(2,6-difluorophenyl)-6-methyl-5-phenylpyridazine; and 3-cyano-4-(2,6-difluorophenyl)-6-methyl-5-phenylpyridazine.

Examples of these other insecticides include the followings:

(1) Organophosphorus Compounds such as acephate, Aluminium phosphide, butathiofos, cadusafos, chlorethoxyfos, chlorfenvinphos, chlorpyrifos, chlorpyrifos-methyl, cyanophos:CYAP, diazinon, DCIP (dichlorodiisopropyl ether), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, Hydrogen phosphide, isofenphos, isoxathion, malathion, mesulfenfos, methidathion:DMTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, phorate, and cadusafos;

(2) Carbamate Compounds such as alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, and aldicarb;

(3) Synthetic Pyrethroid Compounds such as acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, beta-cypermethrin, theta-cypermethrin, zeta-cypermethrin, lambda-cyhalothrin, gamma-cyhalothrin, furamethrin, tau-fluvalinate, halfenprox, protrifenbute, 2,3,5,6-tetrafluoro-4-(methoxymethylbenzyl(EZ-(1RS,3RS; 1RS,3SR-2,2-dimethyl-3-prop-1-enylcyclopropanecarboxylate, 2,3,5,6-tetrafluoro-4-methylbenzyl(EZ-(1RS,3RS;1RS,3SR)-2,2-dimethyl-3-prop-1-enylcyclopropanecarboxylate, and 2,3,5,6-tetrafluoro-4-(methoxymethylbenzyl(1RS,3RS;1RS, 3SR)-2,2-dimethyl-3-(2-methyl-1-propenylcyclopropanecarboxylate;

(4) Nereistoxin Compounds such as cartap, bensultap, thiocyclam, monosultap, and bisultap;

(5) Neonicotinoid Compounds such as imidacloprid, nitenpyram, acetamiprid, thiamethoxam, thiacloprid, dinotefuran, and clothianidin;

(6) Benzoylurea Compounds such as chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron;

(7) Phenylpyrazole Compounds such as acetoprole, ethiprole, fipronil, vaniliprole, pyriprole, and pyrafluprole;

(8) Bt Toxin Insecticides such as live spores derived from and crystal toxins produced from *Bacillus* thuringiesis, and a mixture thereof;

(9) Hydrazine Compounds such as chromafenozide, halofenozide, methoxyfenozide, and tebufenozide;

(10) Organochlorine Compounds such as aldrin, dieldrin, dienochlor, endosulfan, and methoxychlor;

(11) Natural Insecticides such as machine oil and nicotine-sulfate;

(12) Other Insecticides such as avermectin-B, bromopropylate, buprofezin, chlorphenapyr, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, doramectin, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, spiromesifen, Sulfur, metaflumizone, spirotetramat, pyrifluquinazone, spinetoram, chlorantraniliprole, cyantraniliprole, cyclaniliprole, sulfoxaflor, and flupyradifurone.

Examples of these other acaricides (acaricidally active ingredients) include acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite:BPPS, polynactins, pyridaben, Pyrimidifen, tebufenpyrad, tetradifon, spirodiclofen, spiromesifen, spirotetramat, amidoflumet, and cyenopyrafen.

Examples of other nematicides (nematicidally active compounds) include DCIP, fosthiazate, levamisol hydrochloride, methyisothiocyanate, morantel tartarate, imicyafos, and fluensulfone.

Examples of these other plant growth regulators include the followings:

ethephon, chlormequat-chloride, mepiquat-chloride, Gibberellin A typified by Gibberellin A3, abscisic acid, Kinetin, benzyladenine, 1,3-diphenylurea, forchlorfenuron, thidiazuron, 4-oxo-4-(2-phenylethylaminobutyric acid, methyl 5-(trifluoromethylbenzo[b]thiophene-2-carboxylate, and 5-(trifluoromethylbenzo[b]thiophene-2-carboxylic acid.

The application dose of the present compound varies depending on weather conditions, dosage forms, timing of application, methods of application, areas to be applied, target diseases, target crops, and the like, and is usually within a range of 1 to 500 g, and preferably 2 to 200 g, per 1,000 m² of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound is usually within a range of 0.001 to 100 g, and preferably 0.01 to 50 g, per 1 kg of the seeds.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present compound can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), apiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers; Ornamental foliage plants;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese medlar, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir tree, hemlock, juniper, *Pinus, Picea,* and *Taxus cuspidate*); and the like.

The above-mentioned "plants" include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), yellow spot (*Pyrenophora tritici-repentis*), seeding blight caused by *rhizoctonia* fungus (*Rhizoctonia solani*), and take-all disease (*Gaeumannomyces graminis*); Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and seeding blight caused by *rhizoctonia* fungus (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum graminicola*), gray leaf spot (*Cercospora zeaemaydis*), eyespot (*Kabatiella zeae*), and *phaeosphaeria* leaf spot (*Phaeosphaeria maydis*); Cotton diseases: anthracnose (*Colletotrichum gossypii*), grey mildew (*Ramuraria areola*), and *alternaria* leaf spot (*Alternaria macrospora, A. gossypii*); Coffee diseases: rust (*Hemileia vastatrix*); Rape seed diseases: sclerotinia rot (*Sclerotinia sclerotiorum*), gray leaf spot (*Alternaria brassicae*), and root rot (*Phoma lingam*); Citrus diseases: melanose (*Diaporthe citri*), scab (*Elsinoe fawcetti*), and green mold (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata, Colletotrichum acutatum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), *Corynespora* leaf spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans); Eggplant diseases: brown spot (Phomopsis vexans) and powdery mildew (Erysiphe cichoracearum); Cruciferous vegetables diseases: alternaria leaf spot (Alternaria japonica), white spot (Cercosporella brassicae), clubroot (Plasmodiophora brassicae), and downy mildew (Peronospora parasitica); Welsh onion diseases: rust (Puccinia allii); Soybean diseases: purple stain (Cercospora kikuchii), sphaceloma scad (Elsinoe glycines), pod and stem blight (Diaporthe phaseolorum var. sojae), rust (phakopsora pachyrhizi), target spot (Corynespora cassiicola), anthracnose (Colletotrithum glycines, C. truncatum), Rhizoctonia rot (Rhizoctonia solani), septoria brown spot (Septoria glycines), and frog eye leaf spot (Cercospora sojina); Kindney bean diseases: anthracnose (Colletotrichum lindemuthianum); Peanut diseases: leaf spot (Cercospora personata), brown leaf spot (Cercospora arachidicola), and southern blight (Sclerotium rolfsii); Garden pea diseases: powdery mildew (Erysiphe pisi); Potato diseases: early blight (Alternaria solani), late blight (Phytophthora infestans), and verticillium wilt (verticillium albo-atrum, V. dahliae, V. nigrescens); Strawberry diseases: powdery mildew (Sphaerotheca humuli); Tea diseases: net blister blight (Exobasidium reticulatum), white scab (Elsinoe leucospila), gray blight (Pestalotiopsis sp.), and anthracnose (Colletotrichum theae-sinensis); Tabacco diseases: brown spot (Alternaria longipes), powdery mildew (Erysiphe cichoracearum), anthracnose (Colletotrichum tabacum), downy mildew (Peronospora tabacina), and black shank (Phytophthora nicotianae); Sugar beet diseases: cercospora leaf spot (Cercospora beticola), leaf blight (Thanatephorus cucumeris), root rot (Thanatephorus cucumeris), and aphanomyces root rot (Aphanomyces cochlioides); Rose diseases: black spot (Diplocarpon rosae) and powdery mildew (Sphaerotheca pannosa); Chrysanthemum diseases: leaf blight (Septoria chrysanthemi-indici) and white rust (Puccinia horiana); Onion diseases: botrytis leaf blight (Botrytis cinerea, B. byssoidea, B. squamosa), gray-mold neck rot (Botrytis allii), and small sclerotial rot (Botrytis squamosa); various crops diseases: gray mold (Botrytis cinerea) and sclerotinia rot (Sclerotinia sclerotiorum); Japanese radish diseases: alternaria leaf spot (Alternaria brassicicola); Turfgrass diseases: dollar spot (Sclerotinia homoeocarpa) and brown patch and large patch (Rhizoctonia solani); and Banana diseases: Sigatoka disease (Mycosphaerella fijiensis, Mycosphaerella musicola).

Hemiptera: planthoppers (Delphacidae) such as small brown planthopper (Laodelphax striatellus), brown rice planthopper (Nilaparvata lugens), and white-backed rice planthopper (Sogatella furcifera); leafhoppers (Deltocephalidae) such as green rice leafhopper (Nephotettix cincticeps) and green rice leafhopper (Nephotettix virescens); aphids (Aphididae) such as cotton aphid (Aphis gossypii), green peach aphid (Myzus persicae), cabbage aphid (Brevicoryne brassicae), potato aphid (Macrosiphum euphorbiae), foxglove aphid (Aulacorthum solani), oat bird-cherry aphid (Rhopalosiphum padi), and tropical citrus aphid (Toxoptera citricidus); stink bugs (Pentatomidae) such as green stink bug (Nezara antennata), bean bug (Riptortus clavetus), rice bug (Leptocorisa chinensis), white spotted spined bug (Eysarcoris parvus), stink bug (Halyomorpha mista), and tarnished plant bug (Lygus lineolaris); whiteflies (Aleyrodidae) such as greenhouse whitefly (Trialeurodes vaporariorum) and silverleaf whitefly (Bemisia argentifolii); scales (Coccidae) such as California red scale (Aonidiella aurantii), San Jose scale (Comstockaspis perniciosa), citrus north scale (Unaspis citri), red wax scale (Ceroplastes rubens), and cottonycushion scale (Icerya purchasi); lace bugs (Tingidae); jumping plant lice (Homoptera, Psylloidea).

Lepidoptera: pyralid moths (Pyralidae) such as rice stem borer (Chilo suppressalis), yellow rice borer (Tryporyza incertulas), rice leafroller (Cnaphalocrocis medinalis), cotton leafroller (Notarcha derogata), Indian meal moth (Plodia interpunctella), oriental corn borer (Ostrinia furnacalis), cabbage webworm (Hellula undalis), and bluegrass webworm (Pediasia teterrellus); owlet moths (Noctuidae) such as common cutworm (Spodoptera litura), beet armyworm (Spodoptera exigua), armvworm (Pseudaletia separata), cabbage armyworm (Mamestra brassicae), black cutworm (Agrotis ipsilon), beet semi-looper (Plusia nigrisigna), Thoricoplusia spp., Heliothis spp., and Helicoverpa spp.; white butterflies (Pieridae) such as common white (Pieris rapae); tortricid moths (Tortricidae) such as Adoxophyes spp., oriental fruit moth (Grapholita molesta), soybean pod borer (Leguminivora glycinivorella), azuki bean podworm (Matsumuraeses azukivora), summer fruit tortrix (Adoxophyes orana fasciata), smaller tea tortrix (Adoxophyes sp.), oriental tea tortrix (Homona magnanima), apple tortrix (Archips fuscocupreanus), and codling moth (Cydia pomonella); leafblotch miners (Gracillariidae) such as tea leafroller (Caloptilia theivora), and apple leafminer (Phyllonorycter ringoneella); leaf miners (Gracillariidae) such as tea leafroller (Caloptilia theivora) and apple leafminer (Phyllonorycter ringoneella); codling moths (Carposimidae) such as peach fruit moth (Carposina niponensis); lyonetiid moths (Lyonetiidae) such as Lyonetia spp.; tussock moths (Lymantriidae) such as Lymantria spp. and Euproctis spp.; yponomeutid moths (Yponomeutidae) such as diamondback (Plutella xylostella); gelechild moths (Gelechiidae) such as pink bollworm (Pectinophora gossypiella) and potato tubeworm (Phthorimaea operculella); tiger moths and allies (Arctiidae) such as fall webworm (Hyphantria cunea); and tineid moths (Tineidae) such as casemaking clothes moth (Tinea translucens), and webbing clothes moth (Tineola bisselliella).

Thysanoptera: yellow citrus thrips (Frankliniella occidentalis), melon thrips (Thrips palmi), yellow tea thrips (Scirtothrips dorsalis), onion thrips (Thrips tabaci), flower thrips (Frankliniella intonsa), and tobacco thrips (Frankliniella fusca).

Diptera: houseflies (Musca domestica), common mosquito (Culex pipiens pallens), horsefly (Tabanus trigonus), onion maggot (Hylemya anitqua), seedcorn maggot (Hylemya platura), Anopheles sinensis, rice leafminer (Agromyza oryzae), rice leafminer (Hydrellia griseola), rice stem maggot (Chlorops oryzae), melon fly (Dacus cucurbitae), Meditterranean fruit fly (Ceratitis capitata), and legume leafminer (Liriomyza trifolii).

Coleoptera: twenty-eight-spotted ladybirds (Epilachna vigintioctopunctata), cucurbit leaf beetle (Aulacophora femoralis), yellow striped flea beetle (Phyllotreta striolata), rice leaf beetle (Oulema oryzae), rice curculio (Echinocnemus squameus), rice water weevil (Lissorhoptrus oryzophilus), boll weevil (Anthonomus grandis), azuki bean weevil (Callosobruchus chinensis), hunting billbug (Sphenophorus venatus), Japanese beetle (Popillia japonica), cupreous chafer (Anomala cuprea), corn root worms (Diabrotica spp.), Colorado beetle (Leptinotarsa decemlineata), click beetles (Agriotes spp.), cigarette beetle (Lasioderma serricorne), varied carper beetle (Anthrenus verbasci), red flour beetle (Tribolium castaneum), powder post beetle (Lyctus brunneus), white-spotted longicorn beetle (Anoplophora malasiaca), and pine shoot beetle (Tomicus piniperda).

Orthoptera: asiatic locusts (Locusta migratoria), African mole cricket (Gryllotalpa africana), rice grasshopper (Oxya yezoensis), and rice grasshopper (Oxya japonica).

Hymenoptera: cabbage sawflies (*Athalia rosae*), leaf-cutting ant (*Acromyrmex* spp.), and fire ant (*Solenopsis* spp.).

Nematodes: white-tip nematode (*Aphelenchoides besseyi*), strawberry bud nematode (Nothotylenchus acris), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta* America), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (Aculops pelekassi)); Tarsonemidae (for example, broad mite (*Polyphagotarsonemus latus*));

Tenuipalpidae; Tuckerellidae; Tuckerellidae Acaridae (for example, common grain mite (*Tyrophagus putrescentiae*));

Pyroglyphidae (for example, Americal house dust mite (*Dermatophagoides farinae*) and house dust mite (*Dermatophagoides ptrenyssnus*)); Cheyletidae (for example, cheyletid mite (*Cheyletus eruditus*), *Cheyletus malaccensis*, and *Cheyletus moorei*; and Dermanyssidae.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *dermacentor* spp., *Ornithodoros* spp. (for example, *Ornithodoros moubata*), red mite (*Dermahyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp.), *Linognathus* spp., *Haematopinus* spp., *Ctenocephalides* spp. (for example, cat flea (*Ctenocephalides felis*)) *Xenosylla* spp., Pharaoh's ant (*monomorium pharaonis*) and nematodes [for example, hairworm (for example, *Nippostrongylus brasiliensis, Trichostrongylus axei, Trichostrongylus colubriformis*), *Trichinella* spp. (*for example, Trichinella spiriralis*), barber pole worm (*Haemonchus contortus*), *Nematodirus* spp. (for example, *Nematodirus battus*), *Ostertagia circumcincta*, *Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be described.

Production Example 1

A mixture of 0.28 g of 14A mentioned in Reference Production Example 14, 0.17 g of p-hydroxybiphenyl, 0.28 g of potassium carbonate, and 4 mL of acetonitrile was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-[2-(4-phenylphenoxymethyl)-3-methylphenyl]-4-methyl-1,4-dihydrotetrazol-5-one (hereinafter referred to as the present compound 1).

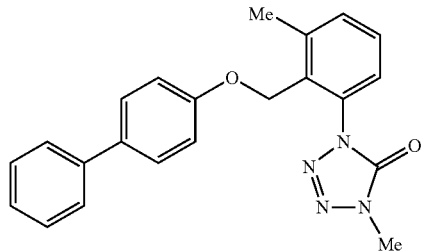

Present Compound 1

¹H-NMR (CDCl3) δ: 7.55-7.47 (4H, m), 7.42-7.37 (4H, m), 7.30-7.27 (2H, m), 6.96-6.92 (2H, m), 5.06 (2H, s), 3.58 (3H, s), 2.49 (3H, s).

In accordance with the reaction mentioned in Production Example 1, the present compounds 59, 92 to 99, and 161 to 163 were synthesized.

The structural formulas and ¹H-NMR data of the thus obtained compounds are shown below.

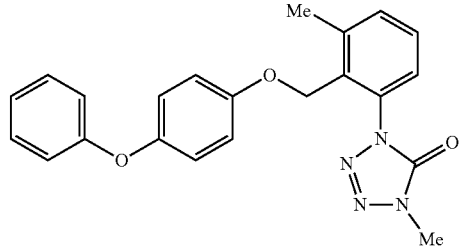

Present Compound 59

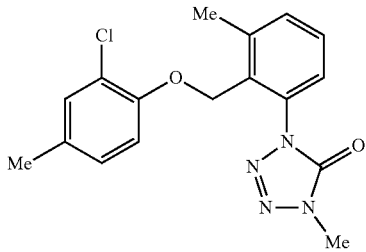

Present Compound 92

-continued
Present Compound 93
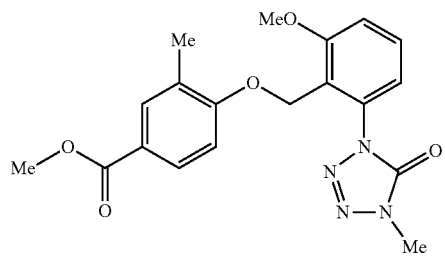
Present Compound 94
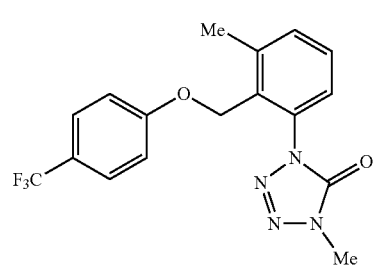
Present Compound 95
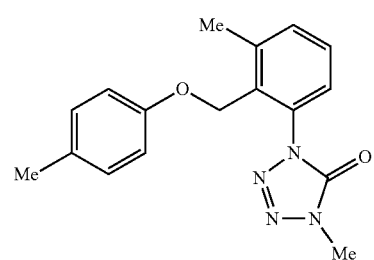
Present Compound 96
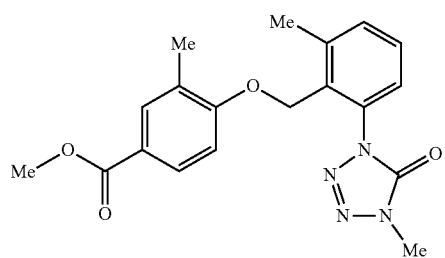
Present Compound 97
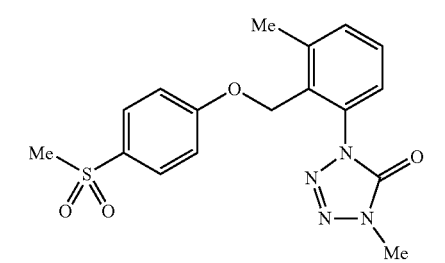
-continued
Present Compound 98
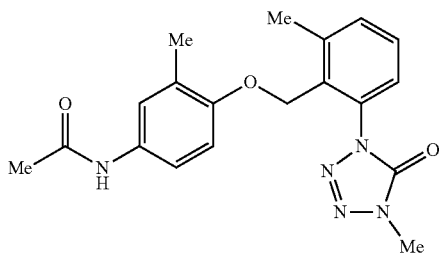
Present Compound 99
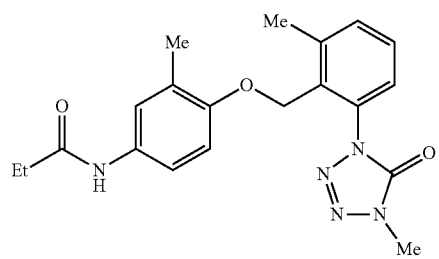
Present Compound 161
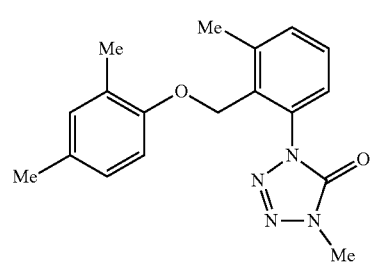
Present Compound 162
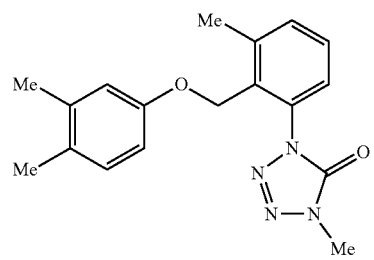
Present Compound 163
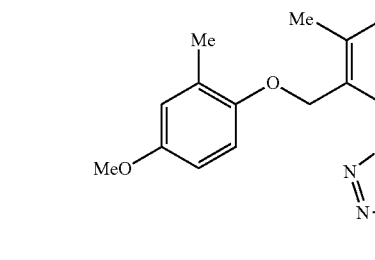
Present Compound 59
$^{1}$H-NMR (CDCl3) δ: 7.44-7.39 (2H, m), 7.32-7.26 (3H, m), 7.05 (1H, t, J=7.4 Hz), 6.97-6.92 (4H, m), 6.87-6.83 (2H, m), 5.01 (2H, s), 3.64 (3H, s), 2.51 (3H, s).
Present Compound 92
1H-NMR (CDCl3) δ: 7.42-7.36 (2H, m), 7.29-7.26 (1H, m), 7.13 (1H, d, J=1.9 Hz), 6.96-6.93 (1H, m), 6.76 (1H, d, J=8.2 Hz), 5.11 (2H, s), 3.66 (3H, s), 2.53 (3H, s), 2.25 (3H, s).

Present Compound 93

1H-NMR (CDCl3) δ: 7.83 (1H, dd, J=8.6, 2.3 Hz), 7.77-7.74 (1H, m), 7.48 (1H, t, J=8.2 Hz), 7.12-7.06 (2H, m), 6.90 (1H, d, J=8.6 Hz), 5.33 (2H, s), 3.94 (3H, s), 3.86 (3H, s), 3.59 (3H, s), 2.00 (3H, s).

Present Compound 94

¹H-NMR (CDCl3) δ: 7.53 (2H, d, J=8.9 Hz), 7.46-7.40 (2H, m), 7.31-7.28 (1H, m), 6.94 (2H, d, J=8.9 Hz), 5.07 (2H, s), 3.61 (3H, s), 2.49 (3H, s).

Present Compound 95

¹H-NMR (CDCl3) δ: 7.43-7.37 (2H, m), 7.28-7.25 (1H, m), 7.06 (2H, d, J=8.7 Hz), 6.79-6.76 (2H, m), 4.99 (2H, s), 3.61 (3H, s), 2.48 (3H, s), 2.28 (3H, s).

Present Compound 96

¹H-NMR (CDCl3) δ: 7.86 (1H, dd, J=8.5, 2.4 Hz), 7.80 (1H, s), 7.46-7.40 (2H, m), 7.30-7.26 (1H, m), 6.86 (1H, d, J=8.5 Hz), 5.10 (2H, s), 3.88 (3H, s), 3.62 (3H, s), 2.50 (3H, s), 2.11 (3H, s).

Present Compound 97

¹H-NMR (CDCl3) δ: 7.85 (2H, d, J=9.1 Hz), 7.47-7.39 (2H, m), 7.32-7.28 (1H, m), 7.00 (2H, d, J=8.8 Hz), 5.09 (2H, s), 3.64 (3H, s), 3.02 (3H, s), 2.48 (3H, s).

Present Compound 98

¹H-NMR (CDCl3) δ: 7.76 (1H, dd, J=8.6, 2.3 Hz), 7.72-7.69 (1H, m), 7.48 (1H, t, J=8.2 Hz), 7.12-7.06 (2H, m), 6.91 (1H, d, J=8.5 Hz), 5.35 (2H, s), 3.94 (3H, s), 3.59 (3H, s), 2.52 (3H, s), 2.02 (3H, s).

Present Compound 99

¹H-NMR (CDCl3) δ: 7.45 (1H, t, J=8.2 Hz), 7.23 (1H, dd, J=8.8, 2.4 Hz), 7.16 (1H, d, J=2.4 Hz), 7.10-7.03 (2H, m), 6.99 (1H, s), 6.80 (1H, d, J=8.7 Hz), 5.22 (2H, s), 3.92 (3H, s), 3.60 (3H, s), 2.34 (2H, q, J=7.6 Hz), 1.98 (3H, s), 1.23 (3H, t, J=7.6 Hz).

Present Compound 162

¹H-NMR (CDCl3) δ: 7.44-7.38 (2H, m), 7.27-7.23 (1H, m), 6.94-6.90 (2H, m), 6.73 (1H, d, J=8.9 Hz), 4.99 (2H, s), 3.63 (3H, s), 2.50 (3H, s), 2.24 (3H, s), 2.06 (3H, s).

Present Compound 163

¹H-NMR (CDCl3) δ: 7.41-7.36 (2H, m), 7.28-7.23 (1H, m), 7.00 (1H, d, J=8.2 Hz), 6.68 (1H, s), 6.62 (1H, d, J=8.2 Hz), 4.97 (2H, s), 3.61 (3H, s), 2.48 (3H, s), 2.21 (3H, s), 2.18 (3H, s).

Present Compound 164

¹H-NMR (CDCl3) δ: 7.43-7.37 (2H, m), 7.27-7.24 (1H, m), 6.75 (1H, d, J=8.7 Hz), 6.70-6.67 (1H, m), 6.63 (1H, dd, J=8.7, 3.1 Hz), 4.97 (2H, s), 3.74 (3H, s), 3.63 (3H, s), 2.50 (3H, s), 2.07 (3H, s).

Production Example 2

A mixture of 0.39 g of 20A mentioned in Reference Production Example 20, 0.15 g of 3,4-dichlorophenylboronic acid, 0.28 g of tripotassium phosphate, 0.4 ml of water, 0.02 g of [1,1'-bis(diphenylphosphino)ferrocene]palladium (II) dichloride dichloromethane adduct, and 4 mL of dioxane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.37 g of 1-[2-(4-(3,4-dichlorophenyl)-2-methylphenoxymethyl)-3-methylphenyl]-4-methyl-1,4-dihydrotetrazol-5-one (hereinafter referred to as the present compound 41).

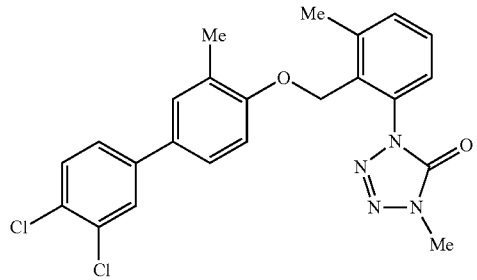

Present Compound 41

Present Compound 41

¹H-NMR (CDCl₃) δ: 7.61 (1H, d, J=2.2 Hz), 7.47-7.40 (3H, m), 7.37-7.27 (4H, m), 6.90 (1H, d, J=8.5 Hz), 5.08 (2H, s), 3.63 (3H, s), 2.52 (3H, s), 2.15 (3H, s).

In accordance with the reaction mentioned in Production Example 2, using the compounds mentioned in Reference Production Examples, or commercially available compounds, the present compounds 2 to 40, 46 to 57, 113 to 148, and 151 to 156 were synthesized.

The structural formulas and ¹H-NMR data of the thus obtained compounds are shown below.

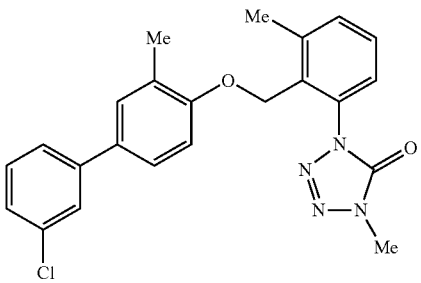

Present Compound 2

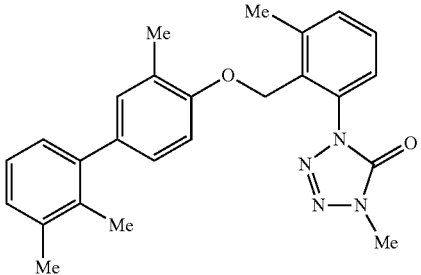

Present Compound 3

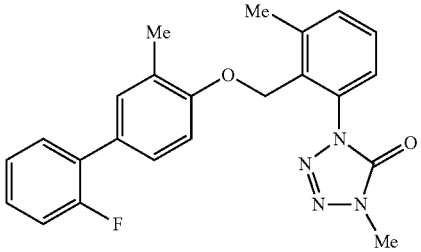

Present Compound 4

-continued
Present Compound 5
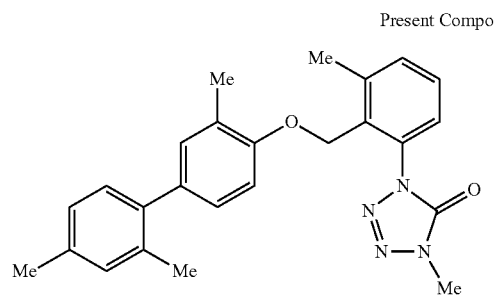
Present Compound 6
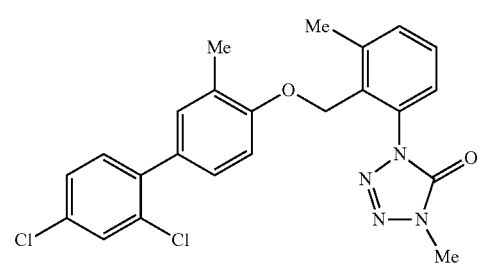
Present Compound 7
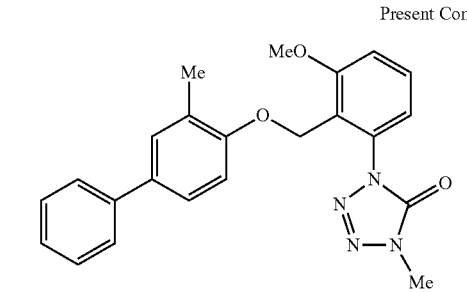
Present Compound 8
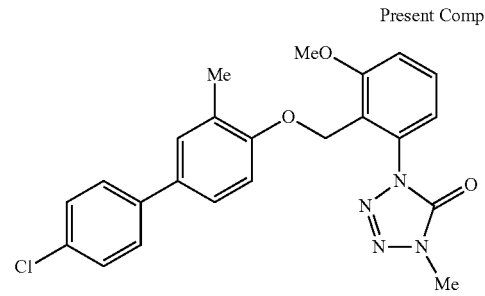
Present Compound 9
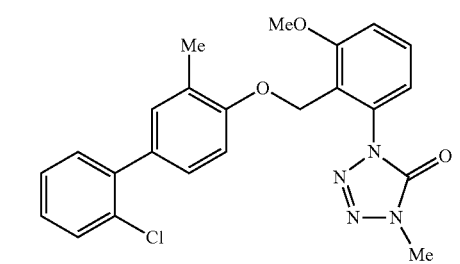
-continued
Present Compound 10
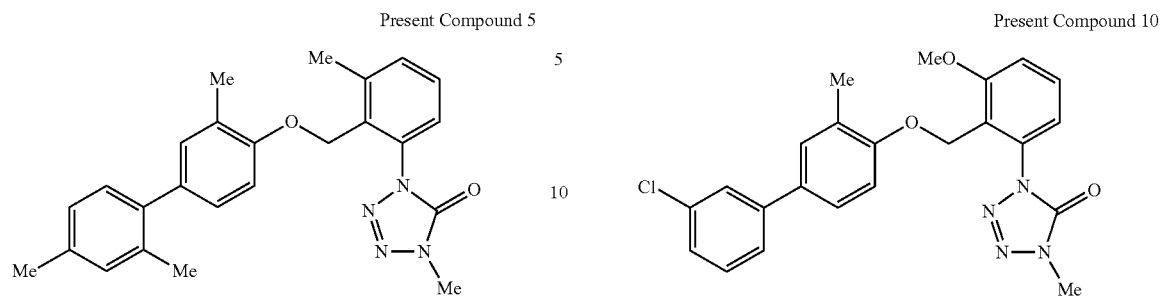
Present Compound 11
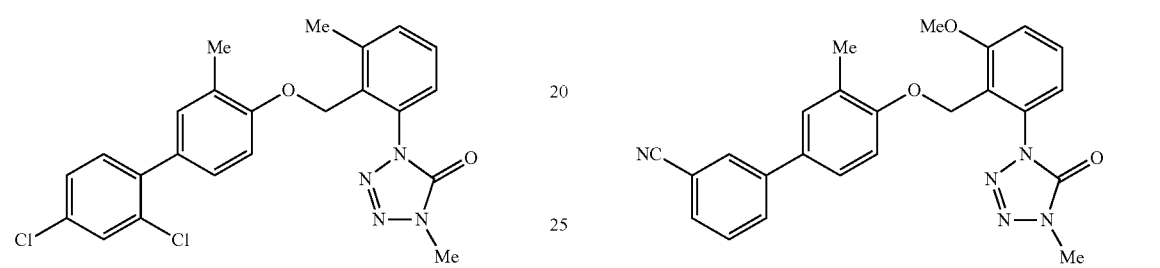
Present Compound 12
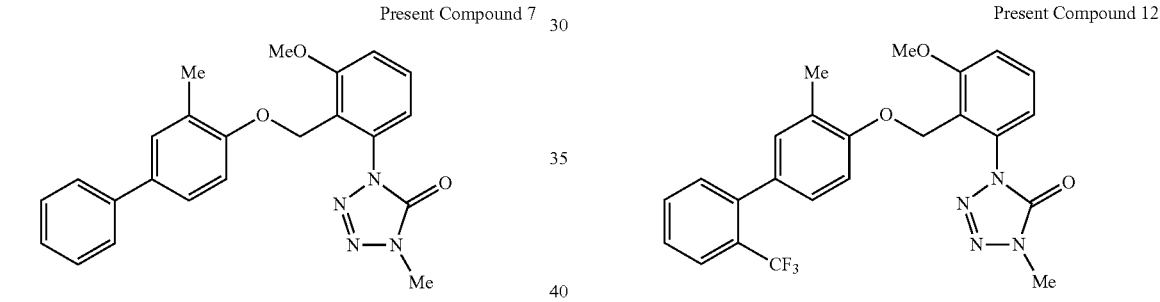
Present Compound 13
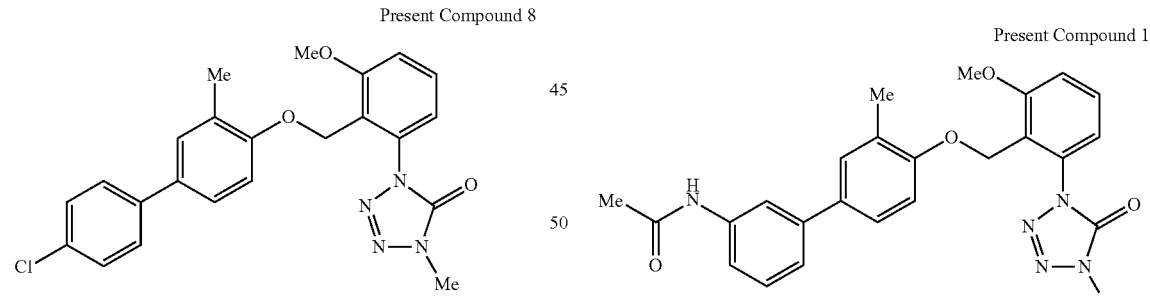
Present Compound 14
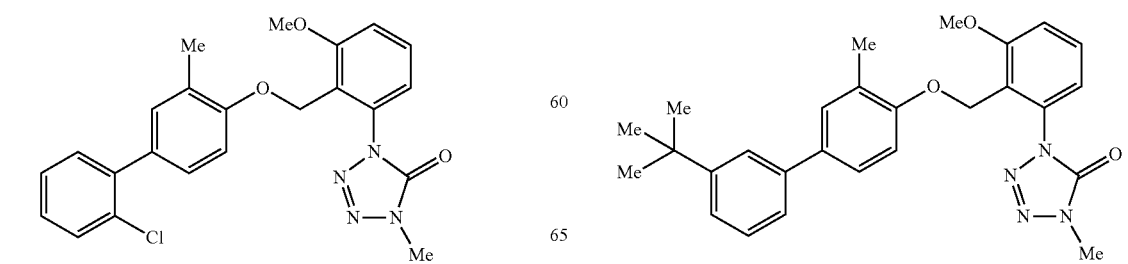

Present Compound 15
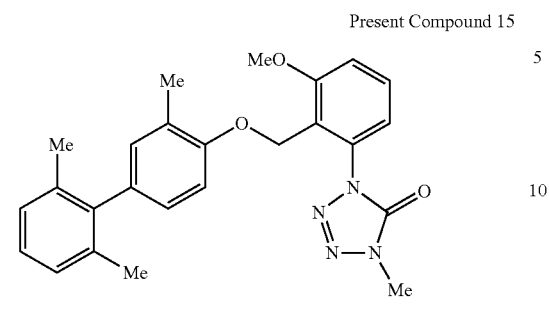
Present Compound 16
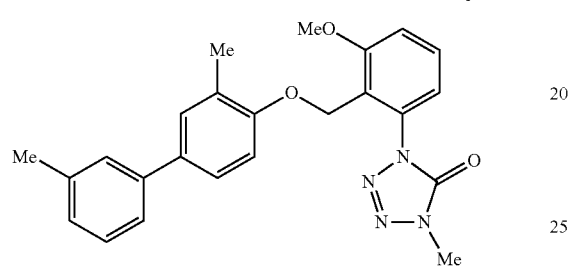
Present Compound 17
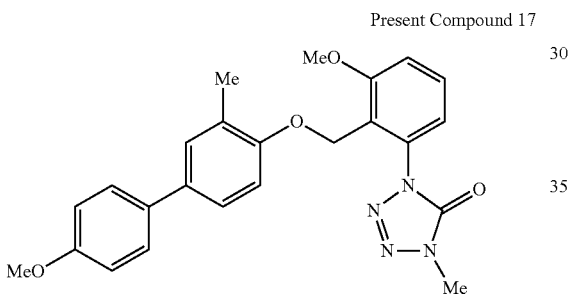
Present Compound 18
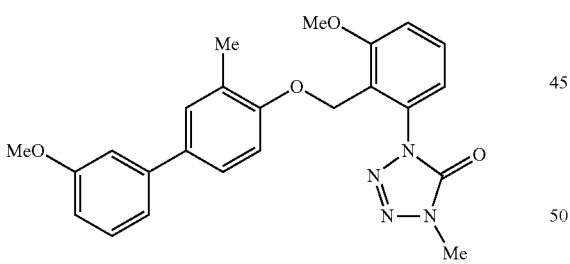
Present Compound 19
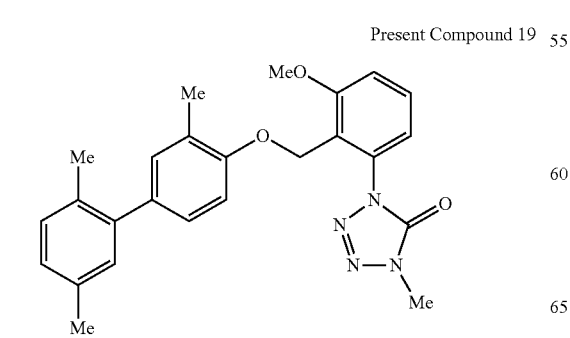
Present Compound 20
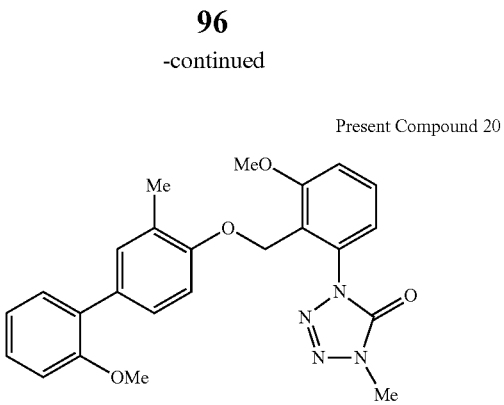
Present Compound 21
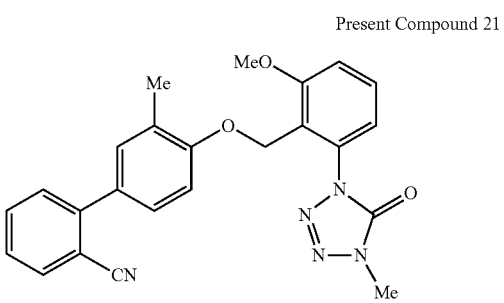 [SMILES: Cc1cccc(-n2nnn(C)c2=O)c1COc1ccc(-c2ccccc2)cc1]
Present Compound 22
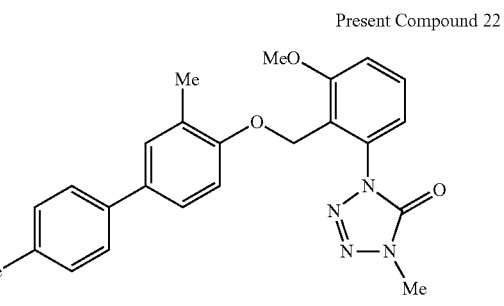
Present Compound 23
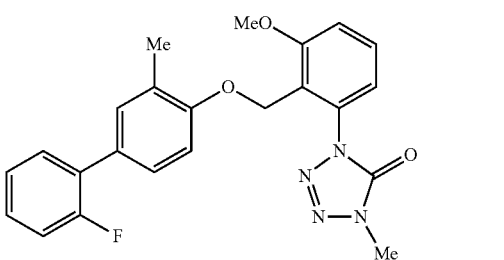
Present Compound 24
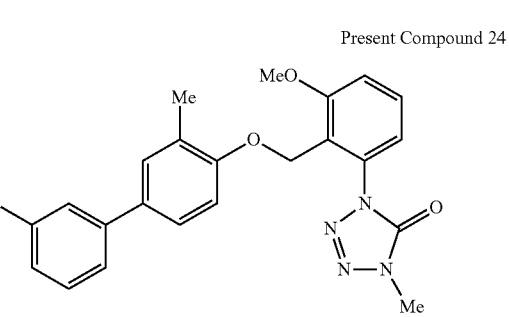

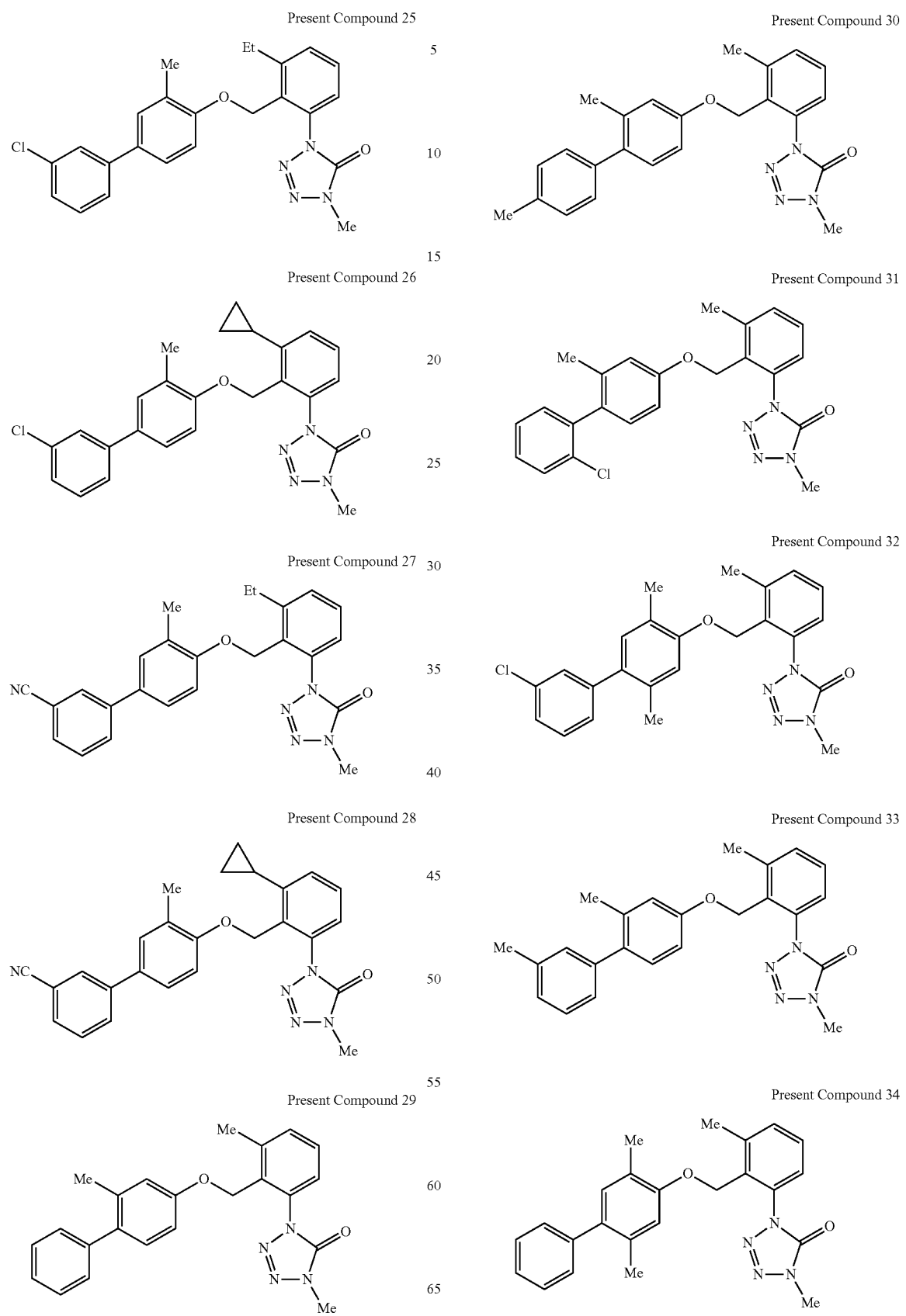

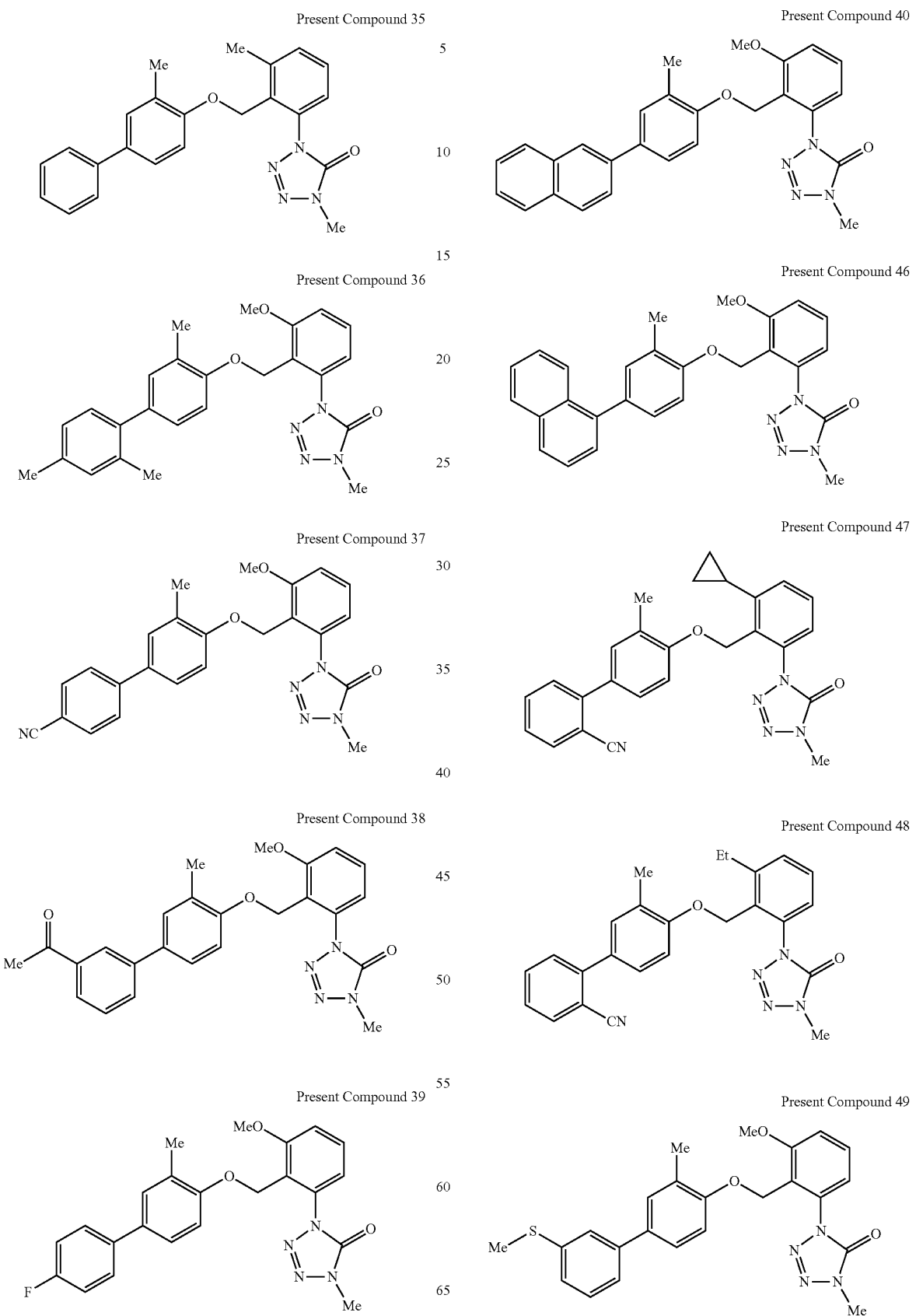

Present Compound 50
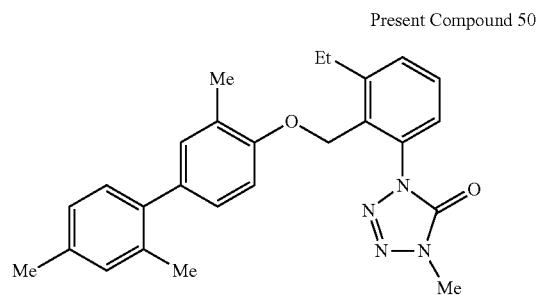
Present Compound 51
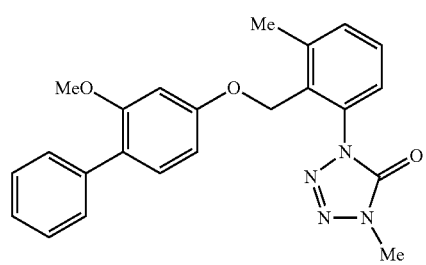
Present Compound 52
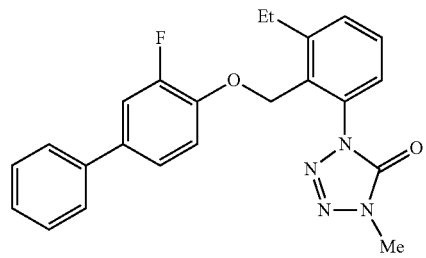
Present Compound 53
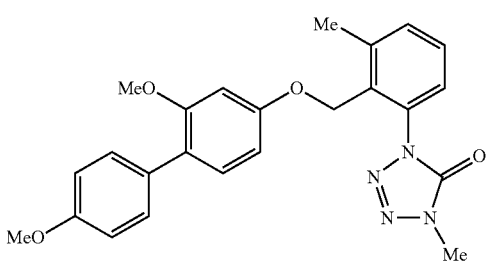
Present Compound 54
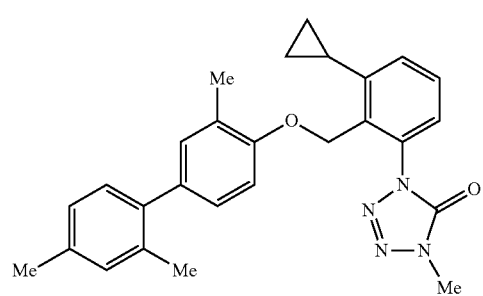
Present Compound 55
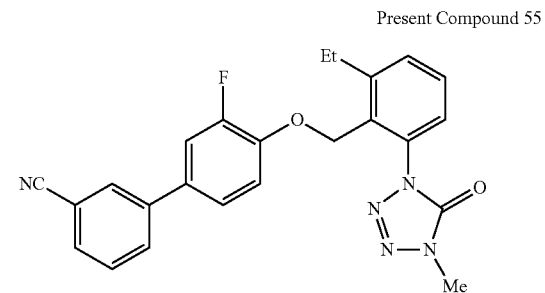
Present Compound 56
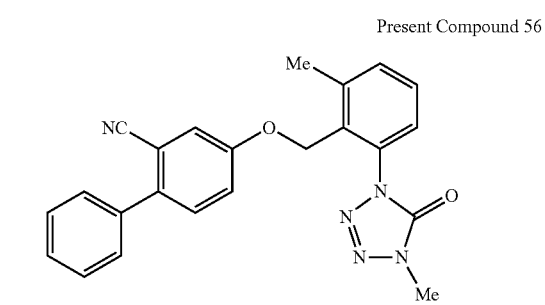
Present Compound 57
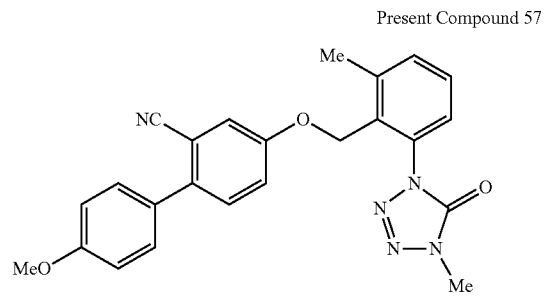
Present Compound 113
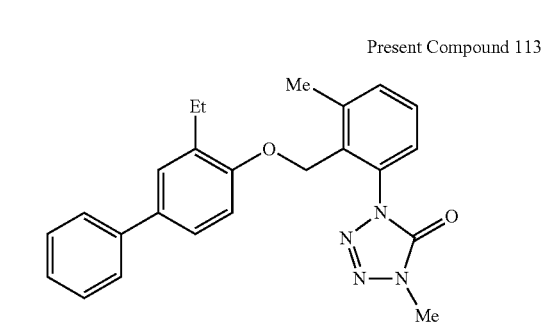
Present Compound 114
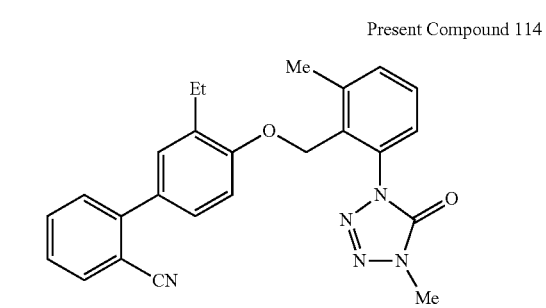

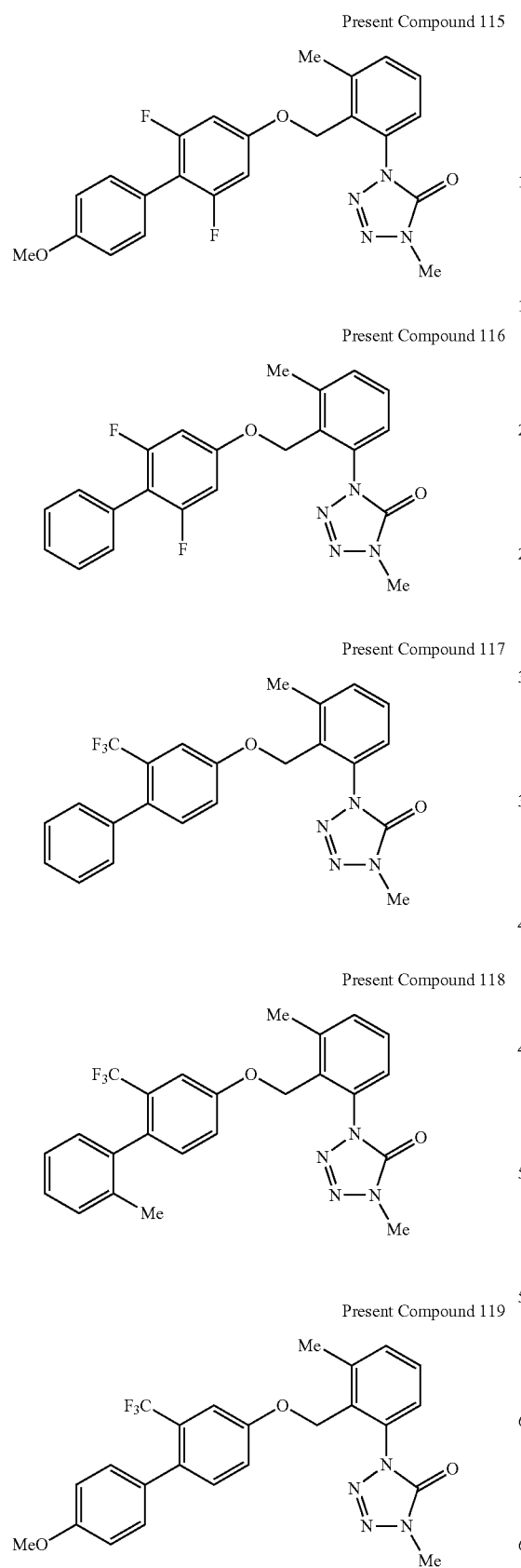
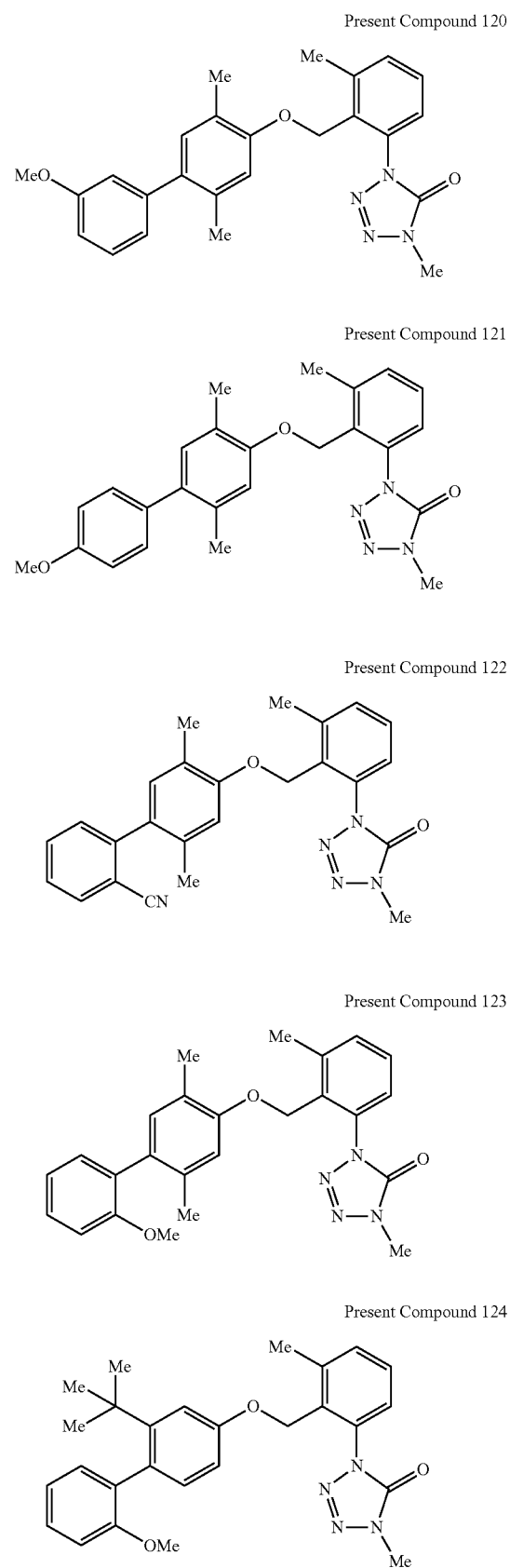

Present Compound 125
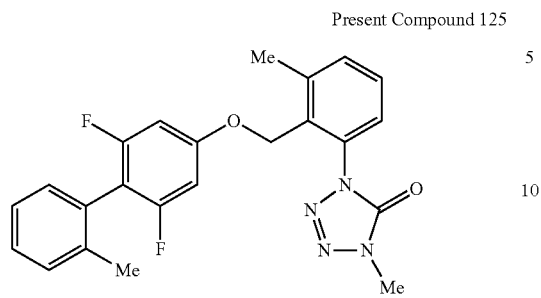
Present Compound 126
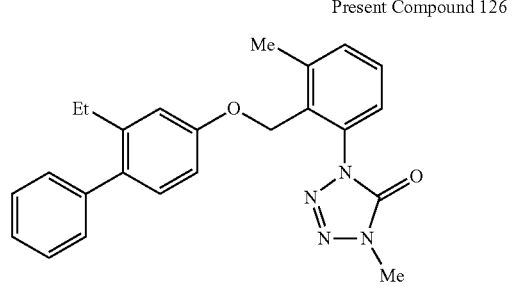
Present Compound 127
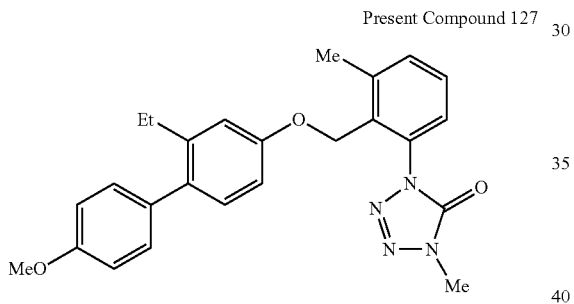
Present Compound 128
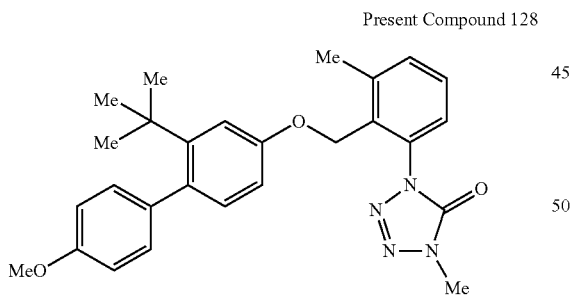
Present Compound 129
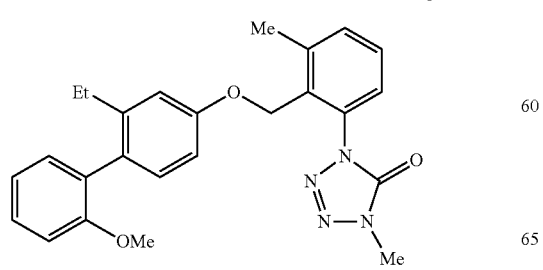
Present Compound 130
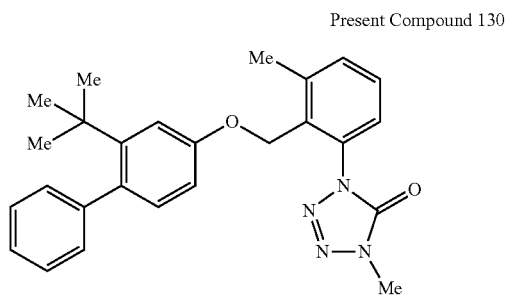
Present Compound 131
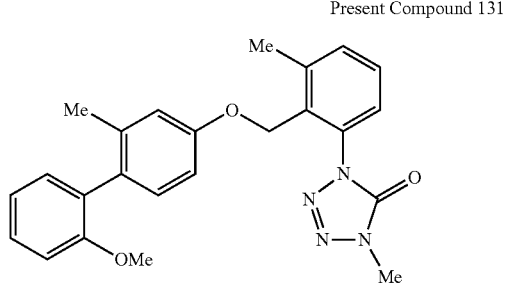
Present Compound 132
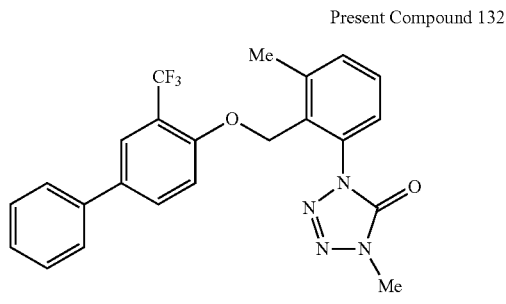
Present Compound 133
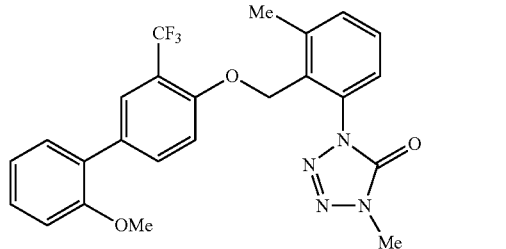
Present Compound 134
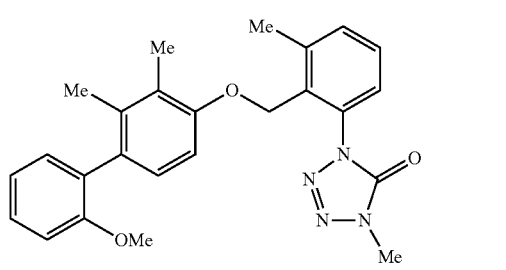

Present Compound 135
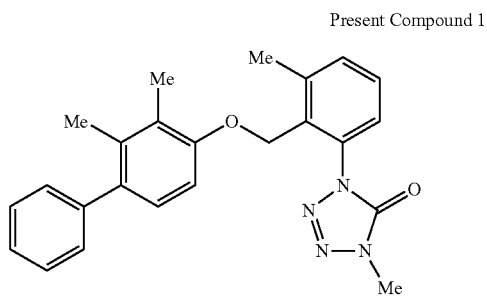
Present Compound 136
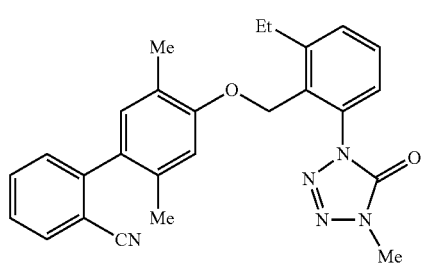
Present Compound 137
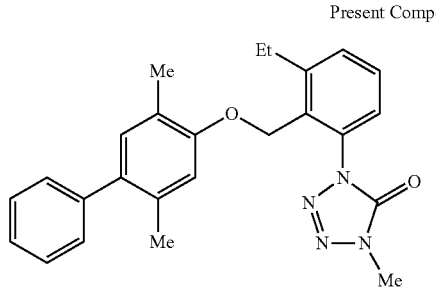
Present Compound 138
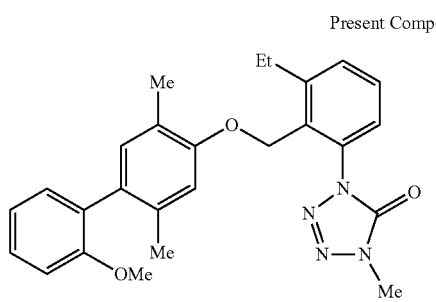
Present Compound 139
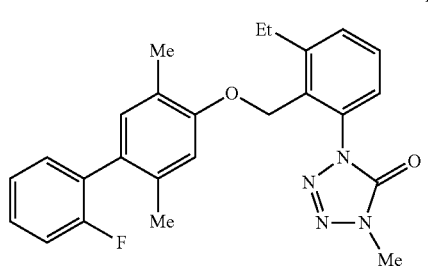
Present Compound 140
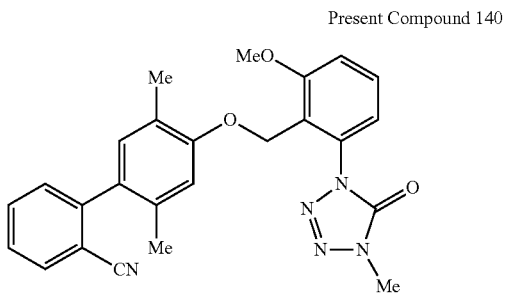
Present Compound 141
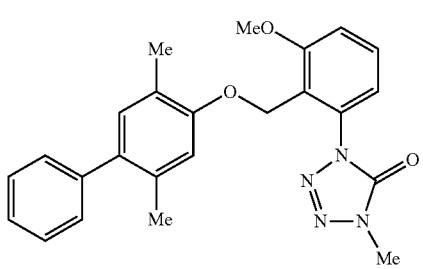
Present Compound 142
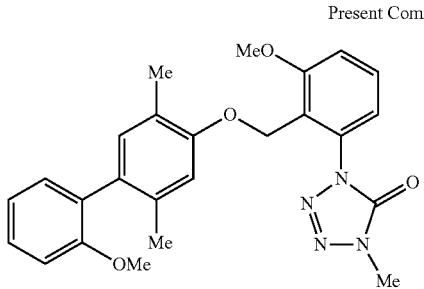
Present Compound 143
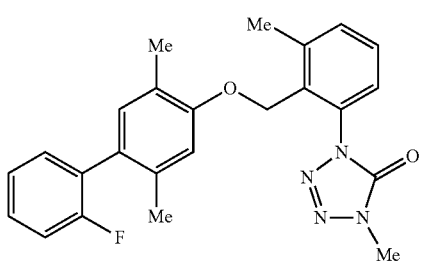
Present Compound 144
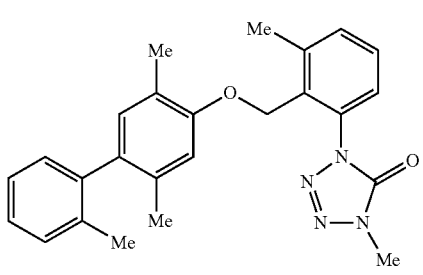

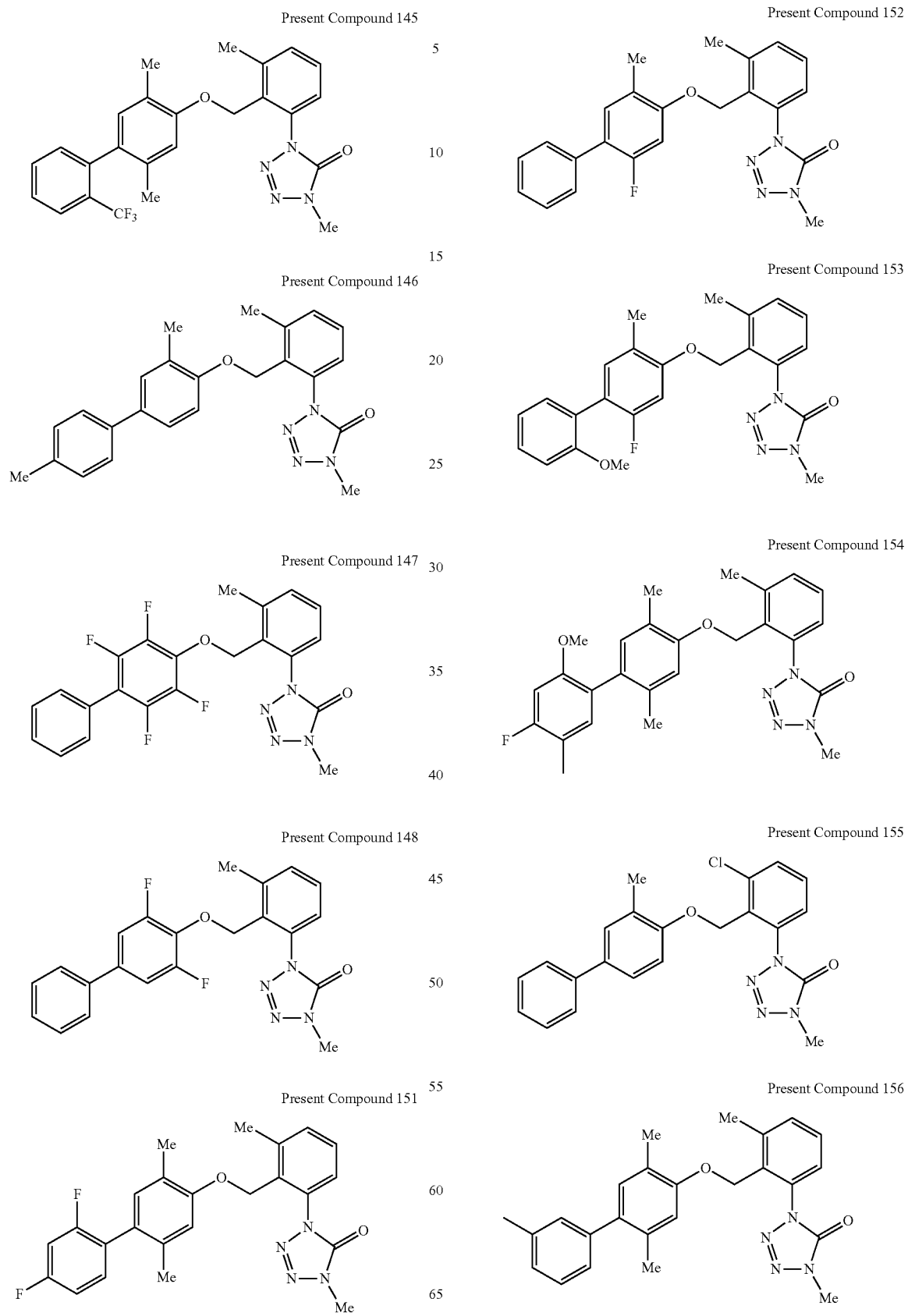

Present Compound 2
¹H-NMR (CDCl₃) δ: 7.52 (1H, t, J=1.8 Hz), 7.46-7.39 (3H, m), 7.36-7.24 (5H, m), 6.91 (1H, d, J=8.4 Hz), 5.08 (2H, s), 3.64 (3H, s), 2.53 (3H, s), 2.16 (3H, s).

Present Compound 3
¹H-NMR (CDCl₃) δ: 7.46-7.40 (2H, m), 7.31-7.27 (1H, m), 7.13-7.05 (5H, m), 6.88 (1H, d, J=8.0 Hz), 5.07 (2H, s), 3.65 (3H, s), 2.54 (3H, s), 2.33 (3H, s), 2.17 (3H, s), 2.13 (3H, s).

Present Compound 4
¹H-NMR (CDCl₃) δ: 7.44-7.26 (7H, m), 7.20-7.10 (2H, m), 6.93 (1H, d, J=8.5 Hz), 5.08 (2H, s), 3.64 (3H, s), 2.53 (3H, s), 2.15 (3H, s).

Present Compound 5
¹H-NMR (CDCl₃) δ: 7.46-7.40 (2H, m), 7.37-7.33 (2H, m), 7.30-7.27 (1H, m), 7.17-7.15 (2H, m), 6.96 (1H, s), 6.90 (1H, d, J=9.2 Hz), 5.08 (2H, s), 3.63 (3H, s), 2.53 (3H, s), 2.37 (6H, s), 2.16 (3H, s).

Present Compound 6
¹H-NMR (CDCl₃) δ: 7.48-7.40 (3H, m), 7.30-7.16 (5H, m), 6.91 (1H, d, J=8.2 Hz), 5.08 (2H, s), 3.65 (3H, s), 2.53 (3H, s), 2.14 (3H, s).

Present Compound 7
¹H-NMR (CDCl₃) δ: 7.59-7.54 (2H, m), 7.51 (1H, t, J=8.2 Hz), 7.43 (2H, t, J=8.2 Hz), 7.40-7.31 (3H, m), 7.13 (2H, t, J=8.2 Hz), 6.99 (1H, d, J=8.2 Hz), 5.34 (2H, s), 3.97 (3H, s), 3.63 (3H, s), 2.10 (3H, s).

Present Compound 8
¹H-NMR (CDCl₃) δ: 7.53-7.47 (3H, m), 7.41-7.37 (2H, m), 7.35-7.29 (2H, m), 7.12 (2H, t, J=8.5 Hz), 6.97 (1H, d, J=8.5 Hz), 5.34 (2H, s), 3.97 (3H, s), 3.64 (3H, s), 2.09 (3H, s).

Present Compound 9
¹H-NMR (CDCl₃) δ: 7.50-7.42 (2H, m), 7.32-7.19 (4H, m), 7.17-7.15 (1H, m), 7.09 (2H, t, J=8.2 Hz), 6.94 (1H, d, J=8.2 Hz), 5.30 (2H, s), 3.93 (3H, s), 3.61 (3H, s), 2.05 (3H, s).

Present Compound 10
¹H-NMR (CDCl₃) δ: 7.52-7.49 (1H, m), 7.46 (1H, d, J=8.0 Hz), 7.41-7.38 (1H, m), 7.33-7.23 (4H, m), 7.09 (2H, t, J=8.5 Hz), 6.94 (1H, d, J=8.5 Hz), 5.31 (2H, s), 3.94 (3H, s), 3.60 (3H, s), 2.06 (3H, s).

Present Compound 11
¹H-NMR (CDCl₃) δ: 7.79 (1H, t, J=1.6 Hz), 7.74 (1H, dt, J=7.8, 1.6 Hz), 7.55 (1H, dt, J=7.6, 1.4 Hz), 7.51-7.45 (2H, m), 7.33-7.27 (2H, m), 7.09 (2H, t, J=8.5 Hz), 6.96 (1H, d, J=8.5 Hz), 5.32 (2H, s), 3.95 (3H, s), 3.61 (3H, s), 2.06 (3H, s).

Present Compound 12
¹H-NMR (CDCl₃) δ: 7.79 (1H, s), 7.72 (1H, d, J=7.1 Hz), 7.58-7.49 (3H, m), 7.40-7.34 (2H, m), 7.13 (2H, t, J=8.2 Hz), 6.99 (1H, d, J=8.2 Hz), 5.35 (2H, s), 3.98 (3H, s), 3.64 (3H, s), 2.10 (3H, s).

Present Compound 13
¹H-NMR (CDCl₃) δ: 7.63 (1H, s), 7.48-7.42 (2H, m), 7.35-7.20 (5H, m), 7.10-7.05 (2H, m), 6.92 (1H, d, J=8.2 Hz), 5.29 (2H, s), 3.93 (3H, s), 3.59 (3H, s), 2.04 (3H, s), 2.04 (3H, s).

Present Compound 14
¹H-NMR (CDCl₃) δ: 7.52 (1H, s), 7.47 (1H, t, J=8.2 Hz), 7.35-7.29 (4H, m), 7.27-7.25 (1H, m), 7.08 (2H, t, J=8.4 Hz), 6.94 (1H, d, J=8.5 Hz), 5.30 (2H, s), 3.93 (3H, s), 3.59 (3H, s), 2.07 (3H, s), 1.36 (9H, s).

Present Compound 15
¹H-NMR (CDCl₃) δ: 7.48 (1H, t, J=8.1 Hz), 7.21-7.05 (5H, m), 6.93-6.82 (3H, m), 5.30 (2H, s), 3.94 (3H, s), 3.62 (3H, s), 2.03 (6H, s), 2.02 (3H, s).

Present Compound 16
¹H-NMR (CDCl₃) δ: 7.47 (1H, t, J=8.1 Hz), 7.35-7.26 (5H, m), 7.11-7.08 (3H, m), 6.94 (1H, d, J=8.2 Hz), 5.30 (2H, s), 3.93 (3H, s), 3.59 (3H, s), 2.40 (3H, s), 2.06 (3H, s).

Present Compound 17
¹H-NMR (CDCl₃) δ: 7.50-7.42 (3H, m), 7.30-7.25 (2H, m), 7.10-7.06 (2H, m), 6.94-6.92 (3H, m), 5.29 (2H, s), 3.93 (3H, s), 3.84 (3H, s), 3.59 (3H, s), 2.05 (3H, s).

Present Compound 18
¹H-NMR (CDCl₃) δ: 7.47 (1H, t, J=8.2 Hz), 7.35-7.29 (3H, m), 7.12-7.05 (4H, m), 6.94 (1H, d, J=8.2 Hz), 6.84 (1H, dd, J=8.2, 2.5 Hz), 5.30 (2H, s), 3.93 (3H, s), 3.85 (3H, s), 3.59 (3H, s), 2.06 (3H, s).

Present Compound 19
¹H-NMR (CDCl₃) δ: 7.48 (1H, t, J=8.1 Hz), 7.14-7.02 (7H, m), 6.91 (1H, d, J=8.2 Hz), 5.29 (2H, s), 3.94 (3H, s), 3.62 (3H, s), 2.33 (3H, s), 2.23 (3H, s), 2.04 (3H, s).

Present Compound 20
¹H-NMR (CDCl₃) δ: 7.47 (1H, t, J=8.2 Hz), 7.30-7.24 (4H, m), 7.10-7.06 (2H, m), 7.01-6.92 (3H, m), 5.28 (2H, s), 3.93 (3H, s), 3.81 (3H, s), 3.62 (3H, s), 2.05 (3H, s).

Present Compound 21
¹H-NMR (CDCl₃) δ: 7.73 (1H, dd, J=7.8, 0.9 Hz), 7.62-7.58 (1H, m), 7.52-7.44 (2H, m), 7.40-7.33 (2H, m), 7.28-7.26 (1H, m), 7.12-7.08 (2H, m), 7.00 (1H, d, J=8.5 Hz), 5.32 (2H, s), 3.95 (3H, s), 3.63 (3H, s), 2.08 (3H, s).

Present Compound 22
¹H-NMR (CDCl₃) δ: 7.45 (1H, t, J=8.1 Hz), 7.41 (2H, dd, J=6.3, 1.7 Hz), 7.33-7.27 (2H, m), 7.19 (2H, d, J=8.0 Hz), 7.09-7.04 (2H, m), 6.92 (1H, d, J=8.2 Hz), 5.28 (2H, s), 3.92 (3H, s), 3.58 (3H, s), 2.36 (3H, s), 2.04 (3H, s).

Present Compound 23
¹H-NMR (CDCl₃) δ: 7.47 (1H, t, J=8.2 Hz), 7.38 (1H, td, J=7.8, 1.8 Hz), 7.32-7.23 (3H, m), 7.18-7.06 (4H, m), 6.95 (1H, d, J=8.5 Hz), 5.30 (2H, s), 3.93 (3H, s), 3.60 (3H, s), 2.05 (3H, s).

Present Compound 24
¹H-NMR (CDCl₃) δ: 7.46 (1H, t, J=8.1 Hz), 7.35-7.17 (5H, m), 7.10-7.05 (2H, m), 6.98-6.90 (2H, m), 5.29 (2H, s), 3.92 (3H, s), 3.58 (3H, s), 2.04 (3H, s).

Present Compound 25
¹H-NMR (CDCl₃) δ: 7.53-7.45 (3H, m), 7.43-7.40 (1H, m), 7.36-7.25 (5H, m), 6.92 (1H, d, J=8.0 Hz), 5.10 (2H, s), 3.60 (3H, s), 2.86 (2H, q, J=7.6 Hz), 2.14 (3H, s), 1.30 (3H, t, J=7.6 Hz).

Present Compound 26
¹H-NMR (CDCl₃) δ: 7.52 (1H, t, J=1.7 Hz), 7.47-7.40 (2H, m), 7.36-7.25 (6H, m), 6.95 (1H, d, J=8.2 Hz), 5.30 (2H, s), 3.62 (3H, s), 2.17-2.12 (4H, m), 1.03-0.97 (2H, m), 0.81-0.75 (2H, m).

Present Compound 27
¹H-NMR (CDCl₃) δ: 7.81 (1H, s), 7.77-7.75 (1H, m), 7.57 (1H, d, J=7.6 Hz), 7.53-7.45 (3H, m), 7.36-7.28 (3H, m), 6.94 (1H, d, J=8.2 Hz), 5.10 (2H, s), 3.61 (3H, s), 2.86 (2H, q, J=7.6 Hz), 2.15 (3H, s), 1.30 (3H, t, J=7.6 Hz).

Present Compound 28
¹H-NMR (CDCl₃) δ: 7.81 (1H, t, J=1.5 Hz), 7.75 (1H, dt, J=7.8, 1.5 Hz), 7.57 (1H, dt, J=7.7, 1.4 Hz), 7.50 (1H, t, J=7.7 Hz), 7.45 (1H, t, J=7.9 Hz), 7.36-7.32 (2H, m), 7.30-7.26 (2H, m), 6.97 (1H, d, J=8.2 Hz), 5.31 (2H, s), 3.62 (3H, s), 2.17-2.13 (4H, m), 1.03-0.98 (2H, m), 0.80-0.76 (2H, m).

Present Compound 29
¹H-NMR (CDCl₃) δ: 7.45-7.37 (4H, m), 7.34-7.26 (4H, m), 7.14 (1H, d, J=8.2 Hz), 6.80-6.75 (2H, m), 5.04 (2H, s), 3.65 (3H, s), 2.52 (3H, s), 2.25 (3H, s).

Present Compound 30
¹H-NMR (CDCl3) δ: 7.45-7.40 (2H, m), 7.30-7.26 (1H, m), 7.23-7.16 (4H, m), 7.13 (1H, d, J=8.2 Hz), 6.80-6.74 (2H, m), 5.04 (2H, s), 3.65 (3H, s), 2.52 (3H, s), 2.40 (3H, s), 2.25 (3H, s).

Present Compound 31
¹H-NMR (CDCl₃) δ: 7.45-7.41 (2H, m), 7.30-7.19 (4H, m), 7.08 (1H, d, J=6.9 Hz), 7.00 (1H, d, J=8.2 Hz), 6.81-6.78 (1H, m), 6.75 (1H, dd, J=8.2, 2.5 Hz), 5.05 (2H, s), 3.65 (3H, s), 2.53 (3H, s), 2.06 (3H, s), 2.02 (3H, s).

Present Compound 32
¹H-NMR (CDCl₃) δ: 7.46-7.40 (2H, m), 7.33-7.26 (4H, m), 7.16 (1H, dt, J=7.0, 1.7 Hz), 6.96 (1H, s), 6.73 (1H, s), 5.05 (2H, s), 3.67 (3H, s), 2.53 (3H, s), 2.24 (3H, s), 2.08 (3H, s).

Present Compound 33
¹H-NMR (CDCl₃) δ: 7.46-7.40 (2H, m), 7.30-7.26 (2H, m), 7.15-7.07 (4H, m), 6.80-6.74 (2H, m), 5.04 (2H, s), 3.65 (3H, s), 2.52 (3H, s), 2.39 (3H, s), 2.25 (3H, s).

Present Compound 34
¹H-NMR (CDCl₃) δ: 7.45-7.25 (8H, m), 7.00 (1H, s), 6.75 (1H, s), 5.06 (2H, s), 3.67 (3H, s), 2.54 (3H, s), 2.26 (3H, s), 2.09 (3H, s).

Present Compound 35
¹H-NMR (CDCl₃) δ: 7.54 (2H, dd, J=8.27, 1.02 Hz), 7.46-7.35 (4H, m), 7.37-7.35 (2H, m), 7.33-7.26 (2H, m), 6.92 (1H, d, J=8.83 Hz), 5.07 (2H, s), 3.63 (3H, s), 2.53 (3H, s), 2.16 (3H, s).

Present Compound 36
¹H-NMR (CDCl₃) δ: 7.47 (1H, t, J=8.2 Hz), 7.11-7.02 (7H, m), 6.90 (1H, d, J=8.4 Hz), 5.29 (2H, s), 3.93 (3H, s), 3.62 (3H, s), 2.35 (3H, s), 2.24 (3H, s), 2.03 (3H, s).

Present Compound 37
¹H-NMR (CDCl₃) δ: 7.68-7.65 (2H, m), 7.62-7.59 (2H, m), 7.48 (1H, t, J=8.2 Hz), 7.36-7.31 (2H, m), 7.12-7.06 (2H, m), 6.96 (1H, d, J=8.6 Hz), 5.32 (2H, s), 3.94 (3H, s), 3.60 (3H, s), 2.05 (3H, s).

Present Compound 38
¹H-NMR (CDCl₃) δ: 8.11 (1H, t, J=1.7 Hz), 7.87 (1H, dt, J=7.8, 1.4 Hz), 7.74-7.71 (1H, m), 7.51-7.45 (2H, m), 7.38-7.34 (2H, m), 7.09 (2H, t, J=8.1 Hz), 6.96 (1H, d, J=8.2 Hz), 5.32 (2H, s), 3.95 (3H, s), 3.61 (3H, s), 2.65 (3H, s), 2.07 (3H, s).

Present Compound 39
¹H-NMR (CDCl₃) δ: 7.50-7.44 (3H, m), 7.30-7.25 (2H, m), 7.12-7.05 (4H, m), 6.93 (1H, d, J=8.2 Hz), 5.30 (2H, s), 3.94 (3H, s), 3.60 (3H, s), 2.06 (3H, s).

Present Compound 40
¹H-NMR (CDCl₃) δ: 7.98 (1H, d, J=1.4 Hz), 7.91-7.83 (3H, m), 7.71 (1H, dd, J=8.5, 1.8 Hz), 7.53-7.41 (6H, m), 7.30 (1H, dd, J=6.5, 2.6 Hz), 6.98-6.95 (1H, m), 5.11 (2H, s), 3.64 (3H, s), 2.55 (3H, s), 2.20 (3H, s).

Present Compound 46
¹H-NMR (CDCl₃) δ: 7.94 (1H, d, J=8.5 Hz), 7.90 (1H, d, J=8.0 Hz), 7.83 (1H, d, J=8.2 Hz), 7.53-7.38 (6H, m), 7.31-7.26 (3H, m), 6.97 (1H, d, J=8.0 Hz), 5.12 (2H, s), 3.67 (3H, s), 2.57 (3H, s), 2.18 (3H, s).

Present Compound 47
¹H-NMR (CDCl₃) δ: 7.74 (1H, dd, J=7.8, 1.4 Hz), 7.61 (1H, td, J=7.7, 1.4 Hz), 7.49-7.37 (4H, m), 7.30-7.26 (3H, m), 7.00 (1H, d, J=8.5 Hz), 5.31 (2H, s), 3.64 (3H, s), 2.17-2.14 (4H, m), 1.05-1.00 (2H, m), 0.81-0.76 (2H, m).

Present Compound 48
¹H-NMR (CDCl₃) δ: 7.73 (1H, dd, J=7.7, 0.9 Hz), 7.63-7.58 (1H, m), 7.51-7.46 (3H, m), 7.41-7.37 (2H, m), 7.31-7.27 (2H, m), 6.97 (1H, d, J=8.4 Hz), 5.10 (2H, s), 3.62 (3H, s), 2.86 (2H, q, J=7.6 Hz), 2.15 (3H, s), 1.30 (3H, t, J=7.6 Hz).

Present Compound 49
¹H-NMR (CDCl₃) δ: 7.47 (1H, t, J=8.3 Hz), 7.41-7.39 (1H, m), 7.33-7.26 (4H, m), 7.17 (1H, dt, J=7.1, 1.8 Hz), 7.10-7.06 (2H, m), 6.94 (1H, d, J=8.4 Hz), 5.30 (2H, s), 3.93 (3H, s), 3.60 (3H, s), 2.52 (3H, s), 2.05 (3H, s).

Present Compound 50
¹H-NMR (CDCl₃) δ: 7.52-7.45 (2H, m), 7.29 (1H, dd, J=6.8, 2.4 Hz), 7.12-7.03 (5H, m), 6.89 (1H, d, J=8.0 Hz), 5.09 (2H, s), 3.62 (3H, s), 2.88 (2H, q, J=7.6 Hz), 2.36 (3H, s), 2.26 (3H, s), 2.12 (3H, s), 1.31 (3H, t, J=7.6 Hz).

Present Compound 51
¹H-NMR (CDCl₃) δ: 7.49-7.37 (6H, m), 7.31-7.21 (3H, m), 6.57 (1H, dd, J=8.4, 2.3 Hz), 6.51 (1H, d, J=2.3 Hz), 5.06 (2H, s), 3.76 (3H, s), 3.63 (3H, s), 2.53 (3H, s).

Present Compound 52
¹H-NMR (CDCl₃) δ: 7.54-7.39 (6H, m), 7.35-7.24 (4H, m), 7.01 (1H, t, J=8.5 Hz), 5.18 (2H, s), 3.65 (3H, s), 2.88 (2H, q, J=7.6 Hz), 1.31 (3H, t, J=7.6 Hz).

Present Compound 53
¹H-NMR (CDCl₃) δ: 7.46-7.36 (4H, m), 7.29 (1H, dd, J=6.6, 2.7 Hz), 7.22-7.19 (3H, m), 6.56 (1H, dd, J=8.4, 2.3 Hz), 6.51 (1H, d, J=2.3 Hz), 5.06 (2H, s), 3.76 (3H, s), 3.63 (3H, s), 2.53 (3H, s), 2.38 (3H, s).

Present Compound 54
¹H-NMR (CDCl₃) δ: 7.46-7.42 (1H, m), 7.29-7.22 (3H, m), 7.12-7.02 (4H, m), 6.92 (1H, d, J=8.2 Hz), 5.29 (2H, s), 3.63 (3H, s), 2.36 (3H, s), 2.26 (3H, s), 2.20-2.11 (4H, m), 1.04-0.98 (2H, m), 0.81-0.75 (2H, m).

Present Compound 55
¹H-NMR (CDCl₃) δ: 7.79 (1H, dd, J=2.4, 1.0 Hz), 7.75-7.71 (1H, m), 7.62 (1H, dt, J=7.7, 1.4 Hz), 7.55-7.44 (3H, m), 7.31-7.22 (3H, m), 7.04 (1H, t, J=8.4 Hz), 5.20 (2H, s), 3.67 (3H, s), 2.88 (2H, q, J=7.6 Hz), 1.32 (3H, t, J=7.6 Hz).

Present Compound 56
¹H-NMR (CDCl₃) δ: 7.53-7.40 (8H, m), 7.31 (1H, dd, J=7.3, 1.8 Hz), 7.23 (1H, d, J=2.5 Hz), 7.15 (1H, dd, J=8.7, 2.5 Hz), 5.08 (2H, s), 3.68 (3H, s), 2.52 (3H, s).

Present Compound 57
¹H-NMR (CDCl₃) δ: 7.48-7.42 (4H, m), 7.38 (1H, d, J=8.7 Hz), 7.31 (1H, dd, J=7.3, 1.8 Hz), 7.20 (1H, d, J=2.8 Hz), 7.12 (1H, dd, J=8.7, 2.7 Hz), 7.02-6.98 (2H, m), 5.06 (2H, s), 3.86 (3H, s), 3.67 (3H, s), 2.51 (3H, s).

Present Compound 113
¹H-NMR (CDCl₃) δ: 7.55 (2H, dd, J=8.0, 1.1 Hz), 7.44-7.37 (6H, m), 7.33-7.27 (2H, m), 6.95 (1H, d, J=9.2 Hz), 5.06 (2H, s), 3.64 (3H, s), 2.57 (2H, q, J=7.6 Hz), 2.53 (3H, s), 1.14 (3H, t, J=7.6 Hz).

Present Compound 114
¹H-NMR (CDCl₃) δ: 7.74 (1H, dd, J=7.8, 0.9 Hz), 7.61 (1H, td, J=7.8, 1.1 Hz), 7.50-7.34 (6H, m), 7.30-7.28 (1H, m), 6.98 (1H, d, J=8.2 Hz), 5.07 (2H, s), 3.66 (3H, s), 2.58 (2H, q, J=7.6 Hz), 2.53 (3H, s), 1.14 (3H, t, J=7.6 Hz).

Present Compound 115
¹H-NMR (CDCl₃) δ: 7.49-7.40 (2H, m), 7.38-7.33 (2H, m), 7.30 (1H, dd, J=7.3, 1.4 Hz), 7.01-6.95 (2H, m), 6.52 (2H, d, J=9.4 Hz), 5.02 (2H, s), 3.85 (3H, s), 3.68 (3H, s), 2.51 (3H, s).

Present Compound 116
¹H-NMR (CDCl₃) δ: 7.47-7.35 (7H, m), 7.30 (1H, dd, J=7.4, 1.7 Hz), 6.53 (2H, d, J=9.3 Hz), 5.02 (2H, s), 3.68 (3H, s), 2.51 (3H, s).

Present Compound 117
¹H-NMR (CDCl₃) δ: 7.47-7.36 (5H, m), 7.32-7.22 (5H, m), 7.05 (1H, dd, J=8.5, 2.6 Hz), 5.09 (2H, s), 3.66 (3H, s), 2.53 (3H, s).

Present Compound 118
¹H-NMR (CDCl₃) δ: 7.48-7.43 (2H, m), 7.33-7.26 (2H, m), 7.25-7.22 (2H, m), 7.21-7.16 (1H, m), 7.16-7.09 (2H, m), 7.05 (1H, dd, J=8.4, 2.6 Hz), 5.10 (2H, s), 3.67 (3H, s), 2.54 (3H, s), 2.04 (3H, s).

Present Compound 119
¹H-NMR (CDCl₃) δ: 7.47-7.41 (2H, m), 7.33-7.19 (5H, m), 7.03 (1H, d, J=8.7 Hz), 6.94-6.89 (2H, m), 5.09 (2H, s), 3.85 (3H, s), 3.66 (3H, s), 2.52 (3H, s).

Present Compound 120
¹H-NMR (CDCl₃) δ: 7.46-7.40 (2H, m), 7.33-7.26 (2H, m), 7.00 (1H, s), 6.89-6.83 (3H, m), 6.74 (1H, s), 5.06 (2H, s), 3.83 (3H, s), 3.67 (3H, s), 2.54 (3H, s), 2.26 (3H, s), 2.09 (3H, s).

Present Compound 121
¹H-NMR (CDCl₃) δ: 7.45-7.39 (2H, m), 7.30-7.26 (1H, m), 7.20 (2H, dd, J=6.6, 2.1 Hz), 6.97 (1H, s), 6.92 (2H, dd, J=6.6, 2.1 Hz), 6.73 (1H, s), 5.05 (2H, s), 3.84 (3H, s), 3.66 (3H, s), 2.53 (3H, s), 2.24 (3H, s), 2.08 (3H, s).

Present Compound 122
¹H-NMR (CDCl₃) δ: 7.72-7.70 (1H, m), 7.62-7.57 (1H, m), 7.46-7.38 (3H, m), 7.35-7.31 (1H, m), 7.30-7.26 (1H, m), 6.94 (1H, s), 6.76 (1H, s), 5.06 (2H, s), 3.67 (3H, s), 2.53 (3H, s), 2.16 (3H, s), 2.08 (3H, s).

Present Compound 123
¹H-NMR (CDCl₃) δ: 7.42-7.40 (2H, m), 7.34-7.26 (2H, m), 7.12 (1H, dd, J=7.5, 1.8 Hz), 7.01-6.92 (3H, m), 6.74 (1H, s), 5.03 (2H, s), 3.77 (3H, s), 3.67 (3H, s), 2.53 (3H, s), 2.11 (3H, s), 2.07 (3H, s).

Present Compound 124
¹H-NMR (CDCl₃) δ: 7.32-7.22 (3H, m), 7.17-7.12 (3H, m), 7.06-7.03 (1H, m), 6.92-6.86 (3H, m), 4.90 (2H, s), 3.65 (3H, s), 3.60 (3H, s), 2.19 (3H, s), 1.30 (9H, s).

Present Compound 125
¹H-NMR (CDCl₃) δ: 7.49-7.41 (2H, m), 7.34-7.29 (3H, m), 7.26-7.23 (1H, m), 7.19 (1H, d, J=7.3 Hz), 6.56-6.49 (2H, m), 5.03 (2H, s), 3.69 (3H, s), 2.52 (3H, s), 2.18 (3H, s).

Present Compound 126
¹H-NMR (CDCl₃) δ: 7.41-7.35 (2H, m), 7.33-7.17 (7H, m), 6.90-6.86 (1H, m), 6.75-6.72 (1H, m), 4.98 (2H, s), 3.59 (3H, s), 2.63 (2H, q, J=7.6 Hz), 2.28 (3H, s), 1.24 (3H, t, J=6.7 Hz).

Present Compound 127
¹H-NMR (CDCl₃) δ: 7.36-7.32 (3H, m), 7.30-7.27 (1H, m), 7.21-7.17 (2H, m), 6.89-6.86 (1H, m), 6.86-6.81 (2H, m), 6.74 (1H, s), 4.96 (2H, s), 3.82 (3H, s), 3.61 (3H, s), 2.63 (2H, q, J=7.6 Hz), 2.32 (3H, s), 1.24 (3H, t, J=7.6 Hz).

Present Compound 128
¹H-NMR (CDCl₃) δ: 7.39-7.26 (4H, m), 7.22-7.16 (2H, m), 7.08-7.04 (1H, m), 6.89-6.84 (3H, m), 4.95 (2H, s), 3.82 (3H, s), 3.58 (3H, s), 2.33 (3H, s), 1.29 (9H, s).

Present Compound 129
¹H-NMR (CDCl₃) δ: 7.33-7.22 (3H, m), 7.17-7.09 (3H, m), 6.92-6.84 (3H, m), 6.75 (1H, d, J=1.4 Hz), 4.94 (2H, s), 3.64 (3H, s), 3.63 (3H, s), 2.65 (2H, q, J=7.6 Hz), 2.20 (3H, s), 1.26 (3H, t, J=7.6 Hz).

Present Compound 130
¹H-NMR (CDCl₃) δ: 7.44-7.17 (9H, m), 7.07 (1H, dd, J=7.9, 1.8 Hz), 6.88 (1H, d, J=1.8 Hz), 4.97 (2H, s), 3.56 (3H, s), 2.30 (3H, s), 1.29 (9H, s).

Present Compound 131
¹H-NMR (CDCl₃) δ: 7.45-7.40 (2H, m), 7.35-7.27 (2H, m), 7.12 (1H, dd, J=7.4, 1.7 Hz), 7.09 (1H, d, J=8.2 Hz), 7.00 (1H, td, J=7.4, 1.0 Hz), 6.95 (1H, dd, J=8.2, 0.7 Hz), 6.80-6.74 (2H, m), 5.03 (2H, s), 3.77 (3H, s), 3.65 (3H, s), 2.52 (3H, s), 2.11 (3H, s).

Present Compound 132
¹H-NMR (CDCl₃) δ: 7.76 (1H, d, J=2.3 Hz), 7.67 (1H, dd, J=8.5, 2.3 Hz), 7.54-7.51 (2H, m), 7.47-7.39 (4H, m), 7.37-7.28 (2H, m), 7.04 (1H, d, J=8.5 Hz), 5.19 (2H, s), 3.69 (3H, s), 2.53 (3H, s).

Present Compound 133
¹H-NMR (CDCl₃) δ: 7.71 (1H, d, J=2.1 Hz), 7.63 (1H, dd, J=8.6, 2.1 Hz), 7.45-7.40 (2H, m), 7.35-7.25 (3H, m), 7.04-7.01 (2H, m), 6.98 (1H, d, J=8.2 Hz), 5.17 (2H, s), 3.82 (3H, s), 3.69 (3H, s), 2.53 (3H, s).

Present Compound 134
¹H-NMR (CDCl₃) δ: 7.29-7.25 (2H, m), 7.16 (1H, d, J=7.6 Hz), 7.13-7.07 (2H, m), 6.95-6.93 (2H, m), 6.91-6.85 (2H, m), 4.58 (2H, s), 3.74 (3H, s), 3.65 (3H, s), 2.25 (3H, s), 1.96-1.93 (6H, m).

Present Compound 135
¹H-NMR (CDCl₃) δ: 7.40-7.36 (2H, m), 7.31-7.25 (4H, m), 7.15 (1H, d, J=7.3 Hz), 7.10 (1H, d, J=7.8 Hz), 7.00 (1H, d, J=7.8 Hz), 6.95 (1H, d, J=7.8 Hz), 4.66 (2H, s), 3.64 (3H, s), 2.24 (3H, s), 2.10 (3H, s), 1.91 (3H, s).

Present Compound 136
¹H-NMR (CDCl₃) δ: 7.72 (1H, dd, J=7.8, 0.6 Hz), 7.63-7.57 (1H, m), 7.57-7.50 (1H, m), 7.50-7.39 (2H, m), 7.34 (1H, d, J=7.8 Hz), 7.29 (1H, dd, J=6.8, 2.4 Hz), 6.94 (1H, s), 6.78 (1H, s), 5.08 (2H, s), 3.64 (3H, s), 2.87 (2H, q, J=7.6 Hz), 2.17 (3H, s), 2.07 (3H, s), 1.31 (3H, t, J=7.6 Hz).

Present Compound 137
¹H-NMR (CDCl₃) δ: 7.51-7.45 (2H, m), 7.41-7.36 (2H, m), 7.32-7.27 (4H, m), 6.99 (1H, s), 6.75 (1H, s), 5.07 (2H, s), 3.64 (3H, s), 2.88 (2H, q, J=7.6 Hz), 2.26 (3H, s), 2.07 (3H, s), 1.30 (3H, t, J=7.6 Hz).

Present Compound 138
¹H-NMR (CDCl₃) δ: 7.51-7.44 (2H, m), 7.34-7.26 (2H, m), 7.15-7.10 (1H, m), 7.01-6.94 (3H, m), 6.76 (1H, s), 5.06 (2H, s), 3.79 (3H, s), 3.66 (3H, s), 2.88 (2H, q, J=7.6 Hz), 2.12 (3H, s), 2.06 (3H, s), 1.30 (3H, t, J=7.6 Hz).

Present Compound 139
¹H-NMR (CDCl₃) δ: 7.51-7.45 (2H, m), 7.34-7.15 (4H, m), 7.14-7.08 (1H, m), 6.97 (1H, s), 6.78 (1H, s), 5.08 (2H, s), 3.64 (3H, s), 2.87 (2H, q, J=7.6 Hz), 2.18 (3H, s), 2.07 (3H, s), 1.30 (3H, t, J=7.6 Hz).

Present Compound 140
¹H-NMR (CDCl₃) δ: 7.71 (1H, dd, J=7.8, 0.6 Hz), 7.59 (1H, td, J=7.7, 1.4 Hz), 7.48 (1H, t, J=8.1 Hz), 7.43-7.38 (1H, m), 7.32 (1H, dd, J=7.7, 0.6 Hz), 7.12-7.07 (2H, m), 6.90 (1H, s), 6.82 (1H, s), 5.28 (2H, s), 3.94 (3H, s), 3.63 (3H, s), 2.15 (3H, s), 1.99 (3H, s).

Present Compound 141
¹H-NMR (CDCl₃) δ: 7.52 (1H, t, J=8.2 Hz), 7.44-7.40 (2H, m), 7.36-7.31 (3H, m), 7.17-7.10 (2H, m), 6.99 (1H, s), 6.84 (1H, s), 5.33 (2H, s), 3.99 (3H, s), 3.68 (3H, s), 2.28 (3H, s), 2.04 (3H, s).

Present Compound 142
¹H-NMR (CDCl₃) δ: 7.52 (1H, t, J=8.2 Hz), 7.38-7.32 (1H, m), 7.16-7.10 (3H, m), 7.05-7.00 (1H, m), 6.98 (1H, dd, J=8.4, 0.8 Hz), 6.93 (1H, s), 6.83 (1H, s), 5.30 (2H, s), 3.98 (3H, s), 3.81 (3H, s), 3.69 (3H, s), 2.14 (3H, s), 2.02 (3H, s).

Present Compound 143
¹H-NMR (CDCl₃) δ: 7.46-7.40 (2H, m), 7.34-7.27 (2H, m), 7.23-7.19 (1H, m), 7.19-7.15 (1H, m), 7.14-7.08 (1H, m), 6.96 (1H, s), 6.76 (1H, s), 5.06 (2H, s), 3.66 (3H, s), 2.53 (3H, s), 2.17 (3H, s), 2.08 (3H, s).

Present Compound 144
¹H-NMR (CDCl₃) δ: 7.44-7.39 (2H, m), 7.30-7.16 (4H, m), 7.09-7.04 (1H, m), 6.86-6.82 (1H, m), 6.74-6.70 (1H, m), 5.05 (2H, s), 3.67 (3H, s), 2.54 (3H, s), 2.08-2.05 (6H, m), 2.02 (3H, s).

Present Compound 145
¹H-NMR (CDCl₃) δ: 7.73 (1H, d, J=7.8 Hz), 7.56-7.50 (1H, m), 7.47-7.39 (3H, m), 7.30-7.26 (1H, m), 7.20 (1H, d, J=7.6 Hz), 6.86 (1H, s), 6.71 (1H, s), 5.12-5.02 (2H, m), 3.65 (3H, s), 2.54 (3H, s), 2.05 (3H, s), 1.98 (3H, s).

Present Compound 146
¹H-NMR (CDCl₃) δ: 7.46-7.40 (4H, m), 7.37-7.33 (2H, m), 7.30-7.27 (1H, m), 7.24-7.20 (2H, m), 6.90 (1H, d, J=9.2 Hz), 5.07 (2H, s), 3.63 (3H, s), 2.52 (3H, s), 2.38 (3H, s), 2.15 (3H, s).

Present Compound 147
¹H-NMR (CDCl₃) δ: 7.48-7.41 (7H, m), 7.24 (1H, t, J=4.6 Hz), 5.29 (2H, s), 3.72 (3H, s), 2.65 (3H, s).
Present Compound 148
¹H-NMR (CDCl₃) δ: 7.51-7.47 (2H, m), 7.46-7.40 (4H, m), 7.39-7.34 (1H, m), 7.26-7.23 (1H, m), 7.07 (2H, d, J=9.5 Hz), 5.18 (2H, s), 3.73 (3H, s), 2.64 (3H, s).
Present Compound 151
¹H-NMR (CDCl₃) δ: 7.46-7.39 (2H, m), 7.30-7.25 (1H, m), 7.20-7.14 (1H, m), 6.95-6.83 (3H, m), 6.75 (1H, s), 5.06 (2H, s), 3.66 (3H, s), 2.53 (3H, s), 2.15 (3H, s), 2.08 (3H, s).
Present Compound 152
¹H-NMR (CDCl₃) δ: 7.53-7.48 (2H, m), 7.47-7.39 (4H, m), 7.36-7.28 (2H, m), 7.17 (1H, dd, J=8.9, 0.5 Hz), 6.68 (1H, d, J=12.1 Hz), 5.05 (2H, s), 3.66 (3H, s), 2.53 (3H, s), 2.09 (3H, s).
Present Compound 153
¹H-NMR (CDCl₃) δ: 7.47-7.41 (2H, m), 7.36-7.32 (1H, m), 7.29 (1H, dd, J=6.9, 2.3 Hz), 7.23 (1H, d, J=6.9 Hz), 7.07 (1H, d, J=8.5 Hz), 7.04-6.96 (2H, m), 6.68 (1H, d, J=11.4 Hz), 5.03 (2H, s), 3.82 (3H, s), 3.68 (3H, s), 2.53 (3H, s), 2.07 (3H, s).
Present Compound 154
¹H-NMR (CDCl₃) δ: 7.47-7.39 (2H, m), 7.30-7.26 (1H, m), 6.94 (1H, t, J=10.0 Hz), 6.88 (1H, s), 6.79-6.71 (2H, m), 5.04 (2H, s), 3.73 (3H, s), 3.68 (3H, s), 2.53 (3H, s), 2.09 (3H, s), 2.07 (3H, s).
Present Compound 155
¹H-NMR (CDCl₃) δ: 7.65-7.61 (1H, m), 7.55-7.51 (2H, m), 7.48 (1H, t, J=8.0 Hz), 7.42-7.36 (4H, m), 7.36-7.33 (1H, m), 7.32-7.28 (1H, m), 6.92 (1H, d, J=8.4 Hz), 5.35 (2H, s), 3.60 (3H, s), 2.09 (3H, s).
Present Compound 156
¹H-NMR (CDCl₃) δ: 7.47-7.40 (2H, m), 7.31-7.25 (3H, m), 7.15-7.07 (3H, m), 6.99 (1H, s), 6.74 (1H, s), 5.06 (2H, s), 3.67 (3H, s), 2.54 (3H, s), 2.39 (3H, s), 2.25 (3H, s), 2.09 (3H, s).

Production Example 3

A mixture of 0.45 g of 28A mentioned in Reference Production Example 28, 0.19 g of 4-bromo-o-xylene, 0.28 g of tripotassium phosphate, 0.40 ml of water, 0.02 g of [1,1'-bis(diphenylphosphino)ferrocene]palladium(II) dichloride dichloromethane adduct, and 4 mL of dioxane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.33 g of 1-[2-{4-(3,4-dimethylphenyl)-2-methylphenoxymethyl}-3-methoxyphenyl]-4-methyl-1,4-dihydrotetrazol-5-one (hereinafter referred to as the present compound 42).

Present Compound 42

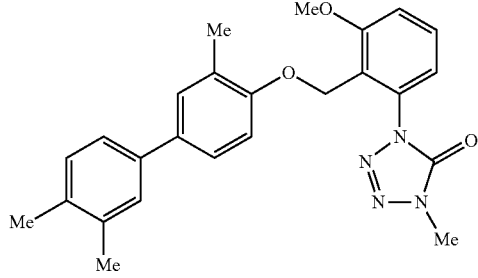

¹H-NMR (CDCl₃) δ: 7.47 (1H, t, J=8.2 Hz), 7.33-7.24 (3H, m), 7.18-7.04 (4H, m), 6.92 (1H, d, J=8.2 Hz), 5.29 (2H, s), 3.93 (3H, s), 3.59 (3H, s), 2.31 (3H, s), 2.28 (3H, s), 2.05 (3H, s).

In accordance with the reaction mentioned in Production Example 3, the present compounds 43 to 45, 149, and 150 were synthesized.

The structural formulas and ¹H-NMR data of the thus obtained compounds are shown below.

Present Compound 43

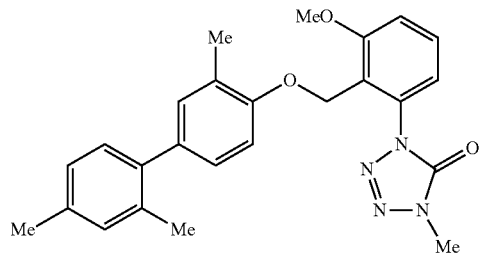

Present Compound 44

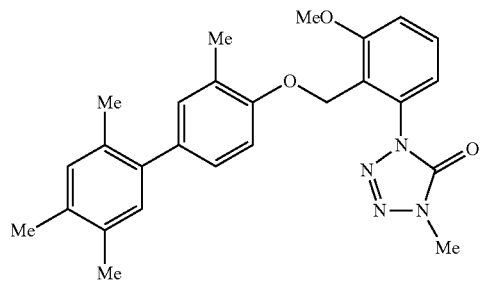

Present Compound 45

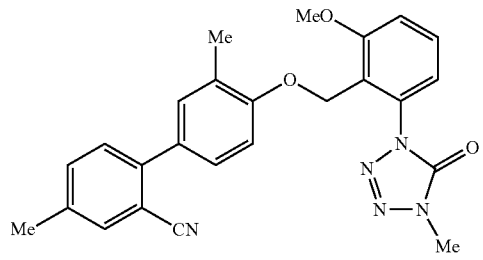

Present Compound 149

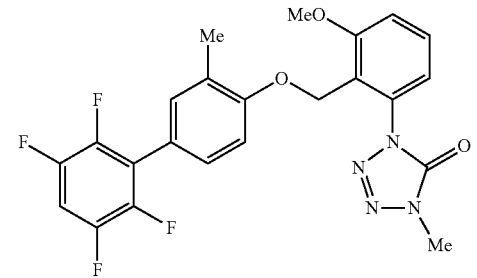

Present Compound 150

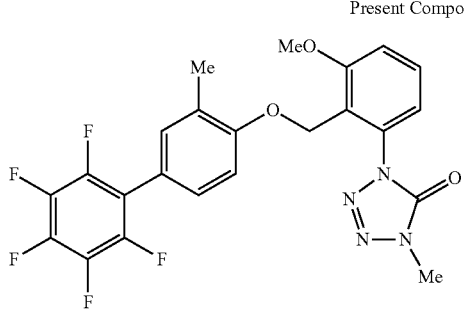

Present Compound 43
¹H-NMR (CDCl₃) δ: 7.47 (1H, t, J=8.2 Hz), 7.34-7.29 (2H, m), 7.15 (2H, s), 7.09 (2H, t, J=7.4 Hz), 6.95-6.91 (2H, m), 5.30 (2H, s), 3.93 (3H, s), 3.59 (3H, s), 2.36 (6H, s), 2.06 (3H, s).

Present Compound 44
¹H-NMR (CDCl₃) δ: 7.47 (1H, t, J=8.3 Hz), 7.11-6.97 (6H, m), 6.90 (1H, d, J=8.4 Hz), 5.28 (2H, s), 3.93 (3H, s), 3.62 (3H, s), 2.26 (3H, s), 2.24 (3H, s), 2.21 (3H, s), 2.03 (3H, s).

Present Compound 45
¹H-NMR (CDCl₃) δ: 7.60 (1H, d, J=8.0 Hz), 7.48 (1H, t, J=8.2 Hz), 7.33 (1H, dd, J=8.2, 2.3 Hz), 7.26-7.24 (2H, m), 7.19-7.17 (1H, m), 7.12-7.06 (2H, m), 6.98 (1H, d, J=8.5 Hz), 5.31 (2H, s), 3.94 (3H, s), 3.62 (3H, s), 2.43 (3H, s), 2.06 (3H, s).

Present Compound 149
¹H-NMR (CDCl₃) δ: 7.47-7.41 (2H, m), 7.31-7.21 (3H, m), 7.04-6.95 (2H, m), 5.09 (2H, s), 3.64 (3H, s), 2.53 (3H, s), 2.15 (3H, s).

Present Compound 150
¹H-NMR (CDCl₃) δ: 7.47-7.41 (2H, m), 7.31-7.16 (3H, m), 6.96 (1H, d, J=8.5 Hz), 5.09 (2H, s), 3.64 (3H, s), 2.53 (3H, s), 2.14 (3H, s).

Production Example 4

A mixture of 1.18 g of the present compound 49, 0.77 g of metachloroperbenzoic acid, and 10 mL of chloroform was stirred at room temperature for 12 hours. The reaction solution was poured into water and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.80 g of 1-[2-{4-(3-methanesulfonyl phenyl)-2-methylphenoxymethyl}-3-methoxyphenyl]-4-methyl-1,4-dihydrotetrazol-5-one (hereinafter referred to as the present compound 58).

Present Compound 58

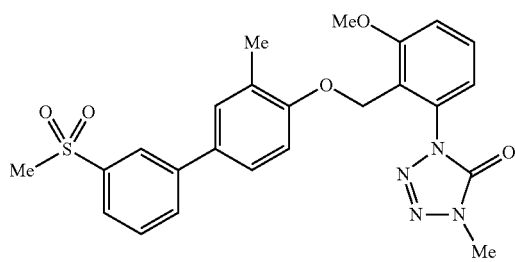

¹H-NMR (CDCl₃) δ: 8.08 (1H, t, J=1.7 Hz), 7.85-7.78 (2H, m), 7.58 (1H, t, J=7.8 Hz), 7.48 (1H, t, J=8.3 Hz), 7.38-7.33 (2H, m), 7.11-7.07 (2H, m), 6.96 (1H, d, J=8.2 Hz), 5.32 (2H, s), 3.95 (3H, s), 3.61 (3H, s), 3.08 (3H, s), 2.06 (3H, s).

Production Example 5

A mixture of 0.41 g of 21A mentioned in Reference Production Example 21, 0.11 g of phenol, 0.04 g of copper iodide, 0.02 g of 2-picolinic acid, 0.42 g of tripotassium phosphate, and 2.5 mL of dimethyl sulfoxide was stirred at 120° C. for 8 hours. The reaction solution was poured into water and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.35 g of 1-[2-{(2-methyl-4-phenoxy)phenoxymethyl}-3-methoxyphenyl]-4-methyl-1,4-dihydrotetrazol-5-one (hereinafter referred to as the present compound 89).

Present Compound 89

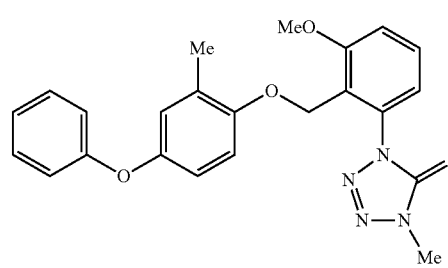

¹H-NMR (CDCl₃) δ: 7.47 (1H, t, J=8.2 Hz), 7.32-7.26 (2H, m), 7.11-7.00 (3H, m), 6.95-6.91 (2H, m), 6.83 (1H, d, J=8.5 Hz), 6.79-6.74 (2H, m), 5.24 (2H, s), 3.93 (3H, s), 3.63 (3H, s), 1.98 (3H, s).

In accordance with the reaction mentioned in Production Example 5, the present compounds 60 to 70 were synthesized.

The structural formulas and ¹H-NMR data of the thus obtained compounds are shown below.

Present Compound 60

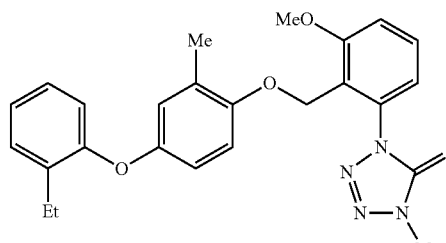

Present Compound 61

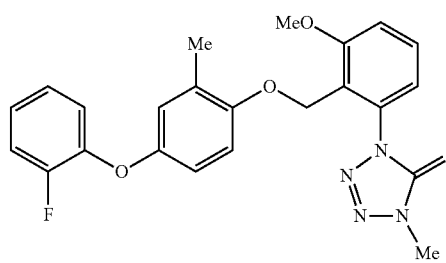

Present Compound 62

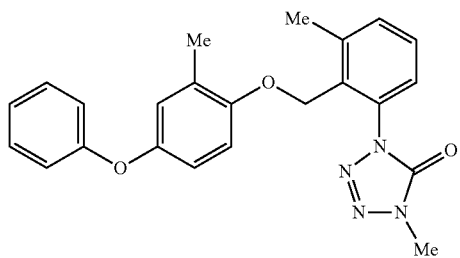

Present Compound 63

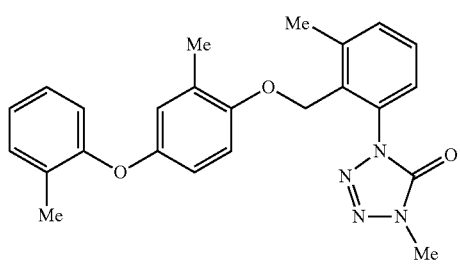

Present Compound 64

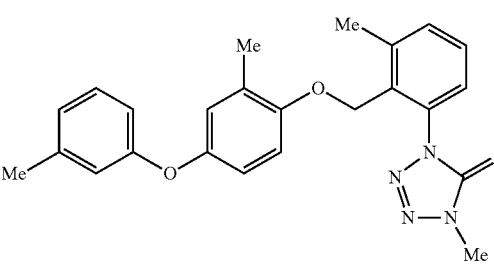

Present Compound 65

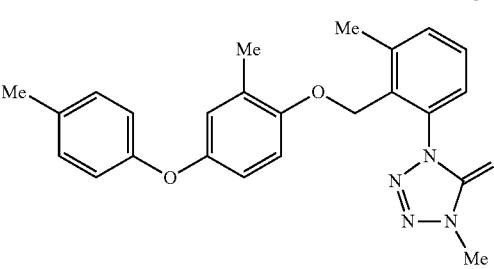

Present Compound 66

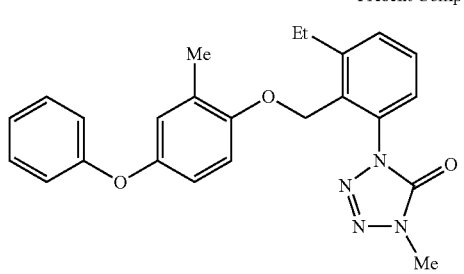

Present Compound 67

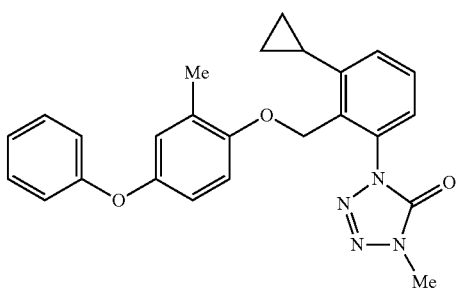

Present Compound 68

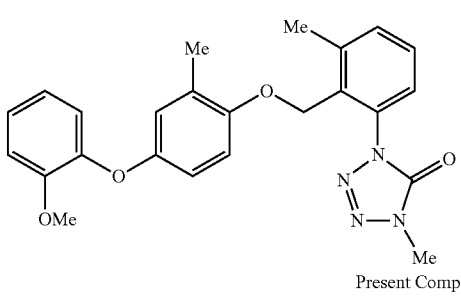

Present Compound 69

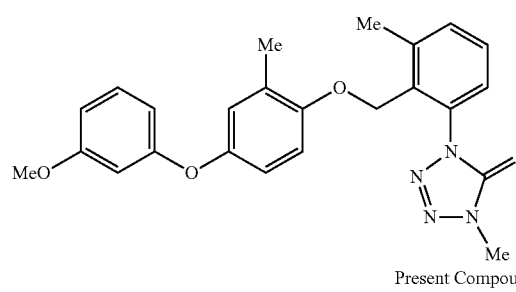

Present Compound 70

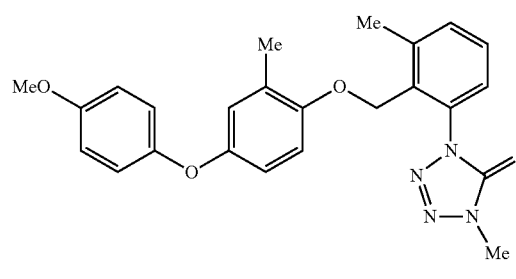

Present Compound 60
$^1$H-NMR (CDCl$_3$) δ: 7.47 (1H, t, J=8.2 Hz), 7.24 (1H, dd, J=7.4, 1.7 Hz), 7.13-7.00 (4H, m), 6.80-6.76 (2H, m), 6.72 (1H, d, J=3.0 Hz), 6.66 (1H, dd, J=8.9, 3.0 Hz), 5.22 (2H, s), 3.92 (3H, s), 3.63 (3H, s), 2.67 (2H, q, J=7.6 Hz), 1.97 (3H, s), 1.22 (3H, t, J=7.6 Hz).

Present Compound 61
$^1$H-NMR (CDCl$_3$) δ: 7.47 (1H, t, J=8.2 Hz), 7.18-7.11 (1H, m), 7.10-7.02 (4H, m), 6.97-6.92 (1H, m), 6.81 (1H, d, J=8.9 Hz), 6.78-6.71 (2H, m), 5.22 (2H, s), 3.92 (3H, s), 3.62 (3H, s), 1.98 (3H, s).

Present Compound 62
$^1$H-NMR (CDCl$_3$) δ: 7.45-7.40 (2H, m), 7.33-7.26 (3H, m), 7.06-7.02 (1H, m), 6.96-6.93 (2H, m), 6.82 (1H, s), 6.80-6.78 (2H, m), 5.01 (2H, s), 3.65 (3H, s), 2.52 (3H, s), 2.07 (3H, s).

Present Compound 63
$^1$H-NMR (CDCl$_3$) δ: 7.44-7.39 (2H, m), 7.28-7.25 (1H, m), 7.22 (1H, dd, J=7.3, 0.7 Hz), 7.14-7.10 (1H, m), 7.01 (1H, td, J=7.3, 1.1 Hz), 6.80 (1H, dd, J=8.0, 1.1 Hz), 6.77-6.73 (2H, m), 6.70-6.66 (1H, m), 4.99 (2H, s), 3.65 (3H, s), 2.51 (3H, s), 2.27 (3H, s), 2.05 (3H, s).

Present Compound 64

¹H-NMR (CDCl₃) δ: 7.45-7.40 (3H, m), 7.29-7.25 (1H, m), 7.18 (1H, t, J=7.7 Hz), 6.86-6.74 (5H, m), 5.02 (2H, s), 3.65 (3H, s), 2.53 (3H, s), 2.32 (3H, s), 2.07 (3H, s).

Present Compound 65

¹H-NMR (CDCl₃) δ: 7.45-7.39 (3H, m), 7.29-7.25 (1H, m), 7.14-7.08 (2H, m), 6.87-6.84 (2H, m), 6.80 (1H, s), 6.77 (1H, s), 5.01 (2H, s), 3.65 (3H, s), 2.52 (3H, s), 2.32 (3H, s), 2.06 (3H, s).

Present Compound 66

¹H-NMR (CDCl₃) δ: 7.49-7.45 (2H, m), 7.33-7.26 (4H, m), 7.07-7.03 (1H, m), 6.97-6.93 (2H, m), 6.82-6.79 (2H, m), 5.02 (2H, s), 3.62 (3H, s), 2.85 (2H, q, J=7.6 Hz), 2.05 (3H, s), 1.28 (3H, t, J=7.6 Hz).

Present Compound 67

¹H-NMR (CDCl₃) δ: 7.43 (1H, t, J=7.9 Hz), 7.33-7.25 (4H, m), 7.06-7.02 (1H, m), 6.96-6.93 (2H, m), 6.84-6.79 (3H, m), 5.23 (2H, s), 3.64 (3H, s), 2.17-2.13 (1H, m), 2.06 (3H, s), 1.04-0.98 (2H, m), 0.80-0.74 (2H, m).

Present Compound 68

¹H-NMR (CDCl₃) δ: 7.44-7.38 (2H, m), 7.28-7.24 (1H, m), 7.09-7.04 (1H, m), 7.00-6.97 (1H, m), 6.90-6.83 (2H, m), 6.80-6.71 (3H, m), 4.98 (2H, s), 3.87 (3H, s), 3.64 (3H, s), 2.51 (3H, s), 2.05 (3H, s).

Present Compound 69

¹H-NMR (CDCl₃) δ: 7.45-7.40 (2H, m), 7.28-7.25 (1H, m), 7.20-7.16 (1H, m), 6.82 (1H, s), 6.80-6.78 (2H, m), 6.61-6.58 (1H, m), 6.53-6.50 (2H, m), 5.01 (2H, s), 3.77 (3H, s), 3.65 (3H, s), 2.52 (3H, s), 2.06 (3H, s).

Present Compound 70

¹H-NMR (CDCl₃) δ: 7.44-7.39 (2H, m), 7.28-7.24 (1H, m), 6.93-6.90 (2H, m), 6.87-6.84 (2H, m), 6.76-6.69 (3H, m), 4.99 (2H, s), 3.79 (3H, s), 3.65 (3H, s), 2.51 (3H, s), 2.05 (3H, s).

Production Example 6

A mixture of 0.33 g of 31A mentioned in Reference Production Example 33, 0.18 g of 3-bromofluorobenzene, 0.19 g of copper iodide, 0.06 g of N-butylimidazole, 0.28 g of potassium carbonate, and 2 mL of toluene was stirred at 120° C. for 8 hours. The reaction solution was poured into water and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.02 g of 1-[2-{4-(3-fluorophenoxy)-2-methylphenoxymethyl}-3-methylphenyl]-4-methyl-1,4-dihydrotetrazol-5-one (hereinafter referred to as the present compound 71).

Present Compound 71

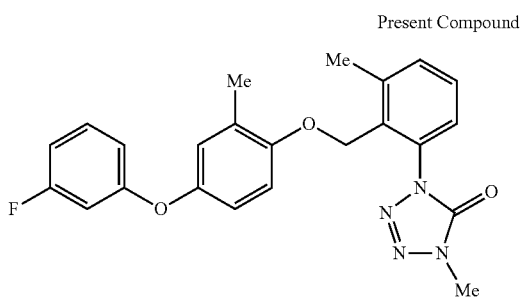

¹H-NMR (CDCl₃) δ: 7.44-7.39 (2H, m), 7.29-7.26 (1H, m), 7.24-7.20 (1H, m), 7.14-7.10 (1H, m), 6.84-6.80 (2H, m), 6.75-6.70 (2H, m), 6.62 (1H, dt, J=10.6, 2.3 Hz), 5.02 (2H, s), 3.65 (3H, s), 2.52 (3H, s), 2.07 (3H, s).

In accordance with the reaction mentioned in Production Example 6, the present compounds 75, 76, and 112 were synthesized.

The structural formulas and ¹H-NMR data of the thus obtained compounds are shown below.

Present Compound 75

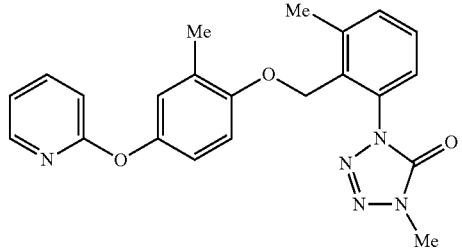

Present Compound 76

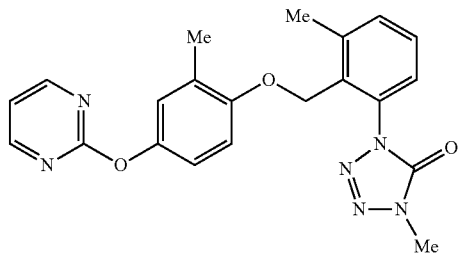

Present Compound 112

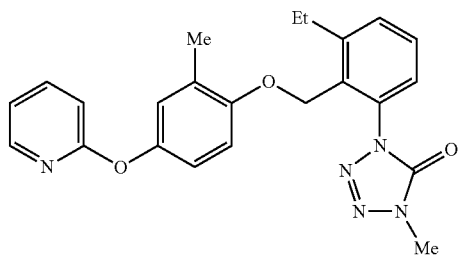

Present Compound 75

¹H-NMR (CDCl₃) δ: 8.18 (1H, dd, J=5.0, 1.0 Hz), 7.68-7.63 (1H, m), 7.45-7.40 (2H, m), 7.29-7.25 (1H, m), 6.97-6.84 (5H, m), 5.01 (2H, s), 3.67 (3H, s), 2.52 (3H, s), 2.10 (3H, s).

Present Compound 76

¹H-NMR (CDCl₃) δ: 8.56 (2H, d, J=4.8 Hz), 7.45-7.38 (3H, m), 7.29-7.26 (1H, m), 7.02-6.96 (3H, m), 5.02 (2H, s), 3.67 (3H, s), 2.51 (3H, s), 2.11 (3H, s).

Present Compound 118

¹H-NMR (CDCl₃) δ: 8.17 (1H, dd, J=5.0, 1.4 Hz), 7.69-7.62 (1H, m), 7.50-7.41 (3H, m), 7.29-7.26 (1H, m), 6.96-6.85 (4H, m), 5.02 (2H, s), 3.64 (3H, s), 2.85 (2H, q, J=7.6 Hz), 2.08 (3H, s), 1.28 (3H, t, J=7.6 Hz).

Production Example 7

A mixture of 0.33 g of 31A mentioned in Reference Production Example 33, 0.12 g of 2-fluorobenzonitrile, 0.65 g of cesium carbonate, and 2 mL of N,N-dimethylformamide was stirred at 120° C. for 6 hours. The reaction solution was poured into water and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.25 g of 1-[2-{4-(4-cyanophenoxy)-2-methylphenoxymethyl}-3-methylphenyl]-4-methyl-1,4-dihydrotetrazol-5-one (hereinafter referred to as the present compound 72).

Present Compound 72

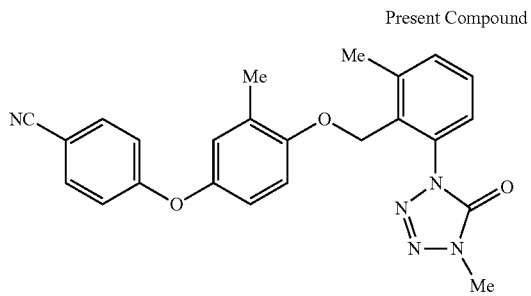

¹H-NMR (CDCl₃) δ: 7.59-7.55 (2H, m), 7.46-7.41 (2H, m), 7.28 (1H, dd, J=7.4, 3.1 Hz), 6.98-6.93 (2H, m), 6.84-6.82 (3H, m), 5.04 (2H, s), 3.66 (3H, s), 2.53 (3H, s), 2.09 (3H, s).

In accordance with the reaction mentioned in Production Example 7, the present compounds 73, 74, and 111 were synthesized.

The structural formulas and ¹H-NMR data of the thus obtained compounds are shown below.

Present Compound 73

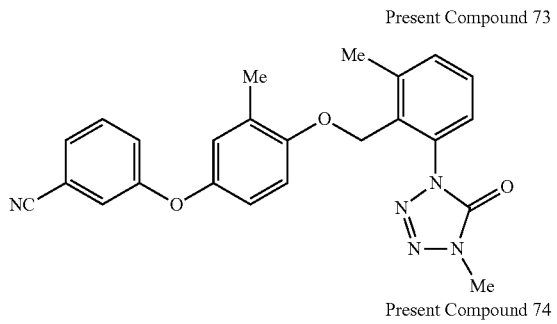

Present Compound 74

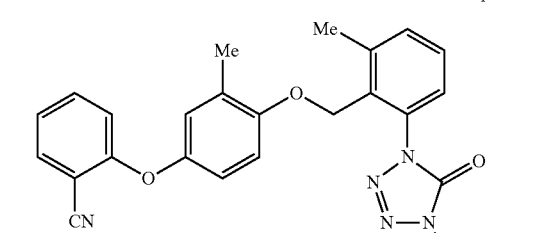

Present Compound 111

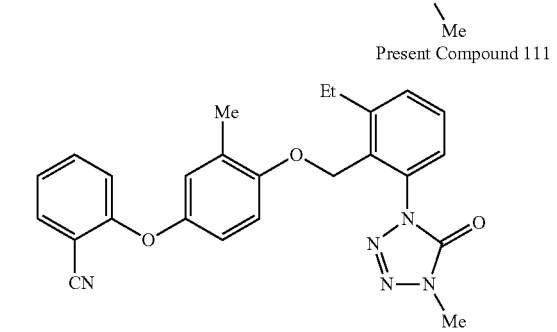

Present Compound 73
¹H-NMR (CDCl₃) δ: 7.44-7.40 (2H, m), 7.37 (1H, d, J=8.2 Hz), 7.32-7.27 (2H, m), 7.21-7.17 (1H, m), 7.13-7.12 (1H, m), 6.83-6.81 (3H, m), 5.04 (2H, s), 3.66 (3H, s), 2.54 (3H, s), 2.09 (3H, s).

Present Compound 74
¹H-NMR (CDCl₃) δ: 7.63 (1H, dd, J=7.7, 1.5 Hz), 7.47-7.41 (3H, m), 7.30-7.26 (1H, m), 7.07 (1H, td, J=7.6, 0.9 Hz), 6.88-6.83 (3H, m), 6.82-6.79 (1H, m), 5.04 (2H, s), 3.66 (3H, s), 2.53 (3H, s), 2.09 (3H, s).

Present Compound 117
¹H-NMR (CDCl₃) δ: 7.63 (1H, dd, J=7.7, 1.7 Hz), 7.51-7.42 (3H, m), 7.29 (1H, dd, J=7.1, 2.1 Hz), 7.08 (1H, td, J=7.7, 0.8 Hz), 6.87-6.79 (4H, m), 5.05 (2H, s), 3.63 (3H, s), 2.86 (2H, q, J=7.6 Hz), 2.07 (3H, s), 1.30 (3H, t, J=7.6 Hz).

Production Example 8

A mixture of 0.41 g of 21A mentioned in Reference Production Example 21, 0.22 g of a benzylboronic acid pinacol ester, 0.43 g of tripotassium phosphate, 0.40 ml of water, 0.08 g of [1,1'-bis(diphenylphosphino)ferrocene]palladium(II) dichloride dichloromethane adduct, and 4 mL of dioxane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 1-[2-(4-benzyl-2-methylphenoxymethyl)-3-methoxyphenyl]-4-methyl-1,4-dihydrotetrazol-5-one (hereinafter referred to as the present compound 90).

Present Compound 90

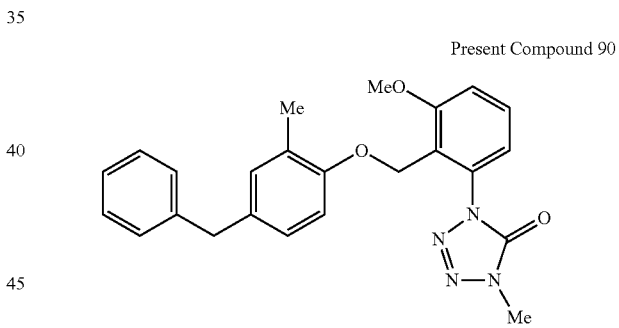

¹H-NMR (CDCl₃) δ: 7.45 (1H, t, J=8.2Hz), 7.29-7.25 (2H, m), 7.21-7.15 (3H, m), 7.10-7.03 (2H, m), 6.91 (2H, d, J=7.8Hz), 6.78 (1H, d, J=8.0Hz), 5.22 (2H, s), 3.91 (3H, s), 3.86 (2H, s), 3.56 (3H, s), 1.96 (3H, s).

Production Example 9

A mixture of 0.39 g of 20A mentioned in Reference Production Example 20, 0.15 g of 2-phenylethylboronic acid, 0.65 g of cesium carbonate, 0.08 g of [1,1'-bis(diphenylphosphino)ferrocene]palladium(II) dichloride dichloromethane adduct, and 4 mL of dimethoxyethane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 1-[2-{4-(2-phenylethyl)-2-methylphenoxymethyl}-3-methylphenyl]-4-methyl-1,4-dihydrotetrazol-5-one (hereinafter referred to as the present compound 91).

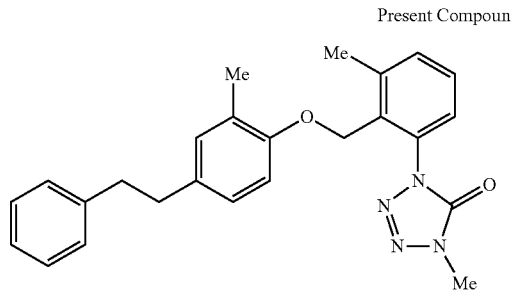

Present Compound 91

¹H-NMR (CDCl₃) δ: 7.45-7.41 (3H, m), 7.35-7.20 (5H, m), 7.00-6.96 (2H, m), 6.79 (1H, d, J=8.5Hz), 5.03 (2H, s), 3.64 (3H, s), 2.93-2.82 (4H, m), 2.52 (3H, s), 2.10 (3H, s).

Production Example 10

A mixture of 0.33 g of 31A mentioned in Reference Production Example 33, 0.17 g of benzylbromide, 0.28 g of potassium carbonate, and 4 mL of acetonitrile was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 1-[2-(4-benzyloxy-2-methylphenoxymethyl)-3-methylphenyl]-4-methyl-1,4-dihydrotetrazol-5-one (hereinafter referred to as the present compound 77).

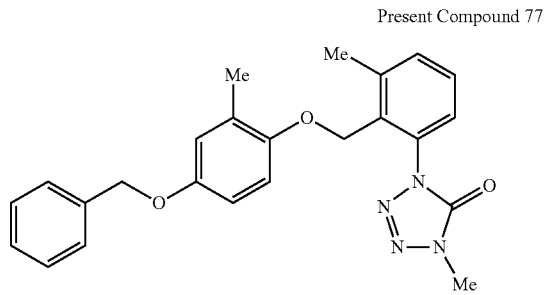 [SMILES: Cc1cc(OCc2ccccc2)ccc1OCc1c(C)cccc1-n1nnn(C)c1=O]

Present Compound 77

¹H-NMR (CDCl₃) δ: 7.43-7.30 (7H, m), 7.28-7.24 (1H, m), 6.79-6.68 (3H, m), 5.00 (2H, s), 4.97 (2H, s), 3.62 (3H, s), 2.50 (3H, s), 2.07 (3H, s).

Production Example 11

A mixture of 0.39 g of 20A mentioned in Reference Production Example 20, 0.11 g of N-methylaniline, 0.29 g of tert-butoxysodium, 0.12 g of 2-(di-tert-butylphosphino)biphenyl, 0.18 g of a palladium dibenzylideneacetone complex, and 4 mL of toluene was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.34 g of 1-[2-{4-(N-methylanilino)-2-methylphenoxymethyl}-3-methylphenyl]-4-methyl-1,4-dihydrotetrazol-5-one (hereinafter referred to as the present compound 78).

Present Compound 78

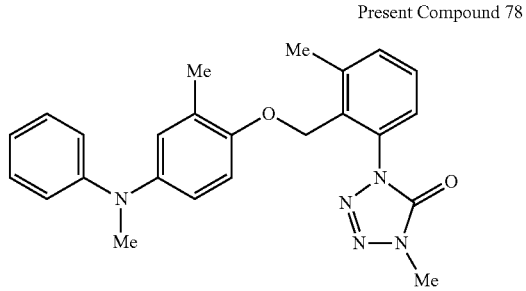 [SMILES: CCN(c1ccccc1)c1ccc(OCc2c(C)cccc2-n2nnn(C)c2=O)c(C)c1]

Present Compound 78

¹H-NMR (CDCl₃) δ: 7.45-7.40 (2H, m), 7.29-7.27 (1H, m), 7.23-7.17 (2H, m), 6.94-6.90 (2H, m), 6.82-6.77 (4H, m), 5.02 (2H, s), 3.67 (3H, s), 3.24 (3H, s), 2.53 (3H, s), 2.06 (3H, s).

In accordance with the reaction mentioned in Production Example 11, the present compound 79 was synthesized.

The structural formula and ¹H-NMR data of the thus obtained compound are shown below.

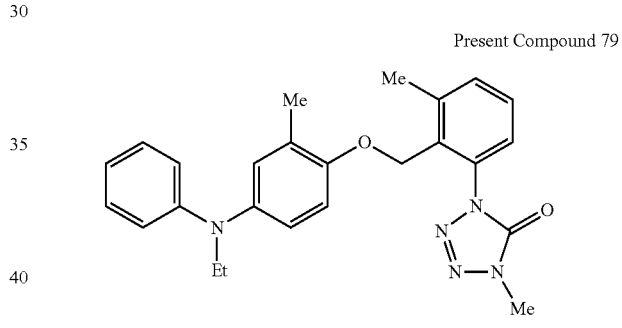

Present Compound 79

¹H-NMR (CDCl₃) δ: 7.44-7.40 (2H, m), 7.28 (1H, dd, J=6.4, 2.7Hz), 7.17 (2H, t, J=7.6Hz), 6.91 (2H, t, J=2.7Hz), 6.83-6.80 (1H, m), 6.75-6.72 (3H, m), 5.02 (2H, s), 3.70-3.68 (5H, m), 2.53 (3H, s), 2.07 (3H, s), 1.20 (3H, t, J=7.0Hz).

Production Example 12

While stirring a mixture of 2.07 g of 32A mentioned in Reference Production Example 32 and 10 mL of methanol at 0° C., 0.76 g of sodium borohydride was added, followed by stirring at room temperature for 4 hours. Water was poured into the reaction solution and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 1.90 g of 1-[2-{4-(hydroxy(phenyl)methyl)-2-methylphenoxymethyl}-3-methylphenyl]-4-methyl-1,4-dihydrotetrazol-5-one (hereinafter referred to as the present compound 80).

Present Compound 80

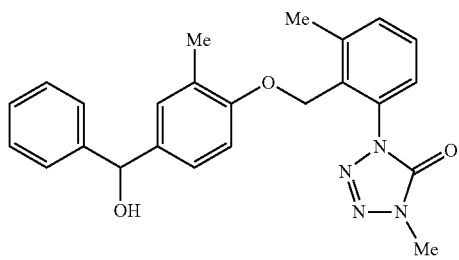

¹H-NMR (CDCl₃) δ: 7.43-7.37 (4H, m), 7.34 (2H, dd, J=8.2, 6.9Hz), 7.27-7.24 (2H, m), 7.13-7.09 (2H, m), 6.78 (1H, d, J=8.9Hz), 5.77 (1H, s), 5.01 (2H, s), 3.60 (3H, s), 2.49 (3H, s), 2.22 (1H, br s), 2.05 (3H, s).

Production Example 13

To a mixture of 0.44 g of sodium hydride and 4 ml of tetrahydrofuran, 0.42 g of the present compound 80 was added, followed by stirring at room temperature for 30 minutes, addition of 0.14 g of iodomethane, and further stirring at room temperature for 4 hours. Water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-[2-{4-(methoxy(phenyl)methyl)-2-methylphenoxymethyl}-3-methylphenyl]-4-methyl-1,4-dihydrotetrazol-5-one (hereinafter referred to as the present compound 81).

Present Compound 81

¹H-NMR (CDCl₃) δ: 7.43-7.38 (2H, m), 7.36-7.29 (4H, m), 7.26-7.22 (2H, m), 7.09-7.06 (2H, m), 6.77 (1H, t, J=4.4Hz), 5.15 (1H, s), 4.98 (2H, s), 3.58 (3H, s), 3.36 (3H, s), 2.47 (3H, s), 2.05 (3H, s).

Production Example 14

To a mixture of 0.54 g of 35A mentioned in Reference Production Example 35 and 4 ml of toluene, 0.28 g of thionyl chloride was added, followed by stirring at 60° C. for 2 hours. Water was poured into the reaction solution and the mixture was extracted with ethyl acetate. The organic layer was washed with water and a saturated saline solution, dried over anhydrous magnesium sulfate, and then concentrated under reduced pressure to obtain 0.54 g of 1-[2-{4-chloromethyl-2-methylphenoxymethyl}-3-methylphenyl]-4-methyl-, 4-dihydrotetrazol-5-one (hereinafter referred to as the present compound 82).

Present Compound 82

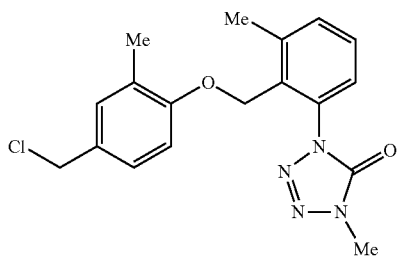

¹H-NMR (CDCl₃) δ: 7.45-7.39 (2H, m), 7.29-7.26 (1H, m), 7.18-7.14 (2H, m), 6.81 (1H, d, J=8.0Hz), 5.03 (2H, s), 4.53 (2H, s), 3.63 (3H, s), 2.50 (3H, s), 2.09 (3H, s).

Production Example 15

A mixture of 0.36 g of the present compound 82, 0.09 g of phenol, 0.28 g of potassium carbonate, and 4 mL of acetonitrile was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 1-[2-(4-phenoxymethyl-2-methylphenoxymethyl)-3-methylphenyl]-4-methyl-1,4-dihydrotetrazol-5-one (hereinafter referred to as the present compound 83).

Present Compound 83

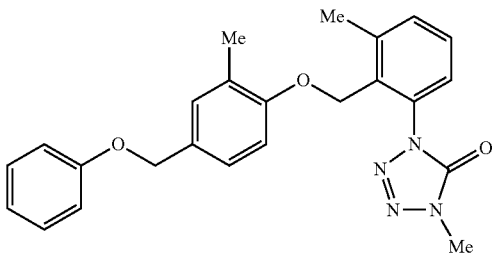

¹H-NMR (CDCl₃) δ: 7.45-7.39 (2H, m), 7.31-7.26 (3H, m), 7.23-7.20 (2H, m), 6.99-6.94 (3H, m), 6.85 (1H, d, J=8.4Hz), 5.03 (2H, s), 4.94 (2H, s), 3.62 (3H, s), 2.50 (3H, s), 2.11 (3H, s).

Production Example 16

To a mixture of 0.22 g of sodium hydride and 2 ml of tetrahydrofuran, 0.17 g of 35A mentioned in Reference Production Example 35 was added, followed by stirring at room temperature for 30 minutes, addition of 0.55 g of bromoethane, and further stirring at room temperature for 4 hours. Water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.05 g of 1-[2-(4-ethoxymethyl-2-methylphenoxymethyl)-3-methylphenyl]-4-methyl-1,4-dihydrotetrazol-5-one (hereinafter referred to as the present compound 84).

Present Compound 84

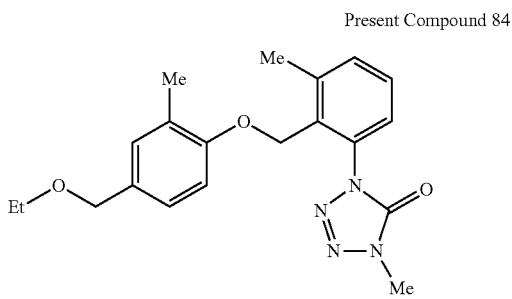 [SMILES: CCOCc1ccc(OCc2c(C)cccc2-n2nnn(C)c2=O)c(C)c1]

¹H-NMR (CDCl₃) δ: 7.44-7.38 (2H, m), 7.28-7.25 (1H, m), 7.13-7.08 (2H, m), 6.80 (1H, d, J=8.8Hz), 5.01 (2H, s), 4.39 (2H, s), 3.63 (3H, s), 3.51 (2H, q, J=7.0Hz), 2.49 (3H, s), 2.08 (3H, s), 1.23 (3H, t, J=7.0Hz).

Production Example 17

To a mixture of 0.44 g of sodium hydride and 2 ml of tetrahydrofuran, 0.35 g of 36A mentioned in Reference Production Example 36 was added, followed by stirring at room temperature for 30 minutes, addition of 0.28 g of iodomethane, and further stirring at room temperature for 4 hours. Water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-[2-{4-(1-methoxyethyl)-2-methylphenoxymethyl}-3-methylphenyl]-4-methyl-1,4-dihydrotetrazol-5-one (hereinafter referred to as the present compound 85).

Present Compound 85

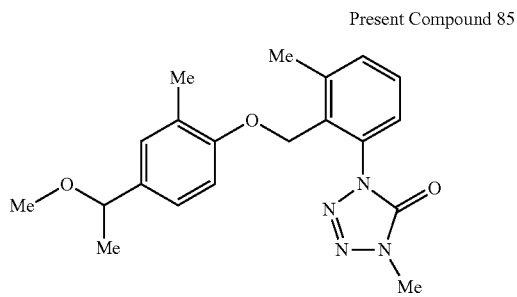 [SMILES: COC(C)c1ccc(OCc2c(C)cccc2-n2nnn(C)c2=O)c(C)c1]

¹H-NMR (CDCl₃) δ: 7.44-7.38 (2H, m), 7.28-7.24 (1H, m), 7.08-7.04 (2H, m), 6.81 (1H, d, J=9.1Hz), 5.01 (2H, s), 4.20 (1H, q, J=6.3Hz), 3.63 (3H, s), 3.19 (3H, s), 2.50 (3H, s), 2.09 (3H, s), 1.40 (3H, d, J=6.3Hz).

Production Example 18

A mixture of 0.33 g of 38A mentioned in Reference Production Example 38 and 5 mL of N,N-dimethylformamide dimethylacetal was stirred with heating at 90° C. for 4 hours. After cooling, the reaction solution was subjected to silica gel column chromatography to obtain 0.10 g of 1-[2-{4-(N,N-dimethylaminomethylidyneamino)-2-methylphenoxymethyl)-3-methylphenyl]-4-methyl-1,4-dihydrotetrazol-5-one (hereinafter referred to as the present compound 86).

Present Compound 86

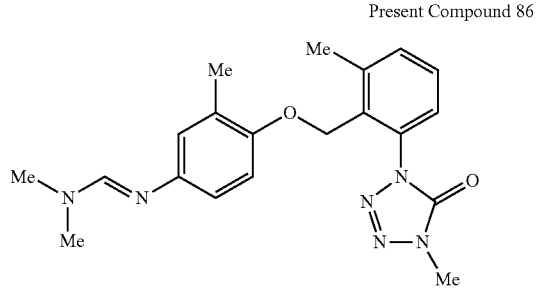 [SMILES: Cc1cc(/N=C/N(C)C)ccc1OCc1c(C)cccc1-n1nnn(C)c1=O]

¹H-NMR (CDCl₃) δ: 7.47 (1H, s), 7.43-7.38 (2H, m), 7.28-7.24 (1H, m), 6.77-6.70 (3H, m), 4.98 (2H, s), 3.63 (3H, s), 3.00 (6H, s), 2.50 (3H, s), 2.05 (3H, s).

Production Example 19

A mixture of 0.33 g of 38A mentioned in Reference Production Example 38, 19 g of p-toluenesulfonic acid monohydrate, and 3 mL of trimethyl orthoformate was stirred with heating at 100° C. for 1 hour. After cooling and concentration under reduced pressure, 0.18 g of N-ethyl-N-methylamine and 3 mL of dimethoxyethane were added to the residue, followed by stirring with heating at 80° C. for 1 hour. The reaction solution was concentrated under reduced pressure and then the residue was subjected to silica gel column chromatography to obtain 0.10 g of 1-[2-{4-(N-ethyl-N-methylaminomethylidyneamino)-2-methylphenoxymethyl)-3-methylphenyl]-4-methyl-1,4-dihydrotetrazol-5-one (hereinafter referred to as the present compound 87).

Present Compound 87

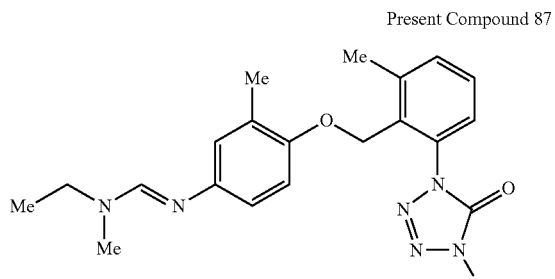

¹H-NMR (CDCl₃) δ: 7.50 (1H, br s), 7.43-7.38 (2H, m), 7.27-7.24 (1H, m), 6.76-6.69 (3H, m), 4.98 (2H, s), 3.63 (3H, s), 3.39-3.27 (2H, m), 2.98 (3H, s), 2.50 (3H, s), 2.06 (3H, s), 1.19 (3H, t, J=7.2Hz).

In accordance with the reaction mentioned in Production Example 19, the present compound 88 was synthesized.

The structural formula and ¹H-NMR data of the thus obtained compound are shown below.

Present Compound 88

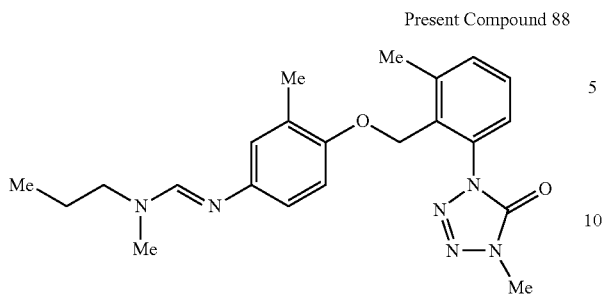

Present Compound 165

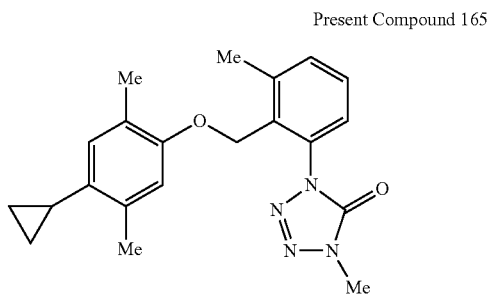 [SMILES: Cc1cc(C2CC2)c(C)cc1OCc1c(C)cccc1-n1nnn(C)c1=O]

Present Compound 88

¹H-NMR (CDCl₃) δ: 7.50 (1H, br s), 7.41-7.37 (2H, m), 7.27-7.24 (1H, m), 6.76-6.70 (3H, m), 4.98 (2H, s), 3.63 (3H, s), 3.25-3.18 (2H, m), 2.98 (3H, s), 2.50 (3H, s), 2.06 (3H, s), 1.61 (2H, dd, J=14.4, 7.3Hz), 0.91 (3H, t, J=7.3Hz).

¹H-NMR (CDCl₃) δ: 7.42-7.37 (2H, m), 7.26-7.23 (1H, m), 6.73 (1H, s), 6.63 (1H, s), 4.98 (2H, s), 3.64 (3H, s), 2.50 (3H, s), 2.37 (3H, s), 2.02 (3H, s), 1.79-1.75 (1H, m), 0.88-0.82 (2H, m), 0.57-0.52 (2H, m).

Production Example 20

A mixture of 0.39 g of 20A mentioned in Reference Production Example 20, 0.13 g of cyclopropylboronic acid, 0.30 g of cesium fluoride, 0.08 g of [1,1'-bis(diphenylphosphino)ferrocene]palladium(II) dichloride dichloromethane adduct, and 5 mL of dioxane was stirred with heating under reflux for 4 hours. After cooling, water was poured into the reaction solution and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.20 g of 1-[2-(4-cyclopropyl-2-methylphenoxymethyl)-3-methylphenyl]-4-methyl-1,4-dihydrotetrazol-5-one (hereinafter referred to as the present compound 100).

Production Example 21

To a mixture of 0.50 g of 52A mentioned in Reference Production Example 52, 0.01 g of N,N-dimethylformamide, and 5 mL of dioxane, 0.18 g of oxalyl chloride and 0.01 g of N,N-dimethylformamide were added, followed by stirring at room temperature for 2 hours. After concentration under reduced pressure, 0.12 g of N-ethyl-N-methylamine and 0.3 mL of triethylamine were added, followed by stirring at room temperature for 3 hours. Water was poured into the reaction solution and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.42 g of N-ethyl-3,N-dimethyl-4-[2-methoxy-6-(4-methyl-5-oxo-4,5-dihydro-tetrazol-1-yl)-benzyloxy]-benzamide (hereinafter referred to as the present compound 101).

Present Compound 100

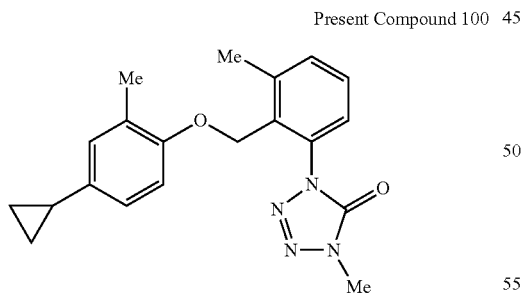

Present Compound 101

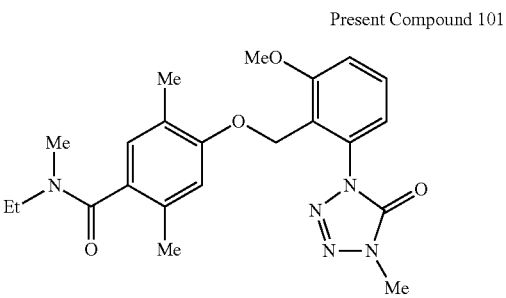 [SMILES: CCN(C)C(=O)c1cc(C)c(OCc2c(OC)cccc2-n2nnn(C)c2=O)cc1C]

¹H-NMR (CDCl₃) δ: 7.43-7.37 (2H, m), 7.26-7.24 (1H, m), 6.87-6.82 (2H, m), 6.73 (1H, d, J=8.0Hz), 4.98 (2H, s), 3.63 (3H, s), 2.49 (3H, s), 2.06 (3H, s), 1.84-1.77 (1H, m), 0.90-0.84 (2H, m), 0.62-0.56 (2H, m).

¹H-NMR (CDCl₃) δ: 7.47 (1H, t, J=8.2Hz), 7.19-7.12 (2H, m), 7.11-7.05 (2H, m), 6.86 (1H, d, J=8.5Hz), 5.28 (2H, s), 3.92 (3H, s), 3.61 (3H, s), 3.57-3.27 (2H, m), 2.99 (3H, s), 1.99 (3H, s), 1.24-1.09 (3H, m).

In accordance with the reaction mentioned in Production Example 20, the present compound 165 was synthesized.

In accordance with the reaction mentioned in Production Example 21, the present compound 102 was synthesized.

The structural formula and ¹H-NMR data of the thus obtained compound are shown below.

The structural formula and ¹H-NMR data of the thus obtained compound are shown below.

Present Compound 102

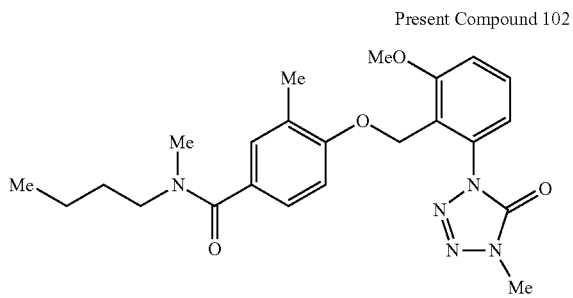 [SMILES: CCCCN(C)C(=O)c1ccc(OCc2c(OC)cccc2-n2nnn(C)c2=O)c(C)c1]

¹H-NMR (CDCl₃) δ: 7.47 (1H, t, J=8.2Hz), 7.20-7.12 (2H, m), 7.11-7.05 (2H, m), 6.86 (1H, d, J=8.5Hz), 5.28 (2H, s), 3.93 (3H, s), 3.61 (3H, s), 3.55-3.19 (2H, m), 3.00 (3H, s), 1.99 (3H, s), 1.61-1.12 (4H, m), 1.04-0.77 (3H, m).

Production Example 22

A mixture of 0.41 g of 21A mentioned in Reference Production Example 21, 0.17 g of 2-(1-methylethenyl)-4,4,5,5-tetramethyl-1,3,2-dioxaborolane, 0.28 g of tripotassium phosphate, 0.08 g of [1,1'-bis(diphenylphosphino)ferrocene]palladium(II) dichloride dichloromethane adduct, and 4 mL of dioxane was stirred with heating under reflux for 4 hours. After cooling, water was poured into the reaction solution and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.29 g of 1-[2-(4-isopropenyl-2-methylphenoxymethyl)-3-methoxyphenyl]-4-methyl-1,4-dihydrotetrazol-5-one (hereinafter referred to as the present compound 103).

Present Compound 103

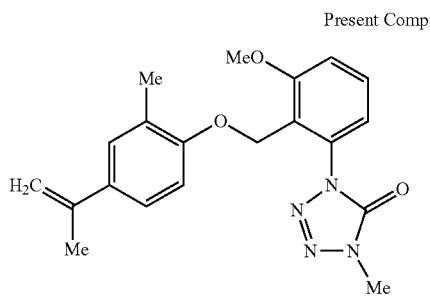

¹H-NMR (CDCl₃) δ: 7.43-7.37 (2H, m), 7.26-7.24 (1H, m), 6.87-6.82 (2H, m), 6.73 (1H, d, J=8.0Hz), 4.98 (2H, s), 3.63 (3H, s), 2.49 (3H, s), 2.06 (3H, s), 1.84-1.77 (1H, m), 0.90-0.84 (2H, m), 0.62-0.56 (2H, m).

In accordance with the reaction mentioned in Production Example 22, the present compound 104 was synthesized.

The structural formula and ¹H-NMR data of the thus obtained compound are shown below.

Present Compound 104

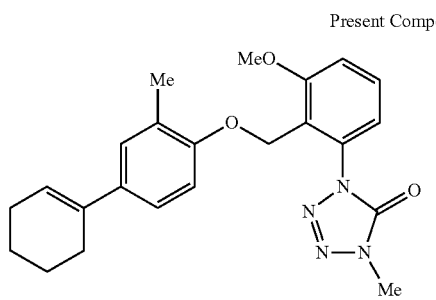

¹H-NMR (CDCl₃) δ: 7.45 (1H, t, J=8.2Hz), 7.12-7.04 (4H, m), 6.82-6.79 (1H, m), 6.00-5.97 (1H, m), 5.24 (2H, s), 3.91 (3H, s), 3.58 (3H, s), 2.36-2.32 (2H, m), 2.19-2.15 (2H, m), 1.99 (3H, s), 1.77-1.72 (2H, m), 1.66-1.61 (2H, m).

Production Example 23

To a mixture of 1.16 g of triphenylpropylphosphonium bromide and 12 mL of tetrahydrofuran, 1.9 mL of n-butyllithium (1.6 M) was added dropwise under ice cooling, followed by stirring at 0° C. for 1 hour. A mixture of 1.06 of 34A mentioned in Reference Production Example 34 and 12 mL of tetrahydrofuran was added, followed by stirring at room temperature for 2 hours. Water was poured into the reaction solution and the mixture was extracted with chloroform. The organic layer was washed with water and a saturated saline solution, dried over anhydrous sodium sulfate, and then concentrated under reduced pressure. The residue thus obtained was subjected to silica gel column chromatography to obtain 0.29 g of 1-{2-[4-(1-methyl-1-buten-1-yl)-2-methylphenoxymethyl]-3-methylphenyl}-4-methyl-1,4-dihydrotetrazol-5-one (hereinafter referred to as the present compound 105).

Present Compound 105

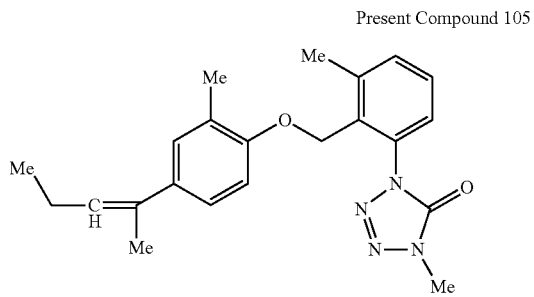 [SMILES: CCC=C(C)c1ccc(OCc2c(C)cccc2-n2nnn(C)c2=O)c(C)c1]

¹H-NMR (CDCl₃) δ: 7.44-7.38 (2H, m), 7.28-7.25 (1H, m), 7.15-7.12 (1H, m), 6.97-6.93 (1H, m), 6.82-6.75 (1H, m), 5.66 (0.3H, t, J=7.1Hz), 5.39 (0.7H, t, J=6.6Hz), 5.02 (2H, s), 3.63-3.62 (3H, m), 2.51-2.50 (3H, m), 2.18 (0.7H, t, J=7.3Hz), 2.09 (3H, s), 2.00 (1.3H, d, J=7.6Hz), 1.97 (3H, s), 1.26 (1H, t, J=7.3Hz), 0.93 (2H, t, J=7.6Hz).

Production Example 24

To a mixture of 0.30 g of the present compound 110 and 15 mL of ethanol, 0.03 g of a palladium-fibroin complex was added, followed by stirring in a hydrogen atmosphere under 1 atom at room temperature for 8 hours. The reaction solution was filtered with Celite (registered trademark) and then the organic layer was concentrated under reduced pressure to obtain 0.25 g of 1-{2-[4-(pentan-2-yl)-2-methylphenoxymethyl]-3-methylphenyl}-4-methyl-1,4-dihydrotetrazol-5-one (hereinafter referred to as the present compound 106).

Present Compound 106

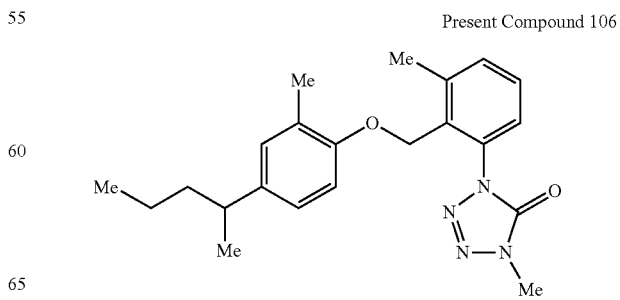

¹H-NMR (CDCl₃) δ: 7.44-7.38 (2H, m), 7.28-7.25 (1H, m), 6.95-6.91 (2H, m), 6.76 (1H, d, J=8.5Hz), 4.99 (2H, s), 3.63 (3H, s), 2.64-132 (1H, m), 2.50 (3H, s), 2.08 (3H, s), 1.53-1.46 (2H, m), 1.26-1.23 (2H, m), 1.19 (3H, d, J=6.9Hz), 0.86 (3H, t, J=7.3Hz).

Production Example 25

To a mixture of 2.82 g of 34A mentioned in Reference Production Example 34 and 16 mL of chloroform, 0.66 g of metachloroperbenzoic acid was added, followed by stirring at room temperature for 72 hours. An aqueous saturated sodium hydrogen carbonate solution was poured into the reaction solution and the mixture was extracted with chloroform. The organic layer was washed with water and a saturated saline solution, dried over anhydrous sodium sulfate, and then concentrated under reduced pressure. The residue thus obtained was subjected to silica gel column chromatography to obtain 1.44 g of 1-[2-(4-acetyloxy-2-methylphenoxymethyl)-3-methylphenyl]-4-methyl-1,4-dihydrotetrazol-5-one (hereinafter referred to as the present compound 107).

Present Compound 107

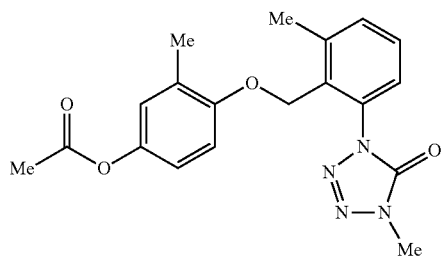

¹H-NMR (CDCl₃) δ: 7.44-7.38 (2H, m), 7.27-7.24 (1H, m), 6.85-6.78 (3H, m), 4.99 (2H, s), 3.63 (3H, s), 2.49 (3H, s), 2.26 (3H, s), 2.07 (3H, s).

Production Example 26

A mixture of 0.34 g of 33A mentioned in Reference Production Example 33, 0.05 g of methylhydrazine, 0.4 mL of acetic acid, and 4 mL of ethanol was stirred at 80° C. for 10 hours. The reaction solution was concentrated under reduced pressure and then the residue thus obtained was subjected to silica gel column chromatography to obtain 0.14 g of 1-[2-{4-(2-methylcarbohydrazonoyl)-2-methylphenoxymethyl}-3-methylphenyl]-4-methyl-1,4-dihydrotetrazol-5-one (hereinafter referred to as the present compound 108).

Present Compound 108

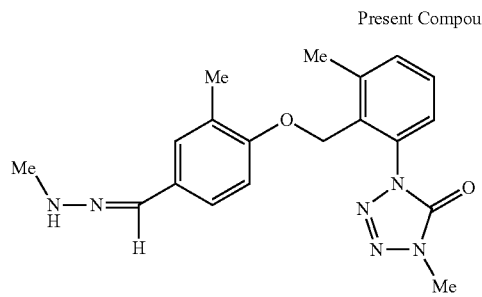

¹H-NMR (CDCl₃) δ: 7.50 (1H, s), 7.42-7.38 (4H, m), 7.29-7.26 (1H, m), 6.81 (1H, d, J=8.5Hz), 5.04 (2H, s), 3.92-3.90 (1H, m), 3.62 (3H, s), 2.95 (3H, s), 2.50 (3H, s), 2.09 (3H, s).

In accordance with the reaction mentioned in Production Example 26, the present compound 109 was synthesized.

The structural formula and ¹H-NMR data of the thus obtained compound are shown below.

Present Compound 109

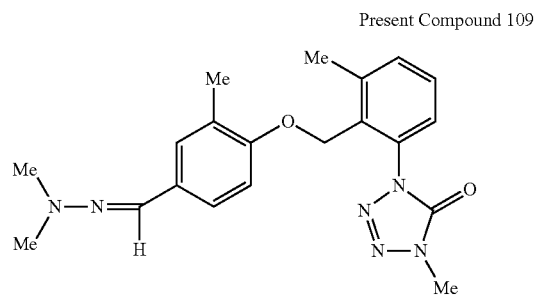 [SMILES: Cc1cc(C=NN(C)C)ccc1OCc1c(C)cccc1-n1nnn(C)c1=O]

¹H-NMR (CDCl₃) δ: 7.45-7.39 (3H, m), 7.31-7.25 (2H, m), 7.23 (1H, s), 6.80 (1H, d, J=8.5Hz), 5.04 (2H, s), 3.61 (3H, s), 2.91 (6H, s), 2.49 (3H, s), 2.08 (3H, s).

Production Example 27

To a mixture of 0.04 g of sodium hydride and 2 ml of N,N-dimethylformamide, 0.35 g of 36A mentioned in Reference Production Example 36 was added, followed by stirring at 0° C. for 30 minutes and addition of 0.55 g of bromoethane, and further stirring at room temperature for 2 hours. Water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-[2-{4-(1-ethoxyethyl)-2-methylphenoxymethyl}-3-methylphenyl]-4-methyl-1,4-dihydrotetrazol-5-one (hereinafter referred to as the present compound 110)

Present Compound 110

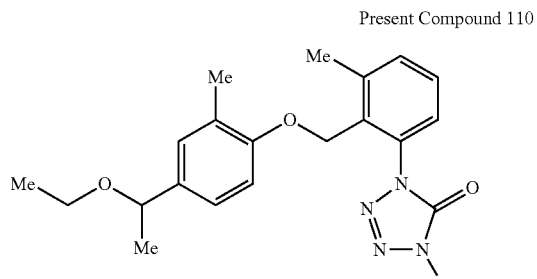

¹H-NMR (CDCl₃) δ: 7.45-7.39 (2H, m), 7.28-7.25 (1H, m), 7.09-7.05 (2H, m), 6.81 (1H, d, J=8.0Hz), 5.01 (2H, s), 4.31 (1H, q, J=6.6Hz), 3.64 (3H, s), 3.36-3.29 (2H, m), 2.50 (3H, s), 2.09 (3H, s), 1.41 (3H, d, J=6.6Hz), 1.17 (3H, t, J=7.1Hz).

Production Example 28

A mixture of 0.41 g of 19-2A mentioned in Reference Production Example 19-2, 0.09 g of phenol, 0.019 g of copper iodide, 0.06 g of N-butylimidazole, 0.28 g of potassium carbonate, and 2 mL of toluene was stirred at 120° C. for 16 hours. The reaction solution was poured into water and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.15 g of 1-[2-{4-phenoxy-2-methylphenoxymethyl}-3-chlorophenyl]-4-methyl-1,4-dihydrotetrazol-5-one (hereinafter referred to as the present compound 157).

Present Compound 157

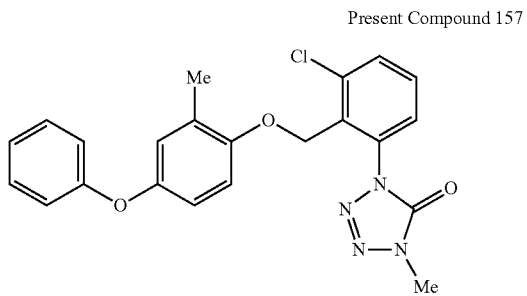 [SMILES: Cc1cc(Oc2ccccc2)ccc1OCc1c(Cl)cccc1-n1nnn(C)c1=O]

$^1$H-NMR (CDCl$_3$) δ: 7.64-7.60 (1H, m), 7.48 (1H, t, J=8.0Hz), 7.40 (1H, dd, J=8.0, 1.1Hz), 7.32-7.28 (2H, m), 7.06-7.02 (1H, m), 6.95-6.93 (2H, m), 6.82-6.79 (3H, m), 5.29 (2H, s), 3.64 (3H, s), 2.02 (3H, s).

In accordance with the reaction mentioned in Production Example 28, the present compound 158 was synthesized.

The structural formula and $^1$H-NMR data of the thus obtained compound are shown below.

Present Compound 158

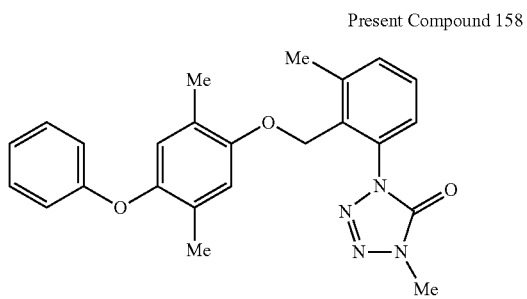 [SMILES: Cc1cc(Oc2ccccn2)c(C)cc1OCc1c(C)cccc1-n1nnn(C)c1=O]

$^1$H-NMR (CDCl$_3$) δ: 7.46-7.38 (3H, m), 7.29-7.23 (3H, m), 7.02-6.97 (1H, m), 6.84 (1H, dd, J=8.7, 1.1Hz), 6.73 (1H, d, J=5.3Hz), 6.69 (1H, s), 5.00 (2H, s), 3.64 (3H, s), 2.49 (3H, s), 2.34 (3H, s), 2.02 (3H, s).

Production Example 29

A mixture of 0.34 g of 57A mentioned in Reference Production Example 57, 0.16 g of 2-bromopyridine, 0.019 g of copper iodide, 0.06 g of N-butylimidazole, 0.28 g of potassium carbonate, and 2 mL of toluene was stirred at 120° C. for 6 hours. The reaction solution was poured into water and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.15 g of 1-[2-{4-(pyridin-2-yl)-2,5-dimethylphenoxymethyl}-3-methylphenyl]-4-methyl-1,4-dihydrotetrazol-5-one (hereinafter referred to as the present compound 159).

Present Compound 159

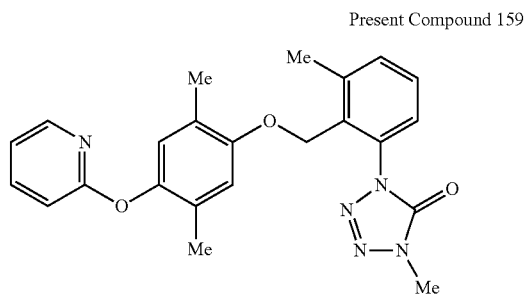

$^1$H-NMR (CDCl$_3$) δ: 8.19-8.14 (1H, m), 7.66-7.62 (1H, m), 7.46-7.39 (2H, m), 7.28-7.25 (1H, m), 6.94-6.91 (1H, m), 6.84 (1H, d, J=8.4Hz), 6.81 (1H, s), 6.71 (1H, s), 5.00 (2H, s), 3.68 (3H, s), 2.52 (3H, s), 2.11 (3H, s), 2.04 (3H, s).

In accordance with the reaction mentioned in Production Example 29, the present compound 160 was synthesized.

The structural formula and 1H-NMR data of the thus obtained compound are shown below.

Present Compound 160

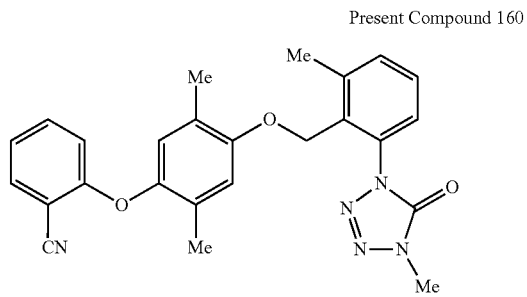 [SMILES: Cc1cc(Oc2ccccc2C#N)c(C)cc1OCc1c(C)cccc1-n1nnn(C)c1=O]

$^1$H-NMR (CDCl$_3$) δ: 7.66-7.62 (1H, m), 7.46-7.39 (2H, m), 7.28-7.25 (1H, m), 6.94-6.91 (1H, m), 6.84 (1H, d, J=8.4Hz), 66.62 (1H, dd, J=8.6, 0.6Hz), 5.03 (2H, s), 3.67 (3H, s), 2.53 (3H, s), 2.13 (3H, s), 2.03 (3H, s).

Production Example 30

A mixture of 0.40 g of 25A mentioned in Reference Production Example 25, 0.12 g of methylboronic acid, 0.98 g of cesium carbonate, 0.08 g of [1,1'-bis(diphenylphosphino)ferrocene]palladium(II) dichloride dichloromethane adduct, and 4 mL of dimethoxyethane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.06 g of 1-[2-{2,4,5-trimethylphenoxymethyl}-3-methoxyphenyl]-4-methyl-1,4-dihydrotetrazol-5-one (hereinafter referred to as the present compound 164).

Present Compound 164

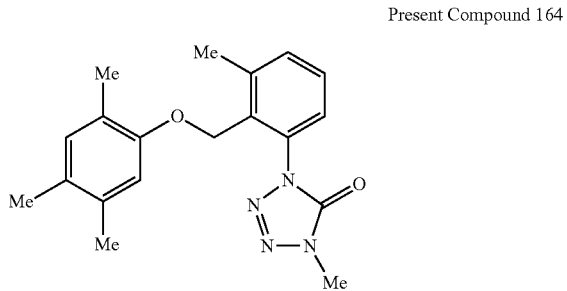 [SMILES: Cc1cc(C)c(OCc2c(C)cccc2-n2nnn(C)c2=O)cc1C]

¹H-NMR (CDCl₃) δ: 7.42-7.36 (2H, m), 7.27-7.22 (1H, m), 6.86 (1H, s), 6.63 (1H, s), 4.98 (2H, s), 3.62 (3H, s), 2.49 (3H, s), 2.21 (3H, s), 2.15 (3H, s), 2.03 (3H, s).

Production Example 31

A mixture of 0.42 g of the present compound 156, 0.49 g of Lawesson's reagent (2,4-Bis(4-methoxyphenyl)-1,3,2,4-dithiadiphosphetane 2,4-disulfide), 0.01 g of triethylamine, and 10 mL of toluene was stirred with heating under reflux for 8 hours, and then concentrated under reduced pressure. The residue thus obtained was subjected to silica gel column chromatography to obtain 0.30 g of 1-{2-[2,5-dimethyl-4-(3-methylphenyl)phenoxymethyl]-3-methylphenyl}-4-methyl-1,4-dihydrotetrazole-5-thione (hereinafter referred to as the present compound 166).

Present Compound 166

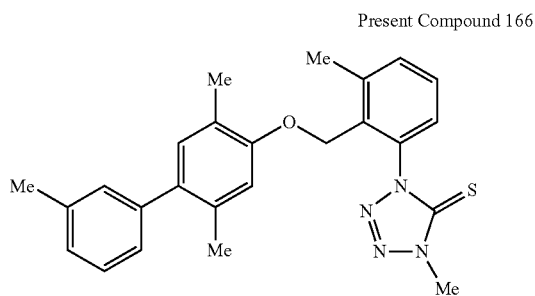 [SMILES: Cc1cccc(-c2cc(C)c(OCc3c(C)cccc3-n3nnn(C)c3=S)cc2C)c1]

1H-NMR (CDCl₃) δ: 7.50-7.45 (2H, m), 7.30-7.24 (2H, m), 7.14-7.05 (3H, m), 6.97 (1H, s), 6.69 (1H, s), 4.95 (2H, s), 3.94 (3H, s), 2.55 (3H, s), 2.38 (3H, s), 2.24 (3H, s), 2.08 (3H, s).

With respect to the production of intermediates for the production of the above-mentioned present compounds, Reference Production Example are shown below.

Reference Production Example 1

Under ice cooling, 21.9 g of anhydrous aluminum chloride was added to 250 mL of N,N-dimethylformamide, followed by stirring for 15 minutes. To this was added 10.7 g of sodium azide and, after stirring for 15 minutes, 25.0 g of 1-chloro-3-isocyanato-2-methylbenzene was added and the mixture was heated at 80° C. for 5 hours. After cooling, the reaction solution was added in a mixture of 35 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one (referred to as 1A).

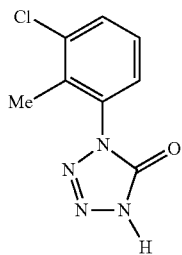

¹H-NMR (CDCl₃) δ(ppm): 2.32 (3H, s), 7.28-7.36 (2H, m), 7.57 (1H, dd, J=6.8, 2.2Hz), 13.08 (1H, s).

Reference Production Example 2

To a mixture of 10.00 g of 1A mentioned in Reference Production Example 1 and 100 mL of N,N-dimethylformamide, 2.30 g of 60% sodium hydride was added under ice cooling. The temperature of the mixture was raised to room temperature, followed by stirring for 1 hour. To the reaction mixture, 3.2 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 1.56 g of 1-(2-methyl-3-chlorophenyl)-4-methyl-1,4-dihydrotetrazol-5-one (referred to as 2A)

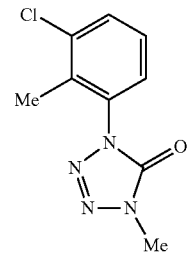

¹H-NMR (CDCl₃) δ(ppm): 2.30 (3H, s), 3.73 (3H, s), 7.27 (1H, d, J=2.7Hz), 7.28 (1H, d, J=7.1Hz), 7.52 (1H, dd, J=2.7, 6.8Hz).

Reference Production Example 3

A mixture of 1.56 g of 2A mentioned in Reference Production Example 2, 0.34 g of 1,1'-azobis(cyclohexane-1-carbonitrile), 1.42 g of N-bromosuccinimide, and 30 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.94 g of 1-(2-bromomethyl-3-chlorophenyl)-4-methyl-1,4-dihydrotetrazol-5-one (referred to as 3A).

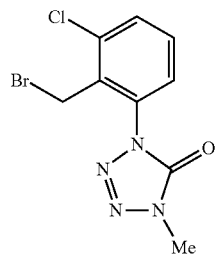 [SMILES: Cn1nnn(-c2cccc(Cl)c2CBr)c1=O]

1H-NMR (CDCl₃) δ(ppm): 3.76 (3H, s), 4.69 (2H, s), 7.35 (1H, dd, J=1.2, 8.1Hz), 7.43 (1H, t, J=8.1Hz), 7.58 (1H, dd, J=1.2, 8.1Hz).

Reference Production Example 4

A mixture of 15.0 g of 3-amino-1-methoxy-2-methylbenzene, 48.7 g of triphosgene, and 350 ml of toluene was stirred with heating under reflux for 3 hours. The reaction mixture allowed to cool was concentrated under reduced pressure to obtain 17.0 g of 1-methoxy-3-isocyanato-2-methylbenzene (referred to as 4A).

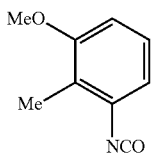

$^1$H-NMR (CDCl$_3$) δ(ppm): 2.19 (3H, s), 3.82 (3H, s), 6.69 (1H, d, J=8.2Hz), 6.72 (1H, dd, J=0.5, 8.0Hz), 7.09 (1H, t, J=8.2Hz).

Reference Production Example 5

Under ice cooling, 16.0 g of anhydrous aluminum chloride was added to 180 mL of N,N-dimethylformamide, followed by stirring for 15 minutes. To this was added 7.8 g of sodium azide and, after stirring for 15 minutes, 17.0 g of 4A mentioned in Reference Production Example 4 was added and the mixture was heated at 80° C. for 4.5 hours. After cooling, the reaction solution was added in a mixture of 25 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one (referred to as 5A).

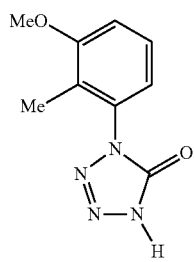

$^1$H-NMR (DMSO-d$_6$) δ(ppm): 1.99 (3H, s), 3.87 (3H, s), 7.01 (1H, d, J=8.1Hz), 7.17 (1H, d, J=8.1Hz). 7.36 (1H, t, J=8.3Hz), 14.63 (1H, s).

Reference Production Example 6

To a mixture of 10.00 g of 5A mentioned in Reference Production Example 5 and 100 mL of N,N-dimethylformamide, 2.47 g of 60% sodium hydride was added under ice cooling. The temperature of the mixture was raised to room temperature, followed by stirring for 1 hour. To the reaction mixture, 3.5 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 2.19 g of 1-(2-methyl-3-methoxyphenyl)-4-methyl-1,4-dihydrotetrazol-5-one (referred to as 6A).

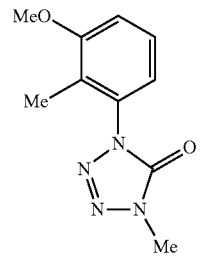 [SMILES: COc1cccc(-n2nnn(C)c2=O)c1C]

$^1$H-NMR (CDCl$_3$) δ(ppm): 2.11 (3H, s), 3.72 (3H, s), 3.88 (3H, s), 6.95 (1H, d, J=8.2Hz), 6.98 (1H, d, J=8.5Hz), 7.29 (1H, t, J=8.2Hz)

Reference Production Example 7

A mixture of 2.19 g of 6A mentioned in Reference Production Example 6, 0.52 g of 1,1'-azobis(cyclohexane-1-carbonitrile), 2.16 g of N-bromosuccinimide, and 40 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.36 g of 1-(2-bromomethyl-3-methoxyphenyl)-4-methyl-1,4-dihydrotetrazol-5-one (referred to as 7A).

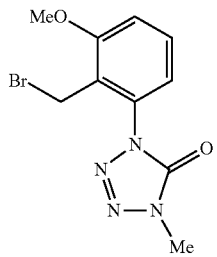 [SMILES: COc1cccc(-n2nnn(C)c2=O)c1CBr]

$^1$H-NMR (CDCl$_3$) δ(ppm): 3.74 (3H, s), 3.96 (3H, s), 4.93 (2H, s), 7.02 (1H, dd, J=1.0, 8.5Hz), 7.04 (1H, d, J=9.0Hz), 7.43 (1H, t, J=8.1Hz).

Reference Production Example 8

A mixture of 25.0 g of 1-bromo-2-methyl-3-aminobenzene, 60.0 g of triphosgene, and 400 ml of toluene was stirred with heating under reflux for 3 hours. The reaction mixture allowed to cool was concentrated under reduced pressure to obtain 30.3 g of 1-bromo-3-isocyanato-2-methylbenzene (referred to as 8A).

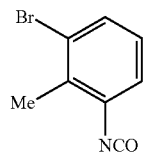

¹H-NMR (CDCl₃) δ(ppm): 2.42 (3H, s), 7.00 (1H, dt, J=0.5, 8.0Hz), 7.05 (1H, dd, J=1.7, 8.0Hz), 7.39 (1H, dd, 1.5, 7.7Hz).

Reference Production Example 9

Under ice cooling, 19.7 g of anhydrous aluminum chloride was added to 220 mL of N,N-dimethylformamide, followed by stirring for 15 minutes. To this was added 9.6 g of sodium azide and, after stirring for 15 minutes, 30.3 g of 8A mentioned in Reference Production Example 8 was added, followed by heating at 80° C. for 5 hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one (referred to as 9A).

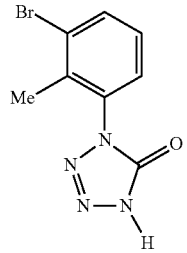

¹H-NMR (DMSO-d₆) δ(ppm): 2.22 (3H, s), 7.34 (1H, t, J=7.2Hz), 7.49 (1H, dd, J=8.2, 1.1Hz), 7.82 (1H, dd, J=8.0, 1.0Hz), 14.72 (1H, s).

Reference Production Example 10

To a mixture of 31.4 g of 9A mentioned in Reference Production Example 9 and 250 mL of N,N-dimethylformamide, 5.90 g of 60% sodium hydride was added under ice cooling. The temperature of the mixture was raised to room temperature, followed by stirring for 1 hour. To the reaction mixture, 8.4 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one (referred to as 10A)

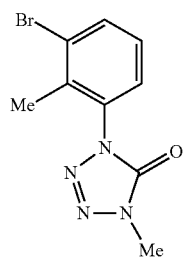

¹H-NMR (CDCl₃) δ(ppm): 2.33 (3H, s), 3.73 (3H, s), 7.21 (1H, dt, J=0.5, 7.8Hz), 7.30 (1H, dd, J=1.0, 8.0Hz), 7.71 (1H, dd, J=1.2, 8.3Hz)

Reference Production Example 11

A mixture of 8.47 g of 10A mentioned in Reference Production Example 10, 1.54 g of 1,1'-azobis(cyclohexane-1-carbonitrile), 6.44 g of N-bromosuccinimide, and 125 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.52 g of 1-(2-bromomethyl-3-bromophenyl)-4-methyl-1,4-dihydrotetrazol-5-one (referred to as 11A).

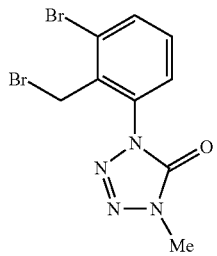

¹H-NMR (CDCl₃) δ(ppm): 3.76 (3H, s), 4.71 (2H, s), 7.34 (1H, t, J=7.8Hz), 7.38 (1H, dd, J=8.0, 1.7Hz), 7.77 (1H, dd, J=7.8, 1.7Hz).

Reference Production Example 12

A mixture of 45.0 g of 11A mentioned in Reference Production Example 11, 37.4 g of sodium methoxide, and 600 mL of tetrahydrofuran was stirred at room temperature for 3 hours. A saturated sodium bicarbonate solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 36.2 g of 1-(2-methoxymethyl-3-bromophenyl)-4-methyl-, 4-dihydrotetrazol-5-one (referred to as 12A).

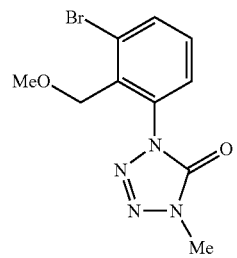

¹H-NMR (CDCl₃) δ(ppm): 3.23 (3H, s), 3.72 (3H, s), 4.67 (2H, s), 7.33 (1H, t, J=7.8Hz), 7.38 (1H, dd, J=1.2, 8.1Hz), 7.76 (1H, dd, J=1.5, 7.8Hz).

Reference Production Example 13

A mixture of 36.2 g of 12A mentioned in Reference Production Example 12, 23.2 g of methylboronic acid, 66.7 g of cesium fluoride, 10.6 g of [1,1'-bis(diphenylphosphino)ferrocene]palladium(II) dichloride dichloromethane adduct, and 500 ml of dioxane was stirred at 90° C. for 5.5 hours. After cooling, the reaction mixture was filtered and the filtrate was concentrated under reduced pressure. The residue thus obtained was subjected to silica gel column chromatography to obtain 132 g of 1-(2-methoxymethyl-3-methylphenyl)-4-methyl-1,4-dihydrotetrazol-5-one (referred to as 13A).

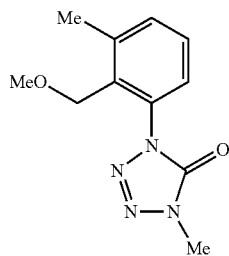

$^1$H-NMR (CDCl$_3$) δ(ppm): 2.48 (3H, s), 3.23 (3H, s), 3.72 (3H, s), 4.42 (2H, s), 7.21 (1H, t, J=5.1Hz), 7.35 (2H, d, J=4.8Hz).

Reference Production Example 14

A mixture of 132 g of 13A mentioned in Reference Production Example 13, 50 mL of acetic acid, and 50 mL of a 25% hydrogen bromide-acetic acid solution was stirred at 65° C. for 1 hour. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 27.9 g of 1-(2-bromomethyl-3-methylphenyl)-4-methyl-1,4-dihydrotetrazol-5-one (referred to as 14A).

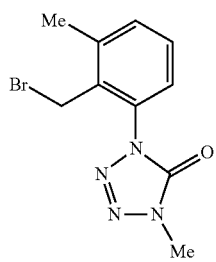 [SMILES: Cc1cccc(-n2nnn(C)c2=O)c1CBr]

$^1$H-NMR (CDCl$_3$) δ(ppm): 2.51 (3H, s), 3.75 (3H, s), 4.51 (2H, s), 7.22-7.24 (1H, m), 7.36-7.39 (2H, m).

Reference Production Example 15

A mixture of 30.1 g of 12A mentioned in Reference Production Example 12, 12.9 g of cyclopropylboronic acid, 46.2 g of cesium fluoride, 8.2 g of [1,1'-bis(diphenylphosphino)ferrocene]palladium(II) dichloride dichloromethane adduct, and 680 ml of dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-(2-methoxymethyl-3-cyclopropylphenyl)-4-methyl-1,4-dihydrotetrazol-5-one (referred to as 15A).

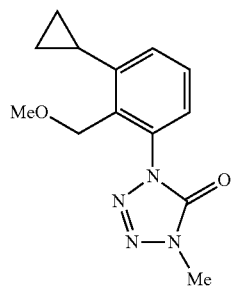 [SMILES: COCc1c(C2CC2)cccc1-n1nnn(C)c1=O]

$^1$H-NMR (CDCl$_3$) δ(ppm): 7.36 (1H, t, J=8.0Hz), 7.20 (2H, d, J=8.0Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 16

A mixture of 26.0 g of 15A mentioned in Reference Production Example 15, 40 mL of acetic acid, and 40 mL of a 25% hydrogen bromide-acetic acid solution was stirred at 65° C. for 2 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 30.8 g of 1-(2-bromomethyl-3-cyclopropylphenyl)-4-methyl-, 4-dihydrotetrazol-5-one (referred to as 16A).

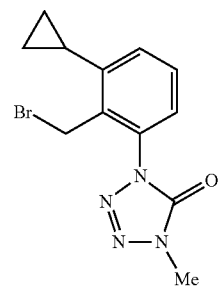 [SMILES: Cn1nnn(-c2cccc(C3CC3)c2CBr)c1=O]

$^1$H-NMR (CDCl$_3$) δ(ppm): 7.38 (1H, t, J=7.8Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 17

A mixture of 29.8 g of 12A mentioned in Reference Production Example 12, 35.2 g of tributylvinyltin, 11.6 g of tetrakistriphenylphosphinepalladium, and 500 mL of toluene was stirred with heating under reflux for 14 hours. After cooling, an aqueous saturated ammonium chloride solution was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 19.7 g of 1-(2-methoxymethyl-3-ethenylphenyl)-4-methyl-1,4-dihydrotetrazol-5-one (referred to as 17A).

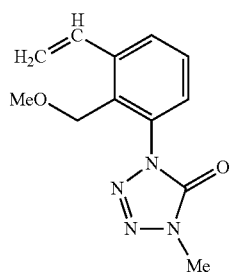 [SMILES: C=Cc1cccc(-n2nnn(C)c2=O)c1COC]

¹H-NMR (CDCl₃) δ(ppm): 7.67 (1H, dd, J=7.8, 1.3Hz), 7.44 (1H, t, J=7.8Hz), 7.29 (1H, dd, J=7.8, 1.3Hz), 7.11 (1H, dd, J=17.4, 11.1Hz), 5.72 (1H, dd, J=17.4, 1.3Hz), 5.44 (1H, dd, J=11.1, 1.3Hz), 4.45 (2H, s), 3.72 (3H, s), 3.23 (3H, s).

Reference Production Example 18

A mixture of 19.7 g of 17A mentioned in Reference Production Example 17, 3.02 g of a palladium-fibroin complex, and 1 L of methanol was stirred in a hydrogen atmosphere at room temperature for 11 hours. The reaction mixture was filtered and the filtrate was concentrated under reduced pressure. The residue thus obtained was subjected to silica gel column chromatography to obtain 19.3 g of 1-(2-methoxymethyl-3-ethylphenyl)-4-methyl-1,4-dihydrotetrazol-5-one (referred to as 18A).

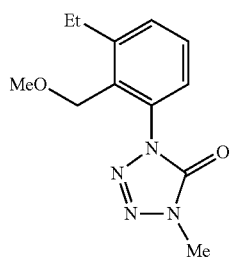 [SMILES: CCc1cccc(-n2nnn(C)c2=O)c1COC]

¹H-NMR (CDCl₃) δ(ppm): 7.42-7.38 (2H, m), 7.23-7.20 (1H, m), 4.44 (2H, s), 3.72 (3H, s), 3.22 (3H, s), 2.82 (2H, q, J=7.6Hz), 1.27 (3H, t, J=7.6Hz).

Reference Production Example 19-1

A mixture of 19.3 g of 18A mentioned in Reference Production Example 18, 40 mL of acetic acid, and 40 mL of a 25% hydrogen bromide-acetic acid solution was stirred at 65° C. for 1.5 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 23.3 g of 1-(2-bromomethyl-3-ethylphenyl)-4-methyl-1,4-dihydrotetrazol-5-one (referred to as 19-1A).

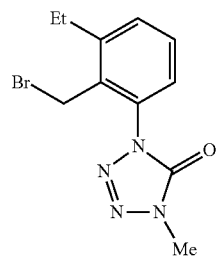

¹H-NMR (CDCl₃) δ(ppm): 7.44-7.37 (2H, m), 7.23 (1H, dd, J=7.1, 2.0Hz), 4.56 (2H, s), 3.75 (3H, s), 2.85 (2H, q, J=7.6Hz), 1.33 (3H, t, J=7.6Hz).

Reference Production Example 19-2

A mixture of 9.11 g of 3A mentioned in Reference Production Example 3, 5.61 g of 4-bromo-2-methylphenol, 8.29 g of potassium carbonate, and 120 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 11.8 g of 1-[2-(4-bromo-2-methylphenoxymethyl)-3-chlorophenyl]-4-methyl-1,4-dihydrotetrazol-5-one (referred to as 19-2A).

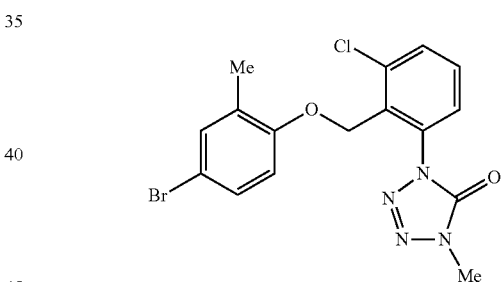

¹H-NMR (CDCl₃) δ: 7.65 (1H, d, J=8.0Hz), 7.51 (1H, t, J=8.0Hz), 7.45-7.42 (1H, m), 7.30-7.24 (2H, m), 6.75 (1H, d, J=8.2Hz), 5.31 (2H, s), 3.65 (3H, s), 2.03 (3H, s).

Reference Production Example 20

A mixture of 23.5 g of 14A mentioned in Reference Production Example 14, 15.5 g of 4-bromo-2-methylphenol, 22.9 g of potassium carbonate, and 330 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 30.1 g of 1-[2-(4-bromo-2-methylphenoxymethyl)-3-methylphenyl]-4-methyl-1,4-dihydrotetrazol-5-one (referred to as 20A).

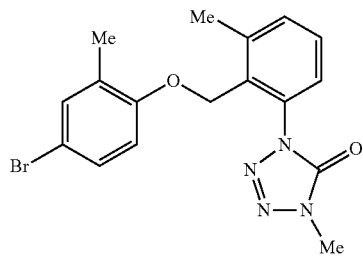

¹H-NMR (CDCl₃) δ: 7.46-7.39 (2H, m), 7.29-7.26 (1H, m), 7.25-7.21 (2H, m), 6.70 (1H, d, J=9.4Hz), 5.00 (2H, s), 3.63 (3H, s), 2.49 (3H, s), 2.06 (3H, s).

Reference Production Example 21

A mixture of 8.97 g of 7A mentioned in Reference Production Example 7, 5.61 g of 4-bromo-2-methylphenol, 8.29 g of potassium carbonate, and 120 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 12.3 g of 1-[2-(4-bromo-2-methylphenoxymethyl)-3-methoxyphenyl]-4-methyl-1,4-dihydrotetrazol-5-one (referred to as 21A).

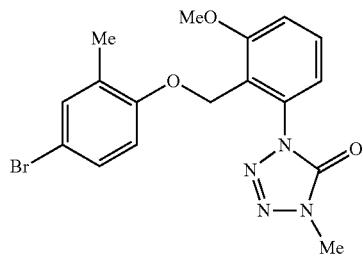

¹H-NMR (CDCl₃) δ: 7.46 (1H, t, J=8.2Hz), 7.20-7.15 (2H, m), 7.10-7.04 (2H, m), 6.73 (1H, d, J=8.2Hz), 5.22 (2H, s), 3.91 (3H, s), 3.59 (3H, s), 1.96 (3H, s).

Reference Production Example 22

A mixture of 8.91 g of 19-1A mentioned in Reference Production Example 19, 5.61 g of 4-bromo-2-methylphenol, 8.29 g of potassium carbonate, and 120 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 12.2 g of 1-[2-(4-bromo-2-methylphenoxymethyl)-3-ethylphenyl]-4-methyl-1,4-dihydrotetrazol-5-one (referred to as 22A).

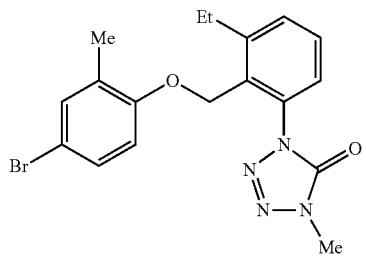

¹H-NMR (CDCl₃) δ: 7.50-7.43 (2H, m), 7.30-7.26 (1H, m), 7.25-7.21 (2H, m), 6.71 (1H, d, J=8.7Hz), 5.02 (2H, s), 3.60 (3H, s), 2.83 (2H, q, J=7.6Hz), 2.04 (3H, s), 1.27 (3H, t, J=7.6Hz).

Reference Production Example 23

A mixture of 9.27 g of 16A mentioned in Reference Production Example 16, 5.61 g of 4-bromo-2-methylphenol, 8.29 g of potassium carbonate, and 120 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 12.8 g of 1-[2-(4-bromo-2-methylphenoxymethyl)-3-cyclopropylphenyl]-4-methyl-1,4-dihydrotetrazol-5-one (referred to as 23A)

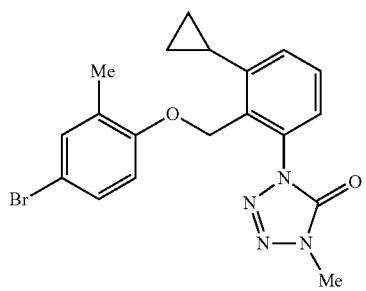 [SMILES: Cc1cc(Br)ccc1OCc1c(C2CC2)cccc1-n1nnn(C)c1=O]

¹H-NMR (CDCl₃) δ: 7.44 (1H, t, J=7.8Hz), 7.26-7.24 (4H, m), 6.75 (1H, d, J=8.2Hz), 5.23 (2H, s), 3.62 (3H, s), 2.12-2.07 (1H, m), 2.05 (3H, s), 1.02-0.96 (2H, m), 0.79-0.73 (2H, m).

Reference Production Example 24

A mixture of 5.66 g of 14A mentioned in Reference Production Example 14, 3.74 g of 4-bromo-3-methylphenol, 5.53 g of potassium carbonate, and 80 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 7.42 g of 1-[2-(4-bromo-3-methylphenoxymethyl)-3-methylphenyl]-4-methyl-1,4-dihydrotetrazol-5-one (referred to as 24A).

153

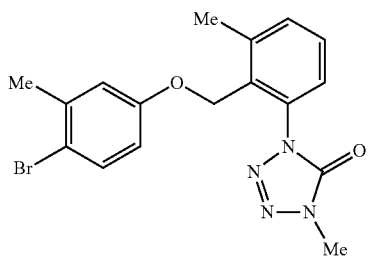

¹H-NMR (CDCl₃) δ: 7.47 (1H, t, J=8.2Hz), 7.21-7.17 (2H, m), 7.10-7.05 (2H, m), 6.74 (1H, d, J=8.5Hz), 5.23 (2H, s), 3.93 (3H, s), 3.60 (3H, s), 1.96 (3H, s).

Reference Production Example 25

A mixture of 4.25 g of 14A mentioned in Reference Production Example 14, 3.02 g of 4-bromo-2,5-dimethylphenol, 4.15 g of potassium carbonate, and 60 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 5.82 g of 1-[2-(4-bromo-2,5-dimethylphenoxymethyl)-3-methylphenyl]-4-methyl-1,4-dihydrotetrazol-5-one (referred to as 25A).

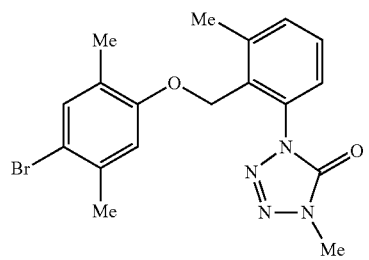 [SMILES: Cc1cc(OCc2c(C)cccc2-n2nnn(C)c2=O)c(C)cc1Br]

¹H-NMR (CDCl₃) δ: 7.45-7.37 (2H, m), 7.28-7.25 (1H, m), 7.23 (1H, s), 6.68 (1H, s), 4.99 (2H, s), 3.64 (3H, s), 2.49 (3H, s), 2.33 (3H, s), 2.01 (3H, s).

Reference Production Example 26

A mixture of 2.97 g of 19-1A mentioned in Reference Production Example 19, 1.91 g of 4-bromo-2-fluorophenol, 2.76 g of potassium carbonate, and 40 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 3.79 g of 1-[2-(4-bromo-2-fluorophenoxymethyl)-3-ethylphenyl]-4-methyl-1,4-dihydrotetrazol-5-one (referred to as 26A).

154

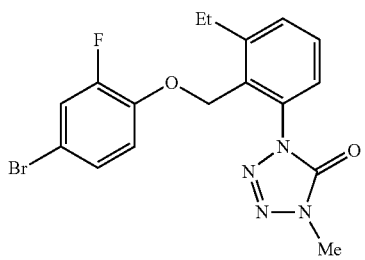 [SMILES: CCc1cccc(-n2nnn(C)c2=O)c1COc1ccc(Br)cc1F]

¹H-NMR (CDCl₃) δ: 7.50-7.42 (2H, m), 7.29 (1H, dd, J=7.4, 1.7Hz), 7.21 (1H, dd, J=10.4, 2.4Hz), 7.18-7.14 (1H, m), 6.83 (1H, t, J=8.7Hz), 5.12 (2H, s), 3.66 (3H, s), 2.84 (2H, q, J=7.6Hz), 1.29 (3H, t, J=7.6Hz).

Reference Production Example 27

A mixture of 2.83 g of 14A mentioned in Reference Production Example 14, 2.03 g of 4-bromo-3-methoxyphenol, 2.76 g of potassium carbonate, and 40 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 3.92 g of 1-[2-(4-bromo-3-methoxyphenoxymethyl)-3-methylphenyl]-4-methyl-1,4-dihydrotetrazol-5-one (referred to as 27A).

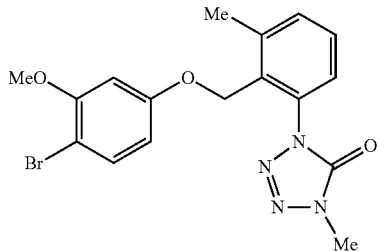 [SMILES: COc1cc(OCc2c(C)cccc2-n2nnn(C)c2=O)ccc1Br]

¹H-NMR (CDCl₃) δ: 7.44-7.39 (3H, m), 7.30-7.26 (1H, m), 6.45-6.38 (2H, m), 5.01 (2H, s), 3.84 (3H, s), 3.63 (3H, s), 2.50 (3H, s).

Reference Production Example 28

A mixture of 4.05 g of 21A mentioned in Reference Production Example 21, 2.79 g of bis(pinacolato)diboron, 0.25 g of [1,1'-bis(diphenylphosphino)ferrocene]palladium (II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 2.92 g of 1-[2-{4-(4,4,5,5-tetramethyl-[1,3,2]dioxaborolan-2-yl)-2-methylphenoxymethyl}-3-methoxyphenyl]-4-methyl-1,4-dihydrotetrazol-5-one (referred to as 28A).

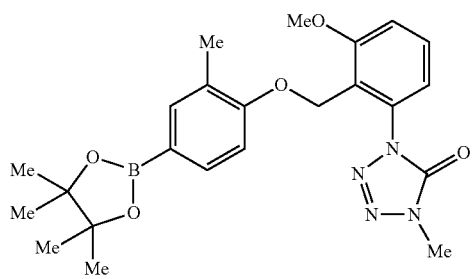 [SMILES: COc1cccc(-n2nnn(C)c2=O)c1COc1ccc(B2OC(C)(C)C(C)(C)O2)cc1C]

¹H-NMR (CDCl₃) δ: 7.58 (1H, dd, J=8.2, 1.4Hz), 7.51 (1H, s), 7.45 (1H, t, J=8.3Hz), 7.08-7.04 (2H, m), 6.87 (1H, d, J=8.2Hz), 5.28 (2H, s), 3.91 (3H, s), 3.57 (3H, s), 1.97 (3H, s), 1.31 (12H, s).

Reference Production Example 29

A mixture of 3.89 g of 20A mentioned in Reference Production Example 20, 2.79 g of bis(pinacolato)diboron, 0.25 g of [1,1'-bis(diphenylphosphino)ferrocene]palladium (II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 3.44 g of 1-[2-{4-(4,4,5,5-tetramethyl-[1,3,2]dioxaborolan-2-yl)-2-methylphenoxymethyl}-3-methylphenyl]-4-methyl-1,4-dihydrotetrazol-5-one (referred to as 29A).

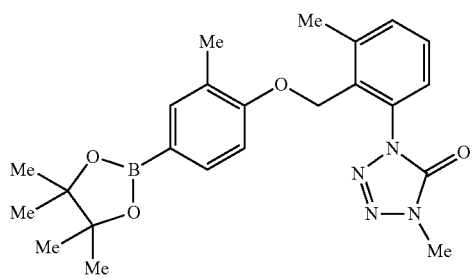 [SMILES: Cc1cc(B2OC(C)(C)C(C)(C)O2)ccc1OCc1c(C)cccc1-n1nnn(C)c1=O]

¹H-NMR (CDCl₃) δ: 7.62 (1H, dd, J=8.0, 1.4Hz), 7.57 (1H, s), 7.44-7.38 (2H, m), 7.29-7.25 (1H, m), 6.85 (1H, d, J=8.2Hz), 5.05 (2H, s), 3.62 (3H, s), 2.49 (3H, s), 2.08 (3H, s), 1.33 (12H, s).

Reference Production Example 30

A mixture of 4.03 g of 22A mentioned in Reference Production Example 22, 2.79 g of bis(pinacolato)diboron, 0.25 g of [1,1'-bis(diphenylphosphino)ferrocene]palladium (II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 3.87 g of 1-[2-{4-(4,4,5,5-tetramethyl-[1,3,2]dioxaborolan-2-yl)-2-methylphenoxymethyl}-3-ethylphenyl]-4-methyl-1,4-dihydrotetrazol-5-one (referred to as 30A).

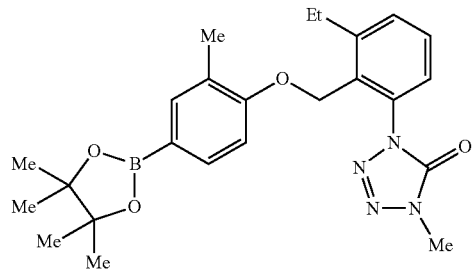 [SMILES: CCc1cccc(-n2nnn(C)c2=O)c1COc1ccc(B2OC(C)(C)C(C)(C)O2)cc1C]

¹H-NMR (CDCl₃) δ: 7.63 (1H, dd, J=8.1, 1.3Hz), 7.56 (1H, s), 7.49-7.43 (2H, m), 7.29-7.25 (1H, m), 6.86 (1H, d, J=8.2Hz), 5.07 (2H, s), 3.59 (3H, s), 2.83 (2H, q, J=7.6Hz), 2.07 (3H, s), 1.33 (12H, s), 1.26 (3H, t, J=7.6Hz).

Reference Production Example 31

While stirring a mixture of 13.1 g of 29A mentioned in Reference Production Example 29, 8.40 g of sodium hydroxide, 60 ml of tetrahydrofuran, and 30 mL of water under ice cooling at 0° C., 17.0 ml of a 30% hydrogen peroxide solution was added, followed by stirring at 0° C. for 1 hour. After raising the temperature to room temperature and further stirring for 1 hour, an aqueous saturated sodium thiosulfate solution was poured into the reaction mixture and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 5.92 g of 1-[2-(4-hydroxy-2-methylphenoxymethyl)-3-methylphenyl]-4-methyl-1,4-dihydrotetrazol-5-one (referred to as 31A).

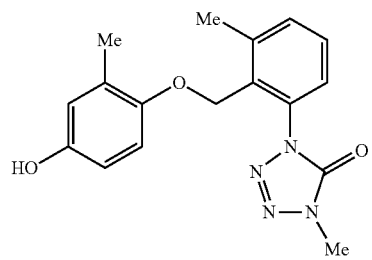 [SMILES: Cc1cc(O)ccc1OCc1c(C)cccc1-n1nnn(C)c1=O]

¹H-NMR (CDCl₃) δ: 7.30 (1H, t, J=7.9Hz), 7.06 (1H, d, J=7.9Hz), 7.02 (1H, d, J=7.8Hz), 6.90 (1H, d, J=8.2Hz), 6.66-6.62 (2H, m), 4.97 (2H, s), 4.48 (1H, br s), 2.41 (3H, s), 2.15 (3H, s), 1.59 (3H, s).

Reference Production Example 32

A mixture of 2.83 g of 14A mentioned in Reference Production Example 14, 2.12 g of 4-hydroxy-3-methylbenzophenone, 2.76 g of potassium carbonate, and 40 mL of acetonitrile was stirred while heating at 80° C. for 2 hours. Water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 4.08 g of 1-[2-(4-benzoyl-2-methyl-phenoxymethyl)-3-methyl-phenyl]-4-methyl-1,4-dihydro-tetrazol-5-one (referred to as 32A).

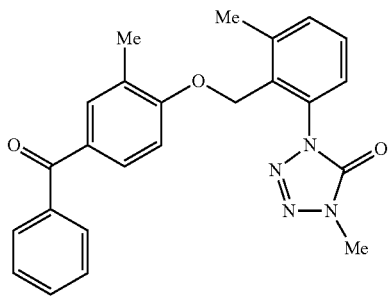 [SMILES: Cc1cc(C(=O)c2ccccc2)ccc1OCc1c(C)cccc1-n1nnn(C)c1=O]

$^1$H-NMR (CDCl$_3$) δ: 7.75 (2H, dd, J=8.2, 1.0Hz), 7.68-7.63 (2H, m), 7.60-7.54 (1H, m), 7.51-7.40 (4H, m), 7.30 (1H, dd, J=7.1, 2.1Hz), 6.89 (1H, d, J=8.2Hz), 5.13 (2H, s), 3.64 (3H, s), 2.52 (3H, s), 2.13 (3H, s).

Reference Production Example 33

A mixture of 2.83 g of 14A mentioned in Reference Production Example 14, 1.36 g of 4-hydroxy-3-methylbenzaldehyde, 2.76 g of potassium carbonate, and 40 mL of acetonitrile was stirred with heating under reflux for 4 hours. After cooling to room temperature, the reaction mixture was filtered and the filtrate was concentrated. The residue thus obtained was subjected to silica gel column chromatography to obtain 2.96 g of 3-methyl-4-{[2-methyl-6-(4-methyl-1,4-dihydrotetrazol-5-on-1-yl)phenyl]methyloxy}benzaldehyde (referred to as 33A).

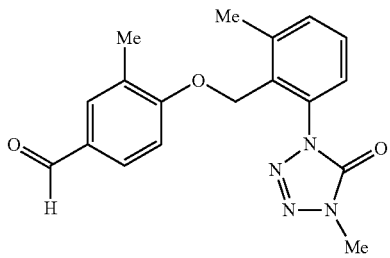 [SMILES: Cc1cc(C=O)ccc1OCc1c(C)cccc1-n1nnn(C)c1=O]

$^1$H-NMR (CDCl$_3$) δ: 9.86 (1H, s), 7.70 (1H, dd, J=8.2, 2.1Hz), 7.68-7.66 (1H, m), 7.48-7.41 (2H, m), 7.30 (1H, dd, J=7.4, 1.7Hz), 6.96 (1H, d, J=8.2Hz), 5.14 (2H, s), 3.63 (3H, s), 2.51 (3H, s), 2.14 (3H, s).

Reference Production Example 34

While stirring a mixture of 5.66 g of 14A mentioned in Reference Production Example 14, 3.00 g of 4'-hydroxy-3'-methyl-acetophenone, 5.53 g of potassium carbonate, and 40 mL of acetonitrile was stirred with heating under reflux for 4 hours. After cooling to room temperature, the reaction mixture was filtered and the filtrate was concentrated. The residue thus obtained was subjected to silica gel column chromatography to obtain 4.73 g of 1-{2-(2-methyl-4-acetyl-phenoxymethyl)-3-methyl-phenyl}-4-methyl-1,4-dihydrotetrazol-5-one (referred to as 34A).

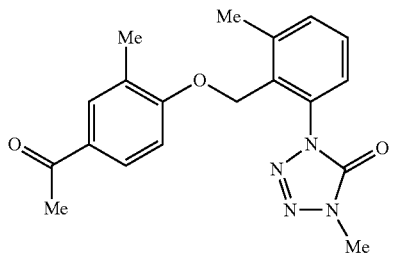 [SMILES: CC(=O)c1ccc(OCc2c(C)cccc2-n2nnn(C)c2=O)c(C)c1]

$^1$H-NMR (CDCl$_3$) δ: 7.79 (1H, dd, J=8.54, 2.24Hz), 7.75 (1H, d, J=1.46Hz), 7.46-7.40 (2H, m), 7.29 (1H, dd, J=7.32, 1.95Hz), 6.86 (1H, d, J=8.54Hz), 5.11 (2H, s), 3.62 (3H, s), 2.54 (3H, s), 2.50 (3H, s), 2.12 (3H, s).

Reference Production Example 35

While stirring a mixture of 1.35 g of 33A mentioned in Reference Production Example 33, and 8 mL of methanol at 0° C., 0.30 g of sodium borohydride was added, followed by stirring at room temperature for 4 hours. Water was poured into the reaction solution and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 1.25 g of 1-[2-{4-hydroxymethyl-2-methylphenoxymethyl}-3-methylphenyl]-4-methyl-1,4-dihydrotetrazol-5-one (referred to as 35A).

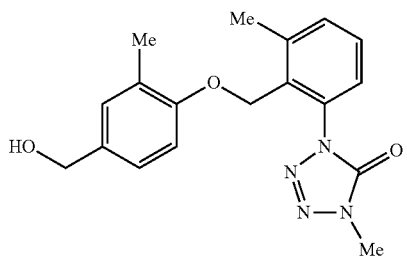 [SMILES: Cc1cc(CO)ccc1OCc1c(C)cccc1-n1nnn(C)c1=O]

$^1$H-NMR (CDCl$_3$) δ: 7.44-7.39 (2H, m), 7.27-7.25 (1H, m), 7.14-7.10 (2H, m), 6.83-6.79 (1H, m), 5.03 (2H, s), 4.58 (2H, d, J=5.7Hz), 3.63 (3H, s), 2.51 (3H, s), 2.08 (3H, s).

Reference Production Example 36

While stirring a mixture of 0.71 g of 34A mentioned in Reference Production Example 34 and 4 mL of methanol at 0° C., 0.15 g of sodium borohydride was added, followed by stirring at room temperature for 4 hours. Water was poured into the reaction solution and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.45 g of 1-[2-{4-(1-hydroxy-ethyl)-2-methylphenoxymethyl}-3-methylphenyl]-4-methyl-1,4-dihydrotetrazol-5-one (referred to as 36A).

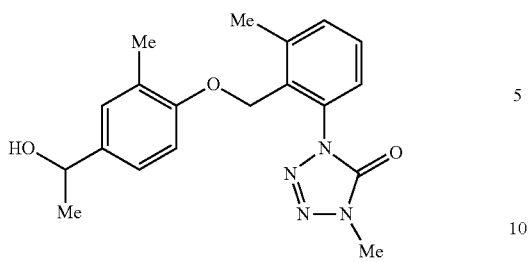

¹H-NMR (CDCl₃) δ: 7.44-7.39 (2H, m), 7.27-7.24 (1H, m), 7.14-7.12 (2H, m), 6.82-6.78 (1H, m), 5.02 (2H, s), 4.84-4.79 (1H, m), 3.64 (3H, s), 2.51 (3H, s), 2.09 (3H, s), 1.73 (1H, d, J=3.4Hz), 1.47 (3H, d, J=6.4Hz).

Reference Production Example 37

A mixture of 8.49 g of 14A mentioned in Reference Production Example 14, 4.59 g of 4-nitro-2-methylphenol, 2.76 g of potassium carbonate, and 120 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 10.4 g of 1-[2-(4-nitro-2-methylphenoxymethyl)-3-methylphenyl]-4-methyl-1,4-dihydrotetrazol-5-one (referred to as 37A).

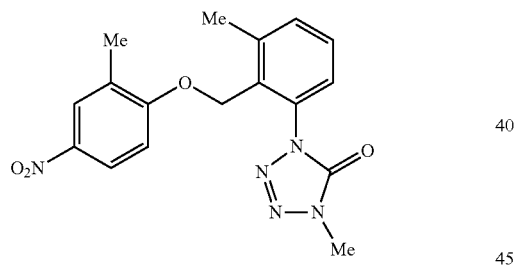

¹H-NMR (CDCl₃) δ: 7.47 (1H, s), 7.43-7.38 (2H, m), 7.27-7.25 (1H, m), 6.76-6.71 (2H, m), 4.98 (2H, s), 3.63 (3H, s), 2.50 (3H, s), 2.06 (3H, s).

Reference Production Example 38

A mixture of 7.11 g of 37A mentioned in Reference Production Example 37, 6.00 g of electrolytic iron, 80 ml of acetic acid, and 20 mL of water was stirred with heating at 60° C. for 2 hours. After concentrating under reduced pressure, an aqueous saturated sodium hydrogen carbonate solution was added to the residue and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 10.4 g of 1-[2-(4-amino-2-methylphenoxymethyl)-3-methylphenyl]-4-methyl-1,4-dihydrotetrazol-5-one (referred to as 38A).

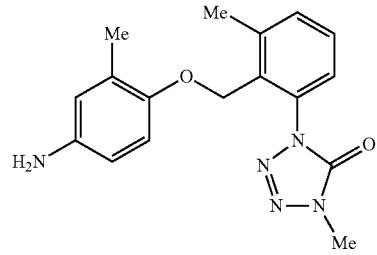 [SMILES: Cc1cc([N+](=O)[O-])ccc1OCc1c(C)cccc1-n1nnn(C)c1=O]

¹H-NMR (CDCl₃) δ: 7.42-7.36 (2H, m), 7.26-7.23 (1H, m), 6.65 (1H, d, J=8.4Hz), 6.49 (1H, d, J=2.5Hz), 6.45 (1H, dd, J=8.5, 2.5Hz), 4.93 (2H, s), 3.64 (3H, s), 3.39 (2H, br s), 2.49 (3H, s), 2.02 (3H, s).

Reference Production Example 39

While stirring a mixture of 2.25 g of 30A mentioned in Reference Production Example 30, 1.40 g of sodium hydroxide, 10 ml of tetrahydrofuran, and 5 mL of water under ice cooling at 0° C., 2.83 ml of a 30% hydrogen peroxide solution was added, followed by stirring at 0° C. for 1 hour. After raising the temperature to room temperature and further stirring for 4 hours, an aqueous saturated sodium thiosulfate solution was poured into the reaction mixture and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 1.47 g of 1-[2-(4-hydroxy-2-methylphenoxymethyl)-3-ethylphenyl]-4-methyl-1,4-dihydrotetrazol-5-one (referred to as 39A).

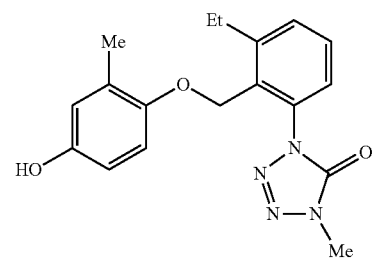 [SMILES: CCc1cccc(-n2nnn(C)c2=O)c1COc1ccc(O)cc1C]

¹H-NMR (CDCl₃) δ: 7.49-7.41 (2H, m), 7.28-7.24 (1H, m), 6.68 (1H, d, J=8.5Hz), 6.61 (1H, d, J=3.0Hz), 6.56 (1H, dd, J=8.5, 3.0Hz), 4.97 (2H, s), 4.58 (1H, br s), 3.61 (3H, s), 2.84 (2H, q, J=7.6Hz), 2.03 (3H, s), 1.27 (3H, t, J=7.6Hz).

Reference Production Example 40

A mixture of 1.42 g of 14A mentioned in Reference Production Example 14, 1.00 g of 4-bromo-2-ethylphenol, 1.38 g of potassium carbonate, and 20 mL of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure. The residue thus obtained was washed with hexane and methyl tert-butyl ketone to obtain 1.90 g of 1-[2-(4-bromo-2-ethylphenoxymethyl)-3-methylphenyl]-4-methyl-1,4-dihydrotetrazol-5-one (referred to as 40A).

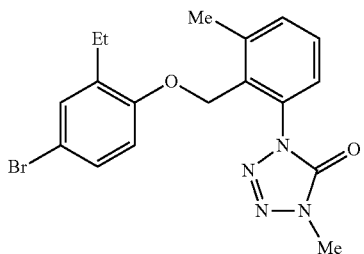 [SMILES: CCc1cc(Br)ccc1OCc1c(C)cccc1-n1nnn(C)c1=O]

¹H-NMR (CDCl₃) δ: 7.46-7.39 (2H, m), 7.30-7.22 (3H, m), 6.73 (1H, d, J=9.4Hz), 4.99 (2H, s), 3.64 (3H, s), 2.51-2.43 (5H, m), 1.08 (3H, t, J=7.6Hz).

Reference Production Example 41

A mixture of 1.42 g of 14A mentioned in Reference Production Example 14, 1.00 g of 4-bromo-3-cyanophenol, 1.38 g of potassium carbonate, and 20 mL of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure. The residue thus obtained was washed with hexane and methyl tert-butyl ketone to obtain 1.94 g of 1-[2-(4-bromo-3-cyanophenoxymethyl)-3-methylphenyl]-4-methyl-1,4-dihydrotetrazol-5-one (referred to as 41A).

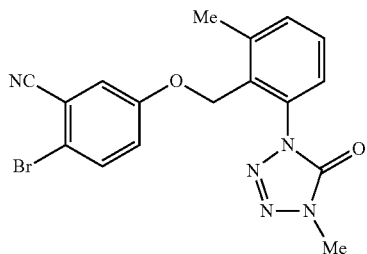 [SMILES: Cc1cccc(-n2nnn(C)c2=O)c1COc1ccc(Br)c(C#N)c1]

¹H-NMR (CDCl₃) δ: 7.53 (1H, d, J=8.9Hz), 7.46 (1H, t, J=7.6Hz), 7.43-7.39 (1H, m), 7.30 (1H, dd, J=7.6, 1.1Hz), 7.14 (1H, d, J=3.0Hz), 6.97 (1H, dd, J=8.9, 3.0Hz), 5.01 (2H, s), 3.67 (3H, s), 2.48 (3H, s).

Reference Production Example 42

A mixture of 1.35 g of 14A mentioned in Reference Production Example 14, 1.00 g of 4-bromo-3,5-difluorophenol, 1.32 g of potassium carbonate, and 19 mL of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure. The residue thus obtained was washed with hexane and methyl tert-butyl ketone to obtain 1.75 g of 1-[2-(4-bromo-3,5-difluorophenoxymethyl)-3-methylphenyl]-4-methyl-1,4-dihydrotetrazol-5-one (referred to as 42A).

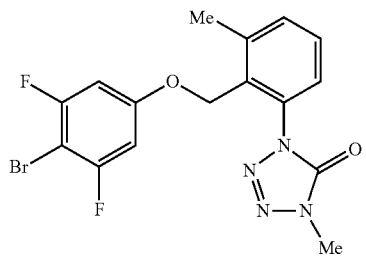 [SMILES: Cc1cccc(-n2nnn(C)c2=O)c1COc1cc(F)c(Br)c(F)c1]

¹H-NMR (CDCl₃) δ: 7.47-7.40 (2H, m), 7.29 (1H, dd, J=7.6, 1.4Hz), 6.55-6.49 (2H, m), 4.98 (2H, s), 3.67 (3H, s), 2.47 (3H, s).

Reference Production Example 43

A mixture of 2.83 g of 14A mentioned in Reference Production Example 14, 2.41 g of 4-bromo-3-trifluoromethylphenol, 2.76 g of potassium carbonate, and 40 mL of acetonitrile stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure. The residue thus obtained was washed with hexane and methyl tert-butyl ketone to obtain 4.20 g of 1-[2-(4-bromo-3-trifluoromethylphenoxymethyl)-3-methylphenyl]-4-methyl-1,4-dihydrotetrazol-5-one (referred to as 43A).

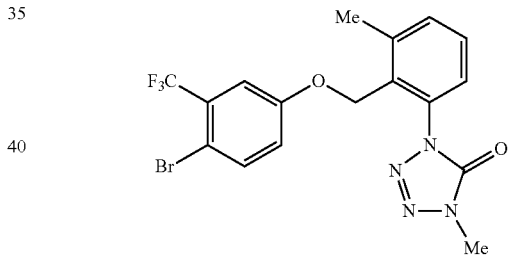

¹H-NMR (CDCl₃) δ: 7.59 (1H, d, J=8.7Hz), 7.50-7.42 (2H, m), 7.32 (1H, dd, J=7.4, 1.5Hz), 7.21 (1H, d, J=3.0Hz), 6.92 (1H, dd, J=8.7, 3.0Hz), 5.06 (2H, s), 3.67 (3H, s), 2.51 (3H, s).

Reference Production Example 44

A mixture of 2.83 g of 14A mentioned in Reference Production Example 14, 2.41 g of 4-bromo-2-trifluoromethylphenol, 2.76 g of potassium carbonate, and 40 mL of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure. The residue thus obtained was washed with hexane and methyl tert-butyl ketone to obtain 4.05 g of 1-[2-(4-bromo-2-trifluoromethylphenoxymethyl)-3-methylphenyl]-4-methyl-1,4-dihydrotetrazol-5-one (referred to as 44A).

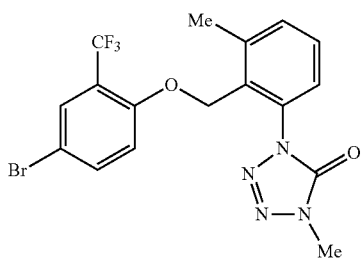

¹H-NMR (CDCl₃) δ: 7.67-7.64 (1H, m), 7.58-7.53 (1H, m), 7.47-7.38 (2H, m), 7.29 (1H, dd, J=7.4, 1.3Hz), 6.86 (1H, d, J=8.7Hz), 5.13 (2H, s), 3.68 (3H, s), 2.49 (3H, s).

Reference Production Example 45

While stirring a mixture of 7.33 g of 3-ethylphenol and 600 mL of chloroform under ice cooling at 0° C., 10.7 g of N-bromosuccinimide was added. After raising the temperature to room temperature and stirring for 2 hours, the reaction solution was concentrated under reduced pressure. The residue thus obtained was subjected to silica gel column chromatography to obtain 7.25 g of 4-bromo-3-ethylphenol (referred to as 45A).

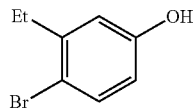

¹H-NMR (CDCl₃) δ: 7.37 (1H, d, J=8.2Hz), 6.90 (1H, d, J=2.1Hz), 6.69 (1H, dd, J=8.2, 2.1Hz), 5.48 (1H, s), 2.61 (2H, q, J=7.6Hz), 1.24 (3H, t, J=7.6Hz).

Reference Production Example 46

While stirring a mixture of 9.01 g of 3-tert-butylphenol and 600 mL of chloroform under ice cooling at 0° C., 10.7 g of N-bromosuccinimide was added. After raising the temperature to room temperature and stirring for 2 hours, the reaction solution was concentrated under reduced pressure. The residue thus obtained was subjected to silica gel column chromatography to obtain 7.59 g of 4-bromo-3-tert-butyl-phenol (referred to as 46A).

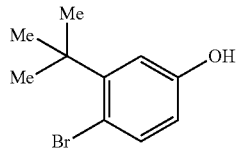

¹H-NMR (CDCl₃) δ: 7.39 (1H, d, J=8.5Hz), 7.09 (1H, d, J=2.3Hz), 6.88 (1H, dd, J=8.5, 2.3Hz), 5.48 (1H, s), 1.32 (9H, s).

Reference Production Example 47

A mixture of 2.83 g of 14A mentioned in Reference Production Example 14, 2.01 g of 45A mentioned in Reference Production Example 45, 2.76 g of potassium carbonate, and 40 mL of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure. The residue thus obtained was washed with hexane and methyl tert-butyl ketone to obtain 3.77 g of 1-[2-(4-bromo-3-ethylphenoxymethyl)-3-methylphenyl]-4-methyl-1,4-dihydrotetrazol-5-one (referred to as 47A).

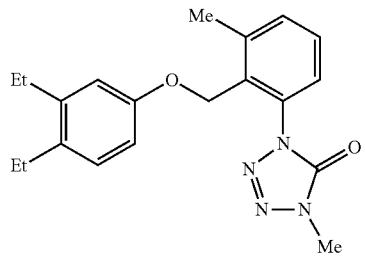 [SMILES: CCc1ccc(OCc2c(C)cccc2-n2nnn(C)c2=O)cc1CC]

¹H-NMR (CDCl₃) δ: 7.44-7.36 (3H, m), 7.28 (1H, dd, J=7.1, 2.1Hz), 6.70-6.66 (2H, m), 5.14 (2H, s), 3.68 (3H, s), 2.57 (2H, q, J=7.6Hz), 2.55 (3H, s), 1.20 (3H, t, J=7.6Hz).

Reference Production Example 48

A mixture of 2.83 g of 14A mentioned in Reference Production Example 14, 2.29 g of 46A mentioned in Reference Production Example 46, 2.76 g of potassium carbonate, and 40 mL of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure. The residue thus obtained was washed with hexane and methyl tert-butyl ketone to obtain 4.00 g of 1-[2-(4-bromo-3-tert-butylphenoxymethyl)-3-methylphenyl]-4-methyl-1,4-dihydrotetrazol-5-one (referred to as 48A).

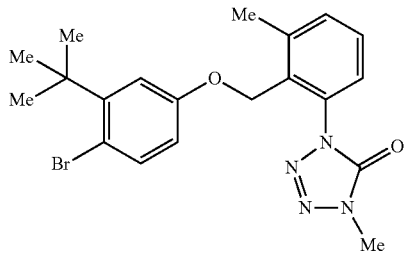 [SMILES: Cc1cccc(-n2nnn(C)c2=O)c1COc1ccc(Br)c(C(C)(C)C)c1]

¹H-NMR (CDCl₃) δ: 7.46-7.40 (3H, m), 7.33-7.30 (1H, m), 6.89 (1H, dd, J=8.4, 2.3Hz), 6.84 (1H, d, J=2.3Hz), 5.20 (2H, s), 3.71 (3H, s), 2.58 (3H, s), 1.28 (9H, s).

Reference Production Example 49

A mixture of 2.83 g of 14A mentioned in Reference Production Example 14, 2.01 g of 4-bromo-2,3-dimethylphenol, 2.76 g of potassium carbonate, and 40 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 1.08 g of 1-[2-(4-bromo-2,3-dimethylphenoxymethyl)-3-methylphenyl]-4-methyl-1,4-dihydrotetrazol-5-one (referred to as 49A).

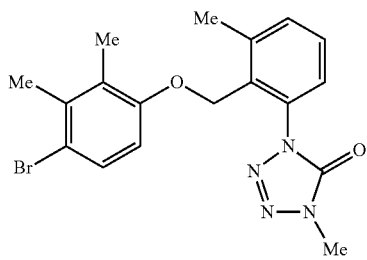 [SMILES: Cc1cccc(-n2nnn(C)c2=O)c1COc1ccc(Br)c(C)c1C]

¹H-NMR (CDCl₃) δ: 7.41-7.38 (2H, m), 7.22-7.17 (2H, m), 6.76 (1H, d, J=8.2Hz), 5.09 (2H, s), 3.63 (3H, s), 2.63 (3H, s), 2.14 (3H, s), 1.86 (3H, s).

Reference Production Example 50

A mixture of 2.23 g of 19-1A mentioned in Reference Production Example 19, 1.51 g of 4-bromo-2,5-dimethylphenol, 2.07 g of potassium carbonate, and 30 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 3.01 g of 1-[2-(4-bromo-2,5-dimethylphenoxymethyl)-3-ethylphenyl]-4-methyl-1,4-dihydrotetrazol-5-one (referred to as 50A).

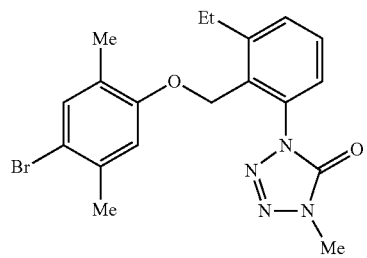 [SMILES: CCc1cccc(-n2nnn(C)c2=O)c1COc1cc(C)c(Br)cc1C]

¹H-NMR (CDCl₃) δ: 7.49-7.43 (2H, m), 7.29-7.26 (1H, m), 7.23 (1H, s), 6.70 (1H, s), 5.00 (2H, s), 3.61 (3H, s), 2.83 (2H, q, J=7.6Hz), 2.34 (3H, s), 2.00 (3H, s), 1.27 (3H, t, J=7.6Hz).

Reference Production Example 51

A mixture of 2.24 g of 7A mentioned in Reference Production Example 7, 1.51 g of 4-bromo-2,5-dimethylphenol, 2.07 g of potassium carbonate, and 30 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 3.02 g of 1-[2-(4-bromo-2,5-dimethylphenoxymethyl)-3-methoxyphenyl]-4-methyl-1,4-dihydrotetrazol-5-one (referred to as 51A).

¹H-NMR (CDCl₃) δ: 7.46 (1H, t, J=8.2Hz), 7.18 (1H, s), 7.09-7.05 (2H, m), 6.74 (1H, s), 5.21 (2H, s), 3.93 (3H, s), 3.60 (3H, s), 2.31 (3H, s), 1.92 (3H, s).

Reference Production Example 52

A mixture of 1.0 g of the present compound 93, 0.19 g of lithium hydroxide, 0.30 g of cesium fluoride, 5 mL of tetrahydrofuran, 5 mL of methanol, and 5 mL of water was stirred at room temperature for 8 hours. After concentrating under reduced pressure, the pH was adjusted to 7 or lower by 12 N hydrochloric acid. The precipitated solid was collected by filtration to obtain 0.64 g of 3-methyl-4-[2-methoxy-6-(4-methyl-5-oxo-4,5-dihydro-tetrazol-1-yl)-benzyloxy]-benzoic acid (referred to as 52A).

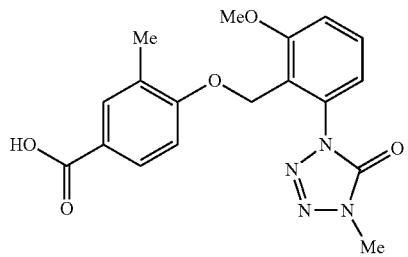 [SMILES: COc1cccc(-n2nnn(C)c2=O)c1COc1ccc(C(=O)O)cc1C]

¹H-NMR (CDCl₃) δ: 7.90 (1H, dd, J=8.6, 2.3Hz), 7.83-7.80 (1H, m), 7.48 (1H, t, J=8.2Hz), 7.13-7.06 (2H, m), 6.92 (1H, d, J=8.6Hz), 5.35 (2H, s), 3.94 (3H, s), 3.60 (3H, s), 2.02 (3H, s).

Reference Production Example 53

A mixture of 2.83 g of 14A mentioned in Reference Production Example 14, 2.09 g of 4-bromo-2,6-difluorophenol, 2.76 g of potassium carbonate, and 40 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 4.26 g of 1-[2-(4-bromo-2,6-difluorophenoxymethyl)-3-methylphenyl]-4-methyl-1,4-dihydrotetrazol-5-one (referred to as 53A).

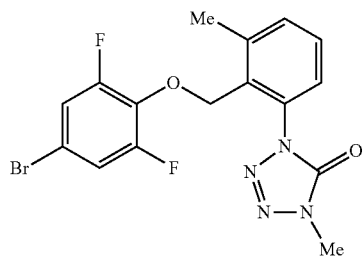 [SMILES: Cc1cccc(-n2nnn(C)c2=O)c1COc1c(F)cc(Br)cc1F]

¹H-NMR (CDCl₃) δ: 7.45-7.40 (2H, m), 7.25-7.21 (1H, m), 7.03 (2H, d, J=7.7Hz), 5.12 (2H, s), 3.72 (3H, s), 2.60 (3H, s).

Reference Production Example 54

A mixture of 2.83 g of 14A mentioned in Reference Production Example 14, 2.45 g of 4-bromo-2,3,5,6-tetrafluorophenol, 2.76 g of potassium carbonate, and 40 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 4.48 g of 1-[2-(4-bromo-2,3,5,6-tetrafluorophenoxymethyl)-3-methylphenyl]-4-methyl-1,4-dihydrotetrazol-5-one (referred to as 54A).

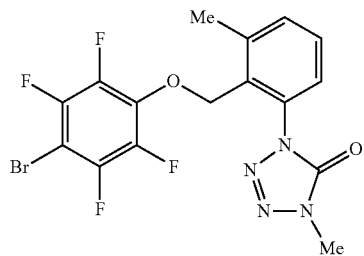 [SMILES: Cc1cccc(-n2nnn(C)c2=O)c1COc1c(F)c(F)c(Br)c(F)c1F]

¹H-NMR (CDCl₃) δ: 7.47-7.41 (2H, m), 7.24-7.21 (1H, m), 5.25 (2H, s), 3.72 (3H, s), 2.62 (3H, s).

Reference Production Example 55

A mixture of 2.83 g of A14 mentioned in Reference Production Example 14, 2.05 g of 4-bromo-5-fluoro-2-methylphenol, 2.76 g of potassium carbonate, and 40 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 3.98 g of 1-[2-(4-bromo-5-fluoro-2-methylphenoxymethyl)-3-methylphenyl]-4-methyl-1,4-dihydrotetrazol-5-one (referred to as 55A).

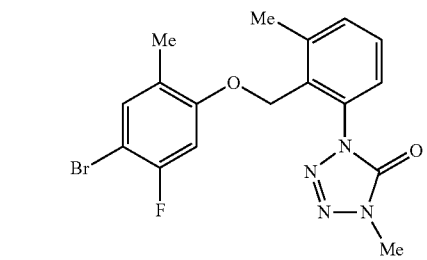 [SMILES: Cc1cc(Br)c(F)cc1OCc1c(C)cccc1-n1nnn(C)c1=O]

¹H-NMR (CDCl₃) δ: 2.02 (3H, s), 2.49 (3H, s), 3.65 (3H, s), 4.98 (2H, s), 6.65 (1H, d, J=10.2Hz), 7.23 (1H, dd, J=7.9, 0.7Hz), 7.29 (1H, dd, J=7.5, 1.7Hz), 7.41 (1H, dd, J=8.4, 1.8Hz), 7.41 (1H, t, J=7.5Hz).

Reference Production Example 56

A mixture of 8.06 g of 25A mentioned in Reference Production Example 25, 5.59 g of bis(pinacolato)diboron, 0.49 g of [1,1'-bis(diphenylphosphino)ferrocene]palladium (II) dichloride dichloromethane adduct, 5.89 g of potassium acetate, and 60 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 8.47 g of 1-[2-{4-(4,4,5,5-tetramethyl-[1,3,2]dioxaborolan-2-yl)-2,5-dimethylphenoxymethyl}-3-methylphenyl]-4-methyl-1,4-dihydrotetrazol-5-one (referred to as 56A).

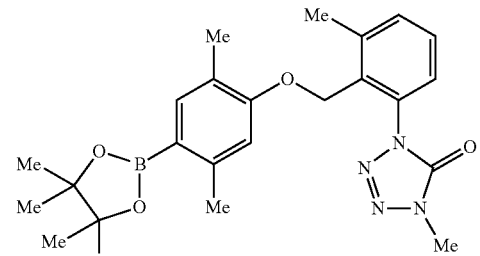

¹H-NMR (CDCl₃) δ: 7.51 (1H, s), 7.44-7.38 (2H, m), 7.29-7.25 (1H, m), 6.65 (1H, s), 5.03 (2H, s), 3.63 (3H, s), 2.51 (3H, s), 2.48 (3H, s), 2.03 (3H, s), 1.32 (12H, s).

Reference Production Example 57

While stirring a mixture of 5.40 g of 56A mentioned in Reference Production Example 56, 3.36 g of sodium hydroxide, 24 ml of tetrahydrofuran, and 12 mL of water under ice cooling at 0° C., 6.8 ml of a 30% hydrogen peroxide solution was added, followed by stirring at 0° C. for 1 hour. After raising the temperature to room temperature and further stirring for 4 hours, an aqueous saturated sodium thiosulfate solution was poured into the reaction mixture and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 3.01 g of 1-[2-(4-hydroxy-2,5-dimethylphenoxymethyl)-3-methylphenyl]-4-methyl-1,4-dihydrotetrazol-5-one (referred to as 57A).

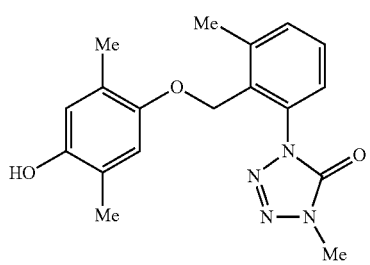
$^1$H-NMR (CDCl$_3$) δ: 7.44-7.37 (2H, m), 7.26-7.23 (1H, m), 6.58 (1H, s), 6.54 (1H, s), 4.95 (2H, s), 4.34 (1H, s), 3.65 (3H, s), 2.50 (3H, s), 2.19 (3H, s), 2.00 (3H, s).
In accordance with the process mentioned above, it is possible to obtain compounds Q1A-001 to Q11L-633.
The compounds Q1A-001 to Q11L-633 are tetrazolinone compounds represented by the following formulas: wherein Y is a substituent corresponding to each of substituent numbers 1 to 633:
(Q1A)
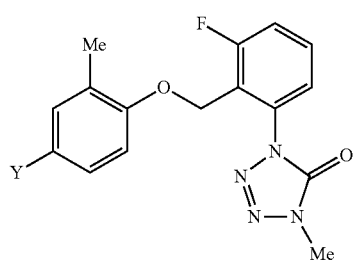
(Q1B)
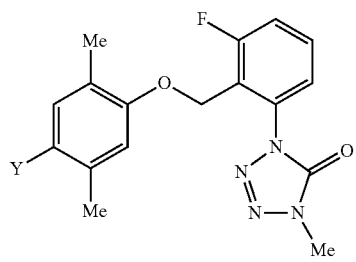
(Q1C)
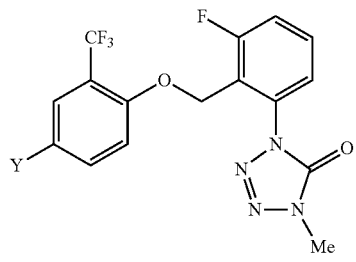
(Q1D)
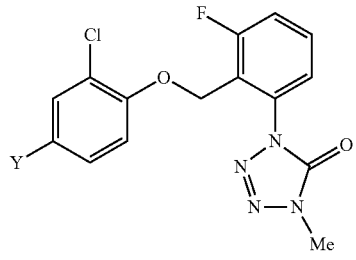
(Q1E)
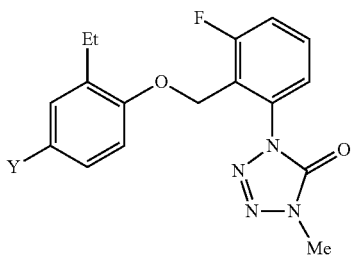
(Q1F)
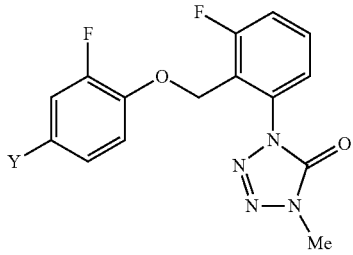
(Q1G)
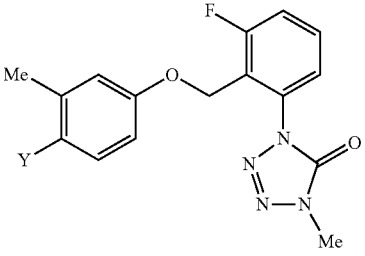
(Q1H)
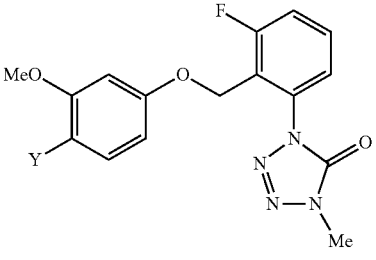
(Q1I)
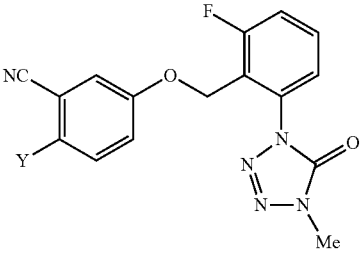
(Q1J)
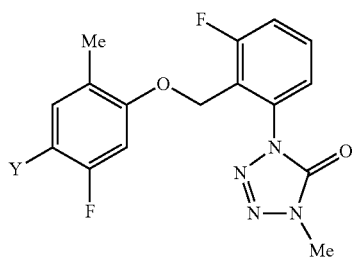

-continued
(Q1K) 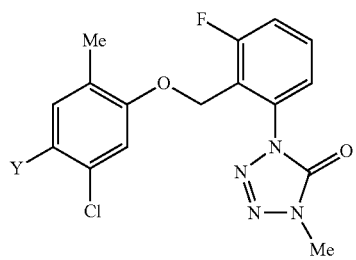
(Q1L) 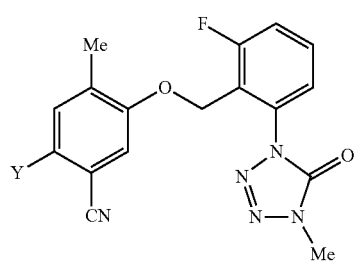
(Q2A) 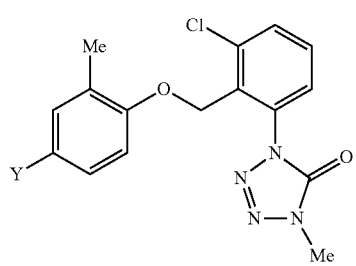
(Q2B) 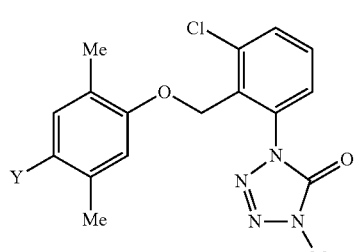
(Q2C) 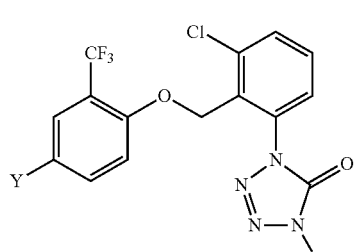
(Q2D) 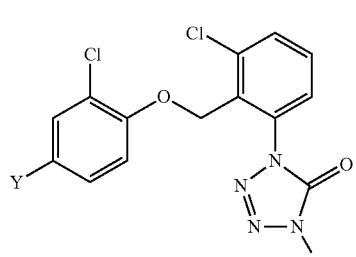
-continued
(Q2E) 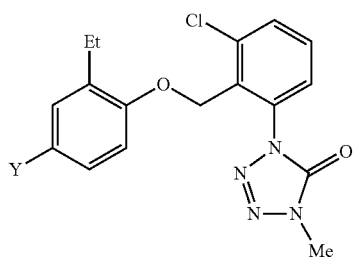
(Q2F) 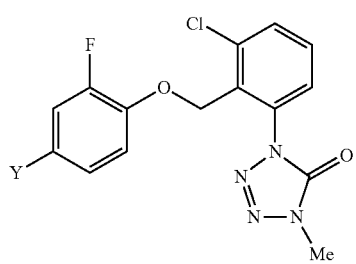
(Q2G) 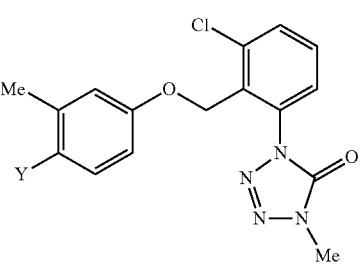
(Q2H) 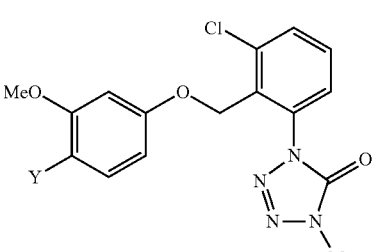
(Q2I) 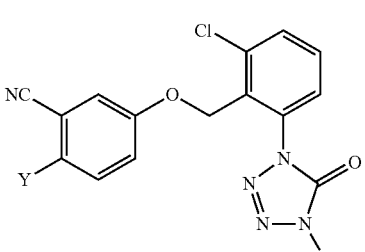
(Q2J) 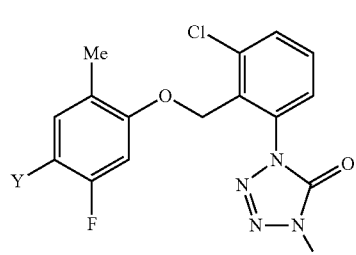

(Q2K) 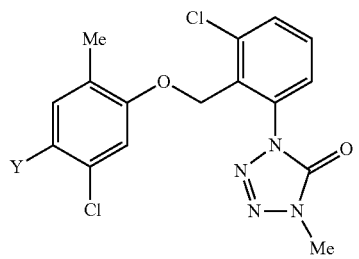
(Q2L) 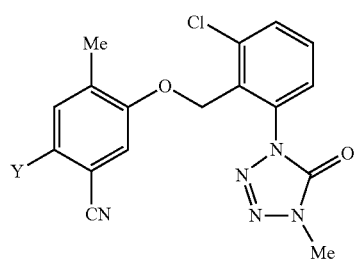
(Q3A) 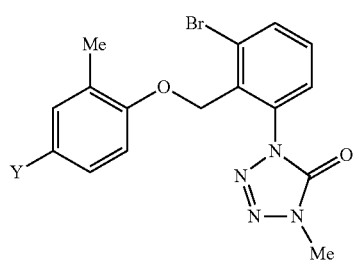
(Q3B) 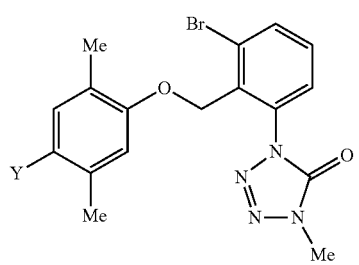
(Q3C) 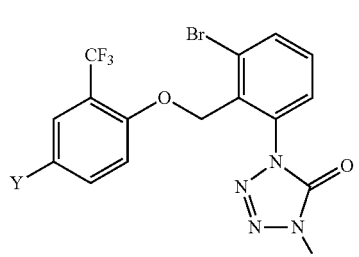
(Q3D) 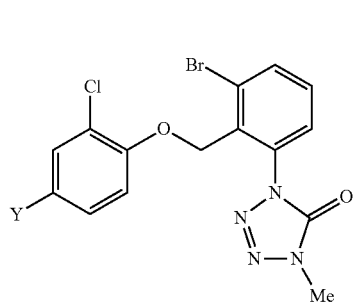
(Q3E) 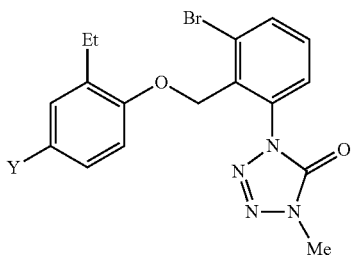
(Q3F) 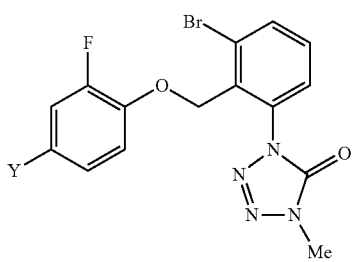
(Q3G) 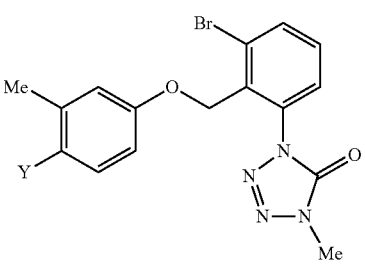
(Q3H) 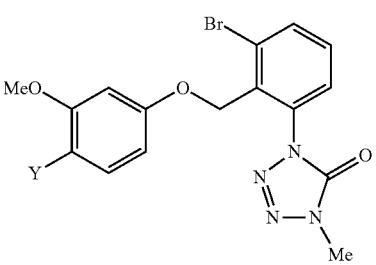
(Q3I) 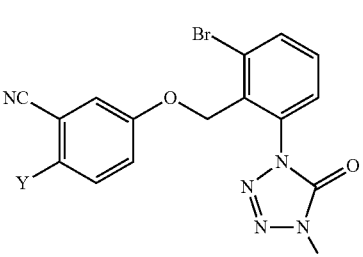
(Q3J) 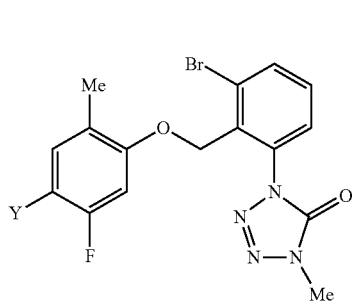

-continued
(Q3K)
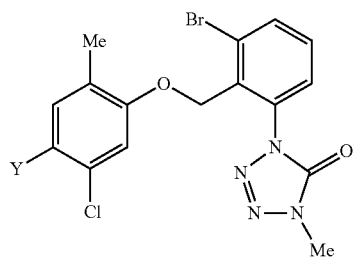
(Q3L)
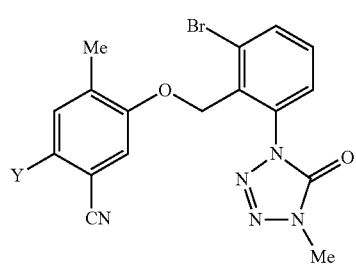
(Q4A)
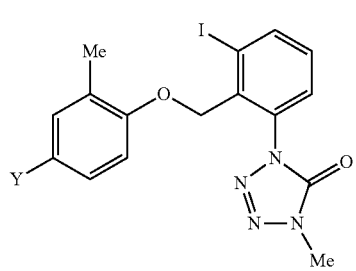
(Q4B)
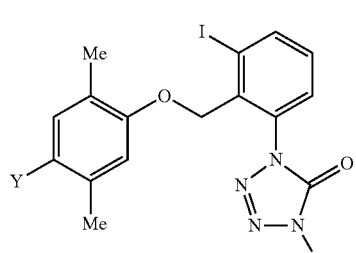
(Q4C)
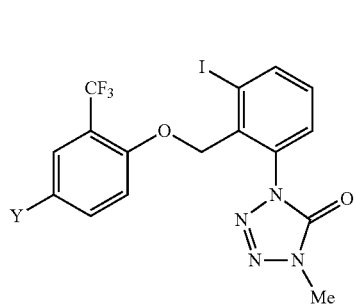
(Q4D)
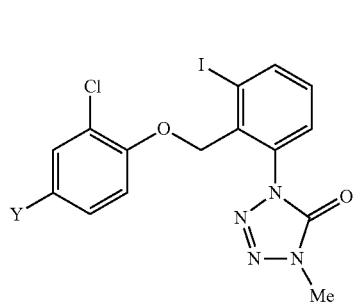
-continued
(Q4E)
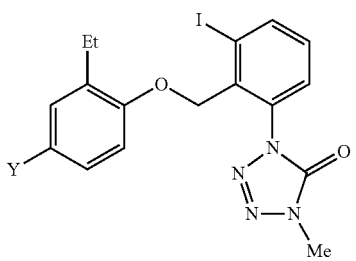
(Q4F)
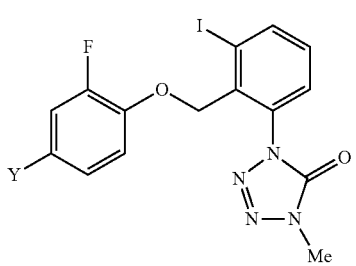
(Q4G)
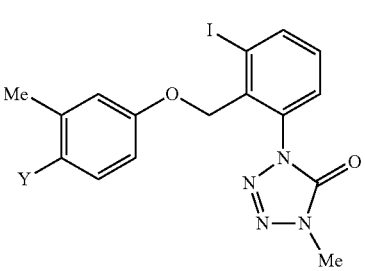
(Q4H)
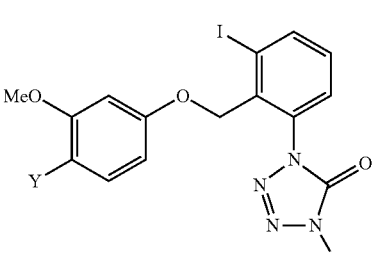
(Q4I)
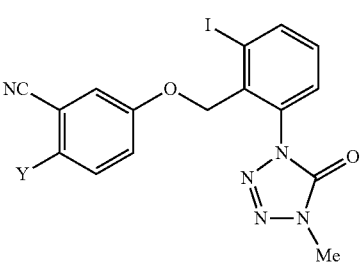
(Q4J)
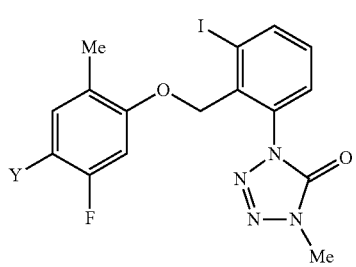

(Q4K)
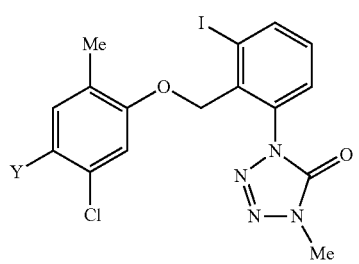
(Q4L)
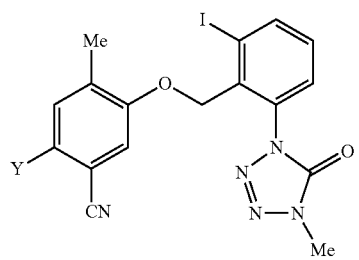
(Q5A)
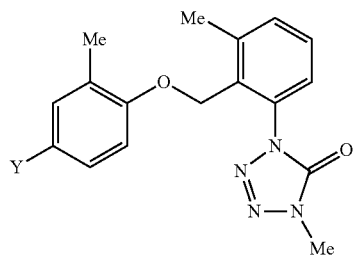
(Q5B)
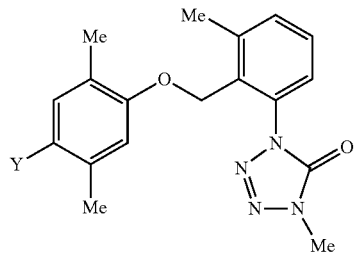
(Q5C)
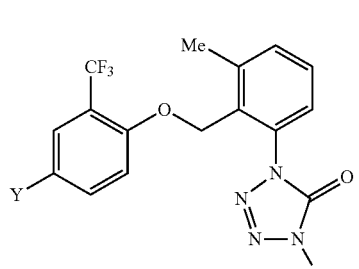
(Q5D)
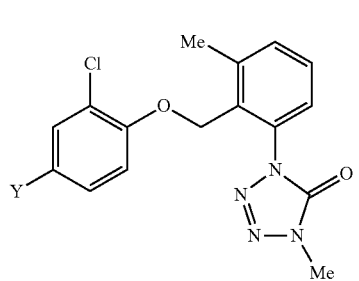
(Q5E)
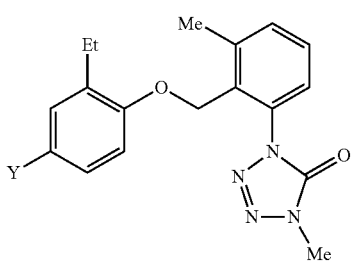
(Q5F)
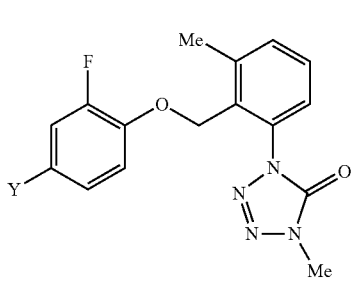
(Q5G)
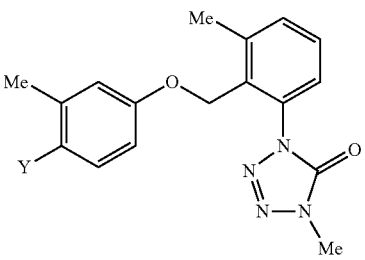
(Q5H)
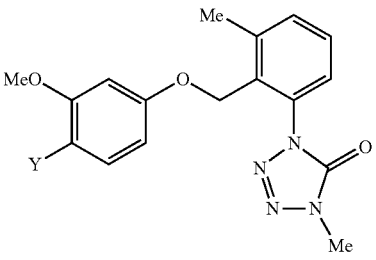
(Q5I)
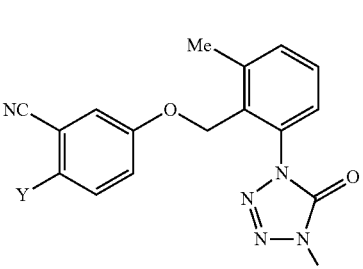
(Q5J)
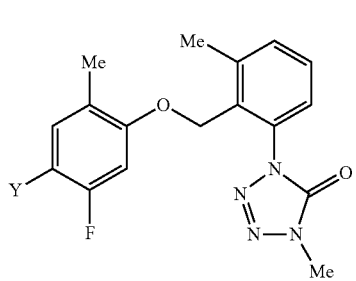

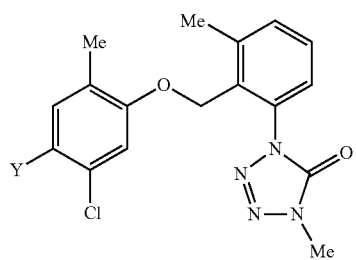 (Q5K)
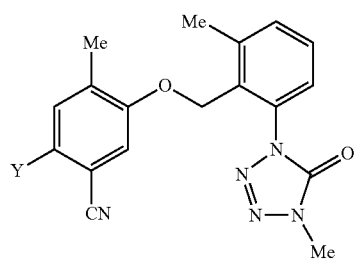 (Q5L)
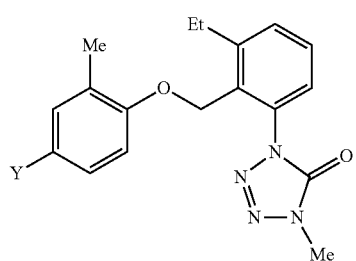 (Q6A)
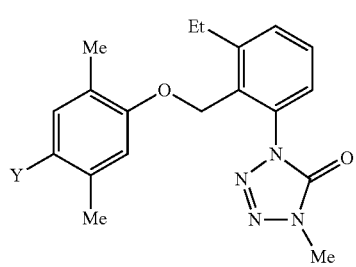 (Q6B)
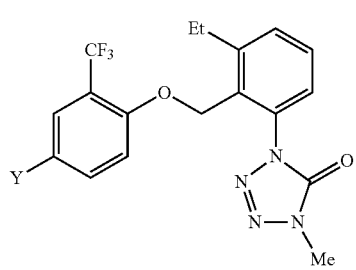 (Q6C)
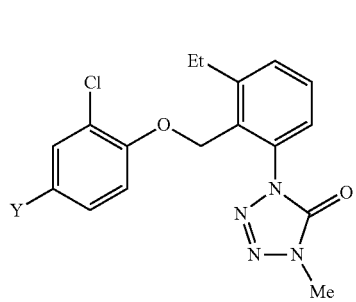 (Q6D)
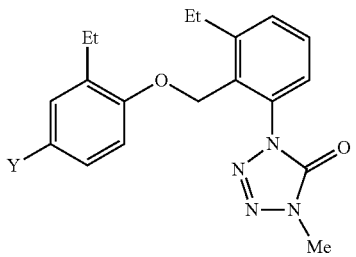 (Q6E)
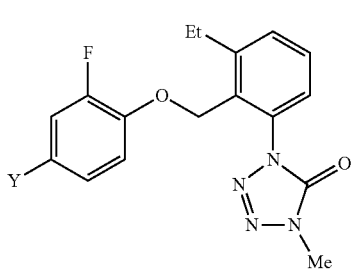 (Q6F)
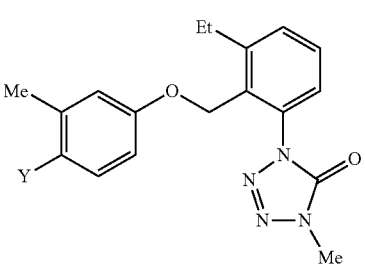 (Q6G)
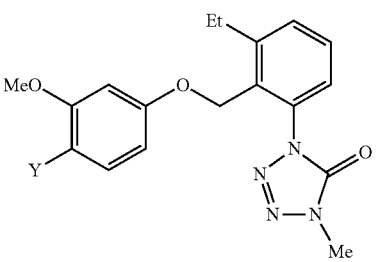 (Q6H)
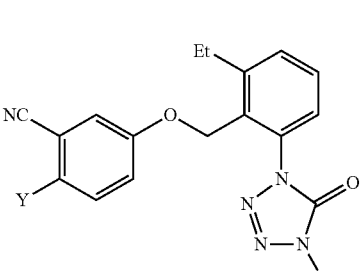 (Q6I)
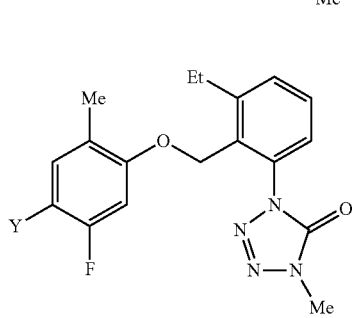 (Q6J)

(Q6K) 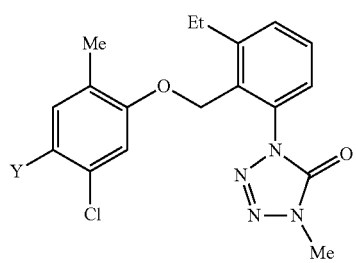
(Q6L) 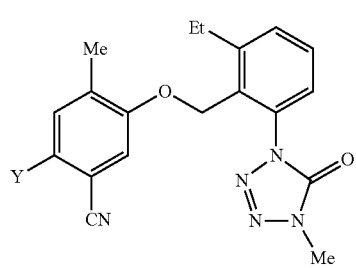
(Q7A) 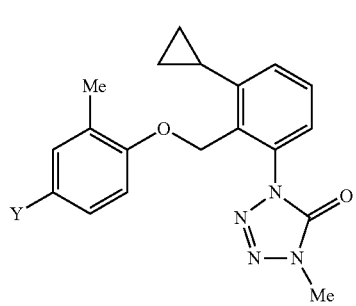
(Q7B) 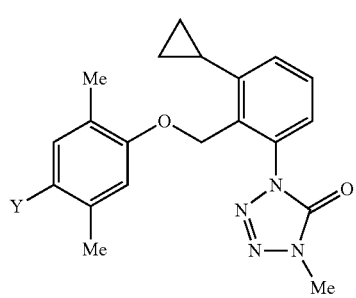
(Q7C) 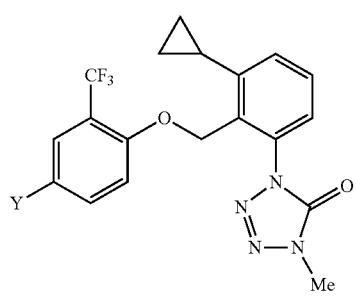
(Q7D) 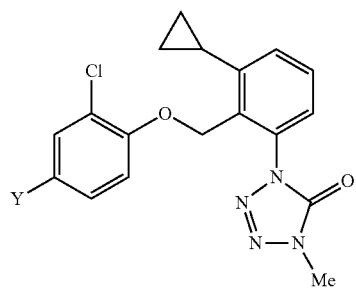
(Q7E) 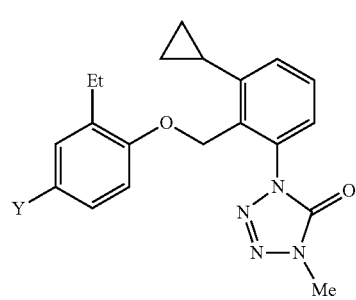
(Q7F) 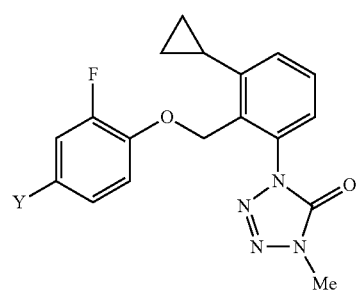
(Q7G) 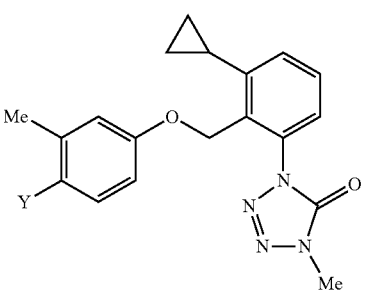
(Q7H) 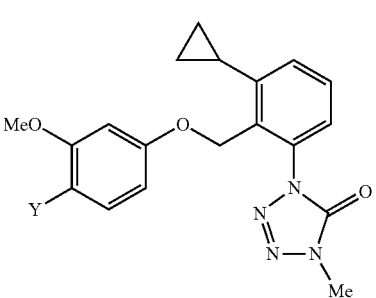

(Q7I) 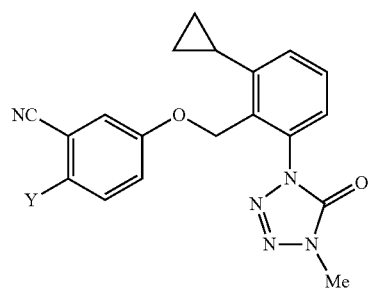
(Q7J) 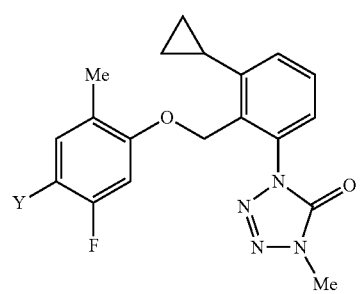
(Q7K) 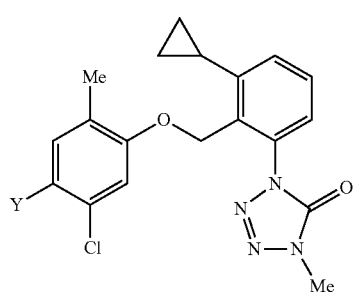
(Q7L) 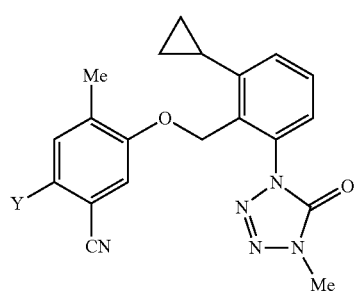
(Q8A) 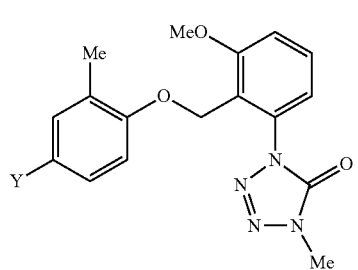
(Q8B) 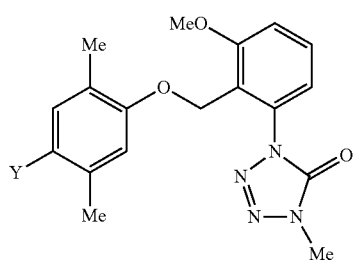
(Q8C) 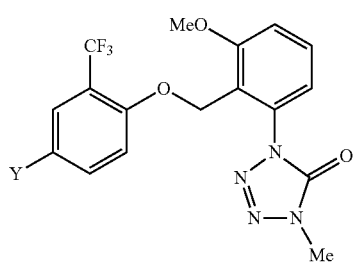
(Q8D) 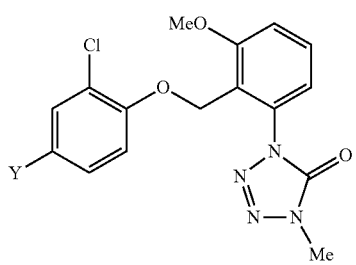
(Q8E) 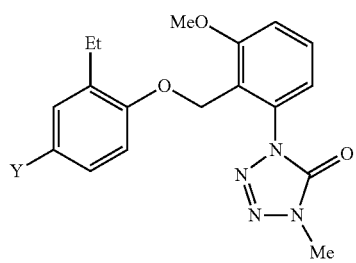
(Q8F) 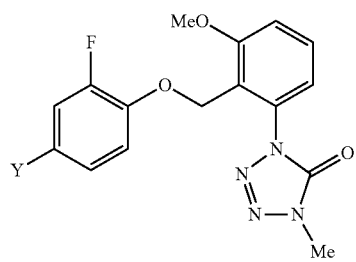
(Q8G) 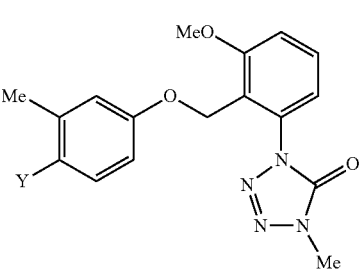

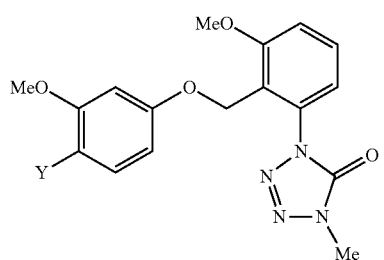 (Q8H)
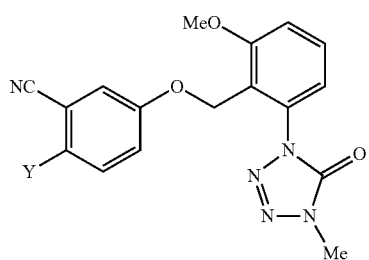 (Q8I)
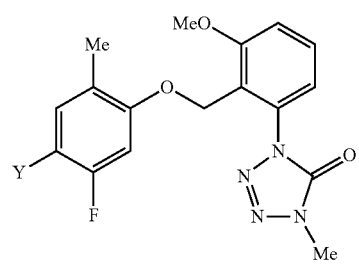 (Q8J)
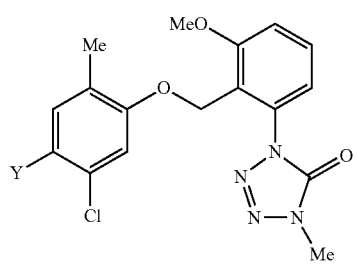 (Q8K)
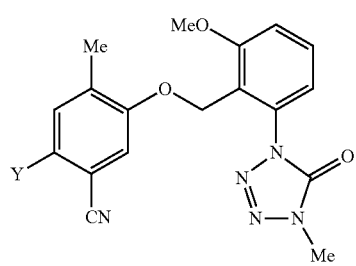 (Q8L)
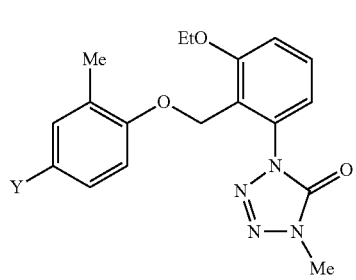 (Q9A)
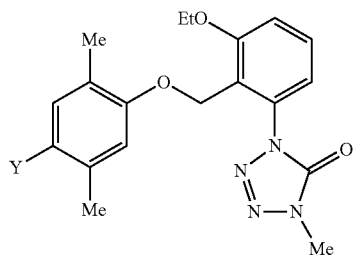 (Q9B)
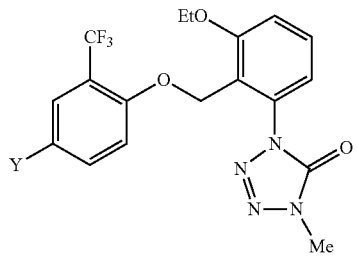 (Q9C)
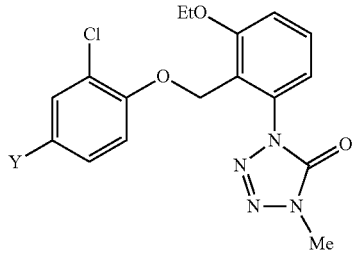 (Q9D)
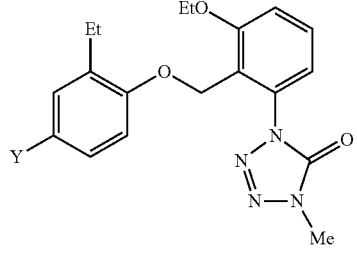 (Q9E)
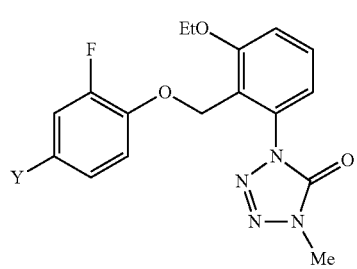 (Q9F)
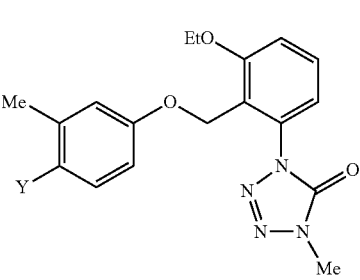 (Q9G)

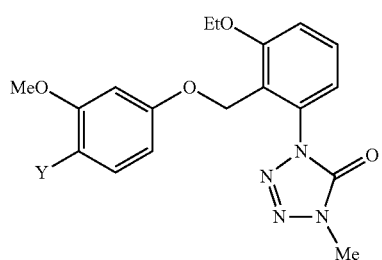
(Q9H)
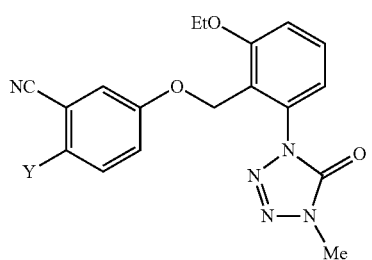
(Q9I)
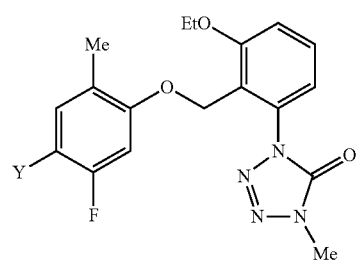
(Q9J)
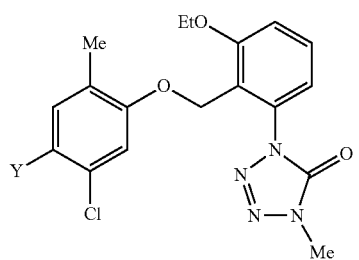
(Q9K)
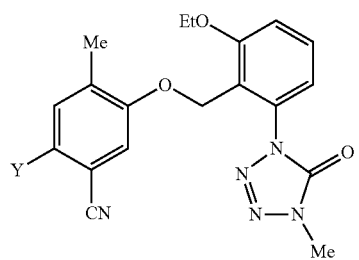
(Q9L)
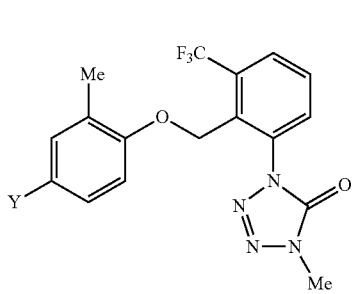
(Q10A)
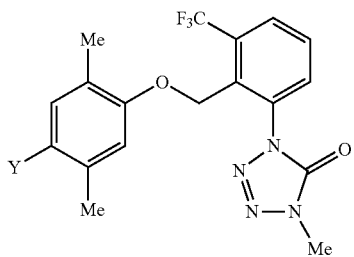
(Q10B)
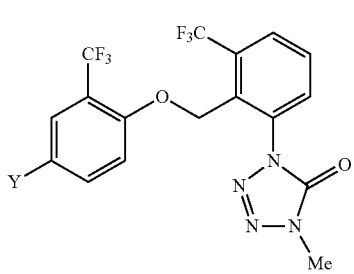
(Q10C)
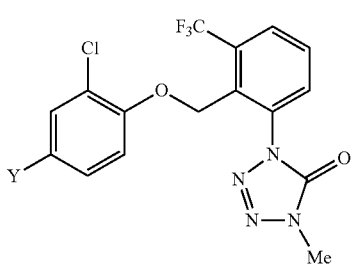
(Q10D)
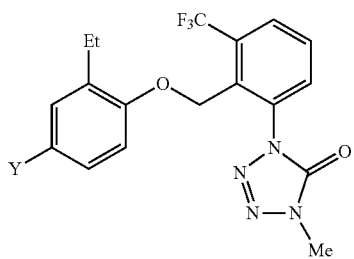
(Q10E)
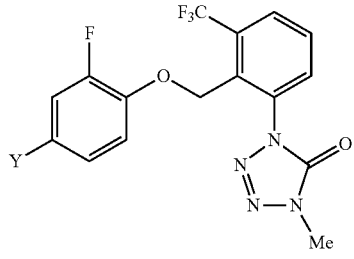
(Q10F)
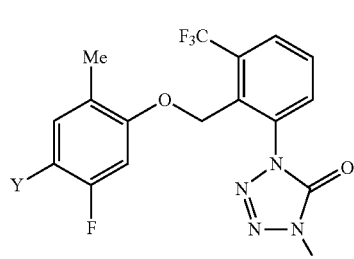
(Q11J)

(Q10K)
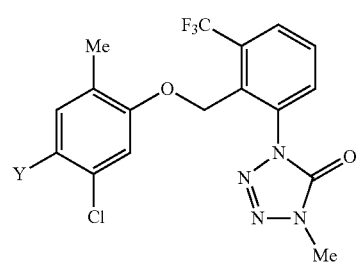
(Q10L)
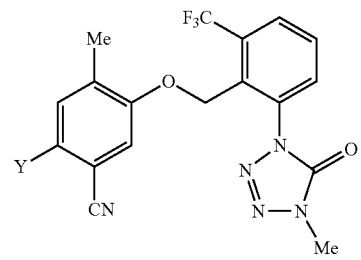
(Q11A)
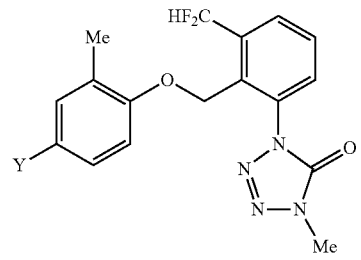
(Q11B)
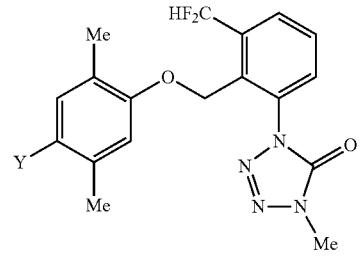
(Q11C)
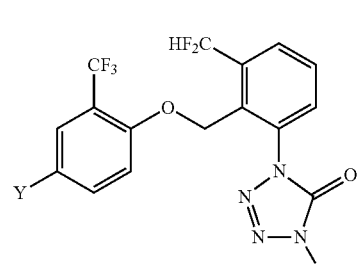
(Q11D)
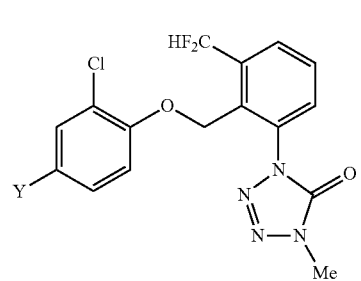
(Q11E)
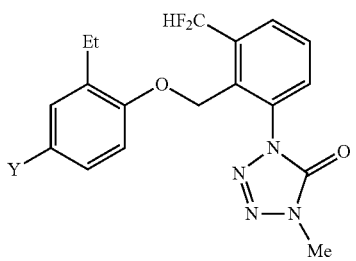
(Q11F)
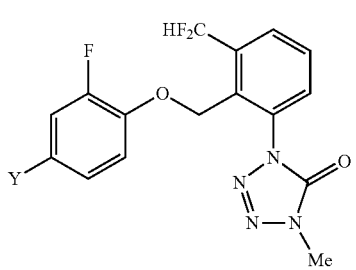
(Q11G)
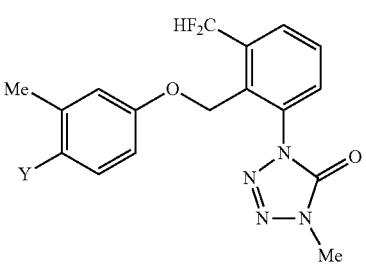
(Q11H)
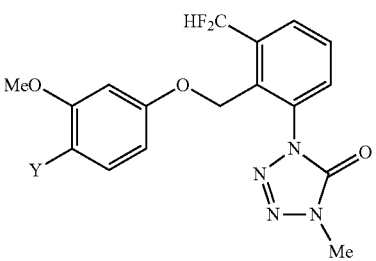
(Q11I)
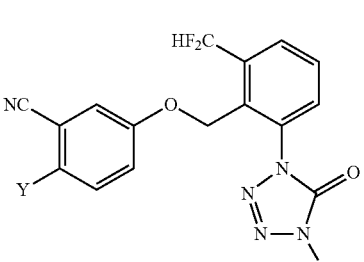
(Q11J)
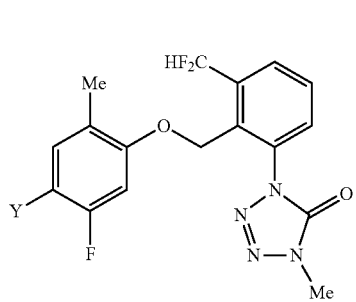

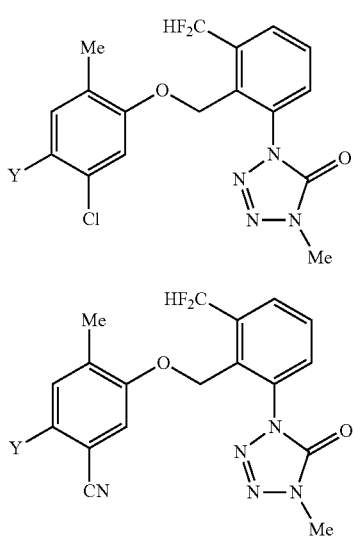

(Q11K)

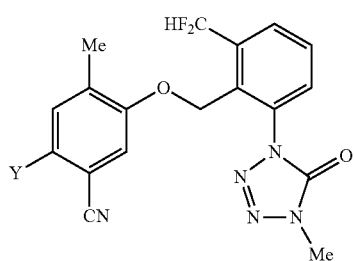

(Q11L)

[substituent number; Y], [1; phenyl group], [2; 2-fluorophenyl group], [3; 3-fluorophenyl group], [4; 4-fluorophenyl group], [5; 2,3-difluorophenyl group], [6; 2,4-difluorophenyl group], [7; 2,5-difluorophenyl group], [8; 2,6-difluorophenyl group], [9; 3,4-difluorophenyl group], [10; 3,5-difluorophenyl group], [11; 2,3,4-trifluorophenyl group], [12; 2,3,5-trifluorophenyl group], [13; 2,3,6-trifluorophenyl group], [14; 2,4,5-trifluorophenyl group], [15; 2,4,6-trifluorophenyl group][16; 3,4,5-trifluorophenyl group], [17; 2,3,4,6-tetrafluorophenyl group], [18; 2,3,5,6-tetrafluorophenyl group], [19; 2,3,4,5,6-pentafluorophenyl group], [20; 2-chlorophenyl group], [21; 3-chlorophenyl group], [22; 4-chlorophenyl group], [23; 2,3-dichlorophenyl group], [24; 2,4-dichlorophenyl group], [25; 2,5-dichlorophenyl group], [26; 2,6-dichlorophenyl group], [27; 3,4-dichlorophenyl group], [28; 3,5-dichlorophenyl group], [29; 2,3,4-trichlorophenyl group]

[substituent number; Y], [30; 2,3,5-trichlorophenyl group], [31; 2,3,6-trichlorophenyl group], [32; 2,4,5-trichlorophenyl group], [33; 2,4,6-trichlorophenyl group], [34; 3,4,5-trichlorophenyl group], [35; 2,3,4,6-tetrachlorophenyl group], [36; 2,3,5,6-tetrachlorophenyl group], [37; 2,3,4,5,6-pentachlorophenyl group], [38; 2-bromophenyl group], [39; 3-bromophenyl group], [40; 4-bromophenyl group], [41; 2,4-dibromophenyl group], [42; 2,5-dibromophenyl group], [43; 2,6-dibromophenyl group], [44; 2,4,6-tribromophenyl group], [45; 2,3,4,5,6-pentabromophenyl group], [46; 2-iodophenyl group], [47; 3-iodophenyl group], [48; 4-iodophenyl group], [49; 2,4-diiodophenyl group], [50; 2-chloro-3-fluorophenyl group], [51; 2-chloro-4-fluorophenyl group], [52; 2-chloro-5-fluorophenyl group], [53; 2-chloro-6-fluorophenyl group], [54; 2-chloro-3-bromophenyl group], [55; 2-chloro-4-bromophenyl group], [56; 2-chloro-5-bromophenyl group], [57; 2-chloro-6-bromophenyl group], [58; 2-bromo-3-chlorophenyl group]

[substituent number; Y], [59; 2-bromo-4-chlorophenyl group], [60; 2-bromo-5-chlorophenyl group], [61; 2-bromo-3-fluorophenyl group], [62; 2-bromo-4-fluorophenyl group], [63; 2-bromo-5-fluorophenyl group], [64; 2-bromo-6-fluorophenyl group], [65; 2-fluoro-3-chlorophenyl group], [66; 2-fluoro-4-chlorophenyl group], [67; 2-fluoro-5-chlorophenyl group], [68; 2-fluoro-4-bromophenyl group], [69; 3-chloro-4-fluorophenyl group], [70; 3-chloro-5-fluorophenyl group], [71; 3-chloro-4-bromophenyl group], [72; 3-chloro-5-bromophenyl group], [73; 3-fluoro-4-chlorophenyl group], [74; 3-fluoro-4-bromophenyl group], [75; 3-bromo-4-chlorophenyl group], [76; 3-bromo-4-fluorophenyl group], [77; 2,6-dichloro-4-bromophenyl group], [78; 2,3-difluoro-4-chlorophenyl group], [79; 2,6-difluoro-4-chlorophenyl group], [80; 2,5-difluoro-4-chlorophenyl group], [81; 3,5-difluoro-4-chlorophenyl group], [82; 2,3,5-trifluoro-4-chlorophenyl group], [83; 2,3,6-trifluoro-4-chlorophenyl group], [84; 2,3,5,6-tetrafluoro-4-chlorophenyl group], [85; 2,3-difluoro-4-bromophenyl group], [86; 2,6-difluoro-4-bromophenyl group], [87; 2,5-difluoro-4-bromophenyl group]

[substituent number; Y], [88; 3,5-difluoro-4-bromophenyl group], [89; 2,3,5-trifluoro-4-bromophenyl group], [90; 2,3,6-trifluoro-4-bromophenyl group], [91; 2,3,5,6-tetrafluoro-4-bromophenyl group], [92; 2-fluoro-4-iodophenyl group], [93; 3-fluoro-4-iodophenyl group], [94; 2,3-difluoro-4-iodophenyl group], [95; 2,6-difluoro-4-iodophenyl group], [96; 2,5-difluoro-4-iodophenyl group], [97; 3,5-difluoro-4-iodophenyl group], [98; 2,3,5-trifluoro-4-iodophenyl group], [99; 2,3,6-trifluoro-4-iodophenyl group], [100; 2,3,5,6-tetrafluoro-4-iodophenyl group], [101; 2-methylphenyl group], [102; 3-methylphenyl group], [103; 4-methylphenyl group], [104; 2,3-dimethylphenyl group], [105; 2,4-dimethylphenyl group], [106; 2,5-dimethylphenyl group], [107; 2,6-dimethylphenyl group], [108; 3,4-dimethylphenyl group], [109; 3,5-dimethylphenyl group], [110; 2,3,5-trimethylphenyl group], [111; 2,3,4-trimethylphenyl group], [112; 2,3,6-trimethylphenyl group], [113; 2,4,5-trimethylphenyl group], [114; 2,4,6-trimethylphenyl group], [115; 3,4,5-trimethylphenyl group], [116; 2,3,4,6-tetramethylphenyl group]

[substituent number; Y], [117; 2,3,5,6-tetramethylphenyl group], [118; 2,3,4,5,6-pentamethylphenyl group], [119; 2-ethylphenyl group], [120; 3-ethylphenyl group], [121; 4-ethylphenyl group], [122; 2,4-diethylphenyl group], [123; 2,6-diethylphenyl group], [124; 3,5-diethylphenyl group], [125; 2,4,6-triethylphenyl group], [126; 2-n-propylphenyl group], [127; 3-n-propylphenyl group], [128; 4-n-propylphenyl group], [129; 2-isopropylphenyl group], [130; 3-isopropylphenyl group], [131; 4-isopropylphenyl group], [132; 2,4-diisopropylphenyl group], [133; 2,6-diisopropylphenyl group], [134; 3,5-diisopropylphenyl group], [135; 2-s-butylphenyl group], [136; 3-s-butylphenyl group], [137; 4-s-butylphenyl group], [138; 2-t-butylphenyl group], [139; 3-t-butylphenyl group], [140; 4-t-butylphenyl group], [141; 4-n-butylphenyl group], [142; 4-n-nonylphenyl group], [143; 2-methyl-4-t-butylphenyl group], [144; 2-methyl-6-t-butylphenyl group], [145; 2-methyl-4-isopropylphenyl group]

[substituent number; Y], [146; 2-methyl-5-isopropylphenyl group], [147; 3-methyl-4-isopropylphenyl group], [148; 2-cyclopropylphenyl group], [149; 3-cyclopropylphenyl group], [150; 4-cyclopropylphenyl group], [151; 4-cyclobutylphenyl group], [152; 4-cyclopentylphenyl group], [153; 4-hydroxyl phenyl group], [154; 2-methoxyphenyl group], [155; 3-methoxyphenyl group], [156; 4-methoxyphenyl group], [157; 2-ethoxyphenyl group], [158; 3-ethoxyphenyl group], [159; 4-ethoxyphenyl group], [160; 2-n-propyloxyphenyl group], [161; 3-n-propyloxyphenyl group], [162; 4-n-propyloxyphenyl group], [163; 2-isopropyloxyphenyl group], [164; 3-isopropyloxyphenyl group], [165; 4-isopropyloxyphenyl group], [166; benzyl group], [167; 2-phenylethyl group], [168; benzyloxy group], [169; phenoxymethyl group], [170; phenoxyethyl group], [171; phenoxy group], [172; 2,3-dimethoxyphenyl group], [173; 2,4-dimethoxyphenyl group], [174; 2,5-dimethoxyphenyl group]

[substituent number; Y], [175; 2,6-dimethoxyphenyl group], [176; 3,4-dimethoxyphenyl group], [177; 3,5-dimethoxyphenyl group], [178; 2-t-butoxyphenyl group], [179; 3-t-butoxyphenyl group], [180; 4-t-butoxyphenyl group], [181; 2-trifluoromethoxyphenyl group], [182; 3-trifluoromethoxyphenyl group], [183; 4-trifluoromethoxyphenyl group], [184; 2-pentafluoroethoxyphenyl group], [185; 3-pentafluoroethoxyphenyl group], [186; 4-pentafluoroethoxyphenyl group], [187; N-methylanilino group], [188; N-ethylanilino group], [189; N-propylanilino group], [190; N-methyl-2-methylanilino group], [191; N-methyl-3-methylanilino group], [192; N-methyl-4-methylanilino group], [193; 2,3,6-trimethyl-4-fluorophenyl group], [194; 2,3,6-trimethyl-4-chlorophenyl group], [195; 2,3,6-trimethyl-4-bromophenyl group], [196; 2,4-dimethyl-6-fluorophenyl group], [197; 2,4-dimethyl-6-chlorophenyl group], [198; 2,4-dimethyl-6-bromophenyl group], [199; 2-isopropyl-4-chloro-5-methylphenyl group], [200; 2-methyl-5-isopropyl-4-chlorophenyl group], [201; 3-fluoro-2-methoxyphenyl group], [202; 4-fluoro-2-methoxyphenyl group], [203; 5-fluoro-2-methoxyphenyl group]

[substituent number; Y], [204; 6-fluoro-2-methoxyphenyl group], [205; 2-fluoro-3-methoxyphenyl group], [206; 4-fluoro-3-methoxyphenyl group], [207; 5-fluoro-3-methoxyphenyl group], [208; 6-fluoro-3-methoxyphenyl group], [209; 2-fluoro-4-methoxyphenyl group], [210; 3-fluoro-4-methoxyphenyl group], [211; 3,4-difluoro-2-methoxyphenyl group], [212; 3,5-difluoro-2-methoxyphenyl group], [213; 3,6-difluoro-2-methoxyphenyl group], [214; 4,5-difluoro-2-methoxyphenyl group], [215; 4,6-difluoro-2-methoxyphenyl group], [216; 5,6-difluoro-2-methoxyphenyl group], [217; 2,4-difluoro-3-methoxyphenyl group], [218; 2,5-difluoro-3-methoxyphenyl group], [219; 2,6-difluoro-3-methoxyphenyl group], [220; 4,5-difluoro-3-methoxyphenyl group], [221; 4,6-difluoro-3-methoxyphenyl group], [22132-difluoro-3-methoxyphenyl group], [223; 2,3-difluoro-4-methoxyphenyl group], [224; 2,5-difluoro-4-methoxyphenyl group], [225; 2,6-difluoro-4-methoxyphenyl group], [226; 3,5-difluoro-4-methoxyphenyl group], [227; 3,6-difluoro-4-methoxyphenyl group], [228; 2,3,5-trifluoro-4-methoxyphenyl group], [229; 2,3,5,6-tetrafluoro-4-methoxyphenyl group], [230; 3-chloro-2-methoxyphenyl group], [231; 4-chloro-2-methoxyphenyl group], [232; 5-chloro-2-methoxyphenyl group]

[substituent number; Y], [233; 6-chloro-2-methoxyphenyl group], [234; 2-chloro-3-methoxyphenyl group], [235; 4-chloro-3-methoxyphenyl group], [236; 5-chloro-3-methoxyphenyl group], [237; 6-chloro-3-methoxyphenyl group], [238; 2-chloro-4-methoxyphenyl group], [239; 3-chloro-4-methoxyphenyl group], [240; 3,4-dichloro-2-methoxyphenyl group], [241; 3,5-dichloro-2-methoxyphenyl group], [242; 3,6-dichloro-2-methoxyphenyl group], [243; 4,5-dichloro-2-methoxyphenyl group], [244; 4,6-dichloro-2-methoxyphenyl group], [245; 5,6-dichloro-2-methoxyphenyl group], [246; 2,4-dichloro-3-methoxyphenyl group], [247; 2,5-dichloro-3-methoxyphenyl group], [248; 2,6-dichloro-3-methoxyphenyl group], [249; 4,5-dichloro-3-methoxyphenyl group], [250; 4,6-dichloro-3-methoxyphenyl group], [251; 5,6-dichloro-3-methoxyphenyl group], [252; 2,3-dichloro-4-methoxyphenyl group], [253; 2,5-dichloro-4-methoxyphenyl group], [254; 2,6-dichloro-4-methoxyphenyl group], [255; 3,5-dichloro-4-methoxyphenyl group], [132; 3,6-dichloro-4-methoxyphenyl group], [257; 3-fluoro-2-trifluoromethoxyphenyl group], [258; 4-fluoro-2-trifluoromethoxyphenyl group], [259; 5-fluoro-2-trifluoromethoxyphenyl group], [260; 6-fluoro-2-trifluoromethoxyphenyl group], [261; 2-fluoro-3-trifluoromethoxyphenyl group]

[substituent number; Y], [262; 4-fluoro-3-trifluoromethoxyphenyl group], [263; 5-fluoro-3-trifluoromethoxyphenyl group], [264; 6-fluoro-3-trifluoromethoxyphenyl group], [265; 2-fluoro-4-trifluoromethoxyphenyl group], [266; 3-fluoro-4-trifluoromethoxyphenyl group], [267; 3,4-difluoro-2-trifluoromethoxyphenyl group], [268; 3,5-difluoro-2-trifluoromethoxyphenyl group], [269; 3,6-difluoro-2-trifluoromethoxyphenyl group], [270; 4,5-difluoro-2-trifluoromethoxyphenyl group], [271; 4,6-difluoro-2-trifluoromethoxyphenyl group], [27132-difluoro-2-trifluoromethoxyphenyl group], [273; 2,4-difluoro-3-trifluoromethoxyphenyl group], [274; 2,5-difluoro-3-trifluoromethoxyphenyl group], [275; 2,6-difluoro-3-trifluoromethoxyphenyl group], [276; 4,5-difluoro-3-trifluoromethoxyphenyl group], [277; 4,6-difluoro-3-trifluoromethoxyphenyl group], [278; 5,6-difluoro-3-trifluoromethoxyphenyl group], [279; 2,3-difluoro-4-trifluoromethoxyphenyl group], [280; 2,5-difluoro-4-trifluoromethoxyphenyl group], [281; 2,6-difluoro-4-trifluoromethoxyphenyl group], [282; 3,5-difluoro-4-trifluoromethoxyphenyl group], [283; 3,6-difluoro-4-trifluoromethoxyphenyl group], [284; 2,3,5-trifluoro-4-trifluoromethoxyphenyl group], [285; 2,3,5,6-tetrafluoro-4-trifluoromethoxyphenyl group], [286; 3-chloro-2-trifluoromethoxyphenyl group], [287; 4-chloro-2-trifluoromethoxyphenyl group], [288; 5-chloro-2-trifluoromethoxyphenyl group], [289; 6-chloro-2-trifluoromethoxyphenyl group], [290; 2-chloro-3-trifluoromethoxyphenyl group]

[substituent number; Y], [291; 4-chloro-3-trifluoromethoxyphenyl group], [292; 5-chloro-3-trifluoromethoxyphenyl group], [293; 6-chloro-3-trifluoromethoxyphenyl group], [294; 2-chloro-4-trifluoromethoxyphenyl group], [295; 3-chloro-4-trifluoromethoxyphenyl group], [296; 3,4-dichloro-2-trifluoromethoxyphenyl group], [297; 3,5-dichloro-2-trifluoromethoxyphenyl group], [298; 3,6-dichloro-2-trifluoromethoxyphenyl group], [299; 4,5-dichloro-2-trifluoromethoxyphenyl group], [300; 4,6-dichloro-2-trifluoromethoxyphenyl group], [301; 5,6-dichloro-2-trifluoromethoxyphenyl group], [302; 2,4-dichloro-3-trifluoromethoxyphenyl group], [303; 2,5-dichloro-3-trifluoromethoxyphenyl group], [304; 2,6-dichloro-3-trifluoromethoxyphenyl group], [305; 4,5-dichloro-3-trifluoromethoxyphenyl group], [306; 4,6-dichloro-3-trifluoromethoxyphenyl group], [307; 5,6-dichloro-3-trifluoromethoxyphenyl group], [308; 2,3-dichloro-4-trifluoromethoxyphenyl group], [309; 2,5-dichloro-4-trifluoromethoxyphenyl group], [310; 2,6-dichloro-4-trifluoromethoxyphenyl group], [311; 3,5-dichloro-4-trifluoromethoxyphenyl group], [312; 3,6-dichloro-4-trifluoromethoxyphenyl group], [313; N,N-dimethylamino group], [314; N,N-diethylamino group], [315; N-methyl-N-ethylamino group], [316; 2-(N-methylaminocarbonyl)phenyl group], [317; 3-(N-methylaminocarbonyl)phenyl group], [318; 4-(N-methylaminocarbonyl)phenyl group], [319; 2-(N,N-dimethylaminocarbonyl)phenyl group]

[substituent number; Y], [320; 3-(N,N-dimethylaminocarbonyl)phenyl group], [321; 4-(N,N-dimethylaminocarbonyl)phenyl group], [322; 2-methoxycarbonylphenyl group], [323; 3-methoxycarbonylphenyl group], [324; 4-methoxycarbonylphenyl group], [325; 4-acetoxyphenyl group], [326; 2-methoxymethylphenyl group], [327; 3-methoxymethylphenyl group], [328; 4-methoxymethylphenyl group], [329; methoxy group], [330; ethoxy group], [331; isobutyloxy group], [332; 2-methyl-5-bromophenyl group], [333; 2-methyl-6-bromophenyl group], [334; 2-chloro-3-methylphenyl group], [335; 2-chloro-4-methylphenyl group], [336; 2-chloro-5-methylphenyl group], [337; 2-fluoro-3-methylphenyl group], [338; 2-fluoro-4-methylphenyl group], [339; 2-fluoro-5-methylphenyl group], [340; 2-bromo-3-methylphenyl group], [341; 2-bromo-4-methylphenyl group], [342; 2-bromo-5-methylphenyl group], [343; 3-methyl-4-chlorophenyl group], [344; 3-methyl-5-chlorophenyl group], [345; 3-methyl-4-fluorophenyl group], [346; 3-methyl-5-fluorophenyl group], [347; 3-methyl-4-bromophenyl group], [348; 3-methyl-5-bromophenyl group]

[substituent number; Y], [349; 3-fluoro-4-methylphenyl group], [350; 3-chloro-4-methylphenyl group], [351; 3-bromo-4-methylphenyl group], [352; 2-chloro-4,5-dimethylphenyl group], [353; 2-bromo-4,5-dimethylphenyl group], [354; 2-chloro-3,5-dimethylphenyl group], [355; 2-bromo-3,5-dimethylphenyl group], [356; 2,6-dibromo-4-methylphenyl group], [357; 2,4-dichloro-6-methylphenyl group], [358; 2,4-difluoro-6-methylphenyl group], [359; 2,4-dibromo-6-methylphenyl group], [360; 2,6-dimethyl-4-fluorophenyl group], [361; 2,6-dimethyl-4-chlorophenyl group], [362; 2,6-dimethyl-4-bromophenyl group], [363; 3,5-dimethyl-4-fluorophenyl group], [364; 3,5-dimethyl-4-chlorophenyl group], [365; 3,5-dimethyl-4-bromophenyl group], [366; 2,3-difluoro-4-methylphenyl group], [367; 2,5-difluoro-4-methylphenyl group], [368; 3,5-difluoro-4-methylphenyl group], [369; 2,3,5-trifluoro-4-methylphenyl group], [370; 2,3,6-trifluoro-4-methylphenyl group], [371; 2,3,5,6-tetrafluoro-4-methylphenyl group], [372; 2-fluoro-4-ethylphenyl group], [373; 3-fluoro-4-ethylphenyl group], [374; 2,3-difluoro-4-ethylphenyl group], [375; 2,6-difluoro-4-ethylphenyl group], [376; 2,5-difluoro-4-ethylphenyl group], [377; 3,5-difluoro-4-ethylphenyl group]

[substituent number; Y], [378; 2,3,5-trifluoro-4-ethylphenyl group], [379; 2,3,6-trifluoro-4-ethylphenyl group], [380; 2,3,5,6-tetrafluoro-4-ethylphenyl group], [381; 2-trifluoromethylphenyl group], [382; 3-trifluoromethylphenyl group], [383; 4-trifluoromethylphenyl group], [384; 4-(2,2,2-trifluoro-1-trifluoromethyl-ethyl)phenyl group], [385; 4-(2,2-difluoroethoxy)phenyl group], [386; 4-(2,2,2-trifluoroethoxy)phenyl group], [387; 2-cyanophenyl group], [388; 3-cyanophenyl group], [389; 4-cyanophenyl group], [390; 2-cyano-4-methylphenyl group], [391; 3-cyano-2-methylphenyl group], [392; 4-cyano-2-methylphenyl group], [393; 2-methyl-3-chlorophenyl group], [394; 2-methyl-4-chlorophenyl group], [395; 2-methyl-5-chlorophenyl group], [396; 2-methyl-6-chlorophenyl group], [397; 2-methyl-3-fluorophenyl group], [398; 2-methyl-4-fluorophenyl group], [399; 2-methyl-5-fluorophenyl group], [400; 2-methyl-6-fluorophenyl group], [401; 2-methyl-3-bromophenyl group], [402; 2-methyl-4-bromophenyl group], [403; 4-methylthiophenyl group], [404; 4-methylsulfonyl phenyl group], [405; 4-methylsulfinylphenyl group], [406; 4-trifluoromethylthiophenyl group]

[substituent number; Y], [407; 4-ethynylphenyl group], [408; 4-(1-propynyl)phenyl group], [409; 4-vinylphenyl group], [410; 4-(2,2-dichlorovinyl)phenyl group], [411; 4-(2,2-difluorovinyl)phenyl group], [412; cyclohexyl group], [413; 2-chlorocyclohexyl group], [414; 3-chlorocyclohexyl group], [415; 4-chlorocyclohexyl group], [416; 4,4-dichlorocyclohexyl group], [417; 2-bromocyclohexyl group], [418; 3-bromocyclohexyl group], [419; 4-bromocyclohexyl group], [420; 4,4-dibromocyclohexyl group], [421; 2-iodocyclohexyl group], [422; 3-iodocyclohexyl group], [423; 4-iodocyclohexyl group], [424; 2-fluorocyclohexyl group], [425; 3-fluorocyclohexyl group], [426; 4-fluorocyclohexyl group], [427; 4,4-difluorocyclohexyl group], [428; 4-methylcyclohexyl group], [429; 4-ethylcyclohexyl group], [430; 4-methoxycyclohexyl group], [431; 4-ethoxycyclohexyl group], [432; 4-trifluoromethoxycyclohexyl group], [433; 1-cyclohexenyl group], [434; 2-cyclohexenyl group], [435; 3-cyclohexenyl group]

[substituent number; Y], [436; 4-fluoro-1-cyclohexenyl group], [437; 4-fluoro-2-cyclohexenyl group], [438; 4-fluoro-3-cyclohexenyl group], [439; 2-chloro-1-cyclohexenyl group], [440; 3-chloro-1-cyclohexenyl group], [441; 4-chloro-1-cyclohexenyl group], [442; 5-chloro-1-cyclohexenyl group], [443; 6-chloro-1-cyclohexenyl group], [444; 1-chloro-2-cyclohexenyl group], [445; 2-chloro-2-cyclohexenyl group], [446; 3-chloro-2-cyclohexenyl group], [447; 4-chloro-2-cyclohexenyl group], [448; 5-chloro-2-cyclohexenyl group], [449; 6-chloro-2-cyclohexenyl group], [450; 1-chloro-3-cyclohexenyl group], [451; 2-chloro-3-cyclohexenyl group], [452; 3-chloro-3-cyclohexenyl group], [453; 4-chloro-3-cyclohexenyl group], [454; 5-chloro-3-cyclohexenyl group], [455; 6-chloro-3-cyclohexenyl group], [456; 4-bromo-1-cyclohexenyl group], [457; 4-bromo-2-cyclohexenyl group], [458; 4-bromo-3-cyclohexenyl group], [459; 4-methyl-1-cyclohexenyl group], [460; 4-methyl-2-cyclohexenyl group], [461; 4-methyl-3-cyclohexenyl group], [462; 4-ethyl-1-cyclohexenyl group], [463; 4-ethyl-2-cyclohexenyl group], [464; 4-ethyl-3-cyclohexenyl group]

[substituent number; Y], [465; 4-methoxy-1-cyclohexenyl group], [466; 4-methoxy-2-cyclohexenyl group], [467; 4-trifluoromethoxy-1-cyclohexenyl group], [468; 4-trifluoromethoxy-2-cyclohexenyl group], [469; 2-fluorophenoxy group], [470; 3-fluorophenoxy group], [471; 4-fluorophenoxy group], [472; 2-chlorophenoxy group], [473; 3-chlorophenoxy group], [474; 4-chlorophenoxy group], [475; 2-bromophenoxy group], [476; 3-bromophenoxy group], [477; 4-bromophenoxy group], [478; 2-iodophenoxy group], [479; 3-iodophenoxy group], [480; 4-iodophenoxy group], [481; 2-methylphenoxy group], [482; 3-methylphenoxy group], [483; 4-methylphenoxy group], [484; 2-pyrimidyloxy group], [485; 3-pyridazinyloxy group], [486; 2-pyridyloxy group], [487; 3-pyridyloxy group], [488; 4-pyridyloxy group], [489; 5-methoxy-2-pyridyloxy group], [490; 5-trifluoromethoxy-2-pyridyloxy group], [491; 5-fluoro-2-pyridyloxy group], [492; 5-chloro-2-pyridyloxy group], [493; 6-methoxy-3-pyridyloxy group]

[substituent number; Y], [494; 6-trifluoromethoxy-3-pyridyloxy group], [495; 6-fluoro-3-pyridyloxy group], [496; 6-chloro-3-pyridyloxy group], [497; 5-methoxy-2-pyrazinyloxy group], [498; 5-trifluoromethoxy-2-pyrazinyloxy group], [499; 5-fluoro-2-pyrazinyloxy group], [500; 5-chloro-2-pyrazinyloxy group], [501; 5-methoxy-2-pyrimidinyloxy group], [502; 5-trifluoromethoxy-2-pyrimidinyloxy group], [503; 5-fluoro-2-pyrimidinyloxy group], [504; 5-chloro-2-pyrimidinyloxy group], [505; 6-methoxy-3-pyridazinyloxy group], [506; 6-trifluoromethoxy-3-pyridazinyloxy group], [507; 6-fluoro-3-pyridazinyloxy group], [508; 6-chloro-3-pyridazinyloxy group], [509; 1-naphthyloxy group], [510; 2-naphthyloxy group], [511; 2-quinolyloxy group], [512; 3-quinolyloxy group], [513; 4-quinolyloxy group], [514; 5-quinolyloxy group], [515; 6-quinolyloxy group], [516; 7-quinolyloxy group], [517; 8-quinolyloxy group], [518; 3-isoquinolyloxy group], [519; 6-isoquinolyloxy group], [520; 7-isoquinolyloxy group], [521; 2-pyrazinyloxy group]

[substituent number; Y], [522; 2-ethylphenoxy group], [523; 3-ethylphenoxy group], [524; 4-ethylphenoxy group],

[525; 2-propylphenoxy group], [526; 3-propylphenoxy group], [527; 4-propylphenoxy group], [528; 2,3-difluorophenoxy group], [529; 2,4-difluorophenoxy group], [530; 2,5-difluorophenoxy group], [531; 2,6-difluorophenoxy group], [532; 3,4-difluorophenoxy group], [533; 3,5-difluorophenoxy group], [534; 2,3-dichlorophenoxy group], [535; 2,4-dichlorophenoxy group], [536; 2,5-dichlorophenoxy group], [537; 2,6-dichlorophenoxy group], [538; 3,4-dichlorophenoxy group], [539; 3,5-dichlorophenoxy group], [540; 2,3-dimethylphenoxy group], [541; 2,4-dimethylphenoxy group], [542; 2,5-dimethylphenoxy group], [543; 2,6-dimethylphenoxy group], [544; 3,4-dimethylphenoxy group], [545; 3,5-dimethylphenoxy group], [546; 2-methyl-3-fluorophenoxy group], [547; 2-methyl-4-fluorophenoxy group], [548; 2-methyl-5-fluorophenoxy group], [549; 2-fluoro-4-methylphenoxy group], [550; 2-chloro-4,5-difluorophenoxy group]

[substituent number; Y], [550; 2-cyano-3-methylphenoxy group], [551; 2-cyano-4-methylphenoxy group], [552; 2-cyano-5-methylphenoxy group], [553; 2-cyano-6-methylphenoxy group], [554; 2-cyano-3-fluorophenoxy group], [555; 2-cyano-4-fluorophenoxy group], [556; 2-cyano-5-fluorophenoxy group], [557; 2-cyano-6-fluorophenoxy group], [558; 3-cyano-2-methylphenoxy group], [559; 3-cyano-4-methylphenoxy group], [560; 3-cyano-5-methylphenoxy group], [561; 3-cyano-6-methylphenoxy group], [562; 4-cyano-2-methylphenoxy group], [563; 4-cyano-3-methylphenoxy group], [564; 4-cyano-5-methylphenoxy group], [565; 4-cyano-6-methylphenoxy group], [566; methoxymethyl group], [567; ethoxymethyl group], [568; isopropoxymethyl group], [569; methyl-ethoxy-methyl group], [570; methyl-isopropoxy-methyl group], [571; ethyl-ethoxy-methyl group], [572; methoxycarbonyl group], [573; ethoxycarbonyl group], [574; propoxycarbonyl group], [575; methylcarbonyloxy group], [576; ethylcarbonyloxy group], [577; propylcarbonyloxy group], [578; trimethylsilyl group]

[substituent number; Y], [578; phenylthio group], [579; 2-methylphenylthio group], [580; 3-methylphenylthio group], [581; 4-methylphenylthio group], [582; 2-chlorophenylthio group], [583; 3-chlorophenylthio group], [584; 4-chlorophenylthio group], [585; 2-cyanophenylthio group], [586; 3-cyanophenylthio group], [587; 4-cyanophenylthio group], [588; ethylthiomethyl group], [589; isopropylthiomethyl group], [590; methyl-ethylthiomethyl group], [591; $(CH_3)_2N-N=CH-$], [592; $(CH_3CH_2)_2N-N=CH-$], [593; $(CH_3)_2N-C=N-$], [594; $CH_3CH_2N(CH_3)-C=N-$], [595; $CH_3CH_2CH_2N(CH_3)-C=N-$], [596; $CH_3CH_2CH_2CH_2N(CH_3)-C=N-$], [597; $(CH_3CH_2)_2N-C=N-$], [598; N,N-dimethylaminocarbonyl group], [599; N,N-diethylaminocarbonyl group], [600; N-methyl-N-ethylaminocarbonyl group], [601; methylcarbonylamino group], [602; methylcarbonyl-N-methylamino group], [603; ethylcarbonyl-N-methylamino group], [604; methylsulfonyl group], [605; ethylsulfonyl group], [606; propylsulfonyl group]

[substituent number; Y], [606; methylsulfinyl group], [607; ethylsulfinyl group], [608; propylsulfinyl group], [609; hydroxy-phenyl-methyl group], [610; methoxy-phenyl-methyl group], [611; ethoxy-phenyl-methyl group], [612; 3-pyrazolyloxy group], [613; 1-methyl-3-pyrazolyloxy group], [614; 1,4-dimethyl-3-pyrazolyloxy group], [615; 1,5-dimethyl-3-pyrazolyloxy group], [616; 1,4,5-trimethyl-3-pyrazolyloxy group], [617; 2-imidazolyloxy group], [618; 1-methyl-2-imidazolyloxy group], [619; 2-thiazolyloxy group], [620; 4-methyl-2-thiazolyloxy group], [621; 5-methyl-2-thiazolyloxy group], [622; 2-oxazolyloxy group], [623; 4-methyl-2-oxazolyloxy group], [624; 5-methyl-2-oxazolyloxy group], [625; 3-furyloxy group], [626; 3-thiophenoxy group], [627; 4-pyrazolyloxy group], [628; 4-thiazolyloxy group], [629; 5-thiazolyloxy group], [630; 4-oxazolyloxy group], [631; 5-oxazolyloxy group], [632; 2-benzothiazolyloxy group], [633; 2-benzooxazolyloxy group]

In accordance with the process mentioned above, it is possible to obtain compounds EB1A-001 to EG1N-342.

The compounds EB1A-001 to EG1N-342 are tetrazolinone compounds represented by the following formulas:

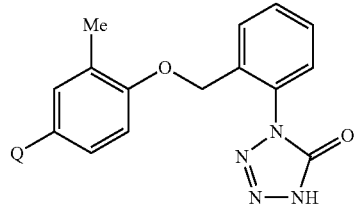
(EB1A)

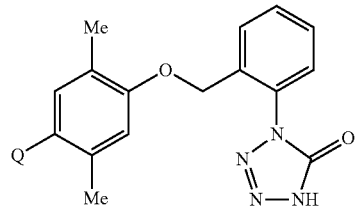
(EB1B)

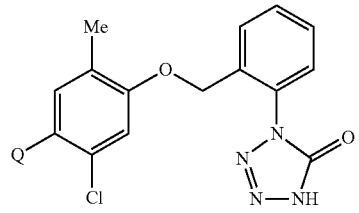
(EB1C)

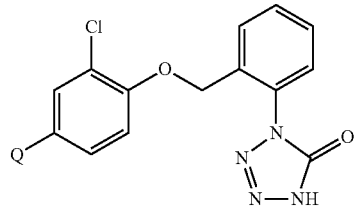
(EB1D)

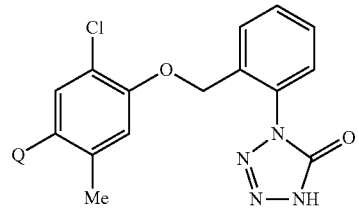
(EB1E)

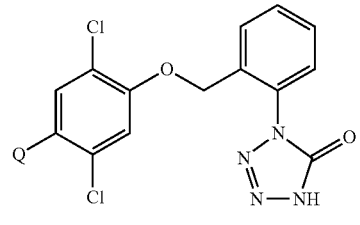
(EB1F)

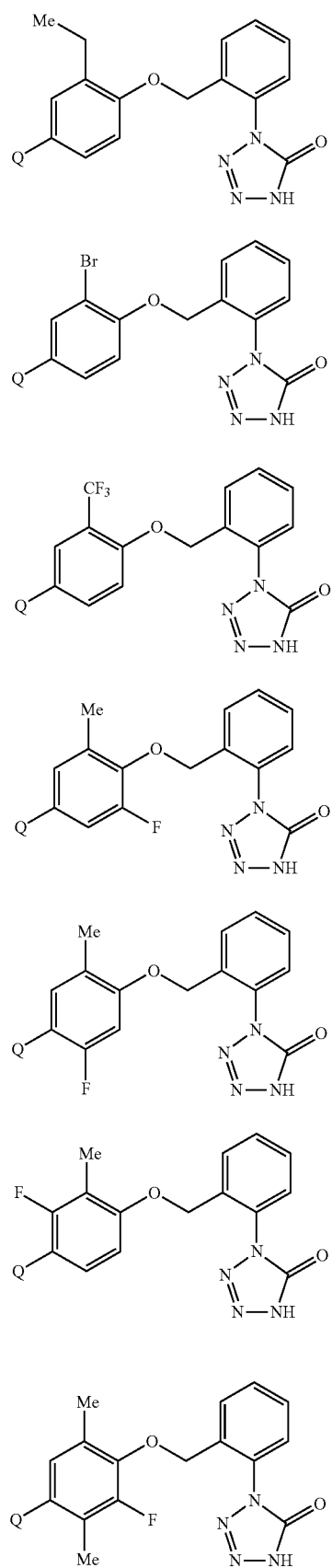
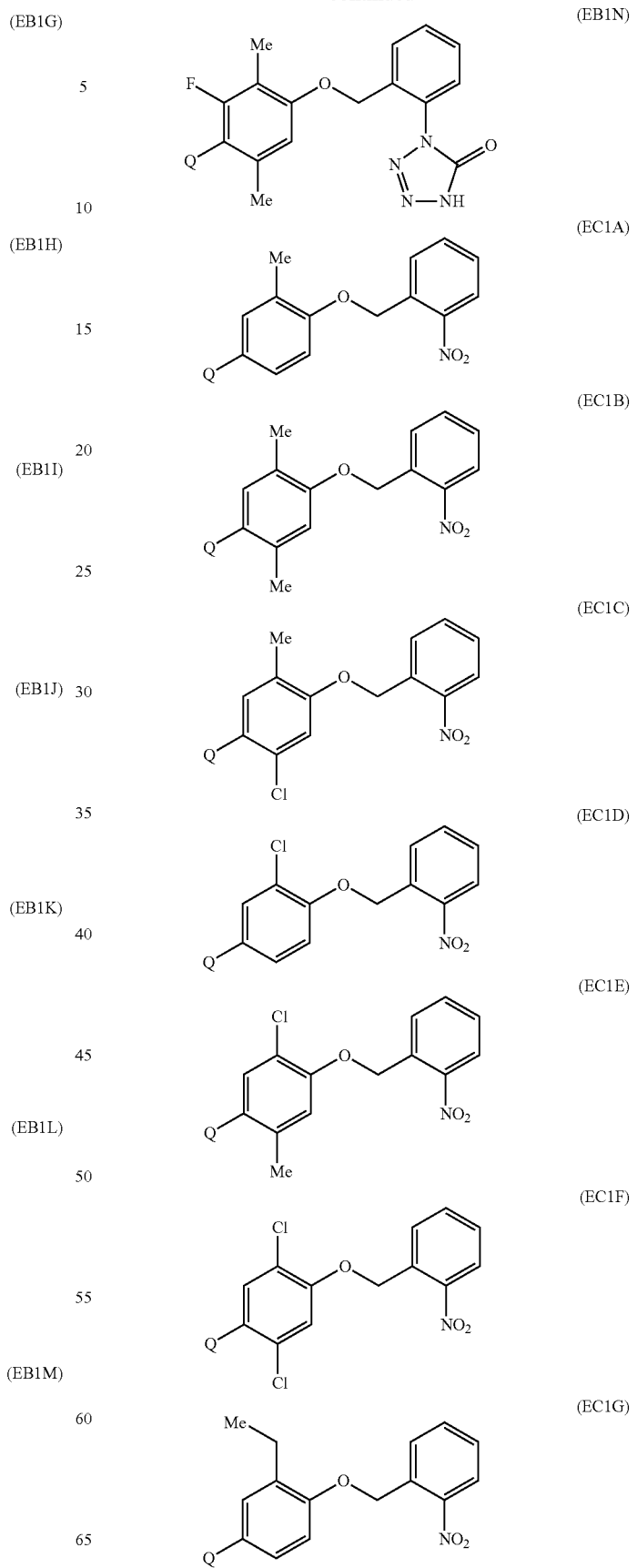

| | |
|---|---|
| (EC1H) 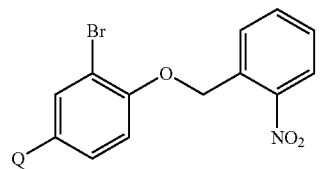 | (ED1B) 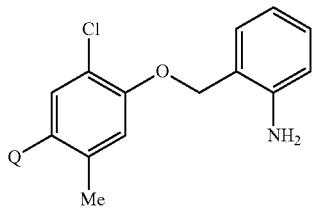 |
| (EC1I) 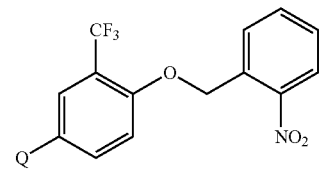 | (ED1C) 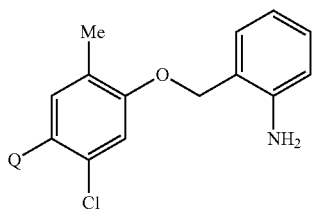 |
| (EC1J) 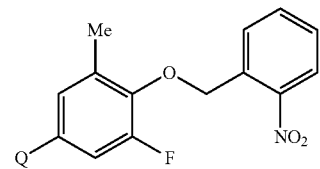 | (ED1D) 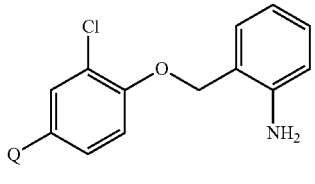 |
| (EC1K) 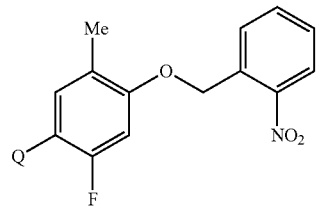 | (ED1E) 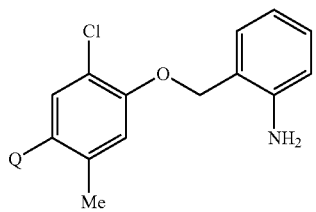 |
| (EC1L) 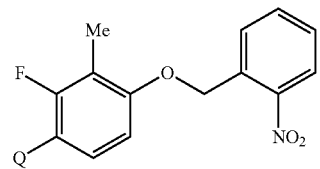 | (ED1F) 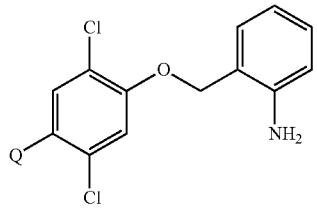 |
| (EC1M) 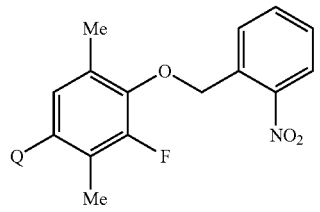 | (ED1G) 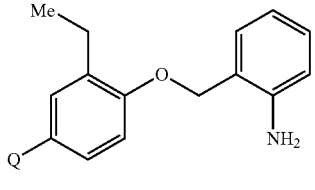 |
| (EC1N) 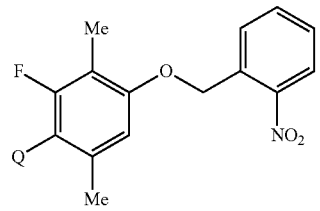 | (ED1H) 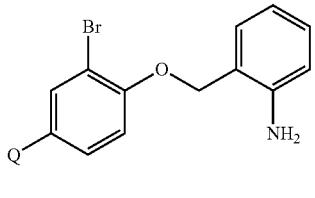 |
| (ED1A) 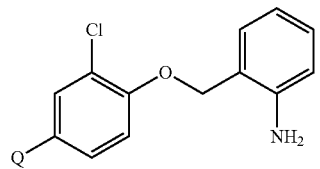 | (ED1I) 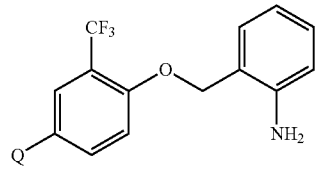 |

(ED1J)
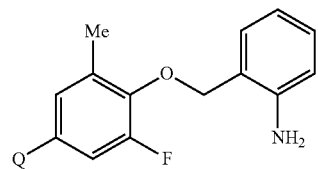
(ED1K)
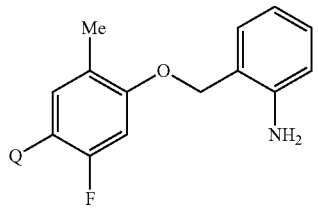
(ED1L)
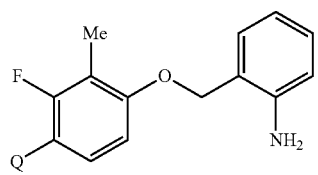
(ED1M)
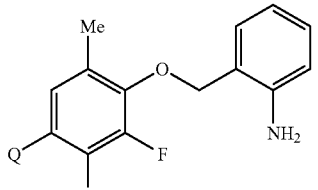
(ED1N)
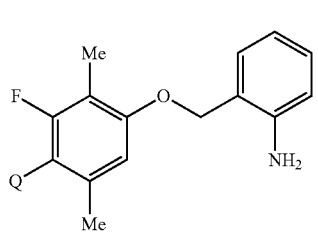
(EE1A)
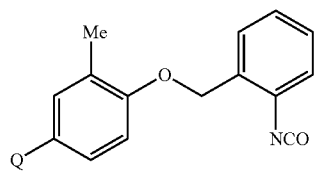
(EE1B)
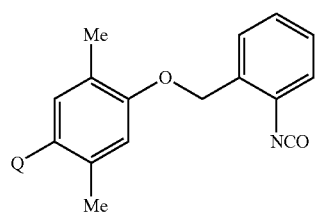
(EE1C)
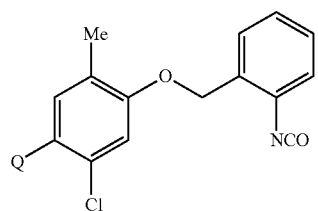
(EE1D)
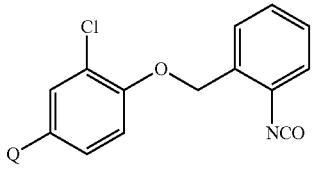
(EE1E)
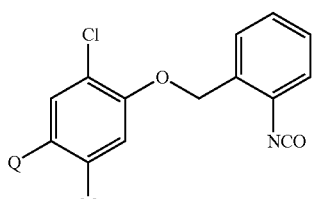
(EE1F)
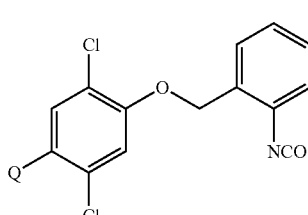
(EE1G)
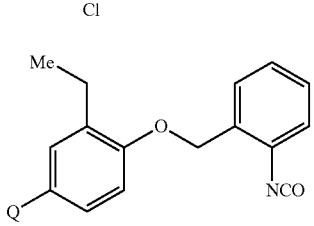
(EE1H)
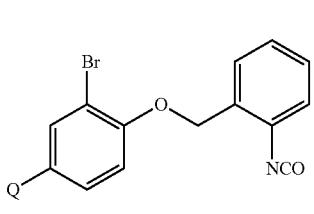
(EE1I)
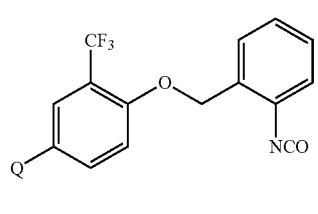
(EE1J)
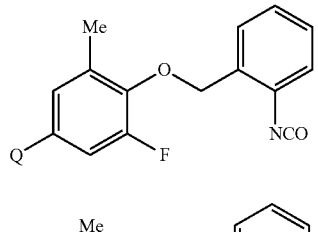
(EE1K)
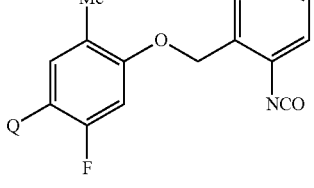

-continued
(EE1L)
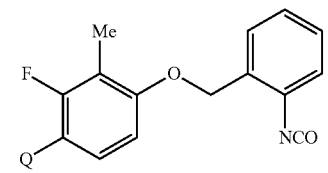
(EF1M)
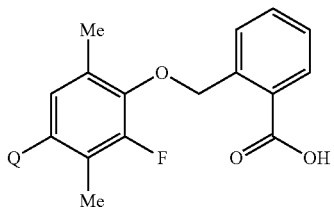
(EF1N)
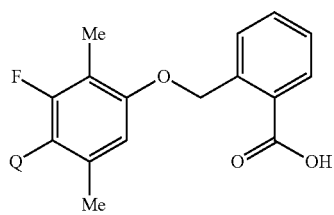
(EF1A)
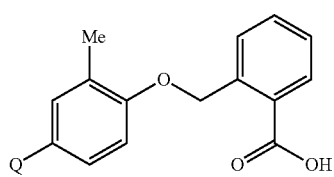
(EF1B)
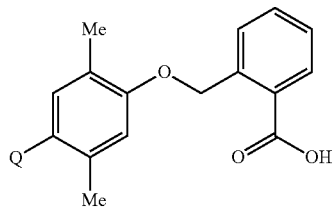
(EF1C)
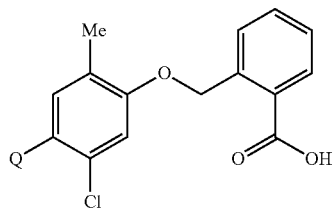
(EF1D)
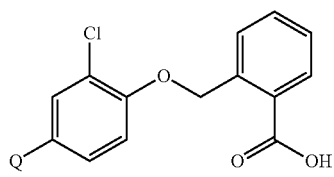
(EF1E)
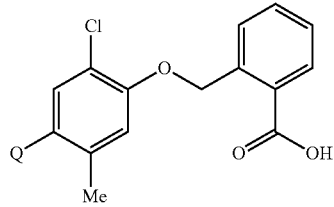
-continued
(EF1F)
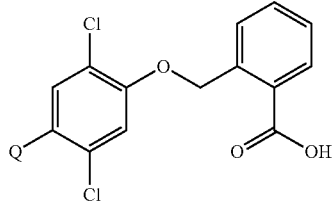
(EF1G)
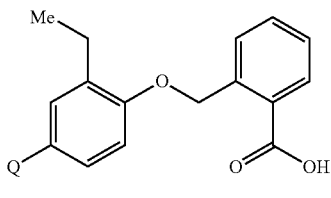
(EF1H)
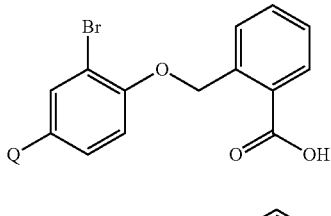
(EF1I)
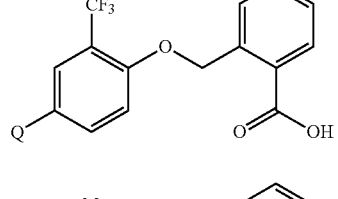
(EF1J)
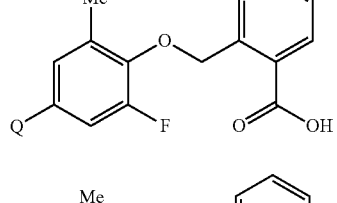
(EF1K)
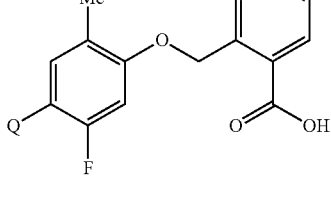
(EF1L)
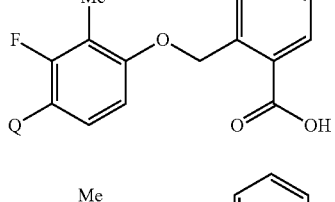
(EF1M)
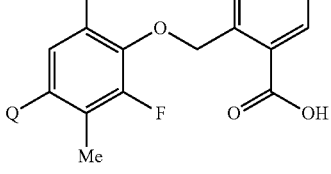

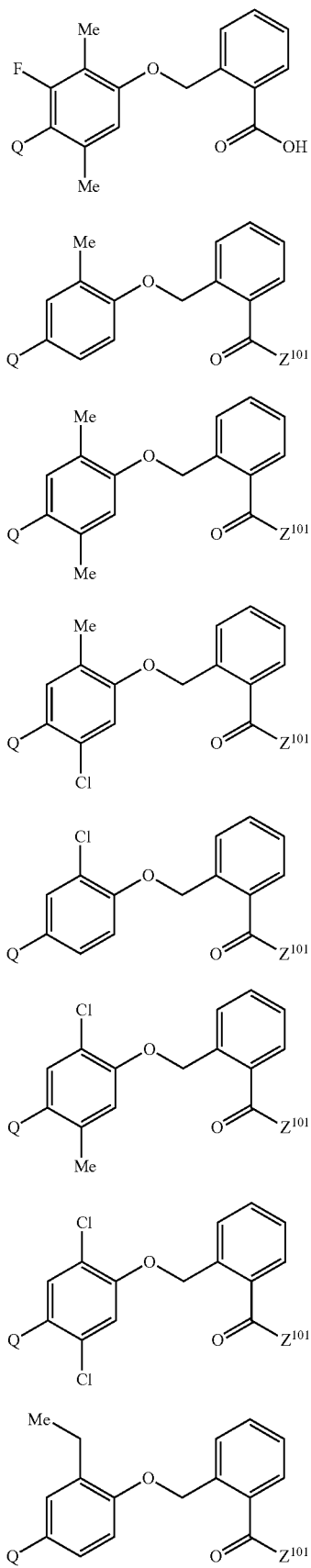
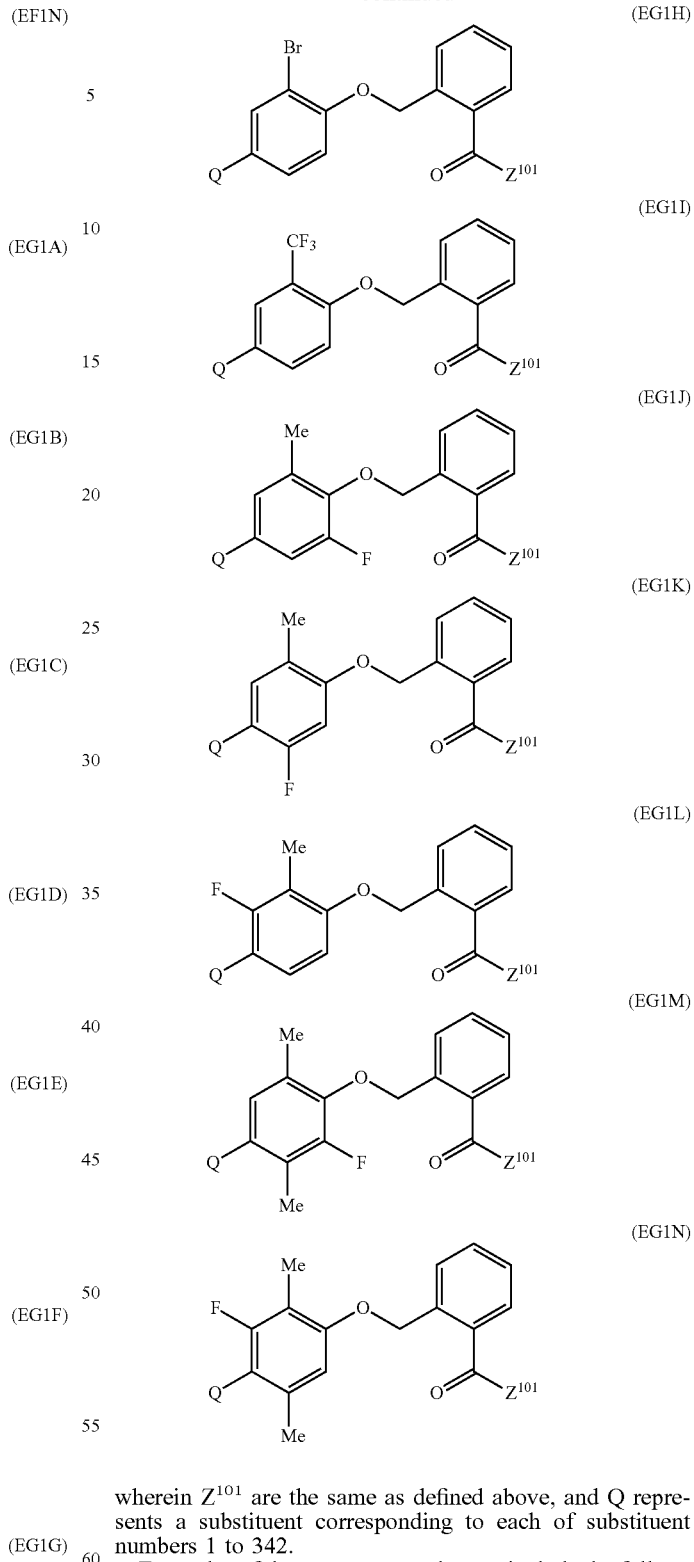

wherein $Z^{101}$ are the same as defined above, and Q represents a substituent corresponding to each of substituent numbers 1 to 342.

Examples of the present control agent include the followings:

a pest control composition comprising any one of the present compounds 1 to 166 and prothioconazole at a ratio of 0.1:1; a pest control composition comprising any one of the present compounds 1 to 166 and prothioconazole at a ratio of 1:1; a pest control composition comprising any one of the present compounds 1 to 166 and prothioconazole at a ratio of 10:1; a pest control composition comprising any one of the present compounds 1 to 166 and bromuconazole at a ratio of 0.1:1; a pest control composition comprising any one of the present compounds 1 to 166 and bromuconazole at a ratio of 1:1; a pest control composition comprising any one of the present compounds 1 to 166 and bromuconazole at a ratio of 10:1; a pest control composition comprising any one of the present compounds 1 to 166 and metconazole at a ratio of 0.1:1; a pest control composition comprising any one of the present compounds 1 to 166 and metconazole at a ratio of 1:1; a pest control composition comprising any one of the present compounds 1 to 166 and metconazole at a ratio of 10:1; a pest control composition comprising any one of the present compounds 1 to 166 and tebuconazole at a ratio of 0.1:1; a pest control composition comprising any one of the present compounds 1 to 166 and tebuconazole at a ratio of 1:1; a pest control composition comprising any one of the present compounds 1 to 166 and tebuconazole at a ratio of 10:1; a pest control composition comprising any one of the present compounds 1 to 166 and tetraconazole at a ratio of 0.1:1; a pest control composition comprising any one of the present compounds 1 to 166 and tetraconazole at a ratio of 1:1; a pest control composition comprising any one of the present compounds 1 to 166 and tetraconazole at a ratio of 10:1; a pest control composition comprising any one of the present compounds 1 to 166 and cyproconazole at a ratio of 0.1:1; a pest control composition comprising any one of the present compounds 1 to 166 and cyproconazole at a ratio of 1:1; a pest control composition comprising any one of the present compounds 1 to 166 and cyproconazole at a ratio of 10:1; a pest control composition comprising any one of the present compounds 1 to 166 and flusilazol at a ratio of 0.1:1; a pest control composition comprising any one of the present compounds 1 to 166 and flusilazol at a ratio of 1:1; a pest control composition comprising any one of the present compounds 1 to 166 and flusilazol at a ratio of 10:1;
a pest control composition comprising any one of the present compounds 1 to 166 and prochloraz at a ratio of 0.1:1; a pest control composition comprising any one of the present compounds 1 to 166 and prochloraz at a ratio of 1:1; a pest control composition comprising any one of the present compounds 1 to 166 and prochloraz at a ratio of 10:1; a pest control composition comprising any one of the present compounds 1 to 166 and imazalil at a ratio of 0.1:1; a pest control composition comprising any one of the present compounds 1 to 166 and imazalil at a ratio of 1:1; a pest control composition comprising any one of the present compounds 1 to 166 and imazalil at a ratio of 10:1; a pest control composition comprising any one of the present compounds 1 to 166 and epoxiconazol at a ratio of 0.1:1; a pest control composition comprising any one of the present compounds 1 to 166 and epoxiconazol at a ratio of 1:1; a pest control composition comprising any one of the present compounds 1 to 166 and epoxiconazol at a ratio of 10:1; a pest control composition comprising any one of the present compounds 1 to 166 and propiconazole at a ratio of 0.1:1; a pest control composition comprising any one of the present compounds 1 to 166 and propiconazole at a ratio of 1:1; a pest control composition comprising any one of the present compounds 1 to 166 and propiconazole at a ratio of 10:1; a pest control composition comprising any one of the present compounds 1 to 166 and difenoconazole at a ratio of 0.1:1; a pest control composition comprising any one of the present compounds 1 to 166 and difenoconazole at a ratio of 1:1; a pest control composition comprising any one of the present compounds 1 to 166 and difenoconazole at a ratio of 10:1; a pest control composition comprising any one of the present compounds 1 to 166 and myclobutanil at a ratio of 0.1:1; a pest control composition comprising any one of the present compounds 1 to 166 and myclobutanil at a ratio of 1:1; a pest control composition comprising any one of the present compounds 1 to 166 and myclobutanil at a ratio of 10:1; a pest control composition comprising any one of the present compounds 1 to 166 and triadimenol at a ratio of 0.1:1; a pest control composition comprising any one of the present compounds 1 to 166 and triadimenol at a ratio of 1:1; a pest control composition comprising any one of the present compounds 1 to 166 and triadimenol at a ratio of 10:1;
A pest control composition comprising any one of the present compounds 1 to 166 and triadimefon at a ratio of 0.1:1; a pest control composition comprising any one of the present compounds 1 to 166 and triadimefon at a ratio of 1:1; a pest control composition comprising any one of the present compounds 1 to 166 and triadimefon at a ratio of 10:1; a pest control composition comprising any one of the present compounds 1 to 166 and fluquinconazole at a ratio of 0.1:1; a pest control composition comprising any one of the present compounds 1 to 166 and fluquinconazole at a ratio of 1:1; a pest control composition comprising any one of the present compounds 1 to 166 and fluquinconazole at a ratio of 10:1; a pest control composition comprising any one of the present compounds 1 to 166 and triticonazole at a ratio of 0.1:1; a pest control composition comprising any one of the present compounds 1 to 166 and triticonazole at a ratio of 1:1; a pest control composition comprising any one of the present compounds 1 to 166 and triticonazole at a ratio of 10:1; a compounds 1 to 166 and ipconazole at a ratio of 0.1:1; a pest control composition comprising any one of the present compounds 1 to 166 and ipconazole at a ratio of 1:1; a pest control composition comprising any one of the present compounds 1 to 166 and ipconazole at a ratio of 10:1; a pest control composition comprising any one of the present compounds 1 to 166 and triflumizol at a ratio of 0.1:1; a pest control composition comprising any one of the present compounds 1 to 166 and triflumizol at a ratio of 1:1; a pest control composition comprising any one of the present compounds 1 to 166 and triflumizol at a ratio of 10:1; a pest control composition comprising any one of the present compounds 1 to 166 and fenbuconazole at a ratio of 0.1:1; a pest control composition comprising any one of the present compounds 1 to 166 and fenbuconazole at a ratio of 1:1; a pest control composition comprising any one of the present compounds 1 to 166 and fenbuconazole at a ratio of 10:1; a pest control composition comprising any one of the present compounds 1 to 166 and hexaconazole at a ratio of 0.1:1;
a pest control composition comprising any one of the present compounds 1 to 166 and hexaconazole at a ratio of 1:1; a pest control composition comprising any one of the present compounds 1 to 166 and hexaconazole at a ratio of 10:1; a pest control composition comprising any one of the present compounds 1 to 166 and bitertanol at a ratio of 0.1:1; a pest control composition comprising any one of the present compounds 1 to 166 and bitertanol at a ratio of 1:1; a pest control composition comprising any one of the present compounds 1 to 166 and bitertanol at a ratio of 10:1; a pest control composition comprising any one of the present compounds 1 to 166 and flutriafol at a ratio of 0.1:1; a pest control composition comprising any one of the present compounds 1 to 166 and flutriafol at a ratio of 1:1; a pest control composition comprising any one of the present compounds 1 to 166 and flutriafol at a ratio of 10:1; a pest control composition comprising any one of the present compounds 1 to 166 and simeconazole at a ratio of 0.1:1; a pest control composition comprising any one of the present compounds 1 to 166 and simeconazole at a ratio of 1:1; a pest control composition comprising any one of the present compounds 1 to 166 and simeconazole at a ratio of 10:1; a pest control composition comprising any one of the present compounds 1 to 166 and imibenconazole at a ratio of 0.1:1; a pest control composition comprising any one of the present compounds 1 to 166 and imibenconazole at a ratio of 1:1; a pest control composition comprising any one of the present compounds 1 to 166 and imibenconazole at a ratio of 10:1; a pest control composition comprising any one of the present compounds 1 to 166 and oxpoconazole at a ratio of 0.1:1; a pest control composition comprising any one of the present compounds 1 to 166 and oxpoconazole at a ratio of 1:1; a pest control composition comprising any one of the present compounds 1 to 166 and oxpoconazole at a ratio of 10:1; a pest control composition comprising any one of the present compounds 1 to 166 and azoxystrobin at a ratio of 0.1:1; a pest control composition comprising any one of the present compounds 1 to 166 and azoxystrobin at a ratio of 1:1; a pest control composition comprising any one of the present compounds 1 to 166 and azoxystrobin at a ratio of 10:1; a pest control composition comprising any one of the present compounds 1 to 166 and pyraclostrobin at a ratio of 0.1:1; a pest control composition comprising any one of the present compounds 1 to 166 and pyraclostrobin at a ratio of 1:1; a pest control composition comprising any one of the present compounds 1 to 166 and pyraclostrobin at a ratio of 10:1; a pest control composition comprising any one of the present compounds 1 to 166 and picoxystrobin at a ratio of 0.1:1; a pest control composition comprising any one of the present compounds 1 to 166 and picoxystrobin at a ratio of 1:1; a pest control composition comprising any one of the present compounds 1 to 166 and picoxystrobin at a ratio of 10:1; a pest control composition comprising any one of the present compounds 1 to 166 and fluoxastrobin at a ratio of 0.1:1; a pest control composition comprising any one of the present compounds 1 to 166 and fluoxastrobin at a ratio of 1:1; a pest control composition comprising any one of the present compounds 1 to 166 and fluoxastrobin at a ratio of 10:1; a pest control composition comprising any one of the present compounds 1 to 166 and trifloxystrobin at a ratio of 0.1:1; a pest control composition comprising any one of the present compounds 1 to 166 and trifloxystrobin at a ratio of 1:1; a pest control composition comprising any one of the present compounds 1 to 166 and trifloxystrobin at a ratio of 10:1; a pest control composition comprising any one of the present compounds 1 to 166 and mandestrobin at a ratio of 0.1:1; a pest control composition comprising any one of the present compounds 1 to 166 and mandestrobin at a ratio of 1:1; a pest compounds 1 to 166 and mandestrobin at a ratio of 10:1; a pest control composition comprising any one of the present compounds 1 to 166 and kresoxim-methyl at a ratio of 0.1:1; a pest control composition comprising any one of the present compounds 1 to 166 and kresoxim-methyl at a ratio of 1:1; a pest control composition comprising any one of the present compounds 1 to 166 and kresoxim-methyl at a ratio of 10:1;

a pest control composition comprising any one of the present compounds 1 to 166 and dimoxystrobin at a ratio of 0.1:1; a pest control composition comprising any one of the present compounds 1 to 166 and dimoxystrobin at a ratio of 1:1; a pest control composition comprising any one of the present compounds 1 to 166 and dimoxystrobin at a ratio of 10:1; a pest control composition comprising any one of the present compounds 1 to 166 and pyribencarb at a ratio of 0.1:1; a pest control composition comprising any one of the present compounds 1 to 166 and pyribencarb at a ratio of 1:1; a pest control composition comprising any one of the present compounds 1 to 166 and pyribencarb at a ratio of 10:1; a pest control composition comprising any one of the present compounds 1 to 166 and famoxadon at a ratio of 0.1:1; a pest control composition comprising any one of the present compounds 1 to 166 and famoxadon at a ratio of 1:1; a pest control composition comprising any one of the present compounds 1 to 166 and famoxadon at a ratio of 10:1; a pest control composition comprising any one of the present compounds 1 to 166 and fenamidone at a ratio of 0.1:1; a pest control composition comprising any one of the present compounds 1 to 166 and fenamidone at a ratio of 1:1; a pest control composition comprising any one of the present compounds 1 to 166 and fenamidone at a ratio of 10:1; a pest control composition comprising any one of the present compounds 1 to 166 and metominostrobin at a ratio of 0.1:1; a pest control composition comprising any one of the present compounds 1 to 166 and metominostrobin at a ratio of 1:1; a pest control composition comprising any one of the present compounds 1 to 166 and metominostrobin at a ratio of 10:1; a pest control composition comprising any one of the present compounds 1 to 166 and orysastrobin at a ratio of 0.1:1; a pest control composition comprising any one of the present compounds 1 to 166 and orysastrobin at a ratio of 1:1; a pest control composition comprising any one of the present compounds 1 to 166 and orysastrobin at a ratio of 10:1; a pest control composition comprising any one of the present compounds 1 to 166 and enestrobin at a ratio of 0.1:1; a pest control composition comprising any one of the present compounds 1 to 166 and enestrobin at a ratio of 1:1;

a pest control composition comprising any one of the present compounds 1 to 166 and enestrobin at a ratio of 10:1; a pest control composition comprising any one of the present compounds 1 to 166 and pyraoxystrobin at a ratio of 0.1:1; a pest control composition comprising any one of the present compounds 1 to 166 and pyraoxystrobin at a ratio of 1:1; a pest control composition comprising any one of the present compounds 1 to 166 and pyraoxystrobin at a ratio of 10:1; a pest control composition comprising any one of the present compounds 1 to 166 and pyrametostrobin at a ratio of 0.1:1; a compounds 1 to 166 and pyrametostrobin at a ratio of 1:1; a pest control composition comprising any one of the present compounds 1 to 166 and pyrametostrobin at a ratio of 10:1; a pest control composition comprising any one of the present compounds 1 to 166 and fenaminstrobin at a ratio of 0.1:1; a pest control composition comprising any one of the present compounds 1 to 166 and fenaminstrobin at a ratio of 1:1; a pest control composition comprising any one of the present compounds 1 to 166 and fenaminstrobin at a ratio of 10:1; a pest control composition comprising any one of the present compounds 1 to 166 and enoxastrobin at a ratio of 0.1:1; a pest control composition comprising any one of the present compounds 1 to 166 and enoxastrobin at a ratio of 1:1; a pest control composition comprising any one of the present compounds 1 to 166 and enoxastrobin at a ratio of 10:1; a pest control composition comprising any one of the present compounds 1 to 166 and coumoxystrobin at a ratio of 0.1:1; a pest control composition comprising any one of the present compounds 1 to 166 and coumoxystrobin at a ratio of 1:1; a pest control composition comprising any one of the present compounds 1 to 166 and coumoxystrobin at a ratio of 10:1; a pest control composition comprising any one of the present compounds 1 to 166 and triclopyricarb at a ratio of 0.1:1; a pest control composition comprising any one of the present compounds 1 to 166 and triclopyricarb at a ratio of 1:1;

a pest control composition comprising any one of the present compounds 1 to 166 and triclopyricarb at a ratio of 10:1; a pest control composition comprising any one of the present compounds 1 to 166 and bixafen at a ratio of 0.1:1; a pest control composition comprising any one of the present compounds 1 to 166 and bixafen at a ratio of 1:1; a pest control composition comprising any one of the present compounds 1 to 166 and bixafen at a ratio of 10:1; a pest control composition comprising any one of the present compounds 1 to 166 and isopyrazam at a ratio of 0.1:1; a pest control composition comprising any one of the present compounds 1 to 166 and isopyrazam at a ratio of 1:1; a pest control composition comprising any one of the present compounds 1 to 166 and isopyrazam at a ratio of 10:1; a pest control composition comprising any one of the present compounds 1 to 166 and fluopyram at a ratio of 0.1:1; a pest control composition comprising any one of the present compounds 1 to 166 and fluopyram at a ratio of 1:1; a pest control composition comprising any one of the present compounds 1 to 166 and fluopyram at a ratio of 10:1; a pest control composition comprising any one of the present compounds 1 to 166 and penthiopyrad at a ratio of 0.1:1; a pest control composition comprising any one of the present compounds 1 to 166 and penthiopyrad at a ratio of 1:1; a pest control composition comprising any one of the present compounds 1 to 166 and penthiopyrad at a ratio of 10:1; a pest control composition comprising any one of the present compounds 1 to 166 and benzovindiflupyr at a ratio of 0.1:1; a pest control composition comprising any one of the present compounds 1 to 166 and benzovindiflupyr at a ratio of 1:1; a pest control composition comprising any one of the present compounds 1 to 166 and benzovindiflupyr at a ratio of 10:1; a pest control composition comprising any one of the present compounds 1 to 166 and fluxapyroxad at a ratio of 0.1:1; a pest control composition comprising any one of the present compounds 1 to 166 and fluxapyroxad at a ratio of 1:1; a pest control composition comprising any one of the present compounds 1 to 166 and fluxapyroxad at a ratio of 10:1; a pest control composition comprising any one of the present compounds 1 to 166 and boscalid at a ratio of 0.1:1;

a pest control composition comprising any one of the present compounds 1 to 166 and boscalid at a ratio of 1:1; a pest control composition comprising any one of the present compounds 1 to 166 and boscalid at a ratio of 10:1; a pest control composition comprising any one of the present compounds 1 to 166 and sedaxane at a ratio of 0.1:1; a pest control composition comprising any one of the present compounds 1 to 166 and sedaxane at a ratio of 1:1; a pest control composition comprising any one of the present compounds 1 to 166 and sedaxane at a ratio of 10:1; a pest control composition comprising any one of the present compounds 1 to 166 and penflufen at a ratio of 0.1:1; a pest control composition comprising any one of the present compounds 1 to 166 and penflufen at a ratio of 1:1; a pest control composition comprising any one of the present compounds 1 to 166 and penflufen at a ratio of 10:1; a pest control composition comprising any one of the present compounds 1 to 166 and carboxin at a ratio of 0.1:1; a pest control composition comprising any one of the present compounds 1 to 166 and carboxin at a ratio of 1:1; a pest control composition comprising any one of the present compounds 1 to 166 and carboxin at a ratio of 10:1; a pest compounds 1 to 166 and mepronil at a ratio of 0.1:1; a pest control composition comprising any one of the present compounds 1 to 166 and mepronil at a ratio of 1:1; a pest control composition comprising any one of the present compounds 1 to 166 and mepronil at a ratio of 10:1; a pest control composition comprising any one of the present compounds 1 to 166 and flutolanil at a ratio of 0.1:1; a pest control composition comprising any one of the present compounds 1 to 166 and flutolanil at a ratio of 1:1; a pest control composition comprising any one of the present compounds 1 to 166 and flutolanil at a ratio of 10:1; a pest control composition comprising any one of the present compounds 1 to 166 and thifluzamide at a ratio of 0.1:1; a pest control composition comprising any one of the present compounds 1 to 166 and thifluzamide at a ratio of 1:1; a pest control composition comprising any one of the present compounds 1 to 166 and thifluzamide at a ratio of 10:1;

a pest control composition comprising any one of the present compounds 1 to 166 and furametpyr at a ratio of 0.1:1; a pest control composition comprising any one of the present compounds 1 to 166 and furametpyr at a ratio of 1:1; a pest control composition comprising any one of the present compounds 1 to 166 and furametpyr at a ratio of 10:1; a pest control composition comprising any one of the present compounds 1 to 166 and isofetamid at a ratio of 0.1:1; a pest control composition comprising any one of the present compounds 1 to 166 and isofetamid at a ratio of 1:1; a pest control composition comprising any one of the present compounds 1 to 166 and isofetamid at a ratio of 10:1; a pest control composition comprising any one of the present compounds 1 to 166 and N-[2-(3,4-difluorophenyl)phenyl]-3-trifluoromethylpyrazine-2-carboxylic acid amide at a ratio of 0.1:1; a pest control composition comprising any one of the present compounds 1 to 166 and N-[2-(3,4-difluorophenyl)phenyl]-3-trifluoromethylpyrazine-2-carboxylic acid amide at a ratio of 1:1; a pest control composition comprising any one of the present compounds 1 to 166 and N-[2-(3,4-difluorophenyl)phenyl]-3-trifluoromethylpyrazine-2-carboxylic acid amide at a ratio of 10:1; a pest control composition comprising any one of the present compounds 1 to 166 and (R)-(−)-N-(1,1,3-trimethylindan-4-yl)-1-methyl-3-difluoromethylpyrazole-4-carboxylic acid amide at a ratio of 0.1:1; a pest control composition comprising any one of the present compounds 1 to 166 and (R)-(−)-N-(1,1,3-trimethylindan-4-yl)-1-methyl-3-difluoromethylpyrazole-4-carboxylic acid amide at a ratio of 1:1; a pest control composition comprising any one of the present compounds 1 to 166 and (R)-(−)-N-(1,1,3-trimethylindan-4-yl)-1-methyl-3-difluoromethylpyrazole-4-carboxylic acid amide at a ratio of 10:1; a pest control composition comprising any one of the present compounds 1 to 166 and 3-chloro-4-(2,6-difluorophenyl)-6-methyl-5-phenylpyridazine at a ratio of 0.1:1;

a pest control composition comprising any one of the present compounds 1 to 166 and 3-chloro-4-(2,6-difluorophenyl)-6-methyl-5-phenylpyridazine at a ratio of 1:1; a pest control composition comprising any one of the present compounds 1 to 166 and 3-chloro-4-(2,6-difluorophenyl)-6-methyl-5-phenylpyridazine at a ratio of 10:1; a pest control composition comprising any one of the present compounds 1 to 166 and 3-cyano-4-(2,6-difluorophenyl)-6-methyl-5-phenylpyridazine at a ratio of 0.1:1; a pest control composition comprising any one of the present compounds 1 to 166 and 3-cyano-4-(2,6-difluorophenyl)-

6-methyl-5-phenylpyridazine at a ratio of 1:1; a pest control composition comprising any one of the present compounds 1 to 166 and 3-cyano-4-(2,6-difluorophenyl)-6-methyl-5-phenylpyridazine at a ratio of 10:1; a pest control composition comprising any one of the present compounds 1 to 166 and fenpropimorph at a ratio of 0.1:1; a pest control composition comprising any one of the present compounds 1 to 166 and fenpropimorph at a ratio of 1:1; a pest control composition comprising any one of the present compounds 1 to 166 and fenpropimorph at a ratio of 10:1; a pest control composition comprising any one of the present compounds 1 to 166 and fenpropidin at a ratio of 0.1:1; a pest control composition comprising any one of the present compounds 1 to 166 and fenpropidin at a ratio of 1:1; a pest control composition comprising any one of the present compounds 1 to 166 and fenpropidin at a ratio of 10:1; a pest control composition comprising any one of the present compounds 1 to 166 and spiroxamine at a ratio of 0.1:1; a pest control composition comprising any one of the present compounds 1 to 166 and spiroxamine at a ratio of 1:1; a pest control composition comprising any one of the present compounds 1 to 166 and spiroxamine at a ratio of 10:1; a pest control composition comprising any one of the present compounds 1 to 166 and tridemorph at a ratio of 0.1:1; a pest compounds 1 to 166 and tridemorph at a ratio of 1:1; a pest control composition comprising any one of the present compounds 1 to 166 and tridemorph at a ratio of 10:1; a pest control composition comprising any one of the present compounds 1 to 166 and cyprodinil at a ratio of 0.1:1; a pest control composition comprising any one of the present compounds 1 to 166 and cyprodinil at a ratio of 1:1; a pest control composition comprising any one of the present compounds 1 to 166 and cyprodinil at a ratio of 10:1; a pest control composition comprising any one of the present compounds 1 to 166 and pyrimethanil at a ratio of 0.1:1; a pest control composition comprising any one of the present compounds 1 to 166 and pyrimethanil at a ratio of 1:1; a pest control composition comprising any one of the present compounds 1 to 166 and pyrimethanil at a ratio of 10:1; a pest control composition comprising any one of the present compounds 1 to 166 and mepanipyrim at a ratio of 0.1:1; a pest control composition comprising any one of the present compounds 1 to 166 and mepanipyrim at a ratio of 1:1; a pest control composition comprising any one of the present compounds 1 to 166 and mepanipyrim at a ratio of 10:1; a pest control composition comprising any one of the present compounds 1 to 166 and fenpiclonil at a ratio of 0.1:1; a pest control composition comprising any one of the present compounds 1 to 166 and fenpiclonil at a ratio of 1:1; a pest control composition comprising any one of the present compounds 1 to 166 and fenpiclonil at a ratio of 10:1; a pest control composition comprising any one of the present compounds 1 to 166 and fludioxonil at a ratio of 0.1:1; a pest control composition comprising any one of the present compounds 1 to 166 and fludioxonil at a ratio of 1:1; a pest control composition comprising any one of the present compounds 1 to 166 and fludioxonil at a ratio of 10:1; a pest control composition comprising any one of the present compounds 1 to 166 and procymidone at a ratio of 0.1:1; a pest control composition comprising any one of the present compounds 1 to 166 and procymidone at a ratio of 1:1; a pest control composition comprising any one of the present compounds 1 to 166 and procymidone at a ratio of 10:1; a pest control composition comprising any one of the present compounds 1 to 166 and iprodione at a ratio of 0.1:1;

a pest control composition comprising any one of the present compounds 1 to 166 and iprodione at a ratio of 1:1; a pest control composition comprising any one of the present compounds 1 to 166 and iprodione at a ratio of 10:1; a pest control composition comprising any one of the present compounds 1 to 166 and vinclozolin at a ratio of 0.1:1; a pest control composition comprising any one of the present compounds 1 to 166 and vinclozolin at a ratio of 1:1; a pest control composition comprising any one of the present compounds 1 to 166 and vinclozolin at a ratio of 10:1; a pest control composition comprising any one of the present compounds 1 to 166 and benomyl at a ratio of 0.1:1; a pest control composition comprising any one of the present compounds 1 to 166 and benomyl at a ratio of 1:1; a pest control composition comprising any one of the present compounds 1 to 166 and benomyl at a ratio of 10:1; a pest compounds 1 to 166 and thiophanate-methyl at a ratio of 0.1:1; a pest control composition comprising any one of the present compounds 1 to 166 and thiophanate-methyl at a ratio of 1:1; a pest control composition comprising any one of the present compounds 1 to 166 and thiophanate-methyl at a ratio of 10:1; a pest control composition comprising any one of the present compounds 1 to 166 and carbendazim at a ratio of 0.1:1; a pest control composition comprising any one of the present compounds 1 to 166 and carbendazim at a ratio of 1:1; a pest control composition comprising any one of the present compounds 1 to 166 and carbendazim at a ratio of 10:1; a pest control composition comprising any one of the present compounds 1 to 166 and diethofencarb at a ratio of 0.1:1; a pest control composition comprising any one of the present compounds 1 to 166 and diethofencarb at a ratio of 1:1; a pest control composition comprising any one of the present compounds 1 to 166 and diethofencarb at a ratio of 10:1; a pest control composition comprising any one of the present compounds 1 to 166 and metalaxyl at a ratio of 0.1:1; a pest control composition comprising any one of the present compounds 1 to 166 and metalaxyl at a ratio of 1:1; a pest control composition comprising any one of the present compounds 1 to 166 and metalaxyl at a ratio of 10:1;

a pest control composition comprising any one of the present compounds 1 to 166 and metalaxyl-M (mefenoxam) at a ratio of 0.1:1; a pest control composition comprising any one of the present compounds 1 to 166 and metalaxyl-M (mefenoxam) at a ratio of 1:1; a pest control composition comprising any one of the present compounds 1 to 166 and metalaxyl-M (mefenoxam) at a ratio of 10:1; a pest control composition comprising any one of the present compounds 1 to 166 and benalaxyl at a ratio of 0.1:1; a pest control composition comprising any one of the present compounds 1 to 166 and benalaxyl at a ratio of 1:1; a pest control composition comprising any one of the present compounds 1 to 166 and benalaxyl at a ratio of 10:1; a pest control composition comprising any one of the present compounds 1 to 166 and benalaxyl-M (kiralaxyl) at a ratio of 0.1:1; a pest control composition comprising any one of the present compounds 1 to 166 and benalaxyl-M (kiralaxyl) at a ratio of 1:1; a pest control composition comprising any one of the present compounds 1 to 166 and benalaxyl-M (kiralaxyl) at a ratio of 10:1; a pest control composition comprising any one of the present compounds 1 to 166 and dimethomorph at a ratio of 0.1:1; a pest control composition comprising any one of the present compounds 1 to 166 and dimethomorph at a ratio of 1:1; a pest control composition comprising any one of the present compounds 1 to 166 and dimethomorph at a ratio of 10:1; a pest control composition comprising any one of the present compounds 1 to 166 and iprovalicarb at a ratio of 0.1:1; a pest control composition comprising any one of the present compounds 1 to 166 and iprovalicarb at a ratio of 1:1; a pest control composition comprising any one of the present compounds 1 to 166 and iprovalicarb at a ratio of 10:1; a pest control composition comprising any one of the present compounds 1 to 166 and benthivalicarb-isopropyl at a ratio of 0.1:1; a pest control composition comprising any one of the present compounds 1 to 166 and benthivalicarb-isopropyl at a ratio of 1:1; a pest control composition comprising any one of the present compounds 1 to 166 and benthivalicarb-isopropyl at a ratio of 10:1; a pest control composition comprising any one of the present compounds 1 to 166 and mandipropamid at a ratio of 0.1:1;

a pest control composition comprising any one of the present compounds 1 to 166 and mandipropamid at a ratio of 1:1; a pest control composition comprising any one of the present compounds 1 to 166 and mandipropamid at a ratio of 10:1; a pest control composition comprising any one of the present compounds 1 to 166 and valifenalate at a ratio of 0.1:1; a pest control composition comprising any one of the present compounds 1 to 166 and valifenalate at a ratio of 1:1; a pest control composition comprising any one of the present compounds 1 to 166 and valifenalate at a ratio of 10:1; a pest control composition comprising any one of the present compounds 1 to 166 and cymoxanil at a ratio of 0.1:1; a pest control composition comprising any one of the present compounds 1 to 166 and cymoxanil at a ratio of 1:1; a pest control composition comprising any one of the present compounds 1 to 166 and cymoxanil at a ratio of 10:1; a pest control composition comprising any one of the present compounds 1 to 166 and fluopicolide at a ratio of 0.1:1; a pest control composition comprising any one of the present compounds 1 to 166 and fluopicolide at a ratio of 1:1; a pest control composition comprising any one of the present compounds 1 to 166 and fluopicolide at a ratio of 10:1; a pest control composition comprising any one of the present compounds 1 to 166 and cyazofamid at a ratio of 0.1:1; a pest control composition comprising any one of the present compounds 1 to 166 and cyazofamid at a ratio of 1:1; a pest control composition comprising any one of the present compounds 1 to 166 and cyazofamid at a ratio of 10:1; a pest control composition comprising any one of the present compounds 1 to 166 and amisulbrom at a ratio of 0.1:1; a pest control composition comprising any one of the present compounds 1 to 166 and amisulbrom at a ratio of 1:1; a pest control composition comprising any one of the present compounds 1 to 166 and amisulbrom at a ratio of 10:1; a pest control composition comprising any one of the present compounds 1 to 166 and ametoctradin at a ratio of 0.1:1; a pest control composition comprising any one of the present compounds 1 to 166 and ametoctradin at a ratio of 1:1;

any one of the present compounds 1 to 166 and ametoctradin at a ratio of 10:1; a pest control composition comprising any one of the present compounds 1 to 166 and ethaboxam at a ratio of 0.1:1; a pest control composition comprising any one of the present compounds 1 to 166 and ethaboxam at a ratio of 1:1; a pest control composition comprising any one of the present compounds 1 to 166 and ethaboxam at a ratio of 10:1; a pest control composition comprising any one of the present compounds 1 to 166 and zoxamide at a ratio of 0.1:1; a pest control composition comprising any one of the present compounds 1 to 166 and zoxamide at a ratio of 1:1; a pest control composition comprising any one of the present compounds 1 to 166 and zoxamide at a ratio of 10:1; a pest control composition comprising any one of the present compounds 1 to 166 and oxathiapiprolin at a ratio of 1:1; a pest control composition comprising any one of the present compounds 1 to 166 and oxathiapiprolin at a ratio of 10:1; a pest control composition comprising any one of the present compounds 1 to 166 and oxathiapiprolin at a ratio of 50:1; a pest control composition comprising any one of the present compounds 1 to 166 and picarbutrazox at a ratio of 0.1:1; a pest control composition comprising any one of the present compounds 1 to 166 and picarbutrazox at a ratio of 1:1; a pest control composition comprising any one of the present compounds 1 to 166 and picarbutrazox at a ratio of 10:1; a pest control composition comprising any one of the present compounds 1 to 166 and fosetylaluminum at a ratio of 0.01:1; a pest control composition comprising any one of the present compounds 1 to 166 and fosetylaluminum at a ratio of 0.1:1; a pest control composition comprising any one of the present compounds 1 to 166 and fosetylaluminum at a ratio of 1:1; a pest control composition comprising any one of the present compounds 1 to 166 and a potassium salt of phosphorous acid at a ratio of 0.01:1; a pest control composition comprising any one of the present compounds 1 to 166 and a potassium salt of phosphorous acid at a ratio of 0.1:1; a pest control composition comprising any one of the present compounds 1 to 166 and a potassium salt of phosphorous acid at a ratio of 1:1; a pest control composition comprising any one of the present compounds 1 to 166 and propamocarb hydrochloride at a ratio of 0.01:1;

any one of the present compounds 1 to 166 and propamocarb hydrochloride at a ratio of 0.1:1; a pest control composition comprising any one of the present compounds 1 to 166 and propamocarb hydrochloride at a ratio of 1:1; a pest control composition comprising any one of the present compounds 1 to 166 and fenpyrazamine at a ratio of 0.1:1; a pest control composition comprising any one of the present compounds 1 to 166 and fenpyrazamine at a ratio of 1:1; a pest control composition comprising any one of the present compounds 1 to 166 and fenpyrazamine at a ratio of 10:1; a pest control composition comprising any one of the present compounds 1 to 166 and fenhexamid at a ratio of 0.1:1; a pest control composition comprising any one of the present compounds 1 to 166 and fenhexamid at a ratio of 1:1; a pest control composition comprising any one of the present compounds 1 to 166 and fenhexamid at a ratio of 10:1; a pest control composition comprising any one of the present compounds 1 to 166 and fluazinam at a ratio of 0.1:1; a pest control composition comprising any one of the present compounds 1 to 166 and fluazinam at a ratio of 1:1; a pest control composition comprising any one of the present compounds 1 to 166 and fluazinam at a ratio of 10:1; a pest control composition comprising any one of the present compounds 1 to 166 and flusulfamide at a ratio of 0.1:1; a pest control composition comprising any one of the present compounds 1 to 166 and flusulfamide at a ratio of 1:1; a pest control composition comprising any one of the present compounds 1 to 166 and flusulfamide at a ratio of 10:1; a pest control composition comprising any one of the present compounds 1 to 166 and ferimzone at a ratio of 0.1:1; a pest control composition comprising any one of the present compounds 1 to 166 and ferimzone at a ratio of 1:1; a pest control composition comprising any one of the present compounds 1 to 166 and ferimzone at a ratio of 10:1; a pest control composition comprising any one of the present compounds 1 to 166 and quinoxyfen at a ratio of 0.1:1; a pest control composition comprising any one of the present compounds 1 to 166 and quinoxyfen at a ratio of 1:1;

a pest control composition comprising any one of the present compounds 1 to 166 and quinoxyfen at a ratio of 10:1; a pest control composition comprising any one of the present compounds 1 to 166 and metrafenone at a ratio of 0.1:1; a pest control composition comprising any one of the present compounds 1 to 166 and metrafenone at a ratio of 1:1; a pest control composition comprising any one of the present compounds 1 to 166 and metrafenone at a ratio of 10:1; a pest control composition comprising any one of the present compounds 1 to 166 and pyriofenone at a ratio of 0.1:1; a pest control composition comprising any one of the present compounds 1 to 166 and pyriofenone at a ratio of 1:1; a pest control composition comprising any one of the present compounds 1 to 166 and pyriofenone at a ratio of 10:1; a pest control composition comprising any one of the present compounds 1 to 166 and proquinazid at a ratio of 0.1:1; a pest control composition comprising any one of the present compounds 1 to 166 and proquinazid at a ratio of 1:1; a pest control composition comprising any one of the present compounds 1 to 166 and proquinazid at a ratio of 10:1; a pest control composition comprising any one of the present compounds 1 to 166 and cyflufenamid at a ratio of 0.1:1; a pest control composition comprising any one of the present compounds 1 to 166 and cyflufenamid at a ratio of 1:1; a pest control composition comprising any one of the present compounds 1 to 166 and cyflufenamid at a ratio of 10:1; a pest control composition comprising any one of the present compounds 1 to 166 and tolclofos-methyl at a ratio of 0.01:1; a pest control composition comprising any one of the present compounds 1 to 166 and tolclofos-methyl at a ratio of 0.1:1; a pest control composition comprising any one of the present compounds 1 to 166 and tolclofos-methyl at a ratio of 1:1; a pest control composition comprising any one of the present compounds 1 to 166 and laminaran at a ratio of 0.1:1; a pest control composition comprising any one of the present compounds 1 to 166 and laminaran at a ratio of 1:1; a pest control composition comprising any one of the present compounds 1 to 166 and laminaran at a ratio of 10:1; a pest control composition comprising any one of the present compounds 1 to 166 and pencycuron at a ratio of 0.1:1;

a pest control composition comprising any one of the present compounds 1 to 166 and pencycuron at a ratio of 1:1; a pest control composition comprising any one of the present compounds 1 to 166 and pencycuron at a ratio of 10:1; a pest control composition comprising any one of the present compounds 1 to 166 and carpropamid at a ratio of 0.1:1; a pest control composition comprising any one of the present compounds 1 to 166 and carpropamid at a ratio of 1:1; a pest control composition comprising any one of the present compounds 1 to 166 and carpropamid at a ratio of 10:1; a pest control composition comprising any one of the present compounds 1 to 166 and diclocymet at a ratio of 0.1:1; a pest control composition comprising any one of the present compounds 1 to 166 and diclocymet at a ratio of 1:1; a pest compounds 1 to 166 and diclocymet at a ratio of 10:1; a pest control composition comprising any one of the present compounds 1 to 166 and tricyclazole at a ratio of 0.1:1; a pest control composition comprising any one of the present compounds 1 to 166 and tricyclazole at a ratio of 1:1; a pest control composition comprising any one of the present compounds 1 to 166 and tricyclazole at a ratio of 10:1; a pest control composition comprising any one of the present compounds 1 to 166 and pyroquilon at a ratio of 0.1:1; a pest control composition comprising any one of the present compounds 1 to 166 and pyroquilon at a ratio of 1:1; a pest control composition comprising any one of the present compounds 1 to 166 and pyroquilon at a ratio of 10:1; a pest control composition comprising any one of the present compounds 1 to 166 and fthalide at a ratio of 0.1:1; a pest control composition comprising any one of the present compounds 1 to 166 and fthalide at a ratio of 1:1; a pest control composition comprising any one of the present compounds 1 to 166 and fthalide at a ratio of 10:1; a pest control composition comprising any one of the present compounds 1 to 166 and probenazole at a ratio of 0.1:1; a pest control composition comprising any one of the present compounds 1 to 166 and probenazole at a ratio of 1:1; a pest control composition comprising any one of the present compounds 1 to 166 and probenazole at a ratio of 10:1; a pest control composition comprising any one of the present compounds 1 to 166 and isotianil at a ratio of 0.1:1;

a pest control composition comprising any one of the present compounds 1 to 166 and isotianil at a ratio of 1:1; a pest control composition comprising any one of the present compounds 1 to 166 and isotianil at a ratio of 10:1; a pest control composition comprising any one of the present compounds 1 to 166 and tiadinil at a ratio of 0.1:1; a pest control composition comprising any one of the present compounds 1 to 166 and tiadinil at a ratio of 1:1; a pest control composition comprising any one of the present compounds 1 to 166 and tiadinil at a ratio of 10:1; a pest control composition comprising any one of the present compounds 1 to 166 and tebufloquin at a ratio of 0.1:1; a pest control composition comprising any one of the present compounds 1 to 166 and tebufloquin at a ratio of 1:1; a pest control composition comprising any one of the present compounds 1 to 166 and tebufloquin at a ratio of 10:1; a pest control composition comprising any one of the present compounds 1 to 166 and tolprocarb at a ratio of 0.1:1; a pest control composition comprising any one of the present compounds 1 to 166 and tolprocarb at a ratio of 1:1; a pest control composition comprising any one of the present compounds 1 to 166 and tolprocarb at a ratio of 10:1; a pest control composition comprising any one of the present compounds 1 to 166 and diclomezine at a ratio of 0.1:1; a pest control composition comprising any one of the present compounds 1 to 166 and diclomezine at a ratio of 1:1; a pest control composition comprising any one of the present compounds 1 to 166 and diclomezine at a ratio of 10:1; a pest control composition comprising any one of the present compounds 1 to 166 and validamycin at a ratio of 0.1:1; a pest control composition comprising any one of the present compounds 1 to 166 and validamycin at a ratio of 1:1; a pest control composition comprising any one of the present compounds 1 to 166 and validamycin at a ratio of 10:1; a pest control composition comprising any one of the present compounds 1 to 166 and isoprothiolane at a ratio of 0.1:1; a pest control composition comprising any one of the present compounds 1 to 166 and isoprothiolane at a ratio of 1:1; a pest control composition comprising any one of the present compounds 1 to 166 and isoprothiolane at a ratio of 10:1;

a pest control composition comprising any one of the present compounds 1 to 166 and hydroxyisoxazole at a ratio of 0.1:1; a pest control composition comprising any one of the present compounds 1 to 166 and hydroxyisoxazole at a ratio of 1:1; a pest control composition comprising any one of the present compounds 1 to 166 and hydroxyisoxazole at a ratio of 10:1; a pest control composition comprising any one of the present compounds 1 to 166 and kasugamycin at a ratio of 0.1:1; a pest control composition comprising any one of the present compounds 1 to 166 and kasugamycin at a ratio of 1:1; a pest control composition comprising any one of the present compounds 1 to 166 and kasugamycin at a ratio of 10:1; a pest control composition comprising any one of the present compounds 1 to 166 and streptomycin at a ratio of 0.1:1; a pest control composition comprising any one of the present compounds 1 to 166 and streptomycin at a ratio of 1:1; a pest control composition comprising any one of the present compounds 1 to 166 and streptomycin at a ratio of 10:1; a pest control composition comprising any one of the present compounds 1 to 166 and oxolinic acid at a ratio of 0.1:1; a compounds 1 to 166 and oxolinic acid at a ratio of 1:1; a pest control composition comprising any one of the present compounds 1 to 166 and oxolinic acid at a ratio of 10:1; a pest control composition comprising any one of the present compounds 1 to 166 and tetracycline at a ratio of 0.1:1; a pest control composition comprising any one of the present compounds 1 to 166 and tetracycline at a ratio of 1:1; a pest control composition comprising any one of the present compounds 1 to 166 and tetracycline at a ratio of 10:1; a pest control composition comprising any one of the present compounds 1 to 166 and oxytetracycline at a ratio of 0.1:1; a pest control composition comprising any one of the present compounds 1 to 166 and oxytetracycline at a ratio of 1:1; a pest control composition comprising any one of the present compounds 1 to 166 and oxytetracycline at a ratio of 10:1; a pest control composition comprising any one of the present compounds 1 to 166 and silthiofam at a ratio of 0.01:1;

a pest control composition comprising any one of the present compounds 1 to 166 and silthiofam at a ratio of 0.1:1; a pest control composition comprising any one of the present compounds 1 to 166 and silthiofam at a ratio of 1:1; a pest control composition comprising any one of the present compounds 1 to 166 and chlorothalonil at a ratio of 0.01:1; a pest control composition comprising any one of the present compounds 1 to 166 and chlorothalonil at a ratio of 0.1:1; a pest control composition comprising any one of the present compounds 1 to 166 and chlorothalonil at a ratio of 1:1; a pest control composition comprising any one of the present compounds 1 to 166 and mancozeb at a ratio of 0.01:1; a pest control composition comprising any one of the present compounds 1 to 166 and mancozeb at a ratio of 0.1:1; a pest control composition comprising any one of the present compounds 1 to 166 and mancozeb at a ratio of 1:1; a pest control composition comprising any one of the present compounds 1 to 166 and folpet at a ratio of 0.01:1; a pest control composition comprising any one of the present compounds 1 to 166 and folpet at a ratio of 0.1:1; a pest control composition comprising any one of the present compounds 1 to 166 and folpet at a ratio of 1:1; a pest control composition comprising any one of the present compounds 1 to 166 and captan at a ratio of 0.01:1; a pest control composition comprising any one of the present compounds 1 to 166 and captan at a ratio of 0.1:1; a pest control composition comprising any one of the present compounds 1 to 166 and captan at a ratio of 1:1; a pest control composition comprising any one of the present compounds 1 to 166 and thiuram at a ratio of 0.01:1; a pest control composition comprising any one of the present compounds 1 to 166 and thiuram at a ratio of 0.1:1; a pest control composition comprising any one of the present compounds 1 to 166 and thiuram at a ratio of 1:1; a pest control composition comprising any one of the present compounds 1 to 166 and metiram at a ratio of 0.01:1; a pest control composition comprising any one of the present compounds 1 to 166 and metiram at a ratio of 0.1:1; a pest control composition comprising any one of the present compounds 1 to 166 and metiram at a ratio of 1:1; a pest control composition comprising any one of the present compounds 1 to 166 and maneb at a ratio of 0.01:1;

a pest control composition comprising any one of the present compounds 1 to 166 and maneb at a ratio of 0.1:1; a pest control composition comprising any one of the present compounds 1 to 166 and maneb at a ratio of 1:1; a pest control composition comprising any one of the present compounds 1 to 166 and iminoctadine acetate at a ratio of 0.1:1; a pest control composition comprising any one of the present compounds 1 to 166 and iminoctadine acetate at a ratio of 1:1; a pest control composition comprising any one of the present compounds 1 to 166 and iminoctadine acetate at a ratio of 10:1; a pest control composition comprising any one of the present compounds 1 to 166 and sulfur at a ratio of 0.01:1; a pest control composition comprising any one of the present compounds 1 to 166 and sulfur at a ratio of 0.1:1; a pest control composition comprising any one of the present compounds 1 to 166 and sulfur at a ratio of 1:1; a pest control composition comprising any one of the present compounds 1 to 166 and copper oxychloride at a ratio of 0.01:1; a pest control composition comprising any one of the present compounds 1 to 166 and copper oxychloride at a ratio of 0.1:1; a pest control composition comprising any one of the present compounds 1 to 166 and copper oxychloride at a ratio of 1:1; a pest control composition comprising any one of the present compounds 1 to 166 and copper hydroxide at a ratio of 0.01:1; a pest control composition comprising any one of the present compounds 1 to 166 and copper hydroxide at a ratio of 0.1:1; a pest control composition comprising any one of the present compounds 1 to 166 and copper hydroxide at a ratio of 1:1; a pest control composition comprising any one of the present compounds 1 to 166 and copper hydroxide sulfate at a ratio of 0.01:1; a pest control composition comprising any one of the present compounds 1 to 166 and copper hydroxide sulfate at a ratio of 0.1:1; a pest control composition comprising any one of the present compounds 1 to 166 and copper hydroxide sulfate at a ratio of 1:1; a pest control composition comprising any one of the present compounds 1 to 166 and Bordeaux mixture at a ratio of 0.01:1; a pest control composition comprising any one of the present compounds 1 to 166 and Bordeaux mixture at a ratio of 0.1:1; a pest control composition comprising any one of the present compounds 1 to 166 and Bordeaux mixture at a ratio of 1:1;

a pest control composition comprising any one of the present compounds 1 to 166 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 0.1:1; a pest control composition comprising any one of the present compounds 1 to 166 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 1:1; a pest control composition comprising any one of the present compounds 1 to 166 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 10:1; a pest control composition comprising any one of the present compounds 1 to 166 and {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 0.1:1; a pest control composition comprising any one of the present compounds 1 to 166 and carboxamide; {[4-methoxy-2-({

[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 1:1; a pest control composition comprising any one of the present compounds 1 to 166 and carboxamide; {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 10:1;
a pest control composition comprising any one of the present compounds 1 to 166 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 0.1:1; a pest control composition comprising any one of the present compounds 1 to 166 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 1:1; a pest control composition comprising any one of the present compounds 1 to 166 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 10:1; a pest control composition comprising any one of the present compounds 1 to 166 and 2,6-dimethyl-1H,5H-[1,4]dithiino[2,3-c:5,6-c']dipyrrole-1,3,5,7 (2H,6H)-tetrone at a ratio of 0.01:1; a pest control composition comprising any one of the present compounds 1 to 166 and 2,6-dimethyl-1H,5H-[1,4]dithiino[2,3-c:5,6-c']dipyrrole-1,3,5,7 (2H,6H)-tetrone at a ratio of 0.1:1; a pest control composition comprising any one of the present compounds 1 to 166 and 2,6-dimethyl-1H,5H-[1,4]dithiino[2,3-c:5,6-c']dipyrrole-1,3,5,7 (2H,6H)-tetrone at a ratio of 1:1; a pest control composition comprising any one of the present compounds 1 to 166 and 3-(4,4-difluoro-3,3-dimethyl-3,4-dihydroisoquinolin-1-yl)quinoline at a ratio of 0.1:1; a pest control composition comprising any one of the present compounds 1 to 166 and 3-(4,4-difluoro-3,3-dimethyl-3,4-dihydroisoquinolin-1-yl)quinoline at a ratio of 1:1; a pest control composition comprising any one of the present compounds 1 to 166 and 3-(4,4-difluoro-3,3-dimethyl-3,4-dihydroisoquinolin-1-yl)quinoline at a ratio of 10:1; a pest control composition comprising any one of the present compounds 1 to 166 and 3-(5-fluoro-3,3,4,4-tetramethyl-3,4-dihydroisoquinolin-1-yl)quinoline at a ratio of 0.1:1;
a pest control composition comprising any one of the present compounds 1 to 166 and 3-(5-fluoro-3,3,4,4-tetramethyl-3,4-dihydroisoquinolin-1-yl)quinoline at a ratio of 1:1; a pest control composition comprising any one of the present compounds 1 to 166 and 3-(5-fluoro-3,3,4,4-tetramethyl-3,4-dihydroisoquinolin-1-yl)quinoline at a ratio of 10:1; a pest control composition comprising any one of the present compounds 1 to 166 and 3-(4,4,5-trifluoro-3,3-dimethyl-3,4-dihydroisoquinolin-1-yl)quinoline at a ratio of 0.1:1; a pest control composition comprising any one of the present compounds 1 to 166 and 3-(4,4,5-trifluoro-3,3-dimethyl-3,4-dihydroisoquinolin-1-yl)quinoline at a ratio of 1:1; a pest control composition comprising any one of the present compounds 1 to 166 and 3-(4,4,5-trifluoro-3,3-dimethyl-3,4-dihydroisoquinolin-1-yl)quinoline at a ratio of 10:1; a pest compounds 1 to 166 and [3-(4-chloro-2-fluorophenyl)-5-(2,4-difluorophenyl)-1,2-oxazol-4-yl](pyridin-3-yl)methanol at a ratio of 0.1:1; a pest control composition comprising any one of the present compounds 1 to 166 and [3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 166 and [3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 166 and (S)-[3-(4-chloro-2-fluorophenyl)-5-(2,4-difluorophenyl)-1,2-oxazol-4-yl](pyridin-3-yl)methanol at a ratio of 0.1:1;
a pest control composition comprising any one of the present compounds 1 to 166 and (S)-[3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 166 and (S)-[3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 166 and (R)-[3-(4-chloro-2-fluorophenyl)-5-(2,4-difluorophenyl)-1,2-oxazol-4-yl](pyridin-3-yl)methanol at a ratio of 0.1:1; a pest control composition comprising any one of the present compounds 1 to 166 and (R)-[3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 166 and (R)-[3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 166 and 2-{[3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 166 and 2-{[3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 166 and 2-{[3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 166 and 2-{[rel-(2R,3S)-3-(2-chlorophenyl)-2-(2,4-difluorophenyl)oxylan-2-yl]methyl}-2,4-dihydro-3H-1,2,4-triazole-3-thione at a ratio of 0.1:1;
a pest control composition comprising any one of the present compounds 1 to 166 and 2-{[rel-(2R,3S)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 166 and 2-{[rel-(2R,3S)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 166 and 2-{[rel-(2R,3R)-3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 166 and 2-{[rel-(2R,3R)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 166 and 2-{[rel-(2R,3R)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 166 and 2-{[(2R,3S)-3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 166 and 2-{[(2R,3S)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 166 and 2-{[(2R,3S)-3-(2-chlorophenyl)-2-(2,4-difluorophenyl)oxylan-2-yl]methyl}-2,4-dihydro-3H-1,2,4-triazole-3-thione at a ratio of 10:1;

a pest control composition comprising any one of the present compounds 1 to 166 and 2-{[(2S,3R)-3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 166 and 2-{[(2S,3R)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 166 and 2-{[(2S,3R)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 166 and 2-{[(2R,3R)-3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 166 and 2-{[(2R,3R)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 166 and 2-{[(2R,3R)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 166 and 2-{[(2S,3S)-3-(2-chlorophenyl)-2-(2,4-difluorophenyl)oxylan-2-yl]methyl}-2,4-dihydro-3H-1,2,4-triazole-3-thione at a ratio of 0.1:1;

a pest control composition comprising any one of the present compounds 1 to 166 and 2-{[(2S,3S)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 166 and 2-{[(2S,3S)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 166 and 1-{[3-(2-chlorophenyl)-2-(2,4-difluorophenyl)oxylan-2-yl]methyl}-1H-1,2,4-triazole-5-thiol at a ratio of 0.1:1; a compounds 1 to 166 and 1-{[3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 166 and 1-{[3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 166 and 1-{[rel-(2R,3S)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 166 and 1-{[rel-(2R,3S)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 166 and 1-{[rel-(2R,3S)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 166 and 1-{[rel-(2R,3R)-3-(2-chlorophenyl)-2-(2,4-difluorophenyl)oxylan-2-yl]methyl}-1H-1,2,4-triazole-5-thiol at a ratio of 0.1:1;

a pest control composition comprising any one of the present compounds 1 to 166 and 1-{[rel-(2R,3R)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 166 and 1-{[rel-(2R,3R)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 166 and 1-{[(2R,3S)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 166 and 1-{[(2R,3S)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 166 and 1-{[(2R,3S)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 166 and 1-{[(2S,3R)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 166 and 1-{[(2S,3R)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 166 and 1-{[(2S,3R)-3-(2-chlorophenyl)-2-(2,4-difluorophenyl)oxylan-2-yl]methyl}-1H-1,2,4-triazole-5-thiol at a ratio of 10:1;

a pest control composition comprising any one of the present compounds 1 to 166 and 1-{[(2R,3R)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 166 and 1-{[(2R,3R)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 166 and 1-{[(2R,3R)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 166 and 1-{[(2S,3S)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 166 and 1-{[(2S,3S)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 166 and 1-{[(2S,3S)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 166 and 1-{[3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 166 and 1-{[3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 166 and 1-{[3-(2-chlorophenyl)-2-(2,4-difluorophenyl)oxylan-2-yl]methyl}-1H-1,2,4-triazol-5-yl thiocyanate at a ratio of 10:1;

a pest control composition comprising any one of the present compounds 1 to 166 and 1-{[rel-(2R,3S)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 166 and 1-{[rel-(2R,3S)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 166 and 1-{[rel-(2R,3S)-3-(2-chlorophenyl)-

2-(2,4-difluorophenyl)oxylan-2-yl]methyl}-1H-1,2,4-triazol-5-yl thiocyanate at a ratio of 10:1; a pest control composition comprising any one of the present compounds 1 to 166 and 1-{[rel-(2R,3R)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 166 and 1-{[rel-(2R,3R)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 166 and 1-{[rel-(2R,3R)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 166 and 1-{[(2R,3S)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 166 and 1-{[(2R,3S)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 166 and 1-{[(2R,3S)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 166 and 1-{[(2S,3R)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 166 and 1-{[(2S,3R)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 166 and 1-([(2S,3R)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 166 and 1-{[(2R,3R)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 166 and 1-{[(2R,3R)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 166 and 1-{[(2R,3R)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 166 and 1-{[(2S,3S)-3-(2-chlorophenyl)-2-(2,4-difluorophenyl)oxylan-2-yl]methyl}-1H-1,2,4-triazol-5-yl thiocyanate at a ratio of 0.1:1;

a pest control composition comprising any one of the present compounds 1 to 166 and 1-{[(2S,3S)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 166 and 1-{[(2S,3S)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 166 and 5-(4-chlorobenzyl)-2-chloromethyl-2-methyl-1-(1H-1,2,4-triazol-1-ylmethyl)cyclopentanol at a ratio of 0.1:1; a pest control composition comprising any one of the present compounds 1 to 166 and 5-(4-chlorobenzyl)-2-chloromethyl-2-methyl-1-(1H-1,2,4-triazol-1-ylmethyl)cyclopentanol at a ratio of 1:1; a pest control composition comprising any one of the present compounds 1 to 166 and 5-(4-chlorobenzyl)-2-chloromethyl-2-methyl-1-(1H-1,2,4-triazol-1-ylmethyl)cyclopentanol at a ratio of 10:1; a pest control composition comprising any one of the present compounds 1 to 166 and (1RS,2SR,5SR)-5-(4-chlorobenzyl)-2-chloromethyl-2-methyl-1-(1H-1,2,4-triazol-1-ylmethyl)cyclopentanol at a ratio of 0.1:1; a pest control composition comprising any one of the present compounds 1 to 166 and (1RS,2SR,5SR)-5-(4-chlorobenzyl)-2-chloromethyl-2-methyl-1-(1H-1,2,4-triazol-1-ylmethyl)cyclopentanol at a ratio of 1:1; a pest control composition comprising any one of the present compounds 1 to 166 and (1RS,2SR,5SR)-5-(4-chlorobenzyl)-2-chloromethyl-2-methyl-1-(1H-1,2,4-triazol-1-ylmethyl)cyclopentanol at a ratio of 10:1;

a pest control composition comprising any one of the present compounds 1 to 166 and (1RS,2RS,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1RS,2RS,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1RS,2RS,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1RS,2RS,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1RS,2RS,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1RS,2SR,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1RS,2SR,5RS)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 166 and (1R,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1R,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1R,2S,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1S,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1S,2R,5R)-2-chloromethyl-5-(4-fluorobenzyl)-2-methyl-1-(1H-1,2,4-triazol-1- ylmethyl)cyclopentanol at a ratio of 1:1; a pest control composition comprising any one of the present compounds 1 to 166 and (1S,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1R,2R,5R)-2-chloromethyl-5-(4-fluorobenzyl)-2-methyl-1-(1H-,1,2,4-triazol-1-ylmethyl)cyclopentanol at a ratio of 0.1:1; a pest control composition comprising any one of the present compounds 1 to 166 and (1R,2R,5R)-2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 166 and (1R,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1S,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1S,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1S,2S,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1R,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1R,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1R,2R,5S)-2-chloromethyl-5-(4-fluorobenzyl)-2-methyl-1-(1H-,1,2,4-triazol-1-ylmethyl)cyclopentanol at a ratio of 10:1; a pest control composition comprising any one of the present compounds 1 to 166 and (1S,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1S,2S,5R)-2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 166 and (1S,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1R,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1R,2S,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1R,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1S,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1S,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1S,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and 2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and 2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 166 and 2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1RS,2SR,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1RS,2SR,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1RS,2SR,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1RS,2RS,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1RS,2RS,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1RS,2RS,5SR)-2-chloromethyl-5-(4-fluorobenzyl)-2-methyl-1-(1H-1,2,4-triazol-1-ylmethyl)cyclopentanol at a ratio of 0.1:1;

a pest control composition comprising any one of the present compounds 1 to 166 and (1RS,2RS,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1RS,2RS,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1RS,2SR,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1RS,2SR,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1R,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1R,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1R,2S,5S)-2-chloromethyl-5-(4-fluorobenzyl)-2-methyl-1-(1H-1,2,4-triazol-1-ylmethyl)cyclopentanol at a ratio of 10:1;
a pest control composition comprising any one of the present compounds 1 to 166 and (1S,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1S,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1S,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1R,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1R,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1R,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1S,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1S,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1S,2S,5S)-2-chloromethyl-5-(4-fluorobenzyl)-2-methyl-1-(1H-1,2,4-triazol-1-ylmethyl)cyclopentanol at a ratio of 10:1;
a pest control composition comprising any one of the present compounds 1 to 166 and (1R,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1R,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1R,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1S,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1S,2S,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1S,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1R,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1R,2S,5R)-2-chloromethyl-5-(4-fluorobenzyl)-2-methyl-1-(1H-1,2,4-triazol-1-ylmethyl)cyclopentanol at a ratio of 1:1;
a pest control composition comprising any one of the present compounds 1 to 166 and (1R,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 166 and (1S,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 166 and (1S,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 166 and (1S,2R,5S)-2-chloromethyl-5-(4-fluorobenzyl)-2-methyl-1-(1H-1,2,4-triazol-1-ylmethyl)cyclopentanol at a ratio of 10:1;
a pest control composition comprising any one of the present compounds 1 to 166 and 5-amino-4-(2-chloro-4-fluorophenyl)-N-(2,6-difluorophenyl)-1,3-dimethyl-1H-pyrazole at a ratio of 0.1:1; a pest control composition comprising any one of the present compounds 1 to 166 and 5-amino-4-(2-chloro-4-fluorophenyl)-N-(2,6-difluorophenyl)-1,3-dimethyl-1H-pyrazole at a ratio of 1:1; a pest control composition comprising any one of the present compounds 1 to 166 and 5-amino-4-(2-chloro-4-fluorophenyl)-N-(2,6-difluorophenyl)-1,3-dimethyl-1H-pyrazole at a ratio of 10:1;
a pest control composition comprising any one of the present compounds 1 to 166 and 5-amino-4-(2-bromo-4-fluorophenyl)-N-(2,6-difluorophenyl)-1,3-dimethyl-1H-pyrazole at a ratio of 0.1:1; a pest control composition comprising any one of the present compounds 1 to 166 and 5-amino-4-(2-bromo-4-fluorophenyl)-N-(2,6-difluorophenyl)-1,3-dimethyl-1H-pyrazole at a ratio of 1:1; a pest control composition comprising any one of the present compounds 1 to 166 and 5-amino-4-(2-bromo-4-fluorophenyl)-N-(2,6-difluorophenyl)-1,3-dimethyl-1H-pyrazole at a ratio of 10:1;
a pest control composition comprising any one of the present compounds 1 to 166 and 5-amino-4-(2-chloro-4-fluorophenyl)-N-(2-chloro-6-fluorophenyl)-1,3-dimethyl-1H-pyrazole at a ratio of 0.1:1; a pest control composition comprising any one of the present compounds 1 to 166 and 5-amino-4-(2-chloro-4-fluorophenyl)-N-(2-chloro-6-fluorophenyl)-1,3-dimethyl-1H-pyrazole at a ratio of 1:1; a pest control composition comprising any one of the present compounds 1 to 166 and 5-amino-4-(2-chloro-4-fluorophenyl)-N-(2-chloro-6-fluorophenyl)-1,3-dimethyl-1H-pyrazole at a ratio of 10:1;
a pest control composition comprising any one of the present compounds 1 to 166 and 5-amino-4-(2-bromo-4-fluorophenyl)-N-(2-chloro-6-fluorophenyl)-1,3-dimethyl-1H-pyrazole at a ratio of 0.1:1; a pest control composition comprising any one of the present compounds 1 to 166 and 5-amino-4-(2-bromo-4-fluorophenyl)-N-(2-chloro-6-fluorophenyl)-1,3-dimethyl-1H-pyrazole at a ratio of 1:1; a pest control composition comprising any one of the present compounds 1 to 166 and 5-amino-4-(2-bromo-4-fluorophenyl)-N-(2-chloro-6-fluorophenyl)-1,3-dimethyl-1H-pyrazole at a ratio of 10:1;
a pest control composition comprising any one of the present compounds 1 to 166 and 5-amino-4-(2-chloro-4-fluorophenyl)-N-(2,6-difluoro-4-methylphenyl)-1,3-dimethyl-1H-pyrazole at a ratio of 0.1:1; a pest control composition comprising any one of the present compounds 1 to 166 and 5-amino-4-(2-chloro-4-fluorophenyl)-N-(2,6-difluoro-4-methylphenyl)-1,3-dimethyl-1H-pyrazole at a ratio of 1:1; a pest control composition comprising any one of the present compounds 1 to 166 and 5-amino-4-(2-chloro-4-fluorophenyl)-N-(2,6-difluoro-4-methylphenyl)-1,3-dimethyl-1H-pyrazole at a ratio of 10:1;
a pest control composition comprising any one of the present compounds 1 to 166 and 5-amino-4-(2-bromo-4-fluorophenyl)-N-(2,6-difluoro-4-methylphenyl)-1,3-dimethyl-1H-pyrazole at a ratio of 0.1:1; a pest control composition comprising any one of the present compounds 1 to 166 and 5-amino-4-(2-bromo-4-fluorophenyl)-N-(2,6-difluoro-4-methylphenyl)-1,3-dimethyl-1H-pyrazole at a ratio of 1:1; a pest control composition comprising any one of the present compounds 1 to 166 and 5-amino-4-(2-bromo-4-fluorophenyl)-N-(2,6-difluoro-4-methylphenyl)-1,3-dimethyl-1H-pyrazole at a ratio of 10:1;
a pest control composition comprising any one of the present compounds 1 to 166 and 5-amino-N-(2-chloro-6-fluoro-4-methylphenyl)-4-(2-chloro-4-fluorophenyl)-1,3-dimethyl-1H-pyrazole at a ratio of 0.1:1; a pest control composition comprising any one of the present compounds 1 to 166 and 5-amino-N-(2-chloro-6-fluoro-4-methylphenyl)-4-(2-chloro-4-fluorophenyl)-1,3-dimethyl-1H-pyrazole at a ratio of 1:1; a pest control composition comprising any one of the present compounds 1 to 166 and 5-amino-N-(2-chloro-6-fluoro-4-methylphenyl)-4-(2-chloro-4-fluorophenyl)-1,3-dimethyl-1H-pyrazole at a ratio of 10:1;
a pest control composition comprising any one of the present compounds 1 to 166 and 5-amino-4-(2-bromo-4-fluorophenyl)-N-(2-chloro-6-fluoro-4-methylphenyl)-1,3-dimethyl-1H-pyrazole at a ratio of 0.1:1; a pest control composition comprising any one of the present compounds 1 to 166 and 5-amino-4-(2-bromo-4-fluorophenyl)-N-(2-chloro-6-fluoro-4-methylphenyl)-1,3-dimethyl-1H-pyrazole at a ratio of 1:1; a pest control composition comprising any one of the present compounds 1 to 166 and 5-amino-4-(2-bromo-4-fluorophenyl)-N-(2-chloro-6-fluoro-4-methylphenyl)-1,3-dimethyl-1H-pyrazole at a ratio of 10:1;
a pest control composition comprising any one of the present compounds 1 to 166 and 9-fluoro-2,3-dihydro-2,2-dimethyl-5-(quinolin-3-yl)-1,4-benzooxazepine at a ratio of 0.1:1; a pest control composition comprising any one of the present compounds 1 to 166 and 9-fluoro-2,3-dihydro-2,2-dimethyl-5-(quinolin-3-yl)-1,4-benzooxazepine at a ratio of 1:1; a pest control composition comprising any one of the present compounds 1 to 166 and 9-fluoro-2,3-dihydro-2,2-dimethyl-5-(quinolin-3-yl)-1,4-benzooxazepine at a ratio of 10:1; a pest compounds 1 to 166 and N-cyclopropyl-3-(difluoromethyl)-5-fluoro-N-(2-isopropylbenzyl)-1-methyl-1H-pyrazole-4-carboxamide at a ratio of 0.1:1; a pest control composition comprising any one of the present compounds 1 to 166 and N-cyclopropyl-3-(difluoromethyl)-5-fluoro-N-(2-isopropylbenzyl)-1-methyl-1H-pyrazole-4-carboxamide at a ratio of 1:1; a pest control composition comprising any one of the present compounds 1 to 166 and N-cyclopropyl-3-(difluoromethyl)-5-fluoro-N-(2-isopropylbenzyl)-1-methyl-1H-pyrazole-4-carboxamide at a ratio of 10:1; a pest control composition comprising any one of the present compounds 1 to 166 and N-cyclopropyl-3-(difluoromethyl)-5-fluoro-N-(5-chloro-2-isopropylbenzyl)-1-methyl-1H-pyrazole-4-carboxamide at a ratio of 0.1:1; a pest control composition comprising any one of the present compounds 1 to 166 and N-cyclopropyl-3-(difluoromethyl)-5-fluoro-N-(5-chloro-2-isopropylbenzyl)-1-methyl-1H-pyrazole-4-carboxamide at a ratio of 1:1; a pest control composition comprising any one of the present compounds 1 to 166 and N-cyclopropyl-3-(difluoromethyl)-5-fluoro-N-(5-chloro-2-isopropylbenzyl)-1-methyl-1H-pyrazole-4-carboxamide at a ratio of 10:1; a pest control composition comprising any one of the present compounds 1 to 166 and N-[1-(2,4-dichlorophenyl)-1-methoxypropan-2-yl]-3-difluoromethyl-1-methyl-1H-pyrazole-4-carboxamide at a ratio of 0.1:1;
a pest control composition comprising any one of the present compounds 1 to 166 and N-[1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and N-[1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and N-[(1R,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and N-[(1R,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and N-[(1R,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and N-[(1R,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and N-[(1R,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and N-[(1R,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and N-[(1S,2R)1-(2,4-dichlorophenyl)-1-methoxypropan-2-yl]-3-difluoromethyl-1-methyl-1H-pyrazole-4-carboxamide at a ratio of 0.1:1;
a pest control composition comprising any one of the present compounds 1 to 166 and N-[(1S,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and N-[(1S,2R) 1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and N-[(1S,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and N-[(1S,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and N-[(1S,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and rel-N-[(1R,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and rel-N-[(1R,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and rel-N-[(1R,2R)1-(2,4-dichlorophenyl)-1-methoxypropan-2-yl]-3-difluoromethyl-1-methyl-1H-pyrazole-4-carboxamide at a ratio of 10:1;

a pest control composition comprising any one of the present compounds 1 to 166 and rel-N-[(1R,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and rel-N-[(1R,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and rel-N-[(1R,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and N-[(1R,2RS)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and N-[(1R,2RS)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and N-[(1R,2RS)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and N-[(1S,2RS)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and N-[(1S,2RS)1-(2,4-dichlorophenyl)-1-methoxypropan-2-yl]-3-difluoromethyl-1-methyl-1H-pyrazole-4-carboxamide at a ratio of 1:1;

a pest control composition comprising any one of the present compounds 1 to 166 and N-[(1S,2RS)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and N-[(1RS,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and N-[(1RS,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and N-[(1RS,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 166 and N-[(1RS,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 166 and N-[(1RS,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 166 and N-[(1RS,2S)1-(2,4-dichlorophenyl)-1-methoxypropan-2-yl]-3-difluoromethyl-1-methyl-1H-pyrazole-4-carboxamide at a ratio of 10:1;

a pest control composition comprising any one of the present compounds 1 to 166 and 3-difluoromethyl-N-methoxy-1-methyl-N-[1-methyl-2-(2,4,6-trichlorophenyl)ethyl]pyrazole-4-carboxamide at a ratio of 0.1:1; a pest control composition comprising any one of the present compounds 1 to 166 and 3-difluoromethyl-N-methoxy-1-methyl-N-[1-methyl-2-(2,4,6-trichlorophenyl)ethyl]pyrazole-4-carboxamide at a ratio of 1:1; a pest control composition comprising any one of the present compounds 1 to 166 and 3-difluoromethyl-N-methoxy-1-methyl-N-[1-methyl-2-(2,4,6-trichlorophenyl)ethyl]pyrazole-4-carboxamide at a ratio of 10:1; a pest control composition comprising any one of the present compounds 1 to 166 and 3-difluoromethyl-N-methoxy-1-methyl-N-[(1R)-1-methyl-2-(2,4,6-trichlorophenyl)ethyl]pyrazole-4-carboxamide at a ratio of 0.1:1; a pest control composition comprising any one of the present compounds 1 to 166 and 3-difluoromethyl-N-methoxy-1-methyl-N-[(1R)-1-methyl-2-(2,4,6-trichlorophenyl)ethyl]pyrazole-4-carboxamide at a ratio of 1:1; a pest control composition comprising any one of the present compounds 1 to 166 and 3-difluoromethyl-N-methoxy-1-methyl-N-[(1R)-1-methyl-2-(2,4,6-trichlorophenyl)ethyl]pyrazole-4-carboxamide at a ratio of 10:1; a pest control composition comprising any one of the present compounds 1 to 166 and 3-difluoromethyl-N-methoxy-1-methyl-N-[(1S)-1-methyl-2-(2,4,6-trichlorophenyl)ethyl]pyrazole-4-carboxamide at a ratio of 0.1:1; a pest control composition comprising any one of the present compounds 1 to 166 and 3-difluoromethyl-N-methoxy-1-methyl-N-[(1S)-1-methyl-2-(2,4,6-trichlorophenyl)ethyl]pyrazole-4-carboxamide at a ratio of 1:1; a pest control composition comprising any one of the present compounds 1 to 166 and 3-difluoromethyl-N-methoxy-1-methyl-N-[(1S)-1-methyl-2-(2,4,6-trichlorophenyl)ethyl]pyrazole-4-carboxamide at a ratio of 10:1;

a pest control composition comprising any one of the present compounds 1 to 166 and 3-butyn-1-yl N-{6-[({(Z)-[(1-methyl-1H-tetrazol-5-yl)phenylmethylene]amino}oxy)methyl]-2-pyridinyl}carbamate at a ratio of 0.1:1; a pest control composition comprising any one of the present compounds 1 to 166 and 3-butyn-1-yl N-{6-[({(Z)-[(1-methyl-1H-tetrazol-5-yl)phenylmethylene]amino}oxy)methyl]-2-pyridinyl}carbamate at a ratio of 1:1; a pest control composition comprising any one of the present compounds 1 to 166 and 3-butyn-1-yl N-{6-[({(Z)-[(1-methyl-1H-tetrazol-5-yl)phenylmethylene]amino}oxy)methyl]-2-pyridinyl}carbamate at a ratio of 10:1; a pest control composition comprising any one of the present compounds 1 to 166 and 5-fluoro-2-[(4-methylphenyl)methoxy]-4-pyrimidineamine at a ratio of 0.1:1; a pest control composition comprising any one of the present compounds 1 to 166 and 5-fluoro-2-[(4-methylphenyl)methoxy]-4-pyrimidineamine at a ratio of 1:1; a pest control composition comprising any one of the present compounds 1 to 166 and 5-fluoro-2-[(4-methylphenyl)methoxy]-4-pyrimidineamine at a ratio of 10:1; a pest control composition comprising any one of the present compounds 1 to 166 and 2-[6-(3-fluoro-4-methoxyphenyl)-5-methylpyridin-2-yl]quinazoline at a ratio of 0.1:1; a pest control composition comprising any one of the present compounds 1 to 166 and 2-[6-(3-fluoro-4-methoxyphenyl)-5-methylpyridin-2-yl]quinazoline at a ratio of 1:1; a pest control composition comprising any one of the present compounds 1 to 166 and 2-[6-(3-fluoro-4-methoxyphenyl)-5-methylpyridin-2-yl]quinazoline at a ratio of 10:1; a pest control composition comprising any one of the present compounds 1 to 166 and azaconazole; a pest control composition comprising any one of the present compounds 1 to 166 and diniconazole-M; a pest control composition comprising any one of the present compounds 1 to 166 and etaconazole; a pest control composition comprising any one of the present compounds 1 to 166 and uniconazole; a pest control composition comprising any one of the present compounds 1 to 166 and s-(+)-N-(1,1,3-trimethylindan-4-yl)-1-methyl-3-difluoromethylpyrazole-4-carboxylic acid amide; a pest control composition comprising any one of the present compounds 1 to 166 and benodanil; a pest control composition comprising any one of the present compounds 1 to 166 and fenfuram; a pest control composition comprising any one of the present co0pounds 1 to 166 and oxycarboxin;

a pest control composition comprising any one of the present compounds 1 to 166 and dodemorph; a pest control composition comprising any one of the present compounds 1 to 166 and piperalin; a pest control composition comprising any one of the present compounds 1 to 166 and thiabendazole; a pest control composition comprising any one of the present compounds 1 to 166 and fuberidazole; a pest control composition comprising any one of the present compounds 1 to 166 and thiophanate; a pest control composition comprising any one of the present compounds 1 to 166 and furalaxyl; a pest control composition comprising any one of the present compounds 1 to 166 and ofurace; a pest control composition comprising any one of the present compounds 1 to 166 and oxadixyl; a pest control composition comprising any one of the present compounds 1 to 166 and flumorph; a pest control composition comprising any one of the present compounds 1 to 166 and dichlofluanid; a pest control composition comprising any one of the present compounds 1 to 166 and fenoxanil; a pest control composition comprising any one of the present compounds 1 to 166 and acibenzolar-S-methyl; a pest control composition comprising any one of the present compounds 1 to 166 and anilazine; a pest control composition comprising any one of the present compounds 1 to 166 and bethoxazine; a pest control composition comprising any one of the present compounds 1 to 166 and binapacryl; a pest control composition comprising any one of the present compounds 1 to 166 and biphenyl; a pest control composition comprising any one of the present compounds 1 to 166 and blastcidin S; a pest control composition comprising any one of the present compounds 1 to 166 and bupirimate; a pest control composition comprising any one of the present compounds 1 to 166 and captafol; a pest control composition comprising any one of the present compounds 1 to 166 and chloroneb; a pest control composition comprising any one of the present compounds 1 to 166 and dichloran; a pest control composition comprising any one of the present compounds 1 to 166 and diflumetorim; a pest control composition comprising any one of the present compounds 1 to 166 and dimethirimol; a pest control composition comprising any one of the present compounds 1 to 166 and dinocap; a pest control composition comprising any one of the present compounds 1 to 166 and dithianon; pest control composition comprising any one of the present compounds 1 to 166 and dodine; a pest control composition comprising any one of the present compounds 1 to 166 and edifenphos; a pest control composition comprising any one of the present compounds 1 to 166 and ethirimol; a pest control composition comprising any one of the present compounds 1 to 166 and etridiazol; a pest control composition comprising any one of the present compounds 1 to 166 and fenarimol; a pest control composition comprising any one of the present compounds 1 to 166 and fentin-acetate; a pest control composition comprising any one of the present compounds 1 to 166 and fentin-hydroxide; a pest control composition comprising any one of the present compounds 1 to 166 and ferbam; a pest control composition comprising any one of the present compounds 1 to 166 and fluoroimide; a pest control composition comprising any one of the present compounds 1 to 166 and flutianil; a pest control composition comprising any one of the present compounds 1 to 166 and furmecyclox; a pest control composition comprising any one of the present compounds 1 to 166 and iodocarb; a pest control composition comprising any one of the present compounds 1 to 166 and iprobenfos; a pest control composition comprising any one of the present compounds 1 to 166 and meptyldinocap; a pest control composition comprising any one of the present compounds 1 to 166 and methasulfocarb; a pest control composition comprising any one of the present compounds 1 to 166 and metiram; a pest control composition comprising any one of the present compounds 1 to 166 and naftifine; a pest control composition comprising any one of the present compounds 1 to 166 and nuarimol; a pest control composition comprising any one of the present compounds 1 to 166 and octhilinone; a pest control composition comprising any one of the present compounds 1 to 166 and pefurazoate; a pest control composition comprising any one of the present compounds 1 to 166 and phosphorous acid; a pest control composition comprising any one of the present compounds 1 to 166 and a sodium salt of phosphorous acid; a pest control composition comprising any one of the present compounds 1 to 166 and an ammonium salt of phosphorous acid; a pest control composition comprising any one of the present compounds 1 to 166 and polyoxin;

a pest control composition comprising any one of the present compounds 1 to 166 and propineb; a pest control composition comprising any one of the present compounds 1 to 166 and prothiocarb; a pest control composition comprising any one of the present compounds 1 to 166 and pyrazophos; a pest control composition comprising any one of the present compounds 1 to 166 and pyributicarb; a pest control composition comprising any one of the present compounds 1 to 166 and pyrifenox; a pest control composition comprising any one of the present compounds 1 to 166 and pyrrolnitrin; a pest control composition comprising any one of the present compounds 1 to 166 and PCNB; a pest control composition comprising any one of the present compounds 1 to 166 and TCNB; a pest control composition comprising any one of the present compounds 1 to 166 and tecloftalam; a pest control composition comprising any one of the present compounds 1 to 166 and terbinafine; a pest control composition comprising any one of the present compounds 1 to 166 and tolylfluanid; a pest control composition comprising any one of the present compounds 1 to 166 and triarimol; a pest control composition comprising any one of the present compounds 1 to 166 and triazoxide; a pest control composition comprising any one of the present compounds 1 to 166 and triforine; a pest control composition comprising any one of the present compounds 1 to 166 and trimorphamide; a pest control composition comprising any one of the present compounds 1 to 166 and zineb; a pest control composition comprising any one of the present compounds 1 to 166 and ziram; a pest control composition comprising any one of the present compounds 1 to 166 and acephate at a ratio of 1:1; a pest control composition comprising any one of the present compounds 1 to 166 and acephate at a ratio of 1:10; a pest control composition comprising any one of the present compounds 1 to 166 and acephate at a ratio of 1:50; a pest control composition comprising any one of the present compounds 1 to 166 and azamethiphos at a ratio of 1:1; a pest control composition comprising any one of the present compounds 1 to 166 and azamethiphos at a ratio of 1:10;

a pest control composition comprising any one of the present compounds 1 to 166 and azamethiphos at a ratio of 1:50; a pest control composition comprising any one of the present compounds 1 to 166 and azinphos-ethyl at a ratio of 1:1; a pest control composition comprising any one of the present compounds 1 to 166 and azinphos-ethyl at a ratio of 1:10; a pest control composition comprising any one of the present compounds 1 to 166 and azinphos-ethyl at a ratio of 1:50; a pest control composition comprising any one of the present compounds 1 to 166 and azinphos-methyl at a ratio of 1:1; a pest control composition comprising any one of the present compounds 1 to 166 and azinphos-methyl at a ratio of 1:10; a pest control composition comprising any one of the present compounds 1 to 166 and azinphos-methyl at a ratio of 1:50; a pest control composition comprising any one of the present compounds 1 to 166 and cadusafos at a ratio of 1:1; a pest control composition comprising any one of the present compounds 1 to 166 and cadusafos at a ratio of 1:10; a pest control composition comprising any one of the present compounds 1 to 166 and cadusafos at a ratio of 1:50; a pest control composition comprising any one of the present compounds 1 to 166 and chlorethoxyfos at a ratio of 1:1; a pest control composition comprising any one of the present compounds 1 to 166 and chlorethoxyfos at a ratio of 1:10; a pest control composition comprising any one of the present compounds 1 to 166 and chlorethoxyfos at a ratio of 1:50; a pest control composition comprising any one of the present compounds 1 to 166 and chlorfenvinphos at a ratio of 1:1; a pest control composition comprising any one of the present compounds 1 to 166 and chlorfenvinphos at a ratio of 1:10; a pest control composition comprising any one of the present compounds 1 to 166 and chlorfenvinphos at a ratio of 1:50; a pest control composition comprising any one of the present compounds 1 to 166 and chlormephos at a ratio of 1:1; a pest control composition comprising any one of the present compounds 1 to 166 and chlormephos at a ratio of 1:10; a pest control composition comprising any one of the present compounds 1 to 166 and chlormephos at a ratio of 1:50; a pest control composition comprising any one of the present compounds 1 to 166 and chlorpyrifos at a ratio of 1:1; a pest control composition comprising any one of the present compounds 1 to 166 and chlorpyrifos at a ratio of 1:10;

a pest control composition comprising any one of the present compounds 1 to 166 and chlorpyrifos at a ratio of 1:50; a pest control composition comprising any one of the present compounds 1 to 166 and chlorpyrifosmethyl at a ratio of 1:1; a pest control composition comprising any one of the present compounds 1 to 166 and chlorpyrifosmethyl at a ratio of 1:10; a pest control composition comprising any one of the present compounds 1 to 166 and chlorpyrifosmethyl at a ratio of 1:50; a pest control composition comprising any one of the present compounds 1 to 166 and coumaphos at a ratio of 1:1; a pest control composition comprising any one of the present compounds 1 to 166 and coumaphos at a ratio of 1:10; a pest control composition comprising any one of the present compounds 1 to 166 and coumaphos at a ratio of 1:50; a pest control composition comprising any one of the present compounds 1 to 166 and cyanophos at a ratio of 1:1; a pest control composition comprising any one of the present compounds 1 to 166 and cyanophos at a ratio of 1:10; a pest control composition comprising any one of the present compounds 1 to 166 and cyanophos at a ratio of 1:50; a pest control composition comprising any one of the present compounds 1 to 166 and demeton-S-methyl at a ratio of 1:1; a pest control composition comprising any one of the present compounds 1 to 166 and demeton-S-methyl at a ratio of 1:10; a pest control composition comprising any one of the present compounds 1 to 166 and demeton-S-methyl at a ratio of 1:50; a compounds 1 to 166 and diazinon at a ratio of 1:1; a pest control composition comprising any one of the present compounds 1 to 166 and diazinon at a ratio of 1:10; a pest control composition comprising any one of the present compounds 1 to 166 and diazinon at a ratio of 1:50; a pest control composition comprising any one of the present compounds 1 to 166 and dichlorvos at a ratio of 1:1; a pest control composition comprising any one of the present compounds 1 to 166 and dichlorvos at a ratio of 1:10; a pest control composition comprising any one of the present compounds 1 to 166 and dichlorvos at a ratio of 1:50;

a pest control composition comprising any one of the present compounds 1 to 166 and dicrotophos at a ratio of 1:1; a pest control composition comprising any one of the present compounds 1 to 166 and dicrotophos at a ratio of 1:10; a pest control composition comprising any one of the present compounds 1 to 166 and dicrotophos at a ratio of 1:50; a pest control composition comprising any one of the present compounds 1 to 166 and dimethoate at a ratio of 1:1; a pest control composition comprising any one of the present compounds 1 to 166 and dimethoate at a ratio of 1:10; a pest control composition comprising any one of the present compounds 1 to 166 and dimethoate at a ratio of 1:50; a pest control composition comprising any one of the present compounds 1 to 166 and dimethylvinphos at a ratio of 1:1; a pest control composition comprising any one of the present compounds 1 to 166 and dimethylvinphos at a ratio of 1:10; a pest control composition comprising any one of the present compounds 1 to 166 and dimethylvinphos at a ratio of 1:50; a pest control composition comprising any one of the present compounds 1 to 166 and disulfoton at a ratio of 1:1; a pest control composition comprising any one of the present compounds 1 to 166 and disulfoton at a ratio of 1:10; a pest control composition comprising any one of the present compounds 1 to 166 and disulfoton at a ratio of 1:50; a pest control composition comprising any one of the present compounds 1 to 166 and EPN at a ratio of 1:1; a pest control composition comprising any one of the present compounds 1 to 166 and EPN at a ratio of 1:10; a pest control composition comprising any one of the present compounds 1 to 166 and EPN at a ratio of 1:50; a pest control composition comprising any one of the present compounds 1 to 166 and ethion at a ratio of 1:1; a pest control composition comprising any one of the present compounds 1 to 166 and ethion at a ratio of 1:10; a pest control composition comprising any one of the present compounds 1 to 166 and ethion at a ratio of 1:50; a pest control composition comprising any one of the present compounds 1 to 166 and ethoprophos at a ratio of 1:1; a pest control composition comprising any one of the present compounds 1 to 166 and ethoprophos at a ratio of 1:10;

pest control composition comprising any one of the present compounds 1 to 166 and ethoprophos at a ratio of 1:50; a pest control composition comprising any one of the present compounds 1 to 166 and famphur at a ratio of 1:1; a pest control composition comprising any one of the present compounds 1 to 166 and famphur at a ratio of 1:10; a pest control composition comprising any one of the present compounds 1 to 166 and famphur at a ratio of 1:50; a pest control composition comprising any one of the present compounds 1 to 166 and fenamiphos at a ratio of 1:1; a pest control composition comprising any one of the present compounds 1 to 166 and fenamiphos at a ratio of 1:10; a pest control composition comprising any one of the present compounds 1 to 166 and fenamiphos at a ratio of 1:50; a pest control composition comprising any one of the present compounds 1 to 166 and fenitrothion at a ratio of 1:1; a pest control composition comprising any one of the present compounds 1 to 166 and fenitrothion at a ratio of 1:10; a pest control composition comprising any one of the present compounds 1 to 166 and fenitrothion at a ratio of 1:50; a pest control composition comprising any one of the present compounds 1 to 166 and fenthion at a ratio of 1:1; a pest control composition comprising any one of the present compounds 1 to 166 and fenthion at a ratio of 1:10; a pest control composition comprising any one of the present compounds 1 to 166 and fenthion at a ratio of 1:50; a pest control composition comprising any one of the present compounds 1 to 166 and heptenophos at a ratio of 1:1; a pest control composition comprising any one of the present compounds 1 to 166 and heptenophos at a ratio of 1:10; a pest control composition comprising any one of the present compounds 1 to 166 and heptenophos at a ratio of 1:50; a pest control composition comprising any one of the present compounds 1 to 166 and isofenphos at a ratio of 1:1; a pest control composition comprising any one of the present compounds 1 to 166 and isofenphos at a ratio of 1:10; a pest control composition comprising any one of the present compounds 1 to 166 and isofenphos at a ratio of 1:50; a pest control composition comprising any one of the present compounds 1 to 166 and isocarbophos at a ratio of 1:1;
a pest control composition comprising any one of the present compounds 1 to 166 and isocarbophos at a ratio of 1:10; a pest control composition comprising any one of the present compounds 1 to 166 and isocarbophos at a ratio of 1:50; a pest control composition comprising any one of the present compounds 1 to 166 and isoxathion at a ratio of 1:1; a pest control composition comprising any one of the present compounds 1 to 166 and isoxathion at a ratio of 1:10; a pest control composition comprising any one of the present compounds 1 to 166 and isoxathion at a ratio of 1:50; a pest control composition comprising any one of the present compounds 1 to 166 and malathion at a ratio of 1:1; a pest control composition comprising any one of the present compounds 1 to 166 and malathion at a ratio of 1:10; a pest control composition comprising any one of the present compounds 1 to 166 and malathion at a ratio of 1:50; a pest control composition comprising any one of the present compounds 1 to 166 and mecarbam at a ratio of 1:1; a pest control composition comprising any one of the present compounds 1 to 166 and mecarbam at a ratio of 1:10; a pest control composition comprising any one of the present compounds 1 to 166 and mecarbam at a ratio of 1:50; a pest control composition comprising any one of the present compounds 1 to 166 and methamidophos at a ratio of 1:1; a pest control composition comprising any one of the present compounds 1 to 166 and methamidophos at a ratio of 1:10; a compounds 1 to 166 and methamidophos at a ratio of 1:50; a pest control composition comprising any one of the present compounds 1 to 166 and methidathion at a ratio of 1:1; a pest control composition comprising any one of the present compounds 1 to 166 and methidathion at a ratio of 1:10; a pest control composition comprising any one of the present compounds 1 to 166 and methidathion at a ratio of 1:50; a pest control composition comprising any one of the present compounds 1 to 166 and mevinphos at a ratio of 1:1; a pest control composition comprising any one of the present compounds 1 to 166 and mevinphos at a ratio of 1:10; a pest control composition comprising any one of the present compounds 1 to 166 and mevinphos at a ratio of 1:50; a pest control composition comprising any one of the present compounds 1 to 166 and monocrotophos at a ratio of 1:1;
a pest control composition comprising any one of the present compounds 1 to 166 and monocrotophos at a ratio of 1:10; a pest control composition comprising any one of the present compounds 1 to 166 and monocrotophos at a ratio of 1:50; a pest control composition comprising any one of the present compounds 1 to 166 and naled at a ratio of 1:1; a pest control composition comprising any one of the present compounds 1 to 166 and naled at a ratio of 1:10; a pest control composition comprising any one of the present compounds 1 to 166 and naled at a ratio of 1:50; a pest control composition comprising any one of the present compounds 1 to 166 and omethoate at a ratio of 1:1; a pest control composition comprising any one of the present compounds 1 to 166 and omethoate at a ratio of 1:10; a compounds 1 to 166 and omethoate at a ratio of 1:50; a pest control composition comprising any one of the present compounds 1 to 166 and oxydemeton-methyl at a ratio of 1:1; a pest control composition comprising any one of the present compounds 1 to 166 and oxydemeton-methyl at a ratio of 1:10; a pest control composition comprising any one of the present compounds 1 to 166 and oxydemeton-methyl at a ratio of 1:50; a pest control composition comprising any one of the present compounds 1 to 166 and parathion at a ratio of 1:1; a pest control composition comprising any one of the present compounds 1 to 166 and parathion at a ratio of 1:10; a pest control composition comprising any one of the present compounds 1 to 166 and parathion at a ratio of 1:50; a pest control composition comprising any one of the present compounds 1 to 166 and methylparathion at a ratio of 1:1; a pest control composition comprising any one of the present compounds 1 to 166 and methylparathion at a ratio of 1:10; a pest control composition comprising any one of the present compounds 1 to 166 and methylparathion at a ratio of 1:50; a pest control composition comprising any one of the present compounds 1 to 166 and phenthoate at a ratio of 1:1; a pest control composition comprising any one of the present compounds 1 to 166 and phenthoate at a ratio of 1:10;
a pest control composition comprising any one of the present compounds 1 to 166 and phenthoate at a ratio of 1:50; a pest control composition comprising any one of the present compounds 1 to 166 and phorate at a ratio of 1:1; a pest control composition comprising any one of the present compounds 1 to 166 and phorate at a ratio of 1:10; a pest control composition comprising any one of the present compounds 1 to 166 and phorate at a ratio of 1:50; a pest control composition comprising any one of the present compounds 1 to 166 and phosalone at a ratio of 1:1; a pest control composition comprising any one of the present compounds 1 to 166 and phosalone at a ratio of 1:10; a pest control composition comprising any one of the present compounds 1 to 166 and phosalone at a ratio of 1:50; a pest control composition comprising any one of the present compounds 1 to 166 and phosmet at a ratio of 1:1; a pest control composition comprising any one of the present compounds 1 to 166 and phosmet at a ratio of 1:10; a pest control composition comprising any one of the present compounds 1 to 166 and phosmet at a ratio of 1:50; a pest control composition comprising any one of the present compounds 1 to 166 and phosphamidon at a ratio of 1:1; a pest control composition comprising any one of the present compounds 1 to 166 and phosphamidon at a ratio of 1:10; a pest control composition comprising any one of the present compounds 1 to 166 and phosphamidon at a ratio of 1:50; a pest control composition comprising any one of the present compounds 1 to 166 and phoxim at a ratio of 1:1; a pest control composition comprising any one of the present compounds 1 to 166 and phoxim at a ratio of 1:10; a pest control composition comprising any one of the present compounds 1 to 166 and phoxim at a ratio of 1:50; a pest control composition comprising any one of the present compounds 1 to 166 and pirimiphos-methyl at a ratio of 1:1; a pest control composition comprising any one of the present compounds 1 to 166 and pirimiphos-methyl at a ratio of 1:10; a pest control composition comprising any one of the present compounds 1 to 166 and pirimiphos-methyl at a ratio of 1:50;

a pest control composition comprising any one of the present compounds 1 to 166 and profenofos at a ratio of 1:1; a pest control composition comprising any one of the present compounds 1 to 166 and profenofos at a ratio of 1:10; a pest control composition comprising any one of the present compounds 1 to 166 and profenofos at a ratio of 1:50; a pest control composition comprising any one of the present compounds 1 to 166 and propetamphos at a ratio of 1:1; a pest control composition comprising any one of the present compounds 1 to 166 and propetamphos at a ratio of 1:10; a pest control composition comprising any one of the present compounds 1 to 166 and propetamphos at a ratio of 1:50; a pest control composition comprising any one of the present compounds 1 to 166 and prothiofos at a ratio of 1:1; a pest control composition comprising any one of the present compounds 1 to 166 and prothiofos at a ratio of 1:10; a pest control composition comprising any one of the present compounds 1 to 166 and prothiofos at a ratio of 1:50; a pest control composition comprising any one of the present compounds 1 to 166 and pyraclofos at a ratio of 1:1; a pest control composition comprising any one of the present compounds 1 to 166 and pyraclofos at a ratio of 1:10; a pest control composition comprising any one of the present compounds 1 to 166 and pyraclofos at a ratio of 1:50; a pest control composition comprising any one of the present compounds 1 to 166 and pyridaphenthion at a ratio of 1:1; a compounds 1 to 166 and pyridaphenthion at a ratio of 1:10; a pest control composition comprising any one of the present compounds 1 to 166 and pyridaphenthion at a ratio of 1:50; a pest control composition comprising any one of the present compounds 1 to 166 and quinalphos at a ratio of 1:1; a pest control composition comprising any one of the present compounds 1 to 166 and quinalphos at a ratio of 1:10; a pest control composition comprising any one of the present compounds 1 to 166 and quinalphos at a ratio of 1:50; a pest control composition comprising any one of the present compounds 1 to 166 and sulfotep at a ratio of 1:1; a pest control composition comprising any one of the present compounds 1 to 166 and sulfotep at a ratio of 1:10; a pest control composition comprising any one of the present compounds 1 to 166 and sulfotep at a ratio of 1:50; a pest control composition comprising any one of the present compounds 1 to 166 and tebupirimfos at a ratio of 1:1;

a pest control composition comprising any one of the present compounds 1 to 166 and tebupirimfos at a ratio of 1:10; a pest control composition comprising any one of the present compounds 1 to 166 and tebupirimfos at a ratio of 1:50; a pest control composition comprising any one of the present compounds 1 to 166 and temephos at a ratio of 1:1; a pest control composition comprising any one of the present compounds 1 to 166 and temephos at a ratio of 1:10; a pest control composition comprising any one of the present compounds 1 to 166 and temephos at a ratio of 1:50; a pest control composition comprising any one of the present compounds 1 to 166 and terbufos at a ratio of 1:1; a pest control composition comprising any one of the present compounds 1 to 166 and terbufos at a ratio of 1:10; a pest control composition comprising any one of the present compounds 1 to 166 and terbufos at a ratio of 1:50; a pest control composition comprising any one of the present compounds 1 to 166 and tetrachlorvinphos at a ratio of 1:1; a pest control composition comprising any one of the present compounds 1 to 166 and tetrachlorvinphos at a ratio of 1:10; a pest control composition comprising any one of the present compounds 1 to 166 and tetrachlorvinphos at a ratio of 1:50; a pest control composition comprising any one of the present compounds 1 to 166 and thiometon at a ratio of 1:1; a pest control composition comprising any one of the present compounds 1 to 166 and thiometon at a ratio of 1:10; a pest control composition comprising any one of the present compounds 1 to 166 and thiometon at a ratio of 1:50; a pest control composition comprising any one of the present compounds 1 to 166 and triazophos at a ratio of 1:1; a pest control composition comprising any one of the present compounds 1 to 166 and triazophos at a ratio of 1:10; a pest control composition comprising any one of the present compounds 1 to 166 and triazophos at a ratio of 1:50; a pest control composition comprising any one of the present compounds 1 to 166 and trichlorfon at a ratio of 1:1; a pest control composition comprising any one of the present compounds 1 to 166 and trichlorfon at a ratio of 1:10; a pest control composition comprising any one of the present compounds 1 to 166 and trichlorfon at a ratio of 1:50;

a pest control composition comprising any one of the present compounds 1 to 166 and vamidothion at a ratio of 1:1; a pest control composition comprising any one of the present compounds 1 to 166 and vamidothion at a ratio of 1:10; a pest control composition comprising any one of the present compounds 1 to 166 and vamidothion at a ratio of 1:50; a pest control composition comprising any one of the present compounds 1 to 166 and alanycarb at a ratio of 1:1; a pest control composition comprising any one of the present compounds 1 to 166 and alanycarb at a ratio of 1:10; a pest control composition comprising any one of the present compounds 1 to 166 and alanycarb at a ratio of 1:50; a pest control composition comprising any one of the present compounds 1 to 166 and aldicarb at a ratio of 1:1; a pest control composition comprising any one of the present compounds 1 to 166 and aldicarb at a ratio of 1:10; a pest control composition comprising any one of the present compounds 1 to 166 and aldicarb at a ratio of 1:50; a pest control composition comprising any one of the present compounds 1 to 166 and bendiocarb at a ratio of 1:1; a pest control composition comprising any one of the present compounds 1 to 166 and bendiocarb at a ratio of 1:10; a pest control composition comprising any one of the present compounds 1 to 166 and bendiocarb at a ratio of 1:50; a pest control composition comprising any one of the present compounds 1 to 166 and benfuracarb at a ratio of 1:1; a pest control composition comprising any one of the present compounds 1 to 166 and benfuracarb at a ratio of 1:10; a pest control composition comprising any one of the present compounds 1 to 166 and benfuracarb at a ratio of 1:50; a pest compounds 1 to 166 and butocarboxim at a ratio of 1:1; a pest control composition comprising any one of the present compounds 1 to 166 and butocarboxim at a ratio of 1:10; a pest control composition comprising any one of the present compounds 1 to 166 and butocarboxim at a ratio of 1:50; a pest control composition comprising any one of the present compounds 1 to 166 and butoxycarboxim at a ratio of 1:1; a pest control composition comprising any one of the present compounds 1 to 166 and butoxycarboxim at a ratio of 1:10; a pest control composition comprising any one of the present compounds 1 to 166 and butoxycarboxim at a ratio of 1:50;

a pest control composition comprising any one of the present compounds 1 to 166 and carbaryl at a ratio of 1:1; a pest control composition comprising any one of the present compounds 1 to 166 and carbaryl at a ratio of 1:10; a pest control composition comprising any one of the present compounds 1 to 166 and carbaryl at a ratio of 1:50; a pest control composition comprising any one of the present compounds 1 to 166 and carbofuran at a ratio of 1:1; a pest control composition comprising any one of the present compounds 1 to 166 and carbofuran at a ratio of 1:10; a pest control composition comprising any one of the present compounds 1 to 166 and carbofuran at a ratio of 1:50; a pest control composition comprising any one of the present compounds 1 to 166 and carbosulfan at a ratio of 1:1; a pest control composition comprising any one of the present compounds 1 to 166 and carbosulfan at a ratio of 1:10; a pest control composition comprising any one of the present compounds 1 to 166 and carbosulfan at a ratio of 1:50; a pest control composition comprising any one of the present compounds 1 to 166 and ethiofencarb at a ratio of 1:1; a pest control composition comprising any one of the present compounds 1 to 166 and ethiofencarb at a ratio of 1:10; a pest control composition comprising any one of the present compounds 1 to 166 and ethiofencarb at a ratio of 1:50; a pest control composition comprising any one of the present compounds 1 to 166 and fenobucarb at a ratio of 1:1; a pest control composition comprising any one of the present compounds 1 to 166 and fenobucarb at a ratio of 1:10; a pest control composition comprising any one of the present compounds 1 to 166 and fenobucarb at a ratio of 1:50; a pest control composition comprising any one of the present compounds 1 to 166 and formetanate at a ratio of 1:1; a pest control composition comprising any one of the present compounds 1 to 166 and formetanate at a ratio of 1:10; a pest control composition comprising any one of the present compounds 1 to 166 and formetanate at a ratio of 1:50; a pest control composition comprising any one of the present compounds 1 to 166 and furathiocarb at a ratio of 1:1;

a pest control composition comprising any one of the present compounds 1 to 166 and furathiocarb at a ratio of 1:10; a pest control composition comprising any one of the present compounds 1 to 166 and furathiocarb at a ratio of 1:50; a pest control composition comprising any one of the present compounds 1 to 166 and isoprocarb at a ratio of 1:1; a pest control composition comprising any one of the present compounds 1 to 166 and isoprocarb at a ratio of 1:10; a pest compounds 1 to 166 and isoprocarb at a ratio of 1:50; a pest control composition comprising any one of the present compounds 1 to 166 and methiocarb at a ratio of 1:1; a pest control composition comprising any one of the present compounds 1 to 166 and methiocarb at a ratio of 1:10; a pest control composition comprising any one of the present compounds 1 to 166 and methiocarb at a ratio of 1:50; a pest control composition comprising any one of the present compounds 1 to 166 and methomyl at a ratio of 1:1; a pest control composition comprising any one of the present compounds 1 to 166 and methomyl at a ratio of 1:10; a pest control composition comprising any one of the present compounds 1 to 166 and methomyl at a ratio of 1:50; a pest control composition comprising any one of the present compounds 1 to 166 and metolcarb at a ratio of 1:1; a pest control composition comprising any one of the present compounds 1 to 166 and metolcarb at a ratio of 1:10; a pest control composition comprising any one of the present compounds 1 to 166 and metolcarb at a ratio of 1:50; a pest control composition comprising any one of the present compounds 1 to 166 and oxamyl at a ratio of 1:1; a pest control composition comprising any one of the present compounds 1 to 166 and oxamyl at a ratio of 1:10; a pest control composition comprising any one of the present compounds 1 to 166 and oxamyl at a ratio of 1:50; a pest control composition comprising any one of the present compounds 1 to 166 and pirimicarb at a ratio of 1:1;

a pest control composition comprising any one of the present compounds 1 to 166 and pirimicarb at a ratio of 1:10; a pest control composition comprising any one of the present compounds 1 to 166 and pirimicarb at a ratio of 1:50; a pest control composition comprising any one of the present compounds 1 to 166 and propoxur at a ratio of 1:1; a pest control composition comprising any one of the present compounds 1 to 166 and propoxur at a ratio of 1:10; a pest control composition comprising any one of the present compounds 1 to 166 and propoxur at a ratio of 1:50; a pest control composition comprising any one of the present compounds 1 to 166 and thiodicarb at a ratio of 1:1; a pest control composition comprising any one of the present compounds 1 to 166 and thiodicarb at a ratio of 1:10; a pest control composition comprising any one of the present compounds 1 to 166 and thiodicarb at a ratio of 1:50; a pest control composition comprising any one of the present compounds 1 to 166 and thiofanox at a ratio of 1:1; a pest control composition comprising any one of the present compounds 1 to 166 and thiofanox at a ratio of 1:10; a pest control composition comprising any one of the present compounds 1 to 166 and thiofanox at a ratio of 1:50; a pest control composition comprising any one of the present compounds 1 to 166 and triazamate at a ratio of 1:1; a pest control composition comprising any one of the present compounds 1 to 166 and triazamate at a ratio of 1:10; a pest control composition comprising any one of the present compounds 1 to 166 and triazamate at a ratio of 1:50; a pest control composition comprising any one of the present compounds 1 to 166 and trimethacarb at a ratio of 1:1; a pest control composition comprising any one of the present compounds 1 to 166 and trimethacarb at a ratio of 1:10; a pest control composition comprising any one of the present compounds 1 to 166 and trimethacarb at a ratio of 1:50; a pest control composition comprising any one of the present compounds 1 to 166 and XMC at a ratio of 1:1; a pest control composition comprising any one of the present compounds 1 to 166 and XMC at a ratio of 1:10; a pest control composition comprising any one of the present compounds 1 to 166 and XMC at a ratio of 1:50;

a pest control composition comprising any one of the present compounds 1 to 166 and xylylcarb at a ratio of 1:1; a pest control composition comprising any one of the present compounds 1 to 166 and xylylcarb at a ratio of 1:10; a pest control composition comprising any one of the present compounds 1 to 166 and xylylcarb at a ratio of 1:50; a pest control composition comprising any one of the present compounds 1 to 166 and acrinathrin at a ratio of 0.1:1; a pest control composition comprising any one of the present compounds 1 to 166 and acrinathrin at a ratio of 1:1; a pest control composition comprising any one of the present compounds 1 to 166 and acrinathrin at a ratio of 1:10; a pest control composition comprising any one of the present compounds 1 to 166 and allethrin at a ratio of 0.1:1; a pest control composition comprising any one of the present compounds 1 to 166 and allethrin at a ratio of 1:1; a pest control composition comprising any one of the present compounds 1 to 166 and allethrin at a ratio of 1:10; a pest control composition comprising any one of the present compounds 1 to 166 and bifenthrin at a ratio of 0.1:1; a pest compounds 1 to 166 and bifenthrin at a ratio of 1:1; a pest control composition comprising any one of the present compounds 1 to 166 and bifenthrin at a ratio of 1:10; a pest control composition comprising any one of the present compounds 1 to 166 and bioallethrin at a ratio of 0.1:1; a pest control composition comprising any one of the present compounds 1 to 166 and bioallethrin at a ratio of 1:1; a pest control composition comprising any one of the present compounds 1 to 166 and bioallethrin at a ratio of 1:10; a pest control composition comprising any one of the present compounds 1 to 166 and bioresmethrin at a ratio of 0.1:1; a pest control composition comprising any one of the present compounds 1 to 166 and bioresmethrin at a ratio of 1:1; a pest control composition comprising any one of the present compounds 1 to 166 and bioresmethrin at a ratio of 1:10; a pest control composition comprising any one of the present compounds 1 to 166 and cycloprothrin at a ratio of 0.1:1; a pest control composition comprising any one of the present compounds 1 to 166 and cycloprothrin at a ratio of 1:1; a pest control composition comprising any one of the present compounds 1 to 166 and cycloprothrin at a ratio of 1:10;

a pest control composition comprising any one of the present compounds 1 to 166 and cyfluthrin at a ratio of 0.1:1; a pest control composition comprising any one of the present compounds 1 to 166 and cyfluthrin at a ratio of 1:1; a pest control composition comprising any one of the present compounds 1 to 166 and cyfluthrin at a ratio of 1:10; a pest control composition comprising any one of the present compounds 1 to 166 and beta-cyfluthrin at a ratio of 0.1:1; a pest control composition comprising any one of the present compounds 1 to 166 and beta-cyfluthrin at a ratio of 1:1; a pest control composition comprising any one of the present compounds 1 to 166 and beta-cyfluthrin at a ratio of 1:10; a pest control composition comprising any one of the present compounds 1 to 166 and cyhalothrin at a ratio of 0.1:1; a pest control composition comprising any one of the present compounds 1 to 166 and cyhalothrin at a ratio of 1:1; a pest control composition comprising any one of the present compounds 1 to 166 and cyhalothrin at a ratio of 1:10; a pest control composition comprising any one of the present compounds 1 to 166 and gamma-cyhalothrin at a ratio of 0.1:1; a pest control composition comprising any one of the present compounds 1 to 166 and gamma-cyhalothrin at a ratio of 1:1; a pest control composition comprising any one of the present compounds 1 to 166 and gamma-cyhalothrin at a ratio of 1:10; a pest control composition comprising any one of the present compounds 1 to 166 and lambda-cyhalothrin at a ratio of 0.1:1; a pest control composition comprising any one of the present compounds 1 to 166 and lambda-cyhalothrin at a ratio of 1:1; a pest control composition comprising any one of the present compounds 1 to 166 and lambda-cyhalothrin at a ratio of 1:10; a pest control composition comprising any one of the present compounds 1 to 166 and cypermethrin at a ratio of 0.1:1; a pest control composition comprising any one of the present compounds 1 to 166 and cypermethrin at a ratio of 1:1; a pest control composition comprising any one of the present compounds 1 to 166 and cypermethrin at a ratio of 1:10; a pest control composition comprising any one of the present compounds 1 to 166 and alpha-cypermethrin at a ratio of 0.1:1;

a pest control composition comprising any one of the present compounds 1 to 166 and alpha-cypermethrin at a ratio of 1:1; a pest control composition comprising any one of the present compounds 1 to 166 and alpha-cypermethrin at a ratio of 1:10; a pest control composition comprising any one of the present compounds 1 to 166 and beta-cypermethrin at a ratio of 0.1:1; a pest control composition comprising any one of the present compounds 1 to 166 and beta-cypermethrin at a ratio of 1:1; a pest control composition comprising any one of the present compounds 1 to 166 and beta-cypermethrin at a ratio of 1:10; a pest control composition comprising any one of the present compounds 1 to 166 and theta-cypermethrin at a ratio of 0.1:1; a pest control composition comprising any one of the present compounds 1 to 166 and theta-cypermethrin at a ratio of 1:1; a pest control composition comprising any one of the present compounds 1 to 166 and theta-cypermethrin at a ratio of 1:10; a pest control composition comprising any one of the present compounds 1 to 166 and zeta-cypermethrin at a ratio of 0.1:1; a pest control composition comprising any one of the present compounds 1 to 166 and zeta-cypermethrin at a ratio of 1:1; a pest control composition comprising any one of the present compounds 1 to 166 and zeta-cypermethrin at a ratio of 1:10; a pest control composition comprising any one of the present compounds 1 to 166 and cyphenothrin at a ratio of 0.1:1; a pest control composition comprising any one of the present compounds 1 to 166 and cyphenothrin at a ratio of 1:1; a pest control composition comprising any one of the present compounds 1 to 166 and cyphenothrin at a ratio of 1:10; a pest compounds 1 to 166 and deltamethrin at a ratio of 0.1:1; a pest control composition comprising any one of the present compounds 1 to 166 and deltamethrin at a ratio of 1:1; a pest control composition comprising any one of the present compounds 1 to 166 and deltamethrin at a ratio of 1:10; a pest control composition comprising any one of the present compounds 1 to 166 and empenthrin at a ratio of 0.1:1; a pest control composition comprising any one of the present compounds 1 to 166 and empenthrin at a ratio of 1:1; a pest control composition comprising any one of the present compounds 1 to 166 and empenthrin at a ratio of 1:10;

a pest control composition comprising any one of the present compounds 1 to 166 and esfenvalerate at a ratio of 0.1:1; a pest control composition comprising any one of the present compounds 1 to 166 and esfenvalerate at a ratio of 1:1; a pest control composition comprising any one of the present compounds 1 to 166 and esfenvalerate at a ratio of 1:10; a pest control composition comprising any one of the present compounds 1 to 166 and etofenprox at a ratio of 0.1:1; a pest control composition comprising any one of the present compounds 1 to 166 and etofenprox at a ratio of 1:1; a pest control composition comprising any one of the present compounds 1 to 166 and etofenprox at a ratio of 1:10; a pest control composition comprising any one of the present compounds 1 to 166 and fenpropathrin at a ratio of 0.1:1; a pest control composition comprising any one of the present compounds 1 to 166 and fenpropathrin at a ratio of 1:1; a pest control composition comprising any one of the present compounds 1 to 166 and fenpropathrin at a ratio of 1:10; a pest control composition comprising any one of the present compounds 1 to 166 and fenvalerate at a ratio of 0.1:1; a pest control composition comprising any one of the present compounds 1 to 166 and fenvalerate at a ratio of 1:1; a pest control composition comprising any one of the present compounds 1 to 166 and fenvalerate at a ratio of 1:10; a pest control composition comprising any one of the present compounds 1 to 166 and flucythrinate at a ratio of 0.1:1; a pest control composition comprising any one of the present compounds 1 to 166 and flucythrinate at a ratio of 1:1; a pest control composition comprising any one of the present compounds 1 to 166 and flucythrinate at a ratio of 1:10; a pest control composition comprising any one of the present compounds 1 to 166 and flumethrin at a ratio of 0.1:1; a pest control composition comprising any one of the present compounds 1 to 166 and flumethrin at a ratio of 1:1; a pest control composition comprising any one of the present compounds 1 to 166 and flumethrin at a ratio of 1:10; a pest control composition comprising any one of the present compounds 1 to 166 and fluvalinate at a ratio of 0.1:1; a pest control composition comprising any one of the present compounds 1 to 166 and fluvalinate at a ratio of 1:1; a pest control composition comprising any one of the present compounds 1 to 166 and fluvalinate at a ratio of 1:10; a pest control composition comprising any one of the present compounds 1 to 166 and tau-fluvalinate at a ratio of 0.1:1;

a pest control composition comprising any one of the present compounds 1 to 166 and tau-fluvalinate at a ratio of 1:1; a compounds 1 to 166 and tau-fluvalinate at a ratio of 1:10; a pest control composition comprising any one of the present compounds 1 to 166 and halfenprox at a ratio of 0.1:1; a pest control composition comprising any one of the present compounds 1 to 166 and halfenprox at a ratio of 1:1; a pest control composition comprising any one of the present compounds 1 to 166 and halfenprox at a ratio of 1:10; a pest control composition comprising any one of the present compounds 1 to 166 and heptafluthrin at a ratio of 0.1:1; a pest control composition comprising any one of the present compounds 1 to 166 and heptafluthrin at a ratio of 1:1; a pest control composition comprising any one of the present compounds 1 to 166 and heptafluthrin at a ratio of 1:10; a pest control composition comprising any one of the present compounds 1 to 166 and imiprothrin at a ratio of 0.1:1; a pest control composition comprising any one of the present compounds 1 to 166 and imiprothrin at a ratio of 1:1; a pest control composition comprising any one of the present compounds 1 to 166 and imiprothrin at a ratio of 1:10; a pest control composition comprising any one of the present compounds 1 to 166 and kadethrin at a ratio of 0.1:1; a pest control composition comprising any one of the present compounds 1 to 166 and kadethrin at a ratio of 1:1; a pest control composition comprising any one of the present compounds 1 to 166 and kadethrin at a ratio of 1:10; a pest control composition comprising any one of the present compounds 1 to 166 and meperfluthrin at a ratio of 0.1:1; a pest control composition comprising any one of the present compounds 1 to 166 and meperfluthrin at a ratio of 1:1;

a pest control composition comprising any one of the present compounds 1 to 166 and meperfluthrin at a ratio of 1:10; a pest control composition comprising any one of the present compounds 1 to 166 and momfluorothrin at a ratio of 0.1:1; a pest control composition comprising any one of the present compounds 1 to 166 and momfluorothrin at a ratio of 1:1; a pest control composition comprising any one of the present compounds 1 to 166 and momfluorothrin at a ratio of 1:10; a pest control composition comprising any one of the present compounds 1 to 166 and permethrin at a ratio of 0.1:1; a pest control composition comprising any one of the present compounds 1 to 166 and permethrin at a ratio of 1:1; a pest control composition comprising any one of the present compounds 1 to 166 and permethrin at a ratio of 1:10; a pest control composition comprising any one of the present compounds 1 to 166 and phenothrin at a ratio of 0.1:1; a pest control composition comprising any one of the present compounds 1 to 166 and phenothrin at a ratio of 1:1; a pest control composition comprising any one of the present compounds 1 to 166 and phenothrin at a ratio of 1:10; a pest control composition comprising any one of the present compounds 1 to 166 and prallethrin at a ratio of 0.1:1; a pest control composition comprising any one of the present compounds 1 to 166 and prallethrin at a ratio of 1:1; a pest control composition comprising any one of the present compounds 1 to 166 and prallethrin at a ratio of 1:10; a pest control composition comprising any one of the present compounds 1 to 166 and pyrethrins at a ratio of 0.1:1; a pest control composition comprising any one of the present compounds 1 to 166 and pyrethrins at a ratio of 1:1; a pest control composition comprising any one of the present compounds 1 to 166 and pyrethrins at a ratio of 1:10; a pest control composition comprising any one of the present compounds 1 to 166 and resmethrin at a ratio of 0.1:1; a pest control composition comprising any one of the present compounds 1 to 166 and resmethrin at a ratio of 1:1; a pest control composition comprising any one of the present compounds 1 to 166 and resmethrin at a ratio of 1:10; a pest control composition comprising any one of the present compounds 1 to 166 and silafluofen at a ratio of 0.1:1;

a pest control composition comprising any one of the present compounds 1 to 166 and silafluofen at a ratio of 1:1; a pest control composition comprising any one of the present compounds 1 to 166 and silafluofen at a ratio of 1:10; a pest control composition comprising any one of the present compounds 1 to 166 and tefluthrin at a ratio of 0.1:1; a pest control composition comprising any one of the present compounds 1 to 166 and tefluthrin at a ratio of 1:1; a pest control composition comprising any one of the present compounds 1 to 166 and tefluthrin at a ratio of 1:10; a pest control composition comprising any one of the present compounds 1 to 166 and tetramethrin at a ratio of 0.1:1; a pest control composition comprising any one of the present compounds 1 to 166 and tetramethrin at a ratio of 1:1; a pest control composition comprising any one of the present compounds 1 to 166 and tetramethrin at a ratio of 1:10; a pest control composition comprising any one of the present compounds 1 to 166 and tetramethylfluthrin at a ratio of 0.1:1; a pest control composition comprising any one of the present compounds 1 to 166 and tetramethylfluthrin at a ratio of 1:1; a pest control composition comprising any one of the present compounds 1 to 166 and tetramethylfluthrin at a ratio of 1:10; a pest control composition comprising any one of the present compounds 1 to 166 and tralomethrin at a ratio of 0.1:1; a pest control composition comprising any one of the present compounds 1 to 166 and tralomethrin at a ratio of 1:1; a pest control composition comprising any one of the present compounds 1 to 166 and tralomethrin at a ratio of 1:10; a pest control composition comprising any one of the present compounds 1 to 166 and transfluthrin at a ratio of 0.1:1; a pest control composition comprising any one of the present compounds 1 to 166 and transfluthrin at a ratio of 1:1; a pest control composition comprising any one of the present compounds 1 to 166 and transfluthrin at a ratio of 1:10; a pest control composition comprising any one of the present compounds 1 to 166 and bensultap at a ratio of 1:1; a pest control composition comprising any one of the present compounds 1 to 166 and bensultap at a ratio of 1:10; a pest control composition comprising any one of the present compounds 1 to 166 and bensultap at a ratio of 1:50; a pest control composition comprising any one of the present compounds 1 to 166 and cartap at a ratio of 1:1; a pest control composition comprising any one of the present compounds 1 to 166 and cartap at a ratio of 1:10; a pest control composition comprising any one of the present compounds 1 to 166 and cartap at a ratio of 1:50; a pest control composition comprising any one of the present compounds 1 to 166 and cartap hydrochloride at a ratio of 1:1; a pest control composition comprising any one of the present compounds 1 to 166 and cartap hydrochloride at a ratio of 1:10; a pest control composition comprising any one of the present compounds 1 to 166 and cartap hydrochloride at a ratio of 1:50; a pest control composition comprising any one of the present compounds 1 to 166 and thiocyclam at a ratio of 1:1; a pest control composition comprising any one of the present compounds 1 to 166 and thiocyclam at a ratio of 1:10; a pest control composition comprising any one of the present compounds 1 to 166 and thiocyclam at a ratio of 1:50; a pest control composition comprising any one of the present compounds 1 to 166 and bisultap at a ratio of 1:1; a pest control composition comprising any one of the present compounds 1 to 166 and bisultap at a ratio of 1:10; a pest control composition comprising any one of the present compounds 1 to 166 and bisultap at a ratio of 1:50; a pest control composition comprising any one of the present compounds 1 to 166 and monosultap at a ratio of 1:1; a pest control composition comprising any one of the present compounds 1 to 166 and monosultap at a ratio of 1:10; a pest control composition comprising any one of the present compounds 1 to 166 and monosultap at a ratio of 1:50; a pest control composition comprising any one of the present compounds 1 to 166 and acetamiprid at a ratio of 1:1; a pest control composition comprising any one of the present compounds 1 to 166 and acetamiprid at a ratio of 1:10; a pest control composition comprising any one of the present compounds 1 to 166 and acetamiprid at a ratio of 1:50; a pest control composition comprising any one of the present compounds 1 to 166 and clothianidin at a ratio of 1:1; a pest control composition comprising any one of the present compounds 1 to 166 and clothianidin at a ratio of 1:10; a pest control composition comprising any one of the present compounds 1 to 166 and clothianidin at a ratio of 1:50;

a pest control composition comprising any one of the present compounds 1 to 166 and imidacloprid at a ratio of 1:1; a pest control composition comprising any one of the present compounds 1 to 166 and imidacloprid at a ratio of 1:10; a pest control composition comprising any one of the present compounds 1 to 166 and imidacloprid at a ratio of 1:50; a pest control composition comprising any one of the present compounds 1 to 166 and thiamethoxam at a ratio of 1:1; a pest control composition comprising any one of the present compounds 1 to 166 and thiamethoxam at a ratio of 1:10; a pest control composition comprising any one of the present compounds 1 to 166 and thiamethoxam at a ratio of 1:50; a pest control composition comprising any one of the present compounds 1 to 166 and dinotefuran at a ratio of 1:1; a pest control composition comprising any one of the present compounds 1 to 166 and dinotefuran at a ratio of 1:10; a pest control composition comprising any one of the present compounds 1 to 166 and dinotefuran at a ratio of 1:50; a pest control composition comprising any one of the present compounds 1 to 166 and sulfoxaflor at a ratio of 1:1; a pest control composition comprising any one of the present compounds 1 to 166 and sulfoxaflor at a ratio of 1:10; a pest control composition comprising any one of the present compounds 1 to 166 and sulfoxaflor at a ratio of 1:50; a pest compounds 1 to 166 and flupyradifurone at a ratio of 1:1; a pest control composition comprising any one of the present compounds 1 to 166 and flupyradifurone at a ratio of 1:10; a pest control composition comprising any one of the present compounds 1 to 166 and flupyradifurone at a ratio of 1:50; a pest control composition comprising any one of the present compounds 1 to 166 and nitenpyram at a ratio of 1:1; a pest control composition comprising any one of the present compounds 1 to 166 and nitenpyram at a ratio of 1:10; a pest control composition comprising any one of the present compounds 1 to 166 and nitenpyram at a ratio of 1:50; a pest control composition comprising any one of the present compounds 1 to 166 and thiacloprid at a ratio of 1:1;

a pest control composition comprising any one of the present compounds 1 to 166 and thiacloprid at a ratio of 1:10; a pest control composition comprising any one of the present compounds 1 to 166 and thiacloprid at a ratio of 1:50; a pest control composition comprising any one of the present compounds 1 to 166 and bistrifluron at a ratio of 0.1:1; a pest control composition comprising any one of the present compounds 1 to 166 and bistrifluron at a ratio of 1:1; a pest control composition comprising any one of the present compounds 1 to 166 and bistrifluron at a ratio of 1:10; a pest control composition comprising any one of the present compounds 1 to 166 and chlorfluazuron at a ratio of 0.1:1; a pest control composition comprising any one of the present compounds 1 to 166 and chlorfluazuron at a ratio of 1:1; a pest control composition comprising any one of the present compounds 1 to 166 and chlorfluazuron at a ratio of 1:10; a pest control composition comprising any one of the present compounds 1 to 166 and diflubenzuron at a ratio of 0.1:1; a pest control composition comprising any one of the present compounds 1 to 166 and diflubenzuron at a ratio of 1:1; a pest control composition comprising any one of the present compounds 1 to 166 and diflubenzuron at a ratio of 1:10; a pest control composition comprising any one of the present compounds 1 to 166 and flucycloxuron at a ratio of 0.1:1; a pest control composition comprising any one of the present compounds 1 to 166 and flucycloxuron at a ratio of 1:1; a pest control composition comprising any one of the present compounds 1 to 166 and flucycloxuron at a ratio of 1:10; a pest control composition comprising any one of the present compounds 1 to 166 and flufenoxuron at a ratio of 0.1:1; a pest control composition comprising any one of the present compounds 1 to 166 and flufenoxuron at a ratio of 1:1; a pest control composition comprising any one of the present compounds 1 to 166 and flufenoxuron at a ratio of 1:10; a pest control composition comprising any one of the present compounds 1 to 166 and hexaflumuron at a ratio of 0.1:1; a pest control composition comprising any one of the present compounds 1 to 166 and hexaflumuron at a ratio of 1:1; a pest control composition comprising any one of the present compounds 1 to 166 and hexaflumuron at a ratio of 1:10;

a pest control composition comprising any one of the present compounds 1 to 166 and lufenuron at a ratio of 0.1:1; a pest control composition comprising any one of the present compounds 1 to 166 and lufenuron at a ratio of 1:1; a pest compounds 1 to 166 and lufenuron at a ratio of 1:10; a pest control composition comprising any one of the present compounds 1 to 166 and novaluron at a ratio of 0.1:1; a pest control composition comprising any one of the present compounds 1 to 166 and novaluron at a ratio of 1:1; a pest control composition comprising any one of the present compounds 1 to 166 and novaluron at a ratio of 1:10; a pest control composition comprising any one of the present compounds 1 to 166 and noviflumuron at a ratio of 0.1:1; a pest control composition comprising any one of the present compounds 1 to 166 and noviflumuron at a ratio of 1:1; a pest control composition comprising any one of the present compounds 1 to 166 and noviflumuron at a ratio of 1:10; a pest control composition comprising any one of the present compounds 1 to 166 and teflubenzuron at a ratio of 0.1:1; a pest control composition comprising any one of the present compounds 1 to 166 and teflubenzuron at a ratio of 1:1; a pest control composition comprising any one of the present compounds 1 to 166 and teflubenzuron at a ratio of 1:10; a pest control composition comprising any one of the present compounds 1 to 166 and triflumuron at a ratio of 0.1:1; a pest control composition comprising any one of the present compounds 1 to 166 and triflumuron at a ratio of 1:1; a pest control composition comprising any one of the present compounds 1 to 166 and triflumuron at a ratio of 1:10; a pest control composition comprising any one of the present compounds 1 to 166 and ethiprole at a ratio of 1:1; a pest control composition comprising any one of the present compounds 1 to 166 and ethiprole at a ratio of 1:10; a pest compounds 1 to 166 and ethiprole at a ratio of 1:50; a pest control composition comprising any one of the present compounds 1 to 166 and fipronil at a ratio of 1:1; a pest control composition comprising any one of the present compounds 1 to 166 and fipronil at a ratio of 1:10;
a pest control composition comprising any one of the present compounds 1 to 166 and fipronil at a ratio of 1:50; a pest control composition comprising any one of the present compounds 1 to 166 and flufiprole at a ratio of 1:1; a pest control composition comprising any one of the present compounds 1 to 166 and flufiprole at a ratio of 1:10; a pest control composition comprising any one of the present compounds 1 to 166 and flufiprole at a ratio of 1:50; a pest control composition comprising any one of the present compounds 1 to 166 and chromafenozide at a ratio of 0.1:1; a pest control composition comprising any one of the present compounds 1 to 166 and chromafenozide at a ratio of 1:1; a pest control composition comprising any one of the present compounds 1 to 166 and chromafenozide at a ratio of 1:10; a pest control composition comprising any one of the present compounds 1 to 166 and halofenozide at a ratio of 0.1:1; a pest control composition comprising any one of the present compounds 1 to 166 and halofenozide at a ratio of 1:1; a pest control composition comprising any one of the present compounds 1 to 166 and halofenozide at a ratio of 1:10; a pest control composition comprising any one of the present compounds 1 to 166 and methoxyfenozide at a ratio of 0.1:1; a pest control composition comprising any one of the present compounds 1 to 166 and methoxyfenozide at a ratio of 1:1; a pest control composition comprising any one of the present compounds 1 to 166 and methoxyfenozide at a ratio of 1:10; a pest control composition comprising any one of the present compounds 1 to 166 and tebufenozide at a ratio of 0.1:1; a pest control composition comprising any one of the present compounds 1 to 166 and tebufenozide at a ratio of 1:1; a pest control composition comprising any one of the present compounds 1 to 166 and tebufenozide at a ratio of 1:10; a pest control composition comprising any one of the present compounds 1 to 166 and chlordane at a ratio of 1:1; a pest control composition comprising any one of the present compounds 1 to 166 and chlordane at a ratio of 1:10; a pest control composition comprising any one of the present compounds 1 to 166 and chlordane at a ratio of 1:50;
a pest control composition comprising any one of the present compounds 1 to 166 and endosulfan at a ratio of 1:1; a pest control composition comprising any one of the present compounds 1 to 166 and endosulfan at a ratio of 1:10; a pest control composition comprising any one of the present compounds 1 to 166 and endosulfan at a ratio of 1:50; a pest control composition comprising any one of the present compounds 1 to 166 and alpha-endosulfan at a ratio of 1:1; a pest control composition comprising any one of the present compounds 1 to 166 and alpha-endosulfan at a ratio of 1:10; a pest control composition comprising any one of the present compounds 1 to 166 and alpha-endosulfan at a ratio of 1:50; a pest control composition comprising any one of the present compounds 1 to 166 and chlorantraniliprole at a ratio of 1:0.1; a pest control composition comprising any one of the present compounds 1 to 166 and chlorantraniliprole at a ratio of 1:1; a pest control composition comprising any one of the present compounds 1 to 166 and chlorantraniliprole at a ratio of 1:10; a pest control composition comprising any one of the present compounds 1 to 166 and chlorantraniliprole at a ratio of 1:50; a pest control composition comprising any one of the present compounds 1 to 166 and cyantraniliprole at a ratio of 1:0.1; a pest control composition comprising any one of the present compounds 1 to 166 and cyantraniliprole at a ratio of 1:1; a pest control composition comprising any one of the present compounds 1 to 166 and cyantraniliprole at a ratio of 1:10; a pest control composition comprising any one of the present compounds 1 to 166 and cyantraniliprole at a ratio of 1:50; a pest control composition comprising any one of the present compounds 1 to 166 and cycloniliprole at a ratio of 1:0.1; a pest control composition comprising any one of the present compounds 1 to 166 and cycloniliprole at a ratio of 1:1; a pest control composition comprising any one of the present compounds 1 to 166 and cycloniliprole at a ratio of 1:10; a pest control composition comprising any one of the present compounds 1 to 166 and cycloniliprole at a ratio of 1:50;
a pest control composition comprising any one of the present compounds 1 to 166 and flubendiamide at a ratio of 1:0.1; a pest control composition comprising any one of the present compounds 1 to 166 and flubendiamide at a ratio of 1:1; a pest control composition comprising any one of the present compounds 1 to 166 and flubendiamide at a ratio of 1:10; a compounds 1 to 166 and flubendiamide at a ratio of 1:50; a pest control composition comprising any one of the present compounds 1 to 166 and tetraniliprole at a ratio of 1:0.1; a pest control composition comprising any one of the present compounds 1 to 166 and tetraniliprole at a ratio of 1:1; a pest control composition comprising any one of the present compounds 1 to 166 and tetraniliprole at a ratio of 1:10; a pest control composition comprising any one of the present compounds 1 to 166 and tetraniliprole at a ratio of 1:50; a pest control composition comprising any one of the present compounds 1 to 166 and *Bacillus thuringiensis aizawai* var. at a ratio of 1:1; a pest control composition comprising any one of the present compounds 1 to 166 and *Bacillus thuringiensis aizawai* var. at a ratio of 1:10; a pest control composition comprising any one of the present compounds 1 to 166 and *Bacillus thuringiensis aizawai* var. at a ratio of 1:50; a pest control composition comprising any one of the present compounds 1 to 166 and *Bacillus thuringiensis* var. *Kurstaki* at a ratio of 1:1; a pest control composition comprising any one of the present compounds 1 to 166 and *Bacillus thuringiensis* var. *Kurstaki* at a ratio of 1:10; a pest control composition comprising any one of the present compounds 1 to 166 and *Bacillus thuringiensis* var. *Kurstaki* at a ratio of 1:50; a pest control composition comprising any one of the present compounds 1 to 166 and *Bacillus thuringiensis* var. *israelensis* at a ratio of 1:1; a pest control composition comprising any one of the present compounds 1 to 166 and *Bacillus thuringiensis* var. *israelensis* at a ratio of 1:10; a pest control composition comprising any one of the present compounds 1 to 166 and *Bacillus thuringiensis* var. *israelensis* at a ratio of 1:50;

a pest control composition comprising any one of the present compounds 1 to 166 and *Bacillus thuringiensis* var. *tenebriosis* at a ratio of 1:1; a pest control composition comprising any one of the present compounds 1 to 166 and *Bacillus thuringiensis* var. *tenebriosis* at a ratio of 1:10; a pest control composition comprising any one of the present compounds 1 to 166 and *Bacillus thuringiensis* var. *tenebriosis* at a ratio of 1:50; a pest control composition comprising any one of the present compounds 1 to 166 and *Bacillus firmus* at a ratio of 1:1; a pest control composition comprising any one of the present compounds 1 to 166 and *Bacillus firmus* at a ratio of 1:10; a pest control composition comprising any one of the present compounds 1 to 166 and *Bacillus firmus* at a ratio of 1:50; a pest control composition comprising any one of the present compounds 1 to 166 and *Bacillus sphaericus* at a ratio of 1:1; a pest control composition comprising any one of the present compounds 1 to 166 and *Bacillus sphaericus* at a ratio of 1:10; a pest control composition comprising any one of the present compounds 1 to 166 and *Bacillus sphaericus* at a ratio of 1:50; a pest control composition comprising any one of the present compounds 1 to 166 and *Beauveria bassiana* at a ratio of 1:1; a pest control composition comprising any one of the present compounds 1 to 166 and *Beauveria bassiana* at a ratio of 1:10; a pest control composition comprising any one of the present compounds 1 to 166 and *Beauveria bassiana* at a ratio of 1:50; a pest control composition comprising any one of the present compounds 1 to 166 and *Beauveria Brongniartii* at a ratio of 1:1; a pest control composition comprising any one of the present compounds 1 to 166 and *Beauveria Brongniartii* at a ratio of 1:10; a pest control composition comprising any one of the present compounds 1 to 166 and *Beauveria Brongniartii* at a ratio of 1:50; a pest control composition comprising any one of the present compounds 1 to 166 and *Paecilomyces fumosoroseus* at a ratio of 1:1; a pest control composition comprising any one of the present compounds 1 to 166 and *Paecilomyces fumosoroseus* at a ratio of 1:10; a pest control composition comprising any one of the present compounds 1 to 166 and *Paecilomyces fumosoroseus* at a ratio of 1:50;

a pest control composition comprising any one of the present compounds 1 to 166 and *Paecilomyces lilacinus* at a ratio of 1:1; a pest control composition comprising any one of the present compounds 1 to 166 and *Paecilomyces lilacinus* at a ratio of 1:10; a pest control composition comprising any one of the present compounds 1 to 166 and *Paecilomyces lilacinus* at a ratio of 1:50; a pest control composition comprising any one of the present compounds 1 to 166 and *Paecilomyces tenuipes* at a ratio of 1:1; a pest control composition comprising any one of the present compounds 1 to 166 and *Paecilomyces tenuipes* at a ratio of 1:10; a pest control composition comprising any one of the present compounds 1 to 166 and *Paecilomyces tenuipes* at a ratio of 1:50; a pest control composition comprising any one of the present compounds 1 to 166 and *Trichoderma harzianum* at a ratio of 1:1; a pest control composition comprising any one of the present compounds 1 to 166 and *Trichoderma harzianum* at a ratio of 1:10; a pest control composition comprising any one of the present compounds 1 to 166 and *Trichoderma harzianum* at a ratio of 1:50; a pest control composition comprising any one of the present compounds 1 to 166 and *Verticillium lecanii* at a ratio of 1:1; a pest control composition comprising any one of the present compounds 1 to 166 and *Verticillium lecanii* at a ratio of 1:10; a pest control composition comprising any one of the present compounds 1 to 166 and *Verticillium lecanii* at a ratio of 1:50; a pest control composition comprising any one of the present compounds 1 to 166 and *Pasteuria penetrans* at a ratio of 1:1; a pest control composition comprising any one of the present compounds 1 to 166 and *Pasteuria penetrans* at a ratio of 1:10; a pest control composition comprising any one of the present compounds 1 to 166 and *Pasteuria penetrans* at a ratio of 1:50; a pest control composition comprising any one of the present compounds 1 to 166 and dazomet at a ratio of 1:1; a pest control composition comprising any one of the present compounds 1 to 166 and dazomet at a ratio of 1:10; a pest control composition comprising any one of the present compounds 1 to 166 and dazomet at a ratio of 1:50; a pest control composition comprising any one of the present compounds 1 to 166 and fluensulfone at a ratio of 1:1;

a pest control composition comprising any one of the present compounds 1 to 166 and fluensulfone at a ratio of 1:10; a pest control composition comprising any one of the present compounds 1 to 166 and fluensulfone at a ratio of 1:50; a pest control composition comprising any one of the present compounds 1 to 166 and fosthiazate at a ratio of 1:1; a pest control composition comprising any one of the present compounds 1 to 166 and fosthiazate at a ratio of 1:10; a pest compounds 1 to 166 and fosthiazate at a ratio of 1:50; a pest control composition comprising any one of the present compounds 1 to 166 and imicyafos at a ratio of 1:1; a pest control composition comprising any one of the present compounds 1 to 166 and imicyafos at a ratio of 1:10; a pest control composition comprising any one of the present compounds 1 to 166 and imicyafos at a ratio of 1:50; a pest control composition comprising any one of the present compounds 1 to 166 and metam at a ratio of 1:1; a pest control composition comprising any one of the present compounds 1 to 166 and metam at a ratio of 1:10; a pest control composition comprising any one of the present compounds 1 to 166 and metam at a ratio of 1:50; a pest control composition comprising any one of the present compounds 1 to 166 and tartar emetic at a ratio of 1:1; a pest control composition comprising any one of the present compounds 1 to 166 and tartar emetic at a ratio of 1:10; a pest control composition comprising any one of the present compounds 1 to 166 and tartar emetic at a ratio of 1:50; a pest control composition comprising any one of the present compounds 1 to 166 and tioxazafen at a ratio of 1:1; a pest control composition comprising any one of the present compounds 1 to 166 and tioxazafen at a ratio of 1:10; a pest control composition comprising any one of the present compounds 1 to 166 and tioxazafen at a ratio of 1:50; a pest control composition comprising any one of the present compounds 1 to 166 and *Arthrobotrys dactyloydes* at a ratio of 1:1; a pest control composition comprising any one of the present compounds 1 to 166 and *Arthrobotrys dactyloydes* at a ratio of 1:10; a pest control composition comprising any one of the present compounds 1 to 166 and Arthrobotrys dactyloydes at a ratio of 1:50; a pest control composition comprising any one of the present compounds 1 to 166 and Bacillus megaterium at a ratio of 1:1; a pest control composition comprising any one of the present compounds 1 to 166 and Bacillus megaterium at a ratio of 1:10; a pest control composition comprising any one of the present compounds 1 to 166 and Bacillus megaterium at a ratio of 1:50; a pest control composition comprising any one of the present compounds 1 to 166 and Hirsutella rhossiliensis at a ratio of 1:1; a pest control composition comprising any one of the present compounds 1 to 166 and Hirsutella rhossiliensis at a ratio of 1:10; a pest control composition comprising any one of the present compounds 1 to 166 and Hirsutella rhossiliensis at a ratio of 1:50; a pest control composition comprising any one of the present compounds 1 to 166 and Hirsutella minnesotensis at a ratio of 1:1; a pest control composition comprising any one of the present compounds 1 to 166 and Hirsutella minnesotensis at a ratio of 1:10; a pest control composition comprising any one of the present compounds 1 to 166 and Hirsutella minnesotensis at a ratio of 1:50; a pest control composition comprising any one of the present compounds 1 to 166 and Monacrosporium phymatopagum at a ratio of 1:1; a pest control composition comprising any one of the present compounds 1 to 166 and Monacrosporium phymatopagum at a ratio of 1:10; a pest control composition comprising any one of the present compounds 1 to 166 and Monacrosporium phymatopagum at a ratio of 1:50; a pest control composition comprising any one of the present compounds 1 to 166 and Pasteuria nishizawae at a ratio of 1:1; a pest control composition comprising any one of the present compounds 1 to 166 and Pasteuria nishizawae at a ratio of 1:10; a pest control composition comprising any one of the present compounds 1 to 166 and Pasteuria nishizawae at a ratio of 1:50; a pest control composition comprising any one of the present compounds 1 to 166 and Pasteuria usgae at a ratio of 1:1; a pest control composition comprising any one of the present compounds 1 to 166 and Pasteuria usgae at a ratio of 1:10; a pest control composition comprising any one of the present compounds 1 to 166 and Pasteuria usgae at a ratio of 1:50;

a pest control composition comprising any one of the present compounds 1 to 166 and Verticillium chlamydosporium at a ratio of 1:1; a pest control composition comprising any one of the present compounds 1 to 166 and Verticillium chlamydosporium at a ratio of 1:10; a pest control composition comprising any one of the present compounds 1 to 166 and Verticillium chlamydosporium at a ratio of 1:50; a pest control composition comprising any one of the present compounds 1 to 166 and Harpin protein at a ratio of 1:1; a pest control composition comprising any one of the present compounds 1 to 166 and Harpin protein at a ratio of 1:10; a pest control composition comprising any one of the present compounds 1 to 166 and Harpin protein at a ratio of 1:50; a pest control composition comprising any one of the present compounds 1 to 166 and 6-bromo-N-{[2-chloro-5-(trifluoromethyl)phenyl]sulfonyl}-imidazo[1,2-a]pyrimidine-2-carboxamide at a ratio of 1:1; a pest control composition comprising any one of the present compounds 1 to 166 and 6-bromo-N-{[2-chloro-5-(trifluoromethyl)phenyl]sulfonyl}-imidazo[1,2-a]pyrimidine-2-carboxamide at a ratio of 1:10; a pest control composition comprising any one of the present compounds 1 to 166 and 6-bromo-N-{[2-chloro-5-(trifluoromethyl)phenyl]sulfonyl}-imidazo[1,2-a]pyrimidine-2-carboxamide at a ratio of 1:50; a pest control composition comprising any one of the present compounds 1 to 166 and 8-chloro-N-[(2-chloro-5-methoxyphenyl)sulfonyl]-6-(trifluoromethyl)-imidazo[1,2-a]pyridine-2-carboxamide at a ratio of 1:1; a pest control composition comprising any one of the present compounds 1 to 166 and 8-chloro-N-[(2-chloro-5-methoxyphenyl)sulfonyl]-6-(trifluoromethyl)-imidazo[1,2-a]pyridine-2-carboxamide at a ratio of 1:10; a pest control composition comprising any one of the present compounds 1 to 166 and 8-chloro-N-[(2-chloro-5-methoxyphenyl)sulfonyl]-6-(trifluoromethyl)-imidazo[1,2-a]pyridine-2-carboxamide at a ratio of 1:50;

a pest control composition comprising any one of the present compounds 1 to 166 and acequinocyl at a ratio of 0.1:1; a pest control composition comprising any one of the present compounds 1 to 166 and acequinocyl at a ratio of 1:1; a pest control composition comprising any one of the present compounds 1 to 166 and acequinocyl at a ratio of 1:10; a pest control composition comprising any one of the present compounds 1 to 166 and amitraz at a ratio of 0.1:1; a pest control composition comprising any one of the present compounds 1 to 166 and amitraz at a ratio of 1:1; a pest control composition comprising any one of the present compounds 1 to 166 and amitraz at a ratio of 1:10; a pest compounds 1 to 166 and Benzoximate at a ratio of 0.1:1; a pest control composition comprising any one of the present compounds 1 to 166 and Benzoximate at a ratio of 1:1; a pest control composition comprising any one of the present compounds 1 to 166 and Benzoximate at a ratio of 1:10; a pest control composition comprising any one of the present compounds 1 to 166 and bifenazate at a ratio of 0.1:1; a pest control composition comprising any one of the present compounds 1 to 166 and bifenazate at a ratio of 1:1; a pest control composition comprising any one of the present compounds 1 to 166 and bifenazate at a ratio of 1:10; a pest control composition comprising any one of the present compounds 1 to 166 and bromopropylate at a ratio of 0.1:1; a pest control composition comprising any one of the present compounds 1 to 166 and bromopropylate at a ratio of 1:1; a pest control composition comprising any one of the present compounds 1 to 166 and bromopropylate at a ratio of 1:10; a pest control composition comprising any one of the present compounds 1 to 166 and chinomethionat at a ratio of 0.1:1; a pest control composition comprising any one of the present compounds 1 to 166 and chinomethionat at a ratio of 1:1; a pest control composition comprising any one of the present compounds 1 to 166 and chinomethionat at a ratio of 1:10; a pest control composition comprising any one of the present compounds 1 to 166 and clofentezine at a ratio of 0.1:1;

any one of the present compounds 1 to 166 and clofentezine at a ratio of 1:1; a pest control composition comprising any one of the present compounds 1 to 166 and clofentezine at a ratio of 1:10; a pest control composition comprising any one of the present compounds 1 to 166 and cyenopyrafen at a ratio of 0.1:1; a pest control composition comprising any one of the present compounds 1 to 166 and cyenopyrafen at a ratio of 1:1; a pest control composition comprising any one of the present compounds 1 to 166 and cyenopyrafen at a ratio of 1:10; a pest control composition comprising any one of the present compounds 1 to 166 and cyflumetofen at a ratio of 0.1:1; a pest control composition comprising any one of the present compounds 1 to 166 and cyflumetofen at a ratio of 1:1; a pest control composition comprising any one of the present compounds 1 to 166 and cyflumetofen at a ratio of 1:10; a pest control composition comprising any one of the present compounds 1 to 166 and cyhexatin at a ratio of 0.1:1; a pest control composition comprising any one of the present compounds 1 to 166 and cyhexatin at a ratio of 1:1; a pest control composition comprising any one of the present compounds 1 to 166 and cyhexatin at a ratio of 1:10; a pest control composition comprising any one of the present compounds 1 to 166 and dicofol at a ratio of 0.1:1; a pest control composition comprising any one of the present compounds 1 to 166 and dicofol at a ratio of 1:1; a pest control composition comprising any one of the present compounds 1 to 166 and dicofol at a ratio of 1:10; a pest control composition comprising any one of the present compounds 1 to 166 and etoxazole at a ratio of 0.1:1; a pest control composition comprising any one of the present compounds 1 to 166 and etoxazole at a ratio of 1:1; a pest control composition comprising any one of the present compounds 1 to 166 and etoxazole at a ratio of 1:10; a pest compounds 1 to 166 and fenazaquin at a ratio of 0.1:1; a pest control composition comprising any one of the present compounds 1 to 166 and fenazaquin at a ratio of 1:1;

a pest control composition comprising any one of the present compounds 1 to 166 and fenazaquin at a ratio of 1:10; a pest control composition comprising any one of the present compounds 1 to 166 and fenbutatin oxide at a ratio of 0.1:1; a pest control composition comprising any one of the present compounds 1 to 166 and fenbutatin oxide at a ratio of 1:1; a pest control composition comprising any one of the present compounds 1 to 166 and fenbutatin oxide at a ratio of 1:10; a pest control composition comprising any one of the present compounds 1 to 166 and fenpyroximate at a ratio of 0.1:1; a pest control composition comprising any one of the present compounds 1 to 166 and fenpyroximate at a ratio of 1:1; a pest control composition comprising any one of the present compounds 1 to 166 and fenpyroximate at a ratio of 1:10; a pest control composition comprising any one of the present compounds 1 to 166 and fluacrypyrim at a ratio of 0.1:1; a pest control composition comprising any one of the present compounds 1 to 166 and fluacrypyrim at a ratio of 1:1; a pest control composition comprising any one of the present compounds 1 to 166 and fluacrypyrim at a ratio of 1:10; a pest control composition comprising any one of the present compounds 1 to 166 and fluazuron at a ratio of 0.1:1; a pest control composition comprising any one of the present compounds 1 to 166 and fluazuron at a ratio of 1:1; a pest control composition comprising any one of the present compounds 1 to 166 and fluazuron at a ratio of 1:10; a pest control composition comprising any one of the present compounds 1 to 166 and flufenoxystrobin at a ratio of 0.1:1; a pest control composition comprising any one of the present compounds 1 to 166 and flufenoxystrobin at a ratio of 1:1; a pest control composition comprising any one of the present compounds 1 to 166 and flufenoxystrobin at a ratio of 1:10; a pest control composition comprising any one of the present compounds 1 to 166 and hexythiazox at a ratio of 0.1:1; a pest control composition comprising any one of the present compounds 1 to 166 and hexythiazox at a ratio of 1:1; a pest control composition comprising any one of the present compounds 1 to 166 and hexythiazox at a ratio of 1:10;

a pest control composition comprising any one of the present compounds 1 to 166 and propargite at a ratio of 0.1:1; a pest control composition comprising any one of the present compounds 1 to 166 and propargite at a ratio of 1:1; a pest control composition comprising any one of the present compounds 1 to 166 and propargite at a ratio of 1:10; a pest control composition comprising any one of the present compounds 1 to 166 and pyflubumide at a ratio of 0.1:1; a pest control composition comprising any one of the present compounds 1 to 166 and pyflubumide at a ratio of 1:1; a pest control composition comprising any one of the present compounds 1 to 166 and pyflubumide at a ratio of 1:10; a pest control composition comprising any one of the present compounds 1 to 166 and pyridaben at a ratio of 0.1:1; a pest control composition comprising any one of the present compounds 1 to 166 and pyridaben at a ratio of 1:1; a pest compounds 1 to 166 and pyridaben at a ratio of 1:10; a pest control composition comprising any one of the present compounds 1 to 166 and Pyrimidifen at a ratio of 0.1:1; a pest control composition comprising any one of the present compounds 1 to 166 and Pyrimidifen at a ratio of 1:1; a pest control composition comprising any one of the present compounds 1 to 166 and Pyrimidifen at a ratio of 1:10; a pest control composition comprising any one of the present compounds 1 to 166 and pyriminostrobin at a ratio of 0.1:1; a pest control composition comprising any one of the present compounds 1 to 166 and pyriminostrobin at a ratio of 1:1; a pest control composition comprising any one of the present compounds 1 to 166 and pyriminostrobin at a ratio of 1:10; a pest control composition comprising any one of the present compounds 1 to 166 and spirodiclofen at a ratio of 0.1:1; a pest control composition comprising any one of the present compounds 1 to 166 and spirodiclofen at a ratio of 1:1; a pest control composition comprising any one of the present compounds 1 to 166 and spirodiclofen at a ratio of 1:10; a pest control composition comprising any one of the present compounds 1 to 166 and spiromesifen at a ratio of 0.1:1; a pest control composition comprising any one of the present compounds 1 to 166 and spiromesifen at a ratio of 1:1; a pest control composition comprising any one of the present compounds 1 to 166 and spiromesifen at a ratio of 1:10;

a pest control composition comprising any one of the present compounds 1 to 166 and tebufenpyrad at a ratio of 0.1:1; a pest control composition comprising any one of the present compounds 1 to 166 and tebufenpyrad at a ratio of 1:1; a pest control composition comprising any one of the present compounds 1 to 166 and tebufenpyrad at a ratio of 1:10; a pest control composition comprising any one of the present compounds 1 to 166 and tetradifon at a ratio of 0.1:1; a pest control composition comprising any one of the present compounds 1 to 166 and tetradifon at a ratio of 1:1; a pest control composition comprising any one of the present compounds 1 to 166 and tetradifon at a ratio of 1:10; a pest control composition comprising any one of the present compounds 1 to 166 and abamectin at a ratio of 1:1; a pest control composition comprising any one of the present compounds 1 to 166 and abamectin at a ratio of 1:10; a pest control composition comprising any one of the present compounds 1 to 166 and abamectin at a ratio of 1:50; a pest control composition comprising any one of the present compounds 1 to 166 and emamectin-benzoate at a ratio of 1:1; a pest control composition comprising any one of the present compounds 1 to 166 and emamectin-benzoate at a ratio of 1:10; a pest control composition comprising any one of the present compounds 1 to 166 and emamectin-benzoate at a ratio of 1:50; a pest control composition comprising any one of the present compounds 1 to 166 and lepimectin at a ratio of 1:1; a pest control composition comprising any one of the present compounds 1 to 166 and lepimectin at a ratio of 1:10; a pest control composition comprising any one of the present compounds 1 to 166 and lepimectin at a ratio of 1:50; a pest control composition comprising any one of the present compounds 1 to 166 and milbemectin at a ratio of 1:1; a pest control composition comprising any one of the present compounds 1 to 166 and milbemectin at a ratio of 1:10; a pest control composition comprising any one of the present compounds 1 to 166 and milbemectin at a ratio of 1:50; a pest control composition comprising any one of the present compounds 1 to 166 and spinetoram at a ratio of 1:1;

a pest control composition comprising any one of the present compounds 1 to 166 and spinetoram at a ratio of 1:10; a pest control composition comprising any one of the present compounds 1 to 166 and spinetoram at a ratio of 1:50; a pest control composition comprising any one of the present compounds 1 to 166 and spinosad at a ratio of 1:1; a pest control composition comprising any one of the present compounds 1 to 166 and spinosad at a ratio of 1:10; a pest control composition comprising any one of the present compounds 1 to 166 and spinosad at a ratio of 1:50; a pest control composition comprising any one of the present compounds 1 to 166 and afidopyropen at a ratio of 1:1; a pest control composition comprising any one of the present compounds 1 to 166 and afidopyropen at a ratio of 1:10; a pest control composition comprising any one of the present compounds 1 to 166 and afidopyropen at a ratio of 1:50; a pest control composition comprising any one of the present compounds 1 to 166 and aluminum phosphide at a ratio of 1:1; a pest control composition comprising any one of the present compounds 1 to 166 and aluminum phosphide at a ratio of 1:10; a pest control composition comprising any one of the present compounds 1 to 166 and aluminum phosphide at a ratio of 1:50; a pest control composition comprising any one of the present compounds 1 to 166 and calcium phosphide at a ratio of 1:1; a compounds 1 to 166 and calcium phosphide at a ratio of 1:10; a pest control composition comprising any one of the present compounds 1 to 166 and calcium phosphide at a ratio of 1:50; a pest control composition comprising any one of the present compounds 1 to 166 and hydrogen phosphide at a ratio of 1:1; a pest control composition comprising any one of the present compounds 1 to 166 and hydrogen phosphide at a ratio of 1:10; a pest control composition comprising any one of the present compounds 1 to 166 and hydrogen phosphide at a ratio of 1:50; a pest control composition comprising any one of the present compounds 1 to 166 and zinc phosphide at a ratio of 1:1; a pest control composition comprising any one of the present compounds 1 to 166 and zinc phosphide at a ratio of 1:10; a pest control composition comprising any one of the present compounds 1 to 166 and zinc phosphide at a ratio of 1:50;

a pest control composition comprising any one of the present compounds 1 to 166 and azadirachtin at a ratio of 1:1; a pest control composition comprising any one of the present compounds 1 to 166 and azadirachtin at a ratio of 1:10; a pest control composition comprising any one of the present compounds 1 to 166 and azadirachtin at a ratio of 1:50; a pest control composition comprising any one of the present compounds 1 to 166 and buprofezin at a ratio of 1:1; a pest control composition comprising any one of the present compounds 1 to 166 and buprofezin at a ratio of 1:10; a pest control composition comprising any one of the present compounds 1 to 166 and buprofezin at a ratio of 1:50; a pest control composition comprising any one of the present compounds 1 to 166 and chlorfenapyr at a ratio of 1:1; a pest control composition comprising any one of the present compounds 1 to 166 and chlorfenapyr at a ratio of 1:10; a pest control composition comprising any one of the present compounds 1 to 166 and chlorfenapyr at a ratio of 1:50; a pest control composition comprising any one of the present compounds 1 to 166 and chloropicrin at a ratio of 1:1; a pest control composition comprising any one of the present compounds 1 to 166 and chloropicrin at a ratio of 1:10; a pest control composition comprising any one of the present compounds 1 to 166 and chloropicrin at a ratio of 1:50; a pest control composition comprising any one of the present compounds 1 to 166 and cyromazine at a ratio of 1:1; a pest control composition comprising any one of the present compounds 1 to 166 and cyromazine at a ratio of 1:10; a pest control composition comprising any one of the present compounds 1 to 166 and cyromazine at a ratio of 1:50; a pest control composition comprising any one of the present compounds 1 to 166 and diafenthiuron at a ratio of 1:1; a pest control composition comprising any one of the present compounds 1 to 166 and diafenthiuron at a ratio of 1:10; a pest control composition comprising any one of the present compounds 1 to 166 and diafenthiuron at a ratio of 1:50; a pest control composition comprising any one of the present compounds 1 to 166 and DNOC at a ratio of 1:1; a pest control composition comprising any one of the present compounds 1 to 166 and DNOC at a ratio of 1:10;

a pest control composition comprising any one of the present compounds 1 to 166 and DNOC at a ratio of 1:50; a pest control composition comprising any one of the present compounds 1 to 166 and fenoxycarb at a ratio of 1:1; a pest control composition comprising any one of the present compounds 1 to 166 and fenoxycarb at a ratio of 1:10; a pest control composition comprising any one of the present compounds 1 to 166 and fenoxycarb at a ratio of 1:50; a pest control composition comprising any one of the present compounds 1 to 166 and flometoquin at a ratio of 1:1; a pest control composition comprising any one of the present compounds 1 to 166 and flometoquin at a ratio of 1:10; a pest control composition comprising any one of the present compounds 1 to 166 and flometoquin at a ratio of 1:50; a pest control composition comprising any one of the present compounds 1 to 166 and flonicamid at a ratio of 1:1; a pest control composition comprising any one of the present compounds 1 to 166 and flonicamid at a ratio of 1:10; a pest control composition comprising any one of the present compounds 1 to 166 and flonicamid at a ratio of 1:50; a pest control composition comprising any one of the present compounds 1 to 166 and hydramethylnon at a ratio of 1:1; a pest control composition comprising any one of the present compounds 1 to 166 and hydramethylnon at a ratio of 1:10; a pest control composition comprising any one of the present compounds 1 to 166 and hydramethylnon at a ratio of 1:50; a pest control composition comprising any one of the present compounds 1 to 166 and hydroprene at a ratio of 1:1; a pest control composition comprising any one of the present compounds 1 to 166 and hydroprene at a ratio of 1:10; a pest control composition comprising any one of the present compounds 1 to 166 and hydroprene at a ratio of 1:50; a pest control composition comprising any one of the present compounds 1 to 166 and indoxacarb at a ratio of 1:1; a pest control composition comprising any one of the present compounds 1 to 166 and indoxacarb at a ratio of 1:10; a pest control composition comprising any one of the present compounds 1 to 166 and indoxacarb at a ratio of 1:50; a pest control composition comprising any one of the present compounds 1 to 166 and kinoprene at a ratio of 1:1;

a pest control composition comprising any one of the present compounds 1 to 166 and kinoprene at a ratio of 1:10; a pest control composition comprising any one of the present compounds 1 to 166 and kinoprene at a ratio of 1:50; a pest control composition comprising any one of the present compounds 1 to 166 and metaflumizone at a ratio of 1:1; a pest control composition comprising any one of the present compounds 1 to 166 and metaflumizone at a ratio of 1:10; a pest control composition comprising any one of the present compounds 1 to 166 and metaflumizone at a ratio of 1:50; a pest control composition comprising any one of the present compounds 1 to 166 and methoprene at a ratio of 1:1; a pest control composition comprising any one of the present compounds 1 to 166 and methoprene at a ratio of 1:10; a pest control composition comprising any one of the present compounds 1 to 166 and methoprene at a ratio of 1:50; a pest control composition comprising any one of the present compounds 1 to 166 and methoxychlor at a ratio of 1:1; a pest control composition comprising any one of the present compounds 1 to 166 and methoxychlor at a ratio of 1:10; a pest control composition comprising any one of the present compounds 1 to 166 and methoxychlor at a ratio of 1:50; a pest control composition comprising any one of the present compounds 1 to 166 and methyl bromide at a ratio of 1:1; a pest control composition comprising any one of the present compounds 1 to 166 and methyl bromide at a ratio of 1:10; a pest control composition comprising any one of the present compounds 1 to 166 and methyl bromide at a ratio of 1:50; a pest control composition comprising any one of the present compounds 1 to 166 and metoxadiazone at a ratio of 1:1; a pest control composition comprising any one of the present compounds 1 to 166 and metoxadiazone at a ratio of 1:10; a pest control composition comprising any one of the present compounds 1 to 166 and metoxadiazone at a ratio of 1:50; a pest control composition comprising any one of the present compounds 1 to 166 and pymetrozine at a ratio of 1:1; a pest control composition comprising any one of the present compounds 1 to 166 and pymetrozine at a ratio of 1:10; a pest control composition comprising any one of the present compounds 1 to 166 and pymetrozine at a ratio of 1:50; a pest control composition comprising any one of the present compounds 1 to 166 and pyrazophos at a ratio of 1:1;

a pest control composition comprising any one of the present compounds 1 to 166 and pyrazophos at a ratio of 1:10; a pest control composition comprising any one of the present compounds 1 to 166 and pyrazophos at a ratio of 1:50; a pest control composition comprising any one of the present compounds 1 to 166 and pyridalyl at a ratio of 1:1; a pest control composition comprising any one of the present compounds 1 to 166 and pyridalyl at a ratio of 1:10; a pest compounds 1 to 166 and pyridalyl at a ratio of 1:50; a pest control composition comprising any one of the present compounds 1 to 166 and pyrifluquinazone at a ratio of 1:1; a pest control composition comprising any one of the present compounds 1 to 166 and pyrifluquinazone at a ratio of 1:10; a pest control composition comprising any one of the present compounds 1 to 166 and pyrifluquinazone at a ratio of 1:50; a pest control composition comprising any one of the present compounds 1 to 166 and pyriproxyfen at a ratio of 1:1; a pest control composition comprising any one of the present compounds 1 to 166 and pyriproxyfen at a ratio of 1:10; a pest control composition comprising any one of the present compounds 1 to 166 and pyriproxyfen at a ratio of 1:50; a pest control composition comprising any one of the present compounds 1 to 166 and sodium aluminum fluoride at a ratio of 1:1; a pest control composition comprising any one of the present compounds 1 to 166 and sodium aluminum fluoride at a ratio of 1:10; a pest control composition comprising any one of the present compounds 1 to 166 and sodium aluminum fluoride at a ratio of 1:50; a pest control composition comprising any one of the present compounds 1 to 166 and spirotetramat at a ratio of 1:1; a pest control composition comprising any one of the present compounds 1 to 166 and spirotetramat at a ratio of 1:10; a pest control composition comprising any one of the present compounds 1 to 166 and spirotetramat at a ratio of 1:50; a pest control composition comprising any one of the present compounds 1 to 166 and sulfluramid at a ratio of 1:1; a pest control composition comprising any one of the present compounds 1 to 166 and sulfluramid at a ratio of 1:10;

a pest control composition comprising any one of the present compounds 1 to 166 and sulfluramid at a ratio of 1:50; a pest control composition comprising any one of the present compounds 1 to 166 and sulfuryl fluoride at a ratio of 1:1; a pest control composition comprising any one of the present compounds 1 to 166 and sulfuryl fluoride at a ratio of 1:10; a pest control composition comprising any one of the present compounds 1 to 166 and sulfuryl fluoride at a ratio of 1:50; a pest control composition comprising any one of the present compounds 1 to 166 and tolfenpyrad at a ratio of 1:1; a pest control composition comprising any one of the present compounds 1 to 166 and tolfenpyrad at a ratio of 1:10; a pest control composition comprising any one of the present compounds 1 to 166 and tolfenpyrad at a ratio of 1:50; a pest control composition comprising any one of the present compounds 1 to 166 and triflumezopyrim at a ratio of 1:1; a pest control composition comprising any one of the present compounds 1 to 166 and triflumezopyrim at a ratio of 1:10; a pest control composition comprising any one of the present compounds 1 to 166 and triflumezopyrim at a ratio of 1:50; a pest control composition comprising any one of the present compounds 1 to 166 and 4-oxo-4-(2-phenylethyl)aminobutyric acid at a ratio of 5:1; a pest control composition comprising any one of the present compounds 1 to 166 and 4-oxo-4-(2-phenylethyl)aminobutyric acid at a ratio of 1:10; a pest control composition comprising any one of the present compounds 1 to 166 and 4-oxo-4-(2-phenylethyl)aminobutyric acid at a ratio of 1:50; a pest control composition comprising any one of the present compounds 1 to 166 and methyl 5-(trifluoromethyl)benzo[b]thiophene-2-carboxylate at a ratio of 5:1; a pest control composition comprising any one of the present compounds 1 to 166 and methyl 5-(trifluoromethyl)benzo[b]thiophene-2-carboxylate at a ratio of 1:10; a pest control composition comprising any one of the present compounds 1 to 166 and methyl 5-(trifluoromethyl)benzo[b]thiophene-2-carboxylate at a ratio of 1:50;

a pest control composition comprising any one of the present compounds 1 to 166 and 5-(trifluoromethyl)benzo[b]thiophene-2-carboxylic acid at a ratio of 5:1; a pest control composition comprising any one of the present compounds 1 to 166 and 5-(trifluoromethyl)benzo[b]thiophene-2-carboxylic acid at a ratio of 1:10; a pest control composition comprising any one of the present compounds 1 to 166 and 5-(trifluoromethyl)benzo[b]thiophene-2-carboxylic acid at a ratio of 1:50; a pest control composition comprising any one of the present compounds 1 to 166 and 2,4-D at a ratio of 0.1:1; a pest control composition comprising any one of the present compounds 1 to 166 and 2,4-D at a ratio of 1:1; a pest control composition comprising any one of the present compounds 1 to 166 and 2,4-D at a ratio of 1:20; a pest control composition comprising any one of the present compounds 1 to 166 and 2,4-DB at a ratio of 0.1:1; a pest control composition comprising any one of the present compounds 1 to 166 and 2,4-DB at a ratio of 1:1; a pest control composition comprising any one of the present compounds 1 to 166 and 2,4-DB at a ratio of 1:20; a pest control composition comprising any one of the present compounds 1 to 166 and acetochlor at a ratio of 0.1:1; a pest control composition comprising any one of the present compounds 1 to 166 and acetochlor at a ratio of 1:1; a pest control composition comprising any one of the present compounds 1 to 166 and acetochlor at a ratio of 1:20; a pest control composition comprising any one of the present compounds 1 to 166 and acifluorfen at a ratio of 0.1:1; a pest control composition comprising any one of the present compounds 1 to 166 and acifluorfen at a ratio of 1:1; a pest control composition comprising any one of the present compounds 1 to 166 and acifluorfen at a ratio of 1:20; a pest control composition comprising any one of the present compounds 1 to 166 and alachlor at a ratio of 0.1:1; a pest control composition comprising any one of the present compounds 1 to 166 and alachlor at a ratio of 1:1; a pest control composition comprising any one of the present compounds 1 to 166 and alachlor at a ratio of 1:20; a pest control composition comprising any one of the present compounds 1 to 166 and ametryn at a ratio of 0.1:1; a pest control composition comprising any one of the present compounds 1 to 166 and ametryn at a ratio of 1:1; a pest control composition comprising any one of the present compounds 1 to 166 and ametryn at a ratio of 1:20;

a pest control composition comprising any one of the present compounds 1 to 166 and amicarbazone at a ratio of 0.1:1; a pest control composition comprising any one of the present compounds 1 to 166 and amicarbazone at a ratio of 1:1; a pest control composition comprising any one of the present compounds 1 to 166 and amicarbazone at a ratio of 1:20; a pest compounds 1 to 166 and aminopyralid at a ratio of 0.1:1; a pest control composition comprising any one of the present compounds 1 to 166 and aminopyralid at a ratio of 1:1; a pest control composition comprising any one of the present compounds 1 to 166 and aminopyralid at a ratio of 1:20; a pest control composition comprising any one of the present compounds 1 to 166 and atrazine at a ratio of 0.1:1; a pest control composition comprising any one of the present compounds 1 to 166 and atrazine at a ratio of 1:1; a pest control composition comprising any one of the present compounds 1 to 166 and atrazine at a ratio of 1:20; a pest control composition comprising any one of the present compounds 1 to 166 and benefin at a ratio of 0.1:1; a pest control composition comprising any one of the present compounds 1 to 166 and benefin at a ratio of 1:1; a pest control composition comprising any one of the present compounds 1 to 166 and benefin at a ratio of 1:20; a pest control composition comprising any one of the present compounds 1 to 166 and bentazon at a ratio of 0.1:1; a pest control composition comprising any one of the present compounds 1 to 166 and bentazon at a ratio of 1:1; a pest control composition comprising any one of the present compounds 1 to 166 and bentazon at a ratio of 1:20; a pest control composition comprising any one of the present compounds 1 to 166 and bromoxynil at a ratio of 0.1:1; a pest control composition comprising any one of the present compounds 1 to 166 and bromoxynil at a ratio of 1:1; a pest control composition comprising any one of the present compounds 1 to 166 and bromoxynil at a ratio of 1:20; a pest compounds 1 to 166 and carfentrazone at a ratio of 0.1:1; a pest control composition comprising any one of the present compounds 1 to 166 and carfentrazone at a ratio of 1:1;

a pest control composition comprising any one of the present compounds 1 to 166 and carfentrazone at a ratio of 1:20; a pest control composition comprising any one of the present compounds 1 to 166 and carfentrazone-ethyl at a ratio of 0.1:1; a pest control composition comprising any one of the present compounds 1 to 166 and carfentrazone-ethyl at a ratio of 1:1; a pest control composition comprising any one of the present compounds 1 to 166 and carfentrazone-ethyl at a ratio of 1:20; a pest control composition comprising any one of the present compounds 1 to 166 and chloransulam at a ratio of 0.1:1; a pest control composition comprising any one of the present compounds 1 to 166 and chloransulam at a ratio of 1:1; a pest control composition comprising any one of the present compounds 1 to 166 and chloransulam at a ratio of 1:20; a pest control composition comprising any one of the present compounds 1 to 166 and chlorimuron at a ratio of 0.1:1; a pest control composition comprising any one of the present compounds 1 to 166 and chlorimuron at a ratio of 1:1; a pest control composition comprising any one of the present compounds 1 to 166 and chlorimuron at a ratio of 1:20; a pest control composition comprising any one of the present compounds 1 to 166 and chlorimuronethyl at a ratio of 0.1:1; a pest control composition comprising any one of the present compounds 1 to 166 and chlorimuronethyl at a ratio of 1:1; a pest control composition comprising any one of the present compounds 1 to 166 and chlorimuronethyl at a ratio of 1:20; a pest control composition comprising any one of the present compounds 1 to 166 and chloridazon at a ratio of 0.1:1; a pest control composition comprising any one of the present compounds 1 to 166 and chloridazon at a ratio of 1:1; a pest control composition comprising any one of the present compounds 1 to 166 and chloridazon at a ratio of 1:20; a pest control composition comprising any one of the present compounds 1 to 166 and clethodim at a ratio of 0.1:1; a pest control composition comprising any one of the present compounds 1 to 166 and clethodim at a ratio of 1:1; a pest control composition comprising any one of the present compounds 1 to 166 and clethodim at a ratio of 1:20; a pest control composition comprising any one of the present compounds 1 to 166 and clodinafop at a ratio of 0.1:1; a pest control composition comprising any one of the present compounds 1 to 166 and clodinafop at a ratio of 1:1;

a pest control composition comprising any one of the present compounds 1 to 166 and clodinafop at a ratio of 1:20; a pest control composition comprising any one of the present compounds 1 to 166 and clomazone at a ratio of 0.1:1; a pest control composition comprising any one of the present compounds 1 to 166 and clomazone at a ratio of 1:1; a pest control composition comprising any one of the present compounds 1 to 166 and clomazone at a ratio of 1:20; a pest control composition comprising any one of the present compounds 1 to 166 and clopyralid at a ratio of 0.1:1; a pest control composition comprising any one of the present compounds 1 to 166 and clopyralid at a ratio of 1:1; a pest compounds 1 to 166 and clopyralid at a ratio of 1:20; a pest control composition comprising any one of the present compounds 1 to 166 and cloransulam-methyl at a ratio of 0.1:1; a pest control composition comprising any one of the present compounds 1 to 166 and cloransulam-methyl at a ratio of 1:1; a pest control composition comprising any one of the present compounds 1 to 166 and cloransulam-methyl at a ratio of 1:20; a pest control composition comprising any one of the present compounds 1 to 166 and desmedipham at a ratio of 0.1:1; a pest control composition comprising any one of the present compounds 1 to 166 and desmedipham at a ratio of 1:1; a pest control composition comprising any one of the present compounds 1 to 166 and desmedipham at a ratio of 1:20; a pest control composition comprising any one of the present compounds 1 to 166 and dicamba at a ratio of 0.1:1; a pest control composition comprising any one of the present compounds 1 to 166 and dicamba at a ratio of 1:1; a pest control composition comprising any one of the present compounds 1 to 166 and dicamba at a ratio of 1:20; a pest control composition comprising any one of the present compounds 1 to 166 and diclofop at a ratio of 0.1:1; a pest control composition comprising any one of the present compounds 1 to 166 and diclofop at a ratio of 1:1; a pest control composition comprising any one of the present compounds 1 to 166 and diclofop at a ratio of 1:20;

a pest control composition comprising any one of the present compounds 1 to 166 and diclosulam at a ratio of 0.1:1; a pest control composition comprising any one of the present compounds 1 to 166 and diclosulam at a ratio of 1:1; a pest control composition comprising any one of the present compounds 1 to 166 and diclosulam at a ratio of 1:20; a pest control composition comprising any one of the present compounds 1 to 166 and diflufenzopyr at a ratio of 0.1:1; a pest control composition comprising any one of the present compounds 1 to 166 and diflufenzopyr at a ratio of 1:1; a pest control composition comprising any one of the present compounds 1 to 166 and diflufenzopyr at a ratio of 1:20; a pest control composition comprising any one of the present compounds 1 to 166 and dimethenamid at a ratio of 0.1:1; a pest control composition comprising any one of the present compounds 1 to 166 and dimethenamid at a ratio of 1:1; a pest control composition comprising any one of the present compounds 1 to 166 and dimethenamid at a ratio of 1:20; a pest control composition comprising any one of the present compounds 1 to 166 and diquat at a ratio of 0.1:1; a pest control composition comprising any one of the present compounds 1 to 166 and diquat at a ratio of 1:1; a pest control composition comprising any one of the present compounds 1 to 166 and diquat at a ratio of 1:20; a pest control composition comprising any one of the present compounds 1 to 166 and diuron at a ratio of 0.1:1; a pest control composition comprising any one of the present compounds 1 to 166 and diuron at a ratio of 1:1; a pest control composition comprising any one of the present compounds 1 to 166 and diuron at a ratio of 1:20; a pest control composition comprising any one of the present compounds 1 to 166 and EPTC at a ratio of 0.1:1; a pest control composition comprising any one of the present compounds 1 to 166 and EPTC at a ratio of 1:1; a pest control composition comprising any one of the present compounds 1 to 166 and EPTC at a ratio of 1:20;

a pest control composition comprising any one of the present compounds 1 to 166 and ethalfluralin at a ratio of 0.1:1; a pest control composition comprising any one of the present compounds 1 to 166 and ethalfluralin at a ratio of 1:1; a pest control composition comprising any one of the present compounds 1 to 166 and ethalfluralin at a ratio of 1:20; a pest control composition comprising any one of the present compounds 1 to 166 and ethofumesate at a ratio of 0.1:1; a pest control composition comprising any one of the present compounds 1 to 166 and ethofumesate at a ratio of 1:1; a pest control composition comprising any one of the present compounds 1 to 166 and ethofumesate at a ratio of 1:20; a pest control composition comprising any one of the present compounds 1 to 166 and fenoxaprop at a ratio of 0.1:1; a pest control composition comprising any one of the present compounds 1 to 166 and fenoxaprop at a ratio of 1:1; a pest control composition comprising any one of the present compounds 1 to 166 and fenoxaprop at a ratio of 1:20; a pest control composition comprising any one of the present compounds 1 to 166 and fenoxaprop-P-ethyl at a ratio of 0.1:1; a pest control composition comprising any one of the present compounds 1 to 166 and fenoxaprop-P-ethyl at a ratio of 1:1; a pest control composition comprising any one of the present compounds 1 to 166 and fenoxaprop-P-ethyl at a ratio of 1:20; a pest control composition comprising any one of the present compounds 1 to 166 and florasulam at a ratio of 0.1:1; a pest compounds 1 to 166 and florasulam at a ratio of 1:1; a pest control composition comprising any one of the present compounds 1 to 166 and florasulam at a ratio of 1:20; a pest control composition comprising any one of the present compounds 1 to 166 and fluazifop-P-butyl at a ratio of 0.1:1; a pest control composition comprising any one of the present compounds 1 to 166 and fluazifop-P-butyl at a ratio of 1:1; a pest control composition comprising any one of the present compounds 1 to 166 and fluazifop-P-butyl at a ratio of 1:20; a pest control composition comprising any one of the present compounds 1 to 166 and flufenacet at a ratio of 0.1:1; a pest control composition comprising any one of the present compounds 1 to 166 and flufenacet at a ratio of 1:1;

a pest control composition comprising any one of the present compounds 1 to 166 and flufenacet at a ratio of 1:20; a pest control composition comprising any one of the present compounds 1 to 166 and flumetsulam at a ratio of 0.1:1; a pest control composition comprising any one of the present compounds 1 to 166 and flumetsulam at a ratio of 1:1; a pest control composition comprising any one of the present compounds 1 to 166 and flumetsulam at a ratio of 1:20; a pest control composition comprising any one of the present compounds 1 to 166 and flumiclorac at a ratio of 0.1:1; a pest control composition comprising any one of the present compounds 1 to 166 and flumiclorac at a ratio of 1:1; a pest control composition comprising any one of the present compounds 1 to 166 and flumiclorac at a ratio of 1:20; a pest control composition comprising any one of the present compounds 1 to 166 and flumioxazin at a ratio of 0.1:1; a pest control composition comprising any one of the present compounds 1 to 166 and flumioxazin at a ratio of 1:1; a pest control composition comprising any one of the present compounds 1 to 166 and flumioxazin at a ratio of 1:20; a pest control composition comprising any one of the present compounds 1 to 166 and fluthiacet at a ratio of 0.1:1; a pest control composition comprising any one of the present compounds 1 to 166 and fluthiacet at a ratio of 1:1; a pest control composition comprising any one of the present compounds 1 to 166 and fluthiacet at a ratio of 1:20; a pest control composition comprising any one of the present compounds 1 to 166 and fomesafen at a ratio of 0.1:1; a pest control composition comprising any one of the present compounds 1 to 166 and fomesafen at a ratio of 1:1; a pest control composition comprising any one of the present compounds 1 to 166 and fomesafen at a ratio of 1:20; a pest control composition comprising any one of the present compounds 1 to 166 and foramsulfuron at a ratio of 0.1:1; a pest control composition comprising any one of the present compounds 1 to 166 and foramsulfuron at a ratio of 1:1; a pest control composition comprising any one of the present compounds 1 to 166 and foramsulfuron at a ratio of 1:20;

a pest control composition comprising any one of the present compounds 1 to 166 and glufosinate at a ratio of 0.1:1; a pest control composition comprising any one of the present compounds 1 to 166 and glufosinate at a ratio of 1:1; a pest control composition comprising any one of the present compounds 1 to 166 and glufosinate at a ratio of 1:20; a pest compounds 1 to 166 and a glufosinate ammonium salt at a ratio of 0.1:1; a pest control composition comprising any one of the present compounds 1 to 166 and a glufosinate ammonium salt at a ratio of 1:1; a pest control composition comprising any one of the present compounds 1 to 166 and a glufosinate ammonium salt at a ratio of 1:20; a pest control composition comprising any one of the present compounds 1 to 166 and glyphosate at a ratio of 0.1:1; a pest control composition comprising any one of the present compounds 1 to 166 and glyphosate at a ratio of 1:1; a pest control composition comprising any one of the present compounds 1 to 166 and glyphosate at a ratio of 1:20; a pest control composition comprising any one of the present compounds 1 to 166 and glyphosate trimesium salt at a ratio of 0.1:1; a pest control composition comprising any one of the present compounds 1 to 166 and glyphosate trimesium salt at a ratio of 1:1; a pest control composition comprising any one of the present compounds 1 to 166 and glyphosate trimesium salt at a ratio of 1:20; a pest control composition comprising any one of the present compounds 1 to 166 and glyphosate isopropylamine salt at a ratio of 0.1:1; a pest control composition comprising any one of the present compounds 1 to 166 and glyphosate isopropylamine salt at a ratio of 1:1; a pest control composition comprising any one of the present compounds 1 to 166 and glyphosate isopropylamine salt at a ratio of 1:20; a pest control composition comprising any one of the present compounds 1 to 166 and glyphosate potassium salt at a ratio of 0.1:1; a pest control composition comprising any one of the present compounds 1 to 166 and glyphosate potassium salt at a ratio of 1:1; a pest control composition comprising any one of the present compounds 1 to 166 and glyphosate potassium salt at a ratio of 1:20; a pest control composition comprising any one of the present compounds 1 to 166 and halosulfuron at a ratio of 0.1:1;

a pest control composition comprising any one of the present compounds 1 to 166 and halosulfuron at a ratio of 1:1; a pest control composition comprising any one of the present compounds 1 to 166 and halosulfuron at a ratio of 1:20; a pest control composition comprising any one of the present compounds 1 to 166 and halosulfuron-methyl at a ratio of 0.1:1; a pest control composition comprising any one of the present compounds 1 to 166 and halosulfuron-methyl at a ratio of 1:1; a pest control composition comprising any one of the present compounds 1 to 166 and halosulfuron-methyl at a ratio of 1:20; a pest control composition comprising any one of the present compounds 1 to 166 and haloxyfop-R-methyl at a ratio of 0.1:1; a pest control composition comprising any one of the present compounds 1 to 166 and haloxyfop-R-methyl at a ratio of 1:1; a pest control composition comprising any one of the present compounds 1 to 166 and haloxyfop-R-methyl at a ratio of 1:20; a pest control composition comprising any one of the present compounds 1 to 166 and hexazinone at a ratio of 0.1:1; a pest control composition comprising any one of the present compounds 1 to 166 and hexazinone at a ratio of 1:1; a pest control composition comprising any one of the present compounds 1 to 166 and hexazinone at a ratio of 1:20; a pest control composition comprising any one of the present compounds 1 to 166 and imazamox at a ratio of 0.1:1; a pest control composition comprising any one of the present compounds 1 to 166 and imazamox at a ratio of 1:1; a pest control composition comprising any one of the present compounds 1 to 166 and imazamox at a ratio of 1:20; a pest control composition comprising any one of the present compounds 1 to 166 and imazapic at a ratio of 0.1:1; a pest control composition comprising any one of the present compounds 1 to 166 and imazapic at a ratio of 1:1; a pest control composition comprising any one of the present compounds 1 to 166 and imazapic at a ratio of 1:20; a pest control composition comprising any one of the present compounds 1 to 166 and imazaquine at a ratio of 0.1:1; a pest control composition comprising any one of the present compounds 1 to 166 and imazaquine at a ratio of 1:1; a pest control composition comprising any one of the present compounds 1 to 166 and imazaquine at a ratio of 1:20;

a pest control composition comprising any one of the present compounds 1 to 166 and imazethapyr at a ratio of 0.1:1; a pest control composition comprising any one of the present compounds 1 to 166 and imazethapyr at a ratio of 1:1; a pest control composition comprising any one of the present compounds 1 to 166 and imazethapyr at a ratio of 1:20; a pest control composition comprising any one of the present compounds 1 to 166 and iodosulfuron at a ratio of 0.1:1; a pest control composition comprising any one of the present compounds 1 to 166 and iodosulfuron at a ratio of 1:1; a pest control composition comprising any one of the present compounds 1 to 166 and iodosulfuron at a ratio of 1:20; a pest control composition comprising any one of the present compounds 1 to 166 and isoxaflutole at a ratio of 0.1:1; a compounds 1 to 166 and isoxaflutole at a ratio of 1:1; a pest control composition comprising any one of the present compounds 1 to 166 and isoxaflutole at a ratio of 1:20; a pest control composition comprising any one of the present compounds 1 to 166 and lactofen at a ratio of 0.1:1; a pest control composition comprising any one of the present compounds 1 to 166 and lactofen at a ratio of 1:1; a pest control composition comprising any one of the present compounds 1 to 166 and lactofen at a ratio of 1:20; a pest control composition comprising any one of the present compounds 1 to 166 and lenacil at a ratio of 0.1:1; a pest control composition comprising any one of the present compounds 1 to 166 and lenacil at a ratio of 1:1; a pest control composition comprising any one of the present compounds 1 to 166 and lenacil at a ratio of 1:20; a pest control composition comprising any one of the present compounds 1 to 166 and linuron at a ratio of 0.1:1; a pest control composition comprising any one of the present compounds 1 to 166 and linuron at a ratio of 1:1; a pest control composition comprising any one of the present compounds 1 to 166 and linuron at a ratio of 1:20; a pest control composition comprising any one of the present compounds 1 to 166 and mesosulfuron at a ratio of 0.1:1;

a pest control composition comprising any one of the present compounds 1 to 166 and mesosulfuron at a ratio of 1:1; a pest control composition comprising any one of the present compounds 1 to 166 and mesosulfuron at a ratio of 1:20; a pest control composition comprising any one of the present compounds 1 to 166 and mesotrione at a ratio of 0.1:1; a pest control composition comprising any one of the present compounds 1 to 166 and mesotrione at a ratio of 1:1; a pest control composition comprising any one of the present compounds 1 to 166 and mesotrione at a ratio of 1:20; a pest control composition comprising any one of the present compounds 1 to 166 and metam at a ratio of 0.1:1; a pest control composition comprising any one of the present compounds 1 to 166 and metam at a ratio of 1:1; a pest control composition comprising any one of the present compounds 1 to 166 and metam at a ratio of 1:20; a pest control composition comprising any one of the present compounds 1 to 166 and metamitron at a ratio of 0.1:1; a pest control composition comprising any one of the present compounds 1 to 166 and metamitron at a ratio of 1:1; a pest control composition comprising any one of the present compounds 1 to 166 and metamitron at a ratio of 1:20; a pest control composition comprising any one of the present compounds 1 to 166 and metolachlor at a ratio of 0.1:1; a pest control composition comprising any one of the present compounds 1 to 166 and metolachlor at a ratio of 1:1; a pest control composition comprising any one of the present compounds 1 to 166 and metolachlor at a ratio of 1:20; a pest control composition comprising any one of the present compounds 1 to 166 and metribuzin at a ratio of 0.1:1; a pest control composition comprising any one of the present compounds 1 to 166 and metribuzin at a ratio of 1:1; a pest control composition comprising any one of the present compounds 1 to 166 and metribuzin at a ratio of 1:20; a pest control composition comprising any one of the present compounds 1 to 166 and metsulfuron at a ratio of 0.1:1; a pest control composition comprising any one of the present compounds 1 to 166 and metsulfuron at a ratio of 1:1; a pest control composition comprising any one of the present compounds 1 to 166 and metsulfuron at a ratio of 1:20;

a pest control composition comprising any one of the present compounds 1 to 166 and MPCA at a ratio of 0.1:1; a pest control composition comprising any one of the present compounds 1 to 166 and MPCA at a ratio of 1:1; a pest control composition comprising any one of the present compounds 1 to 166 and MPCA at a ratio of 1:20; a pest control composition comprising any one of the present compounds 1 to 166 and MSMA at a ratio of 0.1:1; a pest control composition comprising any one of the present compounds 1 to 166 and MSMA at a ratio of 1:1; a pest control composition comprising any one of the present compounds 1 to 166 and MSMA at a ratio of 1:20; a pest control composition comprising any one of the present compounds 1 to 166 and nicosulfuron at a ratio of 0.1:1; a pest control composition comprising any one of the present compounds 1 to 166 and nicosulfuron at a ratio of 1:1; a pest control composition comprising any one of the present compounds 1 to 166 and nicosulfuron at a ratio of 1:20; a pest control composition comprising any one of the present compounds 1 to 166 and oryzalin at a ratio of 0.1:1; a pest control composition comprising any one of the present compounds 1 to 166 and oryzalin at a ratio of 1:1; a pest control composition comprising any one of the present compounds 1 to 166 and oryzalin at a ratio of 1:20; a pest control composition comprising any one of the present compounds 1 to 166 and oxyfluorfen at a ratio of 0.1:1; a pest control composition comprising any one of the present compounds 1 to 166 and oxyfluorfen at a ratio of 1:1; a pest control composition comprising any one of the present compounds 1 to 166 and oxyfluorfen at a ratio of 1:20; a pest control composition comprising any one of the present compounds 1 to 166 and paraquat at a ratio of 0.1:1; a pest control composition comprising any one of the present compounds 1 to 166 and paraquat at a ratio of 1:1; a pest control composition comprising any one of the present compounds 1 to 166 and paraquat at a ratio of 1:20; a pest control composition comprising any one of the present compounds 1 to 166 and pendimethalin at a ratio of 0.1:1; a pest control composition comprising any one of the present compounds 1 to 166 and pendimethalin at a ratio of 1:1;

a pest control composition comprising any one of the present compounds 1 to 166 and pendimethalin at a ratio of 1:20; a pest control composition comprising any one of the present compounds 1 to 166 and phenmedipham at a ratio of 0.1:1; a pest control composition comprising any one of the present compounds 1 to 166 and phenmedipham at a ratio of 1:1; a pest control composition comprising any one of the present compounds 1 to 166 and phenmedipham at a ratio of 1:20; a pest control composition comprising any one of the present compounds 1 to 166 and picloram at a ratio of 0.1:1; a pest control composition comprising any one of the present compounds 1 to 166 and picloram at a ratio of 1:1; a pest control composition comprising any one of the present compounds 1 to 166 and picloram at a ratio of 1:20; a pest compounds 1 to 166 and pyrimisulfuron at a ratio of 0.1:1; a pest control composition comprising any one of the present compounds 1 to 166 and pyrimisulfuron at a ratio of 1:1; a pest control composition comprising any one of the present compounds 1 to 166 and pyrimisulfuron at a ratio of 1:20; a pest control composition comprising any one of the present compounds 1 to 166 and pinoxaden at a ratio of 0.1:1; a pest control composition comprising any one of the present compounds 1 to 166 and pinoxaden at a ratio of 1:1; a pest control composition comprising any one of the present compounds 1 to 166 and pinoxaden at a ratio of 1:20; a pest control composition comprising any one of the present compounds 1 to 166 and prometryn at a ratio of 0.1:1; a pest control composition comprising any one of the present compounds 1 to 166 and prometryn at a ratio of 1:1; a pest control composition comprising any one of the present compounds 1 to 166 and prometryn at a ratio of 1:20; a pest control composition comprising any one of the present compounds 1 to 166 and pyraflufen-ethyl at a ratio of 0.1:1; a pest control composition comprising any one of the present compounds 1 to 166 and pyraflufen-ethyl at a ratio of 1:1; a pest control composition comprising any one of the present compounds 1 to 166 and pyraflufen-ethyl at a ratio of 1:20; a pest control composition comprising any one of the present compounds 1 to 166 and pyrithiobac at a ratio of 0.1:1;

a pest control composition comprising any one of the present compounds 1 to 166 and pyrithiobac at a ratio of 1:1; a pest control composition comprising any one of the present compounds 1 to 166 and pyrithiobac at a ratio of 1:20; a pest control composition comprising any one of the present compounds 1 to 166 and pyroxsulam at a ratio of 0.1:1; a pest control composition comprising any one of the present compounds 1 to 166 and pyroxsulam at a ratio of 1:1; a pest control composition comprising any one of the present compounds 1 to 166 and pyroxsulam at a ratio of 1:20; a pest control composition comprising any one of the present compounds 1 to 166 and pyroxasulfone at a ratio of 0.1:1; a pest control composition comprising any one of the present compounds 1 to 166 and pyroxasulfone at a ratio of 1:1; a pest control composition comprising any one of the present compounds 1 to 166 and pyroxasulfone at a ratio of 1:20; a pest control composition comprising any one of the present compounds 1 to 166 and quizalofop-P-ethyl at a ratio of 0.1:1; a pest control composition comprising any one of the present compounds 1 to 166 and quizalofop-P-ethyl at a ratio of 1:1; a pest control composition comprising any one of the present compounds 1 to 166 and quizalofop-P-ethyl at a ratio of 1:20; a pest control composition comprising any one of the present compounds 1 to 166 and salflufenacil at a ratio of 0.1:1; a pest control composition comprising any one of the present compounds 1 to 166 and salflufenacil at a ratio of 1:1; a pest control composition comprising any one of the present compounds 1 to 166 and salflufenacil at a ratio of 1:20; a pest control composition comprising any one of the present compounds 1 to 166 and sethoxydim at a ratio of 0.1:1; a pest control composition comprising any one of the present compounds 1 to 166 and sethoxydim at a ratio of 1:1; a pest control composition comprising any one of the present compounds 1 to 166 and sethoxydim at a ratio of 1:20; a pest control composition comprising any one of the present compounds 1 to 166 and simazine at a ratio of 0.1:1; a pest control composition comprising any one of the present compounds 1 to 166 and simazine at a ratio of 1:1;
a pest control composition comprising any one of the present compounds 1 to 166 and simazine at a ratio of 1:20; a pest control composition comprising any one of the present compounds 1 to 166 and sulfentrazone at a ratio of 0.1:1; a pest control composition comprising any one of the present compounds 1 to 166 and sulfentrazone at a ratio of 1:1; a pest control composition comprising any one of the present compounds 1 to 166 and sulfentrazone at a ratio of 1:20; a pest control composition comprising any one of the present compounds 1 to 166 and tebuthiuron at a ratio of 0.1:1; a pest control composition comprising any one of the present compounds 1 to 166 and tebuthiuron at a ratio of 1:1; a pest control composition comprising any one of the present compounds 1 to 166 and tebuthiuron at a ratio of 1:20; a pest control composition comprising any one of the present compounds 1 to 166 and tembotrione at a ratio of 0.1:1; a pest control composition comprising any one of the present compounds 1 to 166 and tembotrione at a ratio of 1:1; a pest control composition comprising any one of the present compounds 1 to 166 and tembotrione at a ratio of 1:20; a pest control composition comprising any one of the present compounds 1 to 166 and tepraloxydim at a ratio of 0.1:1; a pest control composition comprising any one of the present compounds 1 to 166 and tepraloxydim at a ratio of 1:1; a pest compounds 1 to 166 and tepraloxydim at a ratio of 1:20; a pest control composition comprising any one of the present compounds 1 to 166 and thifensulfuron at a ratio of 0.1:1; a pest control composition comprising any one of the present compounds 1 to 166 and thifensulfuron at a ratio of 1:1; a pest control composition comprising any one of the present compounds 1 to 166 and thifensulfuron at a ratio of 1:20; a pest control composition comprising any one of the present compounds 1 to 166 and tribenuron-methyl at a ratio of 0.1:1; a pest control composition comprising any one of the present compounds 1 to 166 and tribenuron-methyl at a ratio of 1:1; a pest control composition comprising any one of the present compounds 1 to 166 and tribenuron-methyl at a ratio of 1:20; a pest control composition comprising any one of the present compounds 1 to 166 and triclopyr at a ratio of 0.1:1;
a pest control composition comprising any one of the present compounds 1 to 166 and triclopyr at a ratio of 1:1; a pest control composition comprising any one of the present compounds 1 to 166 and triclopyr at a ratio of 1:20; a pest control composition comprising any one of the present compounds 1 to 166 and trifloxysulfuron at a ratio of 0.1:1; a pest control composition comprising any one of the present compounds 1 to 166 and trifloxysulfuron at a ratio of 1:1; a pest control composition comprising any one of the present compounds 1 to 166 and trifloxysulfuron at a ratio of 1:20; a pest control composition comprising any one of the present compounds 1 to 166 and trifluralin at a ratio of 0.1:1; a pest control composition comprising any one of the present compounds 1 to 166 and trifluralin at a ratio of 1:1; a pest control composition comprising any one of the present compounds 1 to 166 and trifluralin at a ratio of 1:20; a pest control composition comprising any one of the present compounds 1 to 166 and triflusulfuron-methyl at a ratio of 0.1:1; a pest control composition comprising any one of the present compounds 1 to 166 and triflusulfuron-methyl at a ratio of 1:1; and a pest control composition comprising any one of the present compounds 1 to 166 and triflusulfuron-methyl at a ratio of 1:20.

Formulation Examples will be shown below. Parts are by weight.

Formulation Example 1

Fifty parts (50 parts) of any one of the present compounds 1 to 166, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds 1 to 166 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds 1 to 166, 88 parts of kaolin clay, and 10 parts of talc are thoroughly ground and mixed to obtain each formulation.

Formulation Example 4

Five parts (5 parts) of any one of the present compounds 1 to 166, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds 1 to 166, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds 1 to 166, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion spots on each of test plants at the time of investigation, and comparing the area of lesion spots on a plant treated with the present control compound with that on an untreated plant.

Test Example 1

Each of plastic pots was filled with sandy loam and rice (cultivar: NIHONBARE) was sowed and grown in a greenhouse for 20 days. Then, each water dilution containing a surfactant prepared by adjusting so as to contain a predetermined concentration (500 ppm) of any one compound of the present compounds 9, 20, 4, 22, 23, 24, 25, 29, 32, 33, 89, 61, 62, 63, 64, 65, 66, 68, 100, 101, 106, 110, 79, 80, 85, 121, 122, 123, 132, 136, 137, 139, 140, 143, 144, and 91 was sprayed over stems and leaves so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compound 9, 20, 4, 22, 23, 24, 25, 29, 32, 33, 89, 61, 62, 63, 64, 65, 66, 68, 100, 101, 106, 110, 79, 80, 85, 121,122, 123, 132, 136, 137, 139, 140, 143, 144, or 91 were 30% or less with respect to the lesion area on the non-treated plant.

Test Example 2

Each of plastic pots was filled with sandy loam and wheat (cultivar: SHIROGANE) was sowed and grown in a greenhouse for 9 days. Then, each water dilution containing a surfactant prepared by adjusting so as to contain a predetermined concentration (500 ppm) of any one compound of the present compounds 9, 14, 5, 46, 23, 26, 29, 33, 36, 44, 89, 75, 66, 101, 102, 79, 85, 53, 115, 122, 136, 140, 143, 144, 145, and 91 was sprayed over stems and leaves of the wheat so that it sufficiently adhered to the surface of the leaves of the wheat. After spraying, the plant was air-dried so as to dry the dilution on the surface of the leaves. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with the present compound 9, 14, 5, 46, 23, 26, 29, 33, 36, 44, 89, 75, 66, 101, 102, 79, 85, 53, 115, 122, 136, 140, 143, 144, 145, or 91 was 30% or less of that on an untreated plant.

Test Example 3

Each of plastic pots was filled with sandy loam and barley (cultivar: NISHINOHOSHI) was sowed and grown in a greenhouse for 7 days. Then, each water dilution containing a surfactant prepared by adjusting so as to contain a predetermined concentration (500 ppm) of any one compound of the present compounds 7, 8, 9, 10, 11, 12, 13, 14, 15, 16, 17, 18, 19, 20, 41, 2, 3, 4, 5, 40, 46, 6, 21, 22, 23, 24, 25, 26, 28, 29, 30, 31, 32, 33, 34, 36, 37, 38, 39, 44, 42, 43, 45, 59, 89, 60, 61, 62, 63, 64, 65, 75, 76, 66, 67, 68, 69, 70, 72, 73, 74, 100, 98, 99, 93, 94, 95, 101, 102, 103, 104, 105, 106, 90, 110, 96, 78, 77, 107, 79, 80, 85, 81, 83, 91, 97, 113, 115, 116, 117, 118, 120, 121, 122, 123, 126, 131, 132, 133, 136, 137, 138, 139, 140, 141, 142, 144, 145, 146, 147, 148, 149, 150, 151, 152, 153, 154, 156, 157, 158, 159, 160, and 88 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 7, 8, 9, 10, 11, 12, 13, 14, 15, 16, 17, 18, 19, 20, 41, 2, 3, 4, 5, 40, 46, 6, 21, 22, 23, 24, 25, 26, 28, 29, 30, 31, 32, 33, 34, 36, 37, 38, 39, 44, 42, 43, 45, 59, 89, 60, 61, 62, 63, 64, 65, 75, 76, 66, 67, 68, 69, 70, 72, 73, 74, 100, 98, 99, 93, 94, 95, 101, 102, 103, 104, 105, 106, 90, 110, 96, 78, 77, 107, 79, 80, 85, 81, 83, 91, 97, 113, 115, 116, 117, 118, 120, 121, 122, 123, 126, 131, 132, 133, 136, 137, 138, 139, 140, 141, 142, 144, 145, 146, 147, 148, 149, 150, 151, 152, 153, 154, 156, 157, 158, 159, 160, or 88 was 30% or less of that on an untreated plant.

Test Example 4

Each of plastic pots was filled with sandy loam and kidney bean (cultivar: NAGAUZURA SAITOU) was sowed and grown in a greenhouse for 8 days. Then, each water dilution containing a surfactant prepared by adjusting so as to contain a predetermined concentration (500 ppm) of any one compound of the present compounds 7, 8, 9, 10, 11, 12, 14, 15, 16, 17, 18, 19, 20, 2, 3, 4, 40, 46, 6, 21, 22, 23, 24, 29, 30, 32, 33, 34, 35, 1, 39, 44, 43, 89, 61, 62, 63, 64, 65, 75, 76, 68, 69, 92, 100, 93, 94, 95, 102, 103, 104, 105, 106, 90, 110, 78, 77, 80, 85, 91, 87, 122, 123, 131, 136, 140, 141, 143, 144, and 88 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 7, 8, 9, 10, 11, 12, 14, 15, 16, 17, 18, 19, 20, 2, 3, 4, 40, 46, 6, 21, 22, 23, 24, 29, 30, 32, 33, 34, 35, 1, 39, 44, 43, 89, 61, 62, 63, 64, 65, 75, 76, 68, 69, 92, 100, 93, 94, 95, 102, 103, 104, 105, 106, 90, 110, 78, 77, 80, 85, 91, 87, 122, 123, 131, 136, 140, 141, 143, 144, or 88 was 30% or less of that on an untreated plant.

Test Example 5

Each of plastic pots was filled with sandy loam and wheat (cultivar: APOGEE) was sowed and grown in a greenhouse for 10 days. Then, each water dilution containing a surfactant prepared by adjusting so as to contain a predetermined concentration (500 ppm) of any one compound of the present compounds 7, 8, 9, 10, 11, 12, 13, 14, 15, 19, 20, 41, 2, 4, 5, 46, 6, 21, 22, 23, 24, 25, 26, 27, 28, 29, 30, 31, 32, 33, 34, 35, 1, 36, 39, 44, 42, 43, 61, 62, 63, 64, 65, 75, 76, 66, 67, 89, 60, 68, 69, 70, 72, 73, 74, 100, 93, 101, 102, 103, 104, 105, 106, 90, 110, 78, 77, 80, 85, 91, 87, 53, 54, 116, 121, 122, 123, 132, 136, 137, 138, 139, 140, 143, 144, 145, 149, 151, 152, 153, 154, and 88 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound 7, 8, 9, 10, 11, 12, 13, 14, 15, 19, 20, 41, 2, 4, 5, 46, 6, 21, 22, 23, 24, 25, 26, 27, 28, 29, 30, 31, 32, 33, 34, 35, 1, 36, 39, 44, 42, 43, 61, 62, 63, 64, 65, 75, 76, 66, 67, 89, 60, 68, 69, 70, 72, 73, 74, 100, 93, 101, 102, 103, 104, 105, 106, 90, 110, 78, 77, 80, 85, 91, 87, 53, 54, 116, 121, 122, 123, 132, 136, 137, 138, 139, 140, 143, 144, 145, 149, 151, 152, 153, 154, or 88 was 30% or less of that on an untreated plant.

Test Example 6

Each of plastic pots was filled with sandy loam and cucumber (cultivar: SAGAMI HANJIRO) was sowed and grown in a greenhouse for 12 days. Then, each water dilution containing a surfactant prepared by adjusting so as to contain a predetermined concentration (500 ppm) of any one compound of the present compounds 7, 8, 9, 10, 11, 12, 13, 14, 15, 16, 17, 18, 19, 20, 41, 2, 3, 4, 5, 40, 46, 6, 21, 22, 23, 24, 25, 26, 27, 28, 29, 30, 31, 32, 33, 34, 35, 1, 36, 37, 39, 44, 43, 89, 60, 61, 62, 63, 64, 65, 75, 76, 66, 67, 68, 69, 70, 72, 73, 74, 92, 100, 93, 94, 95, 101, 103, 104, 105, 106, 90, 110, 78, 77, 80, 85, 91, 87, 47, 48, 49, 50, 51, 52, 54, 58, 56, 113, 116, 117, 118, 120, 121, 122, 123, 125, 127, 131, 132, 133, 136, 137, 138, 139, 140, 141, 142, 143, 144, 145, 146, 147, 148, 149, 150, 151, 152, 154, 156, 157, 158, 159, 160, and 88 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*). After the inoculation, the plant was cultivated in a greenhouse at 24° C. in the daytime and 20° C. at night for 8 days, and then the area of lesion spots was investigated. As a result, the area of lesion spots on the plant treated with the present compound 7, 8, 9, 10, 11, 12, 13, 14, 15, 16, 17, 18, 19, 20, 41, 2, 3, 4, 5, 40, 46, 6, 21, 22, 23, 24, 25, 26, 27, 28, 29, 30, 31, 32, 33, 34, 35, 1, 36, 37, 39, 44, 43, 89, 60, 61, 62, 63, 64, 65, 75, 76, 66, 67, 68, 69, 70, 72, 73, 74, 92, 100, 93, 94, 95, 101, 103, 104, 105, 106, 90, 110, 78, 77, 80, 85, 91, 87, 47, 48, 49, 50, 51, 52, 54, 58, 56, 113, 116, 117, 118, 120, 121, 122, 123, 125, 127, 131, 132, 133, 136, 137, 138, 139, 140, 141, 142, 143, 144, 145, 146, 147, 148, 149, 150, 151, 152, 154, 156, 157, 158, 159, 160, or 88 was 30% or less of that on an untreated plant.

Test Example 7

Each of plastic pots was filled with sandy loam and soybean (cultivar: KUROSENGOKU) was sowed and grown in a greenhouse for 13 days. Then, each water dilution containing a surfactant prepared by adjusting so as to contain a predetermined concentration (200 ppm) of any one compound of the present compounds 7, 9, 10, 16, 18, 19, 20, 4, 5, 46, 22, 23, 24, 25, 27, 29, 30, 31, 32, 33, 34, 35, 89, 60, 61, 62, 63, 64, 66, 68, 69, 100, 106, 110, 79, 80, 84, 39, 44, 42, 43, 53, 113, 122, 127, 129, 131, 132, 135, 136, 137, 138, 139, 141, and 85 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion spots was investigated. As a result, it has been found that the area of lesion spots on the plant treated with the present compound 7, 9, 10, 16, 18, 19, 20, 4, 5, 46, 22, 23, 24, 25, 27, 29, 30, 31, 32, 33, 34, 35, 89, 60, 61, 62, 63, 64, 66, 68, 69, 100, 106, 110, 79, 80, 84, 39, 44, 42, 43, 53, 113, 122, 127, 129, 131, 132, 135, 136, 137, 138, 139, 141, or 85 was 30% or less of that on an untreated plant.

Test Example 8

Each of plastic pots was filled with sandy loam and barley (cultivar: NISHINOHOSHI) was sowed and grown in a greenhouse for 7 days. Then, each water dilution containing a surfactant prepared by adjusting so as to contain a predetermined concentration (200 ppm) of any one compound of the present compounds 7, 8, 9, 10, 11, 12, 13, 14, 15, 16, 17, 18, 19, 20, 41, 2, 3, 4, 5, 40, 46, 6, 21, 22, 23, 24, 25, 26, 27, 28, 29, 30, 31, 32, 33, 34, 35, 1, 36, 37, 89, 60, 61, 62, 63, 64, 65, 75, 76, 66, 67, 68, 69, 70, 71, 72, 73, 92, 100, 99, 93, 94, 101, 102, 103, 104, 106, 108, 109, 90, 110, 96, 78, 77, 79, 80, 84, 85, 81, 83, 39, 44, 42, 43, 47, 49, 50, 51, 52, 53, 54, 58, 56, 113, 116, 117, 118, 119, 120, 121, 122, 123, 126, 129, 131, 132, 133, 135, 136, 137, 139, 140, 141, and 91 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with of the present compound 7, 8, 9, 10, 11, 12, 13, 14, 15, 16, 17, 18, 19, 20, 41, 2, 3, 4, 5, 40, 46, 6, 21, 22, 23, 24, 25, 26, 27, 28, 29, 30, 31, 32, 33, 34, 35, 1, 36, 37, 89, 60, 61, 62, 63, 64, 65, 75, 76, 66, 67, 68, 69, 70, 71, 72, 73, 92, 100, 99, 93, 94, 101, 102, 103, 104, 106, 108, 109, 90, 110, 96, 78, 77, 79, 80, 84, 85, 81, 83, 39, 44, 42, 43, 47, 49, 50, 51, 52, 53, 54, 58, 56, 113, 116, 117, 118, 119, 120, 121, 122, 123, 126, 129, 131, 132, 133, 135, 136, 137, 139, 140, 141, or 91 was 30% or less of that on an untreated plant.

Test Example 9

Each of plastic pots was filled with sandy loam and cucumber (cultivar: SAGAMI HANJIRO) was sowed and grown in a greenhouse for 19 days. Then, each water dilution containing a surfactant prepared by adjusting so as to contain a predetermined concentration (200 ppm) of any one compound of the present compounds 7, 8, 9, 10, 12, 16, 17, 18, 19, 2, 3, 21, 23, 24, 25, 26, 27, 29, 89, 60, 61, 63, 64, 65, 75, 67, 100, 94, 95, 103, 104, 105, 106, 90, 110, 78, 77, 131, 132, 136, 138, 139, 140, 142, 143, 144, and 145 was sprayed over stems and leaves of the cucumber so that it sufficiently adhered to the surface of the leaves of the cucumber. After spraying, the plant was air-dried. After one day, the plant was inoculated by sprinkling with spores of cucumber target leaf spot fungus (*Corynespora cassiicola*). After the inoculation, the plant was cultivated at 24° C. in the daytime and 20° C. at night under high humidity condition for 7 days. Thereafter, the area of lesion spots was investigated. As a result, the area of lesion spots on the plant treated with the present compound 7, 8, 9, 10, 12, 16, 17, 18, 19, 2, 3, 21, 23, 24, 25, 26, 27, 29, 89, 60, 61, 63, 64, 65, 75, 67, 100, 94, 95, 103, 104, 105, 106, 90, 110, 78, 77, 131, 132, 136, 138, 139, 140, 142, 143, 144, or 145 was 30% or less of that on an untreated plant.

Test Example 10

Each of plastic pots was filled with sandy loam and cucumber (cultivar: SAGAMI HANJIRO) was sowed and grown in a greenhouse for 19 days. Then, each water dilution containing a surfactant prepared by adjusting so as to contain a predetermined concentration (200 ppm) of any one compound of the present compounds 7, 8, 9, 10, 14, 16, 17, 18, 19, 2, 3, 4, 5, 46, 6, 21, 22, 23, 24, 25, 26, 27, 28, 29, 30, 31, 32, 33, 34, 35, 36, 37, 39, 42, 43, 89, 61, 62, 63, 64, 65, 75, 66, 67, 68, 69, 70, 73, 74, 100, 93, 104, 105, 106, 90, 110, 96, 78, 77, 79, 80, 84, 81, 51, 53, 58, 56, 117, 120, 122, 123, 131, 133, and 91 was sprayed over stems and leaves of the cucumber so that it sufficiently adhered to the surface of the leaves of the cucumber. After spraying, the plant was air-dried. After one day, the plant was inoculated by sprinkling with spores of cucumber anthracnose fungus (*Colletotrichum lagenarium*). After the inoculation, the plant was at first left to stand at 23° C. under high humidity condition for one day and then cultivated in a greenhouse at 24° C. in the daytime and 20° C. at night for 6 days. Thereafter, the area of lesion spots was investigated. As a result, the area of lesion spots on the plant treated with the present compound 7, 8, 9, 10, 14, 16, 17, 18, 19, 2, 3, 4, 5, 46, 6, 21, 22, 23, 24, 25, 26, 27, 28, 29, 30, 31, 32, 33, 34, 35, 36, 37, 39, 42, 43, 89, 61, 62, 63, 64, 65, 75, 66, 67, 68, 69, 70, 73, 74, 100, 93, 104, 105, 106, 90, 110, 96, 78, 77, 79, 80, 84, 81, 51, 53, 58, 56, 117, 120, 122, 123, 131, 133, or 91 was 30% or less of that on an untreated plant.

Test Example 11

A water dilution (test chemical solution) containing a surfactant prepared by adjusting so as to contain a predetermined concentration (500 ppm) of any one compound of the present compounds 24, 29, 79, 90, and 93 was used as a test chemical solution.

Thirty (30) heads of cotton aphid (*Aphis gossypii*) (including adults and larvae) were released on the leaves of cucumber (cultivar: SAGAMI HANJIRO FUSHINARI) grown in a polyethylene cup until the first true leaf was developed. Next day, 20 mL of the above test chemical solution was sprayed. After 6 days, the number of the surviving insects was counted and the control value was calculated by the following equation.

Control value (%)={1−($Cb \times Tai$)/($Cai \times Tb$)}×100 wherein symbols in the equation represent the followings:
Cb: Number of insects before spraying chemical solution in untreated area;
Cai: Number of surviving insects in untreated area;
Tb: Number of insects before spraying chemical solution in treated area; and
Tai: Number of surviving insects in treated area.
As a result, the present compounds 24, 29, 79, 90, and 93 showed 90% or more of the control value.

Test Example 12

A water dilution containing a surfactant prepared by adjusting so as to contain a predetermined concentration (500 ppm) of any one compound of the present compounds 20, 29, and 79 was used as a test chemical solution.

The above test chemical solution (0.7 mL) was added to 100 mL of deionized water to adjust the concentration of an active ingredient to 3.5 ppm. Twenty (20) heads of last instar larvae of common house mosquito (*Culex pipiens pallens*) were released in the solution and the number of dead insects was counted after 8 days.

Mortality was determined by the following equation.

Mortality (%)=(number of dead insects/number of test insects)×100

As a result, even when using any test chemical solution containing the present compound 20, 29, or 79, mortality of 100% was exhibited.

Comparative Test Example

Each of plastic pots was filled with sandy loam and cucumber (cultivar: SAGAMI HANJIRO) was sowed and grown in a greenhouse for 12 days. Then, each water dilution containing a surfactant prepared by adjusting so as to contain a predetermined concentration (500 ppm) of any one compound of 1-{2-(4-methylphenoxymethyl)phenyl}-4-methyl-1,4-dihydrotetrazol-5-one was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*). After the inoculation, the plant was cultivated in a greenhouse at 24° C. in the daytime and 20° C. at night for 8 days, and then the area of lesion spots was investigated. As a result, the area of lesion spots on the plant treated with the present compound 1-{2-(4-methylphenoxymethyl)phenyl}-4-methyl-1,4-dihydrotetrazol-5-one was 70% or more of that on an untreated plant.

The invention claimed is:
1. A tetrazolinone compound represented by formula (1):

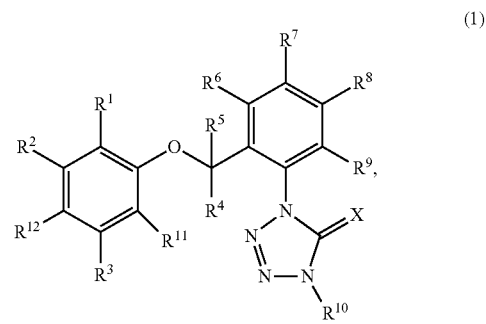

wherein
$R^1$, $R^2$, $R^3$, and $R^{11}$ each independently represents a C1-C6 alkyl group optionally substituted with one or more atoms or groups selected from Group $P^1$, a halogen atom, a hydrogen atom, a C1-C6 alkoxy group optionally substituted with one or more halogen atoms, a cyano group, a nitro group, a C2-C6 alkenyl group optionally substituted with one or more halogen atoms, a C2-C6 alkynyl group optionally substituted with one or more halogen atoms, a C1-C8 alkylamino group optionally substituted with one or more halogen atoms, a C1-C6 alkylthio group optionally substituted with one or more halogen atoms, a C1-C6 alkylsulfinyl group optionally substituted with one or more halogen atoms, a C1-C6 alkylsulfonyl group optionally substituted with one or more halogen atoms, a pentafluorosulfanyl group, a C3-C9 trialkylsilyl group, a C2-C6 alkylcarbonyl group, a C2-C6 alkoxycarbonyl group, or an aminocarbonyl group optionally substituted with a C1-C6 alkyl group;
$R^4$ and $R^5$ each independently represents a hydrogen atom, a halogen atom, or a C1-C3 alkyl group;

$R^6$ represents a C1-C6 alkyl group optionally substituted with one or more halogen atoms, a C1-C6 alkoxy group optionally substituted with one or more halogen atoms, a C3-C6 cycloalkyl group optionally substituted with one or more halogen atoms, a halogen atom, a C2-C6 alkenyl group optionally substituted with one or more halogen atoms, a cyano group, a C1-C6 alkylthio group optionally substituted with one or more halogen atoms, a C2-C6 alkynyl group optionally substituted with one or more halogen atoms, a nitro group, an aminocarbonyl group optionally substituted with one or more C1-C6 alkyl groups, a C3-C6 cycloalkyloxy group optionally substituted with one or more halogen atoms, a C3-C6 cycloalkylthio group optionally substituted with one or more halogen atoms, a C3-C6 alkenyloxy group optionally substituted with one or more halogen atoms, a C3-C6 alkynyloxy group optionally substituted with one or more halogen atoms, a C3-C6 alkynylthio group optionally substituted with one or more halogen atoms, a C2-C6 alkoxycarbonyl group, a hydroxy group, a sulfanyl group, a C1-C8 alkylamino group optionally substituted with one or more halogen atoms, a pentafluorosulfanyl group, a C3-C9 trialkylsilyl group, a C1-C6 alkylsulfonyl group optionally substituted with one or more halogen atoms, a C1-C6 alkylsulfinyl group optionally substituted with one or more halogen atoms, a C2-C6 alkylcarbonyl group, a C2-C5 alkoxyalkyl group, or a C2-C5 alkylthioalkyl group;

$R^7$, $R^8$, and $R^9$ each independently represents a hydrogen atom, a halogen atom, a C1-C3 alkyl group optionally substituted with one or more halogen atoms, a C2-C3 alkenyl group optionally substituted with one or more halogen atoms, or a C1-C3 alkoxy group optionally substituted with one or more halogen atoms;

$R^{10}$ represents a C1-C3 alkyl group optionally substituted with one or more halogen atoms, a C2-C3 alkenyl group optionally substituted with one or more halogen atoms, a C2-C3 alkynyl group optionally substituted with one or more halogen atoms, or a C3-C5 cycloalkyl group optionally substituted with one or more halogen atoms;

$R^{12}$ represents a C6-C16 aryl group optionally substituted with one or more atoms or groups selected from Group $P^2$, a C6-C16 aryloxy group optionally substituted with one or more atoms or groups selected from Group $P^2$, a C6-C16 arylthio group optionally substituted with one or more atoms or groups selected from Group $P^2$, a C7-C18 aralkyl group optionally substituted with one or more atoms or groups selected from Group $P^2$, a C7-C18 aralkyloxy group optionally substituted with one or more atoms or groups selected from Group $P^2$, a C7-C16 aryloxyalkyl group optionally substituted with one or more atoms or groups selected from Group $P^2$, an anilino group optionally substituted with one or more atoms or groups selected from Group $P^2$, a C2-C5 alkylthioalkyl group, a C1-C6 alkyl group optionally substituted with one or more C1-C3 alkoxy groups and/or halogen atoms, a C1-C6 alkoxy group optionally substituted with one or more halogen atoms, a C2-C6 alkenyl group optionally substituted with one or more halogen atoms, a C3-C6 cycloalkyl group optionally substituted with one or more halogen atoms, a C3-C6 cycloalkenyl group optionally substituted with one or more halogen atoms, a C1-C8 alkylamino group optionally substituted with one or more halogen atoms, a C2-C9 heteroaryloxy group optionally substituted with one or more atoms or groups selected from Group $P^2$ (provided that the heteroaryl moiety represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring), $R^{13}R^{14}N$—N=CH—, $R^{13}R^{14}N$—CH=N—, a C1-C6 alkylsulfinyl group optionally substituted with one or more halogen atoms, a C1-C6 alkylsulfonyl group optionally substituted with one or more halogen atoms, a pentafluorosulfanyl group, a C2-C6 alkoxycarbonyl group, a C2-C6 alkylcarbonyloxy group, an aminocarbonyl group optionally substituted with a C1-C6 alkyl group, or a C3-C9 trialkylsilyl group;

$R^{13}$ and $R^{14}$ each independently represents a hydrogen atom or a C1-C3 alkyl group;

X represents an oxygen atom or a sulfur atom:

Group $P^1$ is selected from the group consisting of a halogen atom, a cyano group, a C3-C6 cycloalkyl group optionally substituted with one or more halogen atoms, a C1-C4 alkoxy group optionally substituted with one or more halogen atoms, and a C1-C4 alkylthio group optionally substituted with one or more halogen atoms; and Group $P^2$ is selected from the group consisting of a C1-C6 alkyl group optionally substituted with one or more halogen atoms, a halogen atom, a cyano group, a hydroxyl group, a C3-C6 cycloalkyl group optionally substituted with one or more halogen atoms, a C1-C6 alkoxy group optionally substituted with one or more halogen atoms, a C1-C6 alkylthio group optionally substituted with one or more halogen atoms, a C2-C6 alkenyl group optionally substituted with one or more halogen atoms, a C2-C6 alkynyl group optionally substituted with one or more halogen atoms, a C1-C8 alkylamino group optionally substituted with one or more halogen atoms, a C1-C6 alkylsulfinyl group optionally substituted with one or more halogen atoms, a C1-C6 alkylsulfonyl group optionally substituted with one or more halogen atoms, a pentafluorosulfanyl group, a C2-C6 alkoxycarbonyl group, a C2-C6 alkylcarbonyl group, a C2-C6 alkylcarbonyloxy group, a C2-C6 alkylcarbonylamino group, an aminocarbonyl group optionally substituted with a C1-C6 alkyl group, and a C3-C9 trialkylsilyl group.

2. The tetrazolinone compound according to claim 1, wherein $R^1$ is a C1-C3 alkyl group optionally substituted with one or more halogen atoms, a hydrogen atom, a C2-C3 alkynyl group optionally substituted with one or more halogen atoms, a C3-C5 cycloalkyl group optionally substituted with one or more halogen atoms, or a C1-C3 alkoxy group optionally substituted with one or more halogen atoms;

$R^2$ and $R^3$ represent a hydrogen atom, a halogen atom, a C1-C4 alkyl group optionally substituted with one or more halogen atoms, a C1-C4 alkoxy group optionally substituted with one or more halogen atoms, or a cyano group;

$R^4$, $R^5$, $R^7$, $R^8$, $R^9$, and $R^{11}$ are hydrogen atoms;

$R^6$ is a C1-C4 alkyl group optionally substituted with one or more halogen atoms, a halogen atom, a C1-C4 alkoxy group optionally substituted with one or more halogen atoms, a C3-C5 cycloalkyl group optionally substituted with one or more halogen atoms, a C2-C4 alkenyl group optionally substituted with one or more halogen atoms, or a C2-C4 alkynyl group;

$R^{10}$ is a methyl group; and

X is an oxygen atom.

3. The tetrazolinone compound according to claim 1, wherein $R^{12}$ is a phenyl group optionally substituted with one or more atoms or groups selected from the following Group $P^3$:

Group P³ is selected from the group consisting of a C1-C3 alkyl group optionally substituted with one or more halogen atoms, a halogen atom, a cyano group, a C1-C3 alkoxy group optionally substituted with one or more halogen atoms, a C3-C4 cycloalkyl group optionally substituted with one or more halogen atoms, and a C1-C3 alkylthio group optionally substituted with one or more halogen atoms.

4. The tetrazolinone compound according to claim 1, wherein $R^{12}$ is a phenoxy group optionally substituted with one or more atoms or groups selected from the following Group P³:

Group P³ is selected from the group consisting of a C1-C3 alkyl group optionally substituted with one or more halogen atoms, a halogen atom, a cyano group, a C1-C3 alkoxy group optionally substituted with one or more halogen atoms, a C3-C4 cycloalkyl group optionally substituted with one or more halogen atoms, and a C1-C3 alkylthio group optionally substituted with one or more halogen atoms.

5. The tetrazolinone compound according to claim 1, wherein $R^1$ is a C1-C3 alkyl group optionally substituted with one or more halogen atoms, a hydrogen atom, or a C1-C3 alkoxy group optionally substituted with one or more halogen atoms;

$R^2$ is a hydrogen atom, a halogen atom, a C1-C4 alkyl group optionally substituted with one or more halogen atoms, a C1-C4 alkoxy group optionally substituted with one or more halogen atoms, or a cyano group;

$R^3$ is a hydrogen atom, a halogen atom, or a C1-C4 alkyl group optionally substituted with one or more halogen atoms;

$R^4$, $R^5$, $R^7$, $R^8$, $R^9$, and $R^{11}$ are hydrogen atoms;

$R^6$ is a C1-C4 alkyl group optionally substituted with one or more halogen atoms, a halogen atom, a C1-C4 alkoxy group optionally substituted with one or more halogen atoms, or a C3-C5 cycloalkyl group optionally substituted with one or more halogen atoms;

$R^{10}$ is a methyl group;

X is an oxygen atom;

$R^{12}$ is a phenyl group optionally substituted with one or more atoms or groups selected from the following Group P³, or a phenoxy group optionally substituted with one or more atoms or groups selected from the following Group P³:

Group P³ is selected from the group consisting of a C1-C3 alkyl group optionally substituted with one or more halogen atoms, a halogen atom, a cyano group, and a C1-C3 alkoxy group optionally substituted with one or more halogen atoms.

6. A pest control agent comprising the tetrazolinone compound according to claim 1.

7. A method for controlling pests, which comprises treating plants or soil with an effective amount of the tetrazolinone compound according to claim 1.

* * * * *